United States Patent
Rimkunas et al.

(10) Patent No.: US 11,099,188 B2
(45) Date of Patent: Aug. 24, 2021

(54) ROS KINASE IN LUNG CANCER

(71) Applicant: CELL SIGNALING TECHNOLOGY, INC., Danvers, MA (US)

(72) Inventors: Victoria McGuinness Rimkunas, Reading, MA (US); Herbert Haack, South Hamilton, MA (US); Ting-Lei Gu, Woburn, MA (US); Ailan Guo, Lexington, MA (US); Anthony Paul Possemato, Worcester, MA (US); Katherine Eleanor Crosby, Middleton, MA (US); Meghan Ann Tucker, Salem, MA (US); Cynthia Beaudet, Beverly, MA (US)

(73) Assignee: CELL SIGNALING TECHNOLOGY, INC., Danvers, MA (US)

( * ) Notice: Subject to any disclaimer, the term of this patent is extended or adjusted under 35 U.S.C. 154(b) by 0 days.

(21) Appl. No.: 15/994,165

(22) Filed: May 31, 2018

(65) Prior Publication Data
US 2019/0128889 A1 May 2, 2019

Related U.S. Application Data

(60) Division of application No. 13/113,676, filed on May 23, 2011, now abandoned, which is a continuation-in-part of application No. PCT/US2010/024109, filed on Feb. 12, 2010, and a continuation-in-part of application No. 12/738,210, filed as application No. PCT/US2008/011968 on Oct. 20, 2008, now Pat. No. 9,096,855, said application No. 13/113,676 is a continuation-in-part of application No. 12/581,126, filed on Oct. 17, 2009, now abandoned, which is a continuation-in-part of application No. 12/218,834, filed on Jul. 18, 2008, now Pat. No. 8,383,799, which is a continuation of application No. PCT/US2007/001360, filed on Jan. 19, 2007.

(60) Provisional application No. 61/347,251, filed on May 21, 2010, provisional application No. 61/207,484, filed on Feb. 12, 2009, provisional application No. 60/999,668, filed on Oct. 18, 2007, provisional application No. 60/760,634, filed on Jan. 20, 2006.

(51) Int. Cl.
*G01N 33/574* (2006.01)
*C12Q 1/6886* (2018.01)

(52) U.S. Cl.
CPC ..... *G01N 33/57423* (2013.01); *C12Q 1/6886* (2013.01); *C12Q 2600/106* (2013.01); *C12Q 2600/156* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 2005/0181375 A1 | 8/2005 | Aziz et al. | |
| 2010/0143918 A1 | 6/2010 | Guo et al. | |
| 2010/0221737 A1 | 9/2010 | Gu et al. | |
| 2010/0298404 A1 | 11/2010 | Guo et al. | |
| 2011/0287445 A1 | 11/2011 | Gu et al. | |
| 2012/0208824 A1 | 8/2012 | Rimkunas et al. | |

FOREIGN PATENT DOCUMENTS

| | | |
|---|---|---|
| CN | 101466721 A | 6/2009 |
| CN | 101586155 A | 11/2009 |
| CN | 101466721 B | 8/2013 |
| JP | 2012-517245 A | 8/2012 |
| WO | 2007/084631 A2 | 7/2007 |
| WO | 2008/066498 A1 | 6/2008 |
| WO | 2009/051846 A2 | 4/2009 |
| WO | 2010/093928 A2 | 8/2010 |
| WO | 2011/146945 A2 | 11/2011 |

OTHER PUBLICATIONS

Acquaviva J. et al., "The Multifaceted Roles of the Receptor Tyrosine Kinase ROS in Development and Cancer", Biochimica et Biophysica Acta 1795:37-52 (2009).
Charest A. et al., "Fusion of FIG to the Receptor Tyrosine Kinase ROS in a Glioblastoma With an Interstitial Del(6) (q21q21)", Genes, Chromosomes & Cancer 37:58-71 (2003).
El-Deeb I M et al., "ROS Receptor Tyrosine Kinase: A New Potential Target for Anticancer Drugs", Medicinal Research Reviews 31(5):794-818 (2011).
Falini B. et al., "Porteins Encoded by Genes Involved in Chromosomal Alterations in Lymphoma and Leukemia: Clinical Value of Their Detection by Immunocytochemistry", Blood 99(2):409-426 (Jan. 15, 2002).
Futreal P.A. et al., "A Census of Human Cancer Genes", Nat Rev Cancer 4(3):177-183 (Mar. 2004).
Gu T-L et al., "Survey of Tyrosine Kinase Signaling Reveals ROS Kinase Fusions in Human Cholangiocarcinoma", PLoS ONE 6(1):e15640 (Jan. 2011).

(Continued)

*Primary Examiner* — Robert A Zeman
(74) *Attorney, Agent, or Firm* — Scully, Scott, Murphy & Presser, P.C.

(57) ABSTRACT

The invention provides the identification of the presence of polypeptides with ROS kinase activity in mammalian lung cancer. In some embodiments, the polypeptide with ROS kinase activity is the result of a fusion between a ROS-encoding polynucleotide and a polynucleotide encoding a second (non-ROS) polypeptide. Three different fusion partners of ROS are described, namely proteins encoded by the FIG gene, the SLC34A2 gene, and the CD74 gene. The invention enables new methods for determining the presence of a polypeptide with ROS kinase activity in a biological sample, methods for screening for compounds that inhibit the proteins, and methods for inhibiting the progression of a cancer (e.g., an lung cancer).

4 Claims, 32 Drawing Sheets
(13 of 32 Drawing Sheet(s) Filed in Color)
Specification includes a Sequence Listing.

(56) References Cited

OTHER PUBLICATIONS

Kurzrock R. et al., "The Molecular Genetics of Philadelphia Chromosome-Positive Leukemias", The New England Journal of Medicine 319(15):990-998 (Oct. 13, 1988).

Mitelman F. et al., "The Impact of Translocations and Gene Fusions on Cancer Causation", Nature Reviews—Cancer 7:233-245 (Apr. 2007).

Niwizu T. et al., "CRIZOTINIB, ALK/Met Inhibitor Oncolytic", Drugs of the Future 36(2):91-98 (2011).

Rikova K. et al., "Global Survey of Phosphotyrosine Signaling Identifies Oncogenic Kinases in Lung Cancer", Cell 131:1190-1203 (Dec. 14, 2007).

Ruhe J.E. et al., "Genetic Alterations in the Tyrosine Kinase Transcriptome of Human Cancer Cell Lines", Cancer Research 67(23):11368-11376 (Dec. 1, 2007).

Zhao J-F et al., "Expression of the ROS1 Oncogene for Tyrosine Receptor Kinase in Adult Human Meningiomas", Cancer Genet Cytogenet 83:148-154 (1995).

ROS (C-20): SC-6347, Santa Cruz Biotechnology Inc., retrieved from the Internet: URL:http://datasheets.scbt.com/sc-6347.pdf (1990).

European Supplementary Search Report dated Jul. 25, 2012 received in European Patent Application No. 10 74 1807.

International Search Report dated Sep. 14, 2010 received in International Application No. PCT/US10/24109.

International Search Report and Written Opinion dated Aug. 13, 2012 received in International Application No. PCT/US2012/039108.

Japanese Notice of Reasons for Rejection dated Mar. 1, 2016 received in Japanese Patent Application No. 2014-512072, together with an English-language translation.

Chinese Office Action and Search Report dated Mar. 29, 2019 received in Chinese Patent Application No. 201610542647.6, together with an English-language translation.

Karayan-Tapon L. et al., "Lack of GOPC-ROS1 (FIG-ROS1) Rearrangement in Adult Human Gliomas", European Journal of Cancer 50:2364-2366 (2014).

Lim S M et al., "Lack of ROS1 Gene Rearrangement in Glioblastoma Multiforme", PLoS ONE 10(9):e0137678 (Sep. 14, 2015).

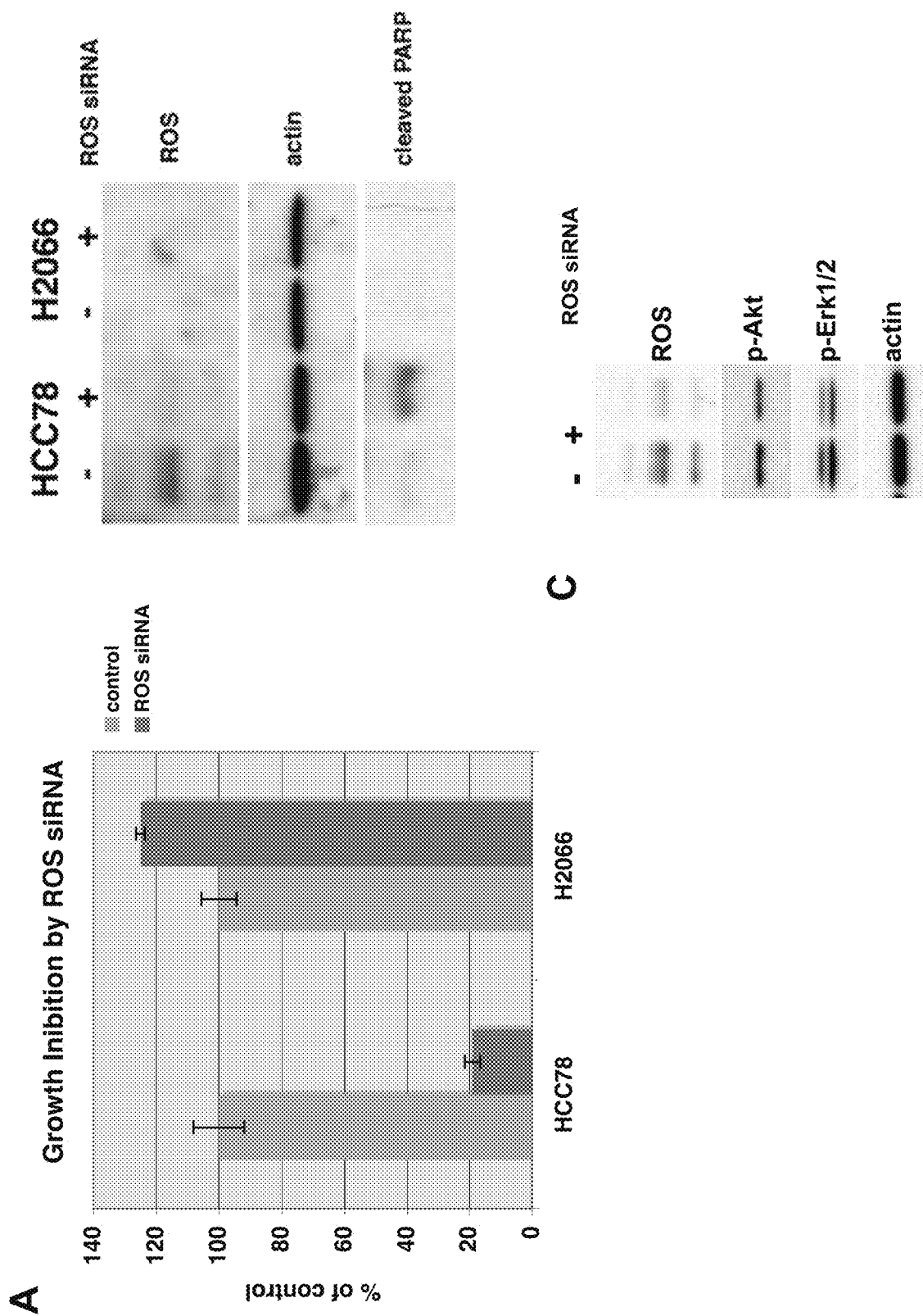
Figure 2A-C

SLC34A2/ROS (long)

SLC34A2/ROS (short)

Figure 4A

MAPWPELGDAQPNPDKYLEGAAGQQPTAPDKSKETNKTDNTEAPVTKIELLPSYSTATLIDEPTEVDDPWNLPTLQDSGI
KWSERDTKGKILCFFQGIGRLILLLGFLYFFVCSLDILSSAFQLVGAGVPNKPGIPKLLEGSKNSIQWEKAEDNGCRITY
YILEIRKSTSNNLQNQNLRWKMTFNGSCSSVCTWKSKNLKGIFQFRVVAANNLGFGEYSGISENIILVGDDFWIPETSFI
LTIIVGIFLVVTIPLTFVWHRRLKNQKSAKEGVTVLINEDKELAELRGLAAGVGLANACYAIHTLPTQEEIENLPAFPRE
**KLTLRLLLGSGAFGEVYEGTAVDILGVGSGEIKVAVKTLKKGSTDQEKIEFLKEAHLMSKFNHPNILKQLGVCLLNEPQY
IILELMEGGDLLTYLRKARMATFYGPLLTLVDLVDLCVDISKGCVYLERMHFIHRDLAARNCLVSVKDYTSPRIVKIGDF
GLARDIYKNDYYRKRGEGLLPVRWMAPESLMDGIFTTQSDVWSFGILIWEILTLGHQPYPAHSNLDVLNYVQTGGRLEPP
RNCPDDLWNLMTQCWAQEPDQRPTFHRIQDQLQLFRNFF**LNSIYKSRDEANNSGVINESFEGEDGDVICLNSDDIMPVAL
METKNREGLNYMVLATECGQGEEKSEGPLGSQESESCGLRKEEKEPHADKDFCQEKQVAYCPSGKPEGLNYACLTHSGYG
DGSD

```
atggctccctggcctgaattgggagatgcccagcccaaccccgataagtacctcgaaggggccgcaggtcagcagcccac
tgcccctgataaaagcaaagagaccaacaaaacagataacactgaggcacctgtaaccaagattgaacttctgccgtcct
actccacggctacactgatagatgagcccactgaggtggatgaccctggaacctacccactcttcaggactcggggatc
aagtggtcagagagagacaccaaagggaagattctctgttcttccaagggattgggagattgattttacttctcggatt
tctctacttttcgtgtgctccctggatattcttagtagcgccttccagctggttggagctggagtcccaataaaccag
gcattcccaaattactagaagggagtaaaaattcaatacagtgggagaaagctgaagataatggatgtagaattacatac
tatatccttgagataagaaagagccacttcaaataatttacagaaccagaatttaaggtggaagatgacatttaatggatc
ctgcagtagtgtttgcacatggaagtccaaaaacctgaaaggaatatttcagttcagagtagtagctgcaaataatctag
ggtttggtgaatatagtggaatcagtgagaatattatattagttggagatgattttggataccagaaacaagtttcata
cttactattatagttggaatatttctggttgttacaatcccactgacctttgtctggcatagaagattaaagaatcaaaa
aagtgccaaggaagggtgacagtgcttataaacgaagacaaagagttggctgagctgcgaggtctggcagccggagtag
gcctggctaatgcctgctatgcaatacatactcttccaacccaagaggagattgaaaatcttcctgccttccctcgggaa
aaactgactctgcgtctcttgctgggaagtggagcctttggagaagtgtatgaaggaacagcagtggacatcttaggagt
tggaagtggagaaatcaaagtagcagtgaagactttgaagaagggttccacagaccaggagaagattgaattcctgaagg
aggcacatctgatgagcaaatttaatcatcccaacattctgaagcagcttggagtttgtctgctgaatgaacccaatac
attatcctggaactgatggagggaggagaccttcttacttatttgcgtaaagcccggatggcaacgttttatggtcctttt
actcaccttggttgaccttgtagacctgtgtgtagatatttcaaaaggctgtgtctacttggaacggatgcatttcattc
acagggatctggcagctagaaattgccttgtttccgtgaaagactataccagtccacggatagtgaagattggagacttt
ggactcgccagagacatctataaaaatgattactatagaaagagaggggaaggcctgctcccagttcggtggatggctcc
agaaagtttgatggatggaatcttcactactcaatctgatgtatggtcttttggaattctgatttgggagattttaactc
ttggtcatcagccttatccagctcattccaaccttgatgtgttaaactatgtgcaaacaggagggagactggagccacca
agaaattgtcctgatgatctgtggaatttaatgacccagtgctgggctcaagaacccgaccaaagacctactttcatag
aattcaggaccaacttcagttattcagaaatttttcttaaatagcatttataagtccagagatgaagcaaacaacagtg
gagtcataaatgaaagctttgaaggtgaagatggcgatgtgatttgtttgaattcagatgacattatgccagttgcttta
atggaaacgaagaaccgagaagggttaaactatatggtacttgctacagaatgtggccaaggtgaagaaaagtctgaggg
tcctctaggctcccaggaatctgaatcttgtggtctgaggaagaagagaaggaaccacatgcagacaaagatttctgcc
aagaaaaacaagtggcttactgcccttctggcaagcctgaaggcctgaactatgcctgtctcactcacagtggatatgga
gatgggtctgattaa
```

Figure 4B

*MAPWPELGDAQPNPDKYLEGAAGQQPTAPDKSKETNKTDNTEAPVTKIELLPSYSTATLIDEPTEVDDPWNLPTLQDSGI*
*KWSERDTKGKILCFFQGIGRLILLLGFLYFFVCSLDILSSAFQLVGDDFWIPETSFILTIIVGIFLVVTIPLTFVWHRRL*
*KNQKSAKEGVTVLINEDKELAELRGLAAGVGLANACYAIHTLPTQEEIENLPAFPREK**LTLRLLLGSGAFGEVYEGTAVD*
*ILGVGSGEIKVAVKTLKKGSTDQEKIEFLKEAHLMSKFNHPNILKQLGVCLLNEPQYIILELMEGGDLLTYLRKARMATF*
*YGPLLTLVDLVDLCVDISKGCVYLERMHFIHRDLAARNCLVSVKDYTSPRIVKIGDFGLARDIYKNDYYRKRGEGLLPVR*
*WMAPESLMDGIFTTQSDVWSFGILIWEILTLGHQPYPAHSNLDVLNYVQTGGRLEPPRNCPDDLWNLMTQCWAQEPDQRP*
*TFHRIQDQLQLFRNFF**LNSIYKSRDEANNSGVINESFEGEDGDVICLNSDDIMPVALMETKNREGLNYMVLATECGQGEE*
*KSEGPLGSQESESCGLRKEEKEPHADKDFCQEKQVAYCPSGKPEGLNYACLTHSGYGDGSD*

*atggctcctggcctgaattgggagatgcccagcccaacccgataagtacctcgaaggggccgcaggtcagcagcccac*
*tgcccctgataaaagcaaagagaccaacaaaacagataacactgaggcacctgtaaccaagattgaacttctgccgtcct*
*actccacggctacactgatagatgagcccactgaggtggatgaccctggaacctacccactcttcaggactcggggatc*
*aagtggtcagagagagacaccaaagggaagattctctgtttcttccaagggattgggagattgattttacttctcggatt*
*tctctacttttcgtgtgctccctggatattcttagtagcgccttccagctggttggagatgattttggataccagaaa*
*caagtttcatacttactattatagttggaatatttctggttgttacaatcccactgacctttgtctggcatagaagatta*
*aagaatcaaaaagtgccaaggaagggtgacagtgcttataaacgaagacaaagagttggctgagctgcgaggtctggc*
*agccggagtaggcctggctaatgcctgctatgcaatacatactcttccaacccaagaggagattgaaaatcttcctgcct*
*tccctcgggaaaactgactctgcgtctcttgctggggaagtggagcctttggagaagtgtatgaaggaacagcagtggac
atcttaggagttggaagtggagaaatcaaagtagcagtgaagactttgaagaagggttccacagaccaggagaagattga
attcctgaaggaggcacatctgatgagcaaatttaatcatcccaacattctgaagcagcttggagtttgtctgctgaatg
aaccccaatacattatcctggaactgatggagggaggagaccttcttacttatttgcgtaaagcccggatggcaacgttt
tatggtcctttactcaccttggttgaccttgtagacctgtgtgtagatatttcaaaaggctgtgtctacttggaacggat
gcatttcattcacagggatctggcagctagaaattgccttgtttccgtgaaagactataccagtccacggatagtgaaga
ttggagactttggactcgccagagacatctataaaaatgattactatagaaagagagggaaggcctgctcccagttcgg
tggatggctccagaaagtttgatggatggaatcttcactactcaatctgatgtatggtcttttggaattctgatttggga
gattttaactcttggtcatcagccttatccagctcattccaaccttgatgtgttaaactatgtgcaaacaggagggagac
tggagccaccaagaaattgtcctgatgatctgtggaatttaatgacccagtgctgggctcaagaacccgaccaaagacct
acttttcatagaattcaggaccaacttcagttattcagaaattttttcttaaatagcatttataagtccagagatgaagc*
*aaacaacagtggagtcataaatgaaagctttgaaggtgaagatggcgatgtgatttgtttgaattcagatgacattatgc*
*cagttgctttaatggaaacgaagaaccgagaagggttaaactatatggtacttgctacagaatgtggccaaggtgaagaa*
*aagtctgagggtcctctaggctcccaggaatctgaatcttgtggtctgaggaagaagagaaggaaccacatgcagacaa*
*agatttctgccaagaaaacaagtggcttactgcccttctggcaagcctgaaggcctgaactatgcctgtctcactcaca*
*gtggatatggagatgggtctgattaa*

Figure 5

MAPWPELGDAQPNPDKYLEGAAGQQPTAPDKSKETNKTDNTEAPVTKIELLPSYSTATLI
DEPTEVDDPWNLPTLQDSGIKWSERDTKGKILCFFQGIGRLILLLGFLYFFVCSLDILSS
AFQLVGGKMAGQFFSNSSIMSNPLLGLIGVLVTVLQSSSTSTSIVVSMVSSSLLTVRA
AIPIIMGANIGTSITNTIVALMQVGDRSEFRRAFAGATVHDFFNWLSVLVLLPVEVATHY
LEIITQLIVESFHFKNGEDAPDLLKVITKPFTKLIVQLDKKVISQIAMNDEKAKNKSLVK
IWCKTFTNKTQINVTVPSTANCTSPSLCWTDGIQNWTMKNVTYKENIAKCQHIFVNFHLP
DLAVGTILLILSLLVLCGCLIMIVKILGSVLKGQVATVIKKTINTDFPFPFAWLTGYLAI
LVGAGMTFIVQSSSVFTSALTPLIGIGVITIERAYPLTLGSNIGTTTTAILAALASPGNA
LRSSLQIALCHFFFNISGILLWYPIPFTRLPIRMAKGLGNISAKYRWFAVFYLIIFFFLI
PLTVFGLSLAGWRVLVGVGVPVVFIIILVLCLRLLQSRCPRVLPKKLQNWNFLPLWMRSL
KPWDAVVSKFTGCFQMRCCYCCRVCCRACCLLCGCPKCCRCSKCCEDLEEAQEGQDVPVK
APETFDNITISREAQGEVPASDSKTECTAL

```
   1 cgggccaggt ttccaggctc ggccgccgcc tccatcccag cacctgcgga gggagcgctg
  61 accatggctc cctggcctga attgggagat gcccagccca acccgataa gtacctcgaa
 121 ggggccgcag gtcagcagcc cactgcccct gataaaagca agagaccaa caaaacagat
 181 aacactgagg cacctgtaac caagattgaa cttctgccgt cctactccac ggctacactg
 241 atagatgagc ccactgaggt ggatgacccc tggaacctac ccactcttca ggactcgggg
 301 atcaagtggt cagagagaga caccaaaggg aagattctct gtttcttcca agggattggg
 361 agattgattt tacttctcgg atttctctac tttttcgtgt gctcctgga tattcttagt
 421 agcgccttcc agctggttgg aggaaaaatg gcaggacagt tcttcagcaa cagctctatt
 481 atgtccaacc ctttgttggg gctggtgatc ggggtgctgg tgaccgtctt ggtgcagagc
 541 tccagcacct caacgtccat cgttgtcagc atggtgtcct cttcattgct cactgttcgg
 601 gctgccatcc ccattatcat ggggccaaac attggaacgt caatcaccaa cactattgtt
 661 gcgctcatgc aggtgggaga tcggagtgag ttcagaagag cttttgcagg agccactgtc
 721 catgacttct tcaactggct gtccgtgttg gtgctcttgc ccgtggaggt ggccacccat
 781 tacctcgaga tcataaccca gcttatagtg gagagcttcc acttcaagaa tggagaagat
 841 gccccagatc ttctgaaagt catcactaag cccttcacaa agctcattgt ccagctggat
 901 aaaaaagtta tcagccaaat tgcaatgaac gatgaaaaag cgaaaaacaa gagtcttgtc
 961 aagatttggt gcaaaacttt taccaacaag acccagatta cgtcactgt tccctcgact
1021 gctaactgca cctcccttc cctctgttgg acggatggca tccaaaactg gaccatgaag
1081 aatgtgacct acaaggagaa catcgccaaa tgccagcata tctttgtgaa tttccacctc
1141 ccggatcttg ctgtgggcac catcttgctc atactctccc tgctggtcct ctgtggttgc
1201 ctgatcatga ttgtcaagat cctgggctct gtgctcaagg gcaggtcgc cactgtcatc
1261 aagaagacca tcaacactga tttccccttt ccctttgcat ggttgactgg ctacctggcc
1321 atcctcgtcg ggcaggcat gaccttcatc gtacagagca gctctgtgtt cacgtcggcc
1381 ttgacccccc tgattggaat cggcgtgata accattgaga gggcttatcc actcacgctg
1441 ggctccaaca tcggcaccac caccaccgcc atcctggccg cttagccag ccctggcaat
1501 gcattgagga gttcactcca gatcgccctg tgccactttt cttcaacat ctccggcatc
1561 ttgctgtggt acccgatccc gttcactcgc ctgccatcc gcatggccaa gggctgggc
1621 aacatctctg ccaagtatcg ctggttcgcc gtcttctacc tgatcatctt cttcttcctg
1681 atcccgctga cggtgtttgg cctctcgctg gccggctggc gggtgctggt tggtgtcggg
1741 gttcccgtcg tcttcatcat catcctggta ctgtgcctcc gactcctgca gtctcgctgc
1801 ccacgcgtcc tgccgaagaa actccagaac tggaacttcc tgccgctgtg gatgcgctcg
1861 ctgaagccct gggatgccgt cgtctccaag ttcaccggct gcttccagat gcgctgctgc
1921 tactgctgcc gcgtgtgctg ccgcgcgtgc tgcttgctgt gtggctgccc caagtgctgc
1981 cgctgcagca agtgctgcga ggacttggag gaggcgcagg aggggcagga tgtccctgtc
2041 aaggctcctg agacctttga taacataacc attagcagag aggctcaggg tgaggtccct
2101 gcctcggact caaagaccga atgcacggcc ttgtagggga cgccccagat tgtcagggat
2161 gggggatgg tccttgagtt ttgcatgctc tcctccctcc cacttctgca ccctttcacc
2221 acctcgagga gatttgctcc ccattagcga atgaaattga tgcagtccta aaaaaaaaa
```

Figure 6A

MKNIYCLIPKLVNFATLGCLWISVVQCTVLNSCLKSCVTNLGQQLDLGTPHNLSEPCIQG
CHFWNSVDQKNCALKCRESCEVGCSSAEGAYEEEVLENADLPTAPFASSIGSHNMTLRWK
SANFSGVKYIIQWKYAQLLGSWTYTKTVSRPSYVVKPLHPFTEYIFRVVWIFTAQLQLYS
PPSPSYRTHPHGVPETAPLIRNIESSSPDTVEVSWDPPQFPGGPILGYNLRLISKNQKLD
AGTQRTSFQFYSTLPNTIYRFSIAAVNEVGEGPEAESSITTSSSAVQQEEQWLFLSRKTS
LRKRSLKHLVDEAHCLRLDAIYHNITGISVDVHQQIVYFSEGTLIWAKKAANMSDVSDLR
IFYRGSGLISSISIDWLYQRMYFIMDELVCVCDLENCSNIEEITPPSISAPQKIVADSYN
GYVFYLLRDGIYRADLPVPSGRCAEAVRIVESCTLKDFAIKPQAKRIIYFNDTAQVFMST
FLDGSASHLILPRIPFADVKSFACENNDFLVTDGKVIFQQDALSFNEFIVGCDLSHIEEF
GFGNLVIFGSSSQLHPLGRPQELSVLFGSHQALVQWKPPALAIGANVILISDIIELFEL
GPSAWQNWTYEVKVSTQDPPEVTHIFLNISGTMLNVPELQSAMKYKVSVRASSPKRPGPW
SEPSVGTTLVPASEPPFIMAVKEDGLWSKPLNSFGPGEFLSSDIGNVSDMDWYNNSLYYS
DTKGDVFVWLLNGTDISENYHLPSIAGAGALAFEWLGHFLYWAGKTYVIQRQSVLTGHTD
IVTHVKLLVNDMVVDSVGGYLYWTTLYSVESTRLNGESSLVLQTQPWFSGKKVIALTLDL
SDGLLYWLVQDSQCIHLYTAVLRGQSTGDTTITEFAAWSTSEISQNALMYYSGRLFWING
FRIITTQEIGQKTSVSVLEPARFNQFTIIQTSLKPLGNFSFTPKVIPDSVQESSFRIEG
NASSFQILWNGPPAVDWGVVFYSVEFSAHSKFLASEQHSLPVFTVEGLEPYALFNLSVTP
YTYWGKGPKTSLSLRAPETVPSAPENPRIFILPSGKCCNKNEVVVEFRWNKPKHENGVLT
KFEIFYNISNQSITNKTCEDWIAVNVTPSVMSFQLEGMSPRCFIAFQVRAFTSKGPGPYA
DVVKSTTSEINPFPHLITLLGNKIVFLDMDQNQVVWTFSAERVISAVCYTADNEMGYYAE
GDSLFLLHLHNRSSSELFQDSLVFDITVITIDWISRHLYFALKESQNGMQVFDVDLEHKV
KYPREVKIHNRNSTIISFSVYPLLSRLYWTEVSNFGYQMFYYSIISHTLHRILQPTATNQ
QNKRNQCSCNVTEFELSGAMAIDTSNLEKPLIYFAKAQEIWAMDLEGCQCWRVITVPAML
AGKTLVSLTVDGDLIYWIITAKDSTQIYQAKKGNGAIVSQVKALRSRHILAYSSVMQPFP
DKAFLSLASDTVEPTILNATNTSLTIRLPLAKTNLTWYGITSPTPTYLVYYAEVNDRKNS
SDLKYRILEFQDSIALIEDLQPFSTYMIQIAVKNYYSDPLEHLPPGKEIWGKTKNGVPEA
VQLINTTVRSDTSLIISWRESHKPNGPKESVRYQLAISHLALIPETPLRQSEFPNGRLTL
LVTRLSGGNIYVLKVLACHSEEMWCTESHPVTVEMFNTPEKPYSLVPENTSLQFNWKAPL
NVNLIRFWVELQKWKYNEFYHVKTSCSQGPAYVCNITNLQPYTSYNVRVVVYKTGENST
SLPESFKTK**AGVPNKPGIPKLLEGSKNSIQWEKAEDNGCRITYYILEIRKSTSNNLQNQN
LRWKMTFNGSCSSVCTWKSKNLKGIFQFRVVAANNLGFGEYSGISENIILVGDDFWIPET
SFILTIIVGIFLVVTIPLTFV**WHRRLKNQKSAKEGVTYLINEDKELAELRGLAAGVGLAN
ACYAIHTLPTQEEIENLPAFPREKLTLRLLLGSGAFGEVYEGTAVDILGVGSGEIKVAVK
TLKKGSTDQEKIEFLKEAHLMSKFNHPNILKQLGVCLLNEPQYIILELMEGGDLLTYLRK
ARMATFYGPLLTLVDLVDLCVDISKGCVYLERMHFIHRDLAARNCLVSVKDYTSPRIVKI
GDFGLARDIYKNDYYRKRGEGLLPVRWMAPESLMDGIFTTQSDVWSFGILIWEILTLGHQ
PYPAHSNLDVLNYVQTGGRLEPPRNCPDDLWNLMTQCWAQEPDQRPTFHRIQNQLQLFRN
FFLNSIYQCRDEANNSGVINESFEGEDGDVICLNSDDIMPVVLMETKNREGLNYMVLATE
CGQGEEKSEGPLGSQESESCGLRKEEKEPHADKDFCQEKQVAYCPSGKPEGLNYACLTHS
GYGDGSD (Underlining, Bolding, and red text distinguish three different fusion proteins.)

Figure 6B

```
   1 caagctttca agcattcaaa ggtctaaatg aaaaaggcta agtattattt caaaaggcaa
  61 gtatatccta atatagcaaa acaaacaaag caaaatccat cagctactcc tccaattgaa
 121 gtgatgaagc ccaaataatt catatagcaa aatggagaaa attagacggg ccatctaaaa
 181 atctgccatt ggtgaagtga tgaagaacat ttactgtctt attccgaagc ttgtcaattt
 241 tgcaactctt ggctgcctat ggatttctgt ggtgcagtgt acagttttaa atagctgcct
 301 aaagtcgtgt gtaactaatc tgggccagca gcttgacctt ggcacaccac ataatctgag
 361 tgaaccgtgt atccaaggat gtcacttttg gaactctgta gatcagaaaa actgtgcttt
 421 aaagtgtcgg gagtcgtgtg aggttggctg tagcagcgcg gaaggtgcat atgaagagga
 481 agtactggaa aatgcagacc taccaactgg tccctttgct tcttccattg gaagccacaa
 541 tatgacatta cgatggaaat ctgcaaactt ctctggagta aaatacatca ttcagtggaa
 601 atatgcacaa cttctgggaa gctggactta tactaagact gtgtccagac cgtcctatgt
 661 ggtcaagccc ctgcacccct tcactgagta cattttccga gtggtttgga tcttcacagc
 721 gcagctgcag ctctactccc ctccaagtcc cagttacagg actcatcctc atggagttcc
 781 tgaaactgca cctttgatta ggaatattga gagctcaagt ccgacactg tggaagtcag
 841 ctgggatcca cctcaattcc caggtggacc tattttgggt tataacttaa ggctgatcag
 901 caaaaatcaa aaattagatg cagggacaca gagaaccagt ttccagtttt actccacttt
 961 accaaatact atctacaggt tttctattgc agcagtaaat gaagttggtg agggtccaga
1021 agcagaatct agtattacca cttcatcttc agcagttcaa caagaggaac agtggctctt
1081 tttatccaga aaaacttctc taagaaagag atctttaaaa catttagtag atgaagcaca
1141 ttgccttcgg ttggatgcta tacccataa tattacagga atatctgttg atgtccacca
1201 gcaaattgtt tatttctctg aaggaactct catatgggcg aagaaggctg ccaacatgtc
1261 tgatgtatct gacctgagaa ttttttacag aggttcagga ttaatttctt ctatctccat
1321 agattggctt tatcaaagaa tgtatttcat catggatgaa ctggtatgtg tctgtgattt
1381 agagaactgc tcaaacatcg aggaaattac tccaccctct attagtgcac ctcaaaaaat
1441 tgtggctgat tcatacaatg ggtatgtctt ttacctcctg agagatggca tttatagagc
1501 agaccttcct gtaccatctg gccggtgtgc agaagctgtg cgtattgtgg agagttgcac
1561 gttaaaggac tttgcaatca agccacaagc caagcgaatc atttacttca atgacactgc
1621 ccaagtcttc atgtcaacat ttctggatgg ctctgcttcc catctcatcc tacctcgcat
1681 cccctttgct gatgtgaaaa gttttgcttg tgaaaacaat gacttcttg tcacagatgg
1741 caaggtcatt ttccaacagg atgctttgtc ttttaatgaa ttcatcgtgg atgtgacct
1801 gagtcacata gaagaatttg ggtttggtaa cttggtcatc tttggctcat cctccagct
1861 gcaccctctg ccaggccgcc cgcaggagct ttcggtgctg tttggctctc accaggctct
1921 tgttcaatgg aagcctcctg cccttgccat aggagccaat gtcatcctga tcagtgatat
1981 tattgaactc tttgaattag gcccttctgc ctggcagaac tggacctatg aggtgaaagt
2041 atccacccaa gaccctcctg aagtcactca tatttcttg aacataagtg gaaccatgct
2101 gaatgtacct gagctgcaga gtgctatgaa atacaaggtt tctgtgagag caagttctcc
2161 aaagaggcca ggcccctggt cagagccctc agtgggtact accctggtgc cagctagtga
2221 accaccattt atcatggctg tgaaagaaga tgggcttggg agtaaaccat taaatagctt
2281 tggccagga gagttcttat cctctgatat aggaaatgtg tcagacatgg attggtataa
2341 caacagcctc tactacagtg acacgaaagg cgacgttttt gtgtggctgc tgaatgggac
2401 ggatatctca gagaattatc acctaccag cattgcagga gcagggcttt agcttttga
2461 gtggctgggt cactttctct actgggctgg aaagacatat gtgatacaaa ggcagtctgt
2521 gttgacggga cacacagaca ttgttaccca cgtgaagcta ttggtgaatg acatggtggt
2581 ggattcagtt ggtggatatc tctactggac cacactctat tcagtggaaa gcaccagact
2641 aaatggggaa agttcccttg tactacagac acagccttgg ttttctggga aaaggtaat
2701 tgctctaact ttagacctca gtgatggct cctgtattgg ttggttcaag acagtcaatg
2761 tattcacctg tacacagctg ttcttcgggg acagagcact ggggatacca ccatcacaga
2821 atttgcagcc tggagtactt ctgaaatttc ccagaatgca ctgatgtact atagtggtcg
2881 gctgttctgg atcaatggct taggattat cacaactcaa gaaataggtc agaaaaccag
2941 tgtctctgtt ttggaaccag ccagatttaa tcagttcaca attattcaga catcccttaa
3001 gcccctgcca gggaactttt cctttacccc taaggttatt ccagattctg ttcaagagtc
3061 ttcatttagg attgaaggaa atgcttcaag ttttcaaatc ctgtggaatg tcccctgc
3121 ggtagactgg ggtgtagttt tctacagtgt agaatttagt gctcattcta gttcttggc
3181 tagtgaacaa cactctttac ctgtatttac tgtggaagga ctggaacctt atgccttatt
3241 taatctttct gtcactcctt ataccctactg gggaaagggc cccaaaacat ctctgtcact
3301 tcgagcacct gaaacagttc catcagcacc agagaacccc agaatattta tattaccaag
3361 tggaaaatgc tgcaacaaga atgaagttgt ggtggaattt aggtggaaca aacctaagca
3421 tgaaaatggg gtgttaacaa aatttgaaat tttctacaat atatccaatc aaagtattac
3481 aaacaaaaca tgtgaagact ggattgctgt caatgtcact ccctcagtga tgtcttttca
3541 acttgaaggc atgagtccca atgctttat tgccttccag gttagggcct ttacatctaa
3601 ggggccagga ccatatgctg acgttgtaaa gtctacaaca tcagaaatca acccattcc
3661 tcacctcata actcttcttg gtaacaagat agtttttta gatatggatc aaaatcaagt
3721 tgtgtggacg ttttcagcag aaagagttat cagtgccgtt tgctacacag ctgataatga
```

Figure 6B (cont.)

```
3781 gatgggatat tatgctgaag gggactcact ctttcttctg cacttgcaca atcgctctag
3841 ctctgagctt ttccaagatt cactggtttt tgatatcaca gttattacaa ttgactggat
3901 ttcaaggcac ctctactttg cactgaaaga atcacaaaat ggaatgcaag tatttgatgt
3961 tgatcttgaa cacaaggtga aatatcccag agaggtgaag attcacaata ggaattcaac
4021 aataatttct ttttctgtat atcctctttt aagtcgcttg tattggacag aagtttccaa
4081 ttttggctac cagatgttct actacagtat tatcagtcac accttgcacc gaattctgca
4141 acccacagct acaaaccaac aaaacaaaag gaatcaatgt tcttgtaatg tgactgaatt
4201 tgagttaagt ggagcaatgg ctattgatac ctctaaccta gagaaaccat tgatatactt
4261 tgccaaagca caagagatct gggcaatgga tctggaaggc tgtcagtgtt ggagagttat
4321 cacagtacct gctatgctcg caggaaaaac ccttgttagc ttaactgtgg atggagatct
4381 tatatactgg atcatcacag caaaggacag cacacagatt tatcaggcaa agaaaggaaa
4441 tggggccatc gtttcccagg tgaaggccct aaggagtagg catatcttgg cttacagttc
4501 agttatgcag ccttttccag ataaagcgtt tctgtctcta gcttcagaca ctgtggaacc
4561 aactatactt aatgccacta acactagcct cacaatcaga ttacctctgg ccaagacaaa
4621 cctcacatgg tatggcatca ccagccctac tccaacatac ctggtttatt atgcagaagt
4681 taatgacagg aaaaacagct ctgacttgaa atatagaatt ctggaatttc aggacagtat
4741 agctcttatt gaagatttac aaccattttc aactacatg atacagatag ctgtaaaaaa
4801 ttattattca gatcctttgg aacatttacc accaggaaaa gagatttggg gaaaaactaa
4861 aaatggagta ccagaggcag tgcagctcat taatacaact gtgcggtcag acaccagcct
4921 cattatatct tggagagaat ctcacaagcc aaatggacct aaagaatcag tccgttatca
4981 gttggcaatc tcacacctgg ccctaattcc tgaaactcct ctaagacaaa gtgaatttcc
5041 aaatggaagg ctcactctcc ttgttactag actgtctggt ggaaatattt atgtgttaaa
5101 ggttcttgcc tgccactctg aggaaatgtg gtgtacagag agtcatcctg tcactgtgga
5161 aatgtttaac acaccagaga aaccttattc cttggttcca gagaacacta gtttgcaatt
5221 taattggaag gctccattga atgttaacct catcagattt tgggttgagc tacagaagtg
5281 gaaatacaat gagttttacc atgttaaaac ttcatgcagc caaggtcctg cttatgtctg
5341 taatatcaca aatctacaac cttatacttc atataatgtc agagtagtgg tggtttataa
5401 gacgggagaa aatagcacct cacttccaga aagctttaag acaaaagctg gagtcccaaa
5461 taaaccagcc attcccaaat tactagaagg gagtaaaaat tcaatacagt gggagaaagc
5521 tgaagataat ggatgtagaa ttacatacta tatccttgag ataagaaaga gcacttcaaa
5581 taatttacag aaccagaatt taaggtggaa gatgacattt aatggatcct cagtagtgt
5641 ttgcacatgg aagtccaaaa acctgaaagg aatatttcag ttcagagtag tagctgcaaa
5701 taatctaggg tttggtgaat atagtggaat cagtgagaat attatattag ttggagatga
5761 ttttggata ccagaaacaa gtttcatact tactattata gttggaatat ttctggttgt
5821 tacaatccca ctgacctttg TCTGGCATAG AAGATTAAAG AATCAAAAAA GTGCCAAGGA
5881 AGGGGTGACA GTGCTTATAA ACGAAGACAA AGAGTTGGCT GAGCTGCGAG GTCTGGCAGC
5941 CGGAGTAGGC CTGGCTAATG CCTGCTATGC AATACATACT CTTCCAACCC AAGAGGAGAT
6001 TGAAAATCTT CCTGCCTTCC CTCGGGAAAA ACTGACTCTG CGTCTCTTGC TGGGAAGTGG
6061 AGCCTTTGGA GAAGTGTATG AAGGAACAGC AGTGGACATC TTAGGAGTTG GAAGTGGAGA
6121 AATCAAAGTA GCAGTGAAGA CTTTGAAGGA GGGTTCCACA GACCAGGAGA AGATTGAATT
6181 CCTGAAGGAG GCACATCTGA TGAGCAAATT TAATCATCCC AACATTCTGA AGCAGCTTGG
6241 AGTTTGTCTG CTGAATGAAC CCCAATACAT TATCCTGGAA CTGATGGAGG GAGGAGACCT
6301 TCTTACTTAT TTGCGTAAAG CCCGGATGGC AACGTTTTAT GGTCCTTTAC TCACCTTGGT
6361 TGACCTTGTA GACCTGTGTG TAGATATTTC AAAAGGCTGT GTCTACTTGG AACGGATGCA
6421 TTTCATTCAC AGGGATCTGG CAGCTAGAAA TTGCCTTGTT TCCGTGAAAG ACTATACCAG
6481 TCCACGGATA GTGAAGATTG GAGACTTTGG ACTCGCCAGA GACATCTATA AAAATGATTA
6541 CTATAGAAAG AGAGGGGAAG GCCTGCTCCC AGTTCGGTGG ATGGCTCCAG AAAGTTTGAT
6601 GGATGGAATC TTCACTACTC AATCTGATGT ATGGTCTTTT GGAATTCTGA TTTGGGAGAT
6661 TTTAACTCTT GGTCATCAGC CTTATCCAGC TCATTCCAAC CTTGATGTGT TAAACTATGT
6721 GCAAACAGGA GGGAGACTGG AGCCACCAAG AAATTGTCCT GATGATCTGT GGAATTTAAT
6781 GACCCAGTGC TGGGCTCAAG AACCCGACCA AAGACCTACT TTTCATAGAA TTCAGGACCA
6841 ACTTCAGTTA TTCAGAAATT TTTTCTTAAT TAGCATTTAT AAGTCCAGAG ATGAAGCAAA
6901 CAACAGTGGA GTCATAAATG AAAGCTTTGA AGGTGAAGAT GGCGATGTGA TTTGTTTGAA
6961 TTCAGATGAC ATTATGCCAG TTGCTTTAAT GGAAACGAAG AACCGAGAAG GGTTAAACTA
7021 TATGGTACTT GCTACAGAAT GTGGCCAAGG TGAAGAAAAG TCTGAGGGTC CTCTAGGCTC
7081 CCAGGAATCT GAATCTTGTG GTCTGAGGAA AGAAGAGAAG GAACCACATG CAGACAAAGA
7141 TTTCTGCCAA GAAAAACAAG TGGCTTACTG CCCTTCTGGC AAGCCTGAAG GCCTGAACTA
7201 TGCCTGTCTC ACTCACAGTG GATATGGAGA TGGGTCTGAT TAATAGCGTT GTTTGGGAAA
7261 TAGAGAGTTG AGATAAACAC TCTCATTCAG TAGTTACTGA AAGAAAACTC TGCTAGAATG
7321 ATAAATGTCA TGGTGGTCTA TAACTCCAAA TAAACAATGC AACGTTCC
```

Figure 8A-C
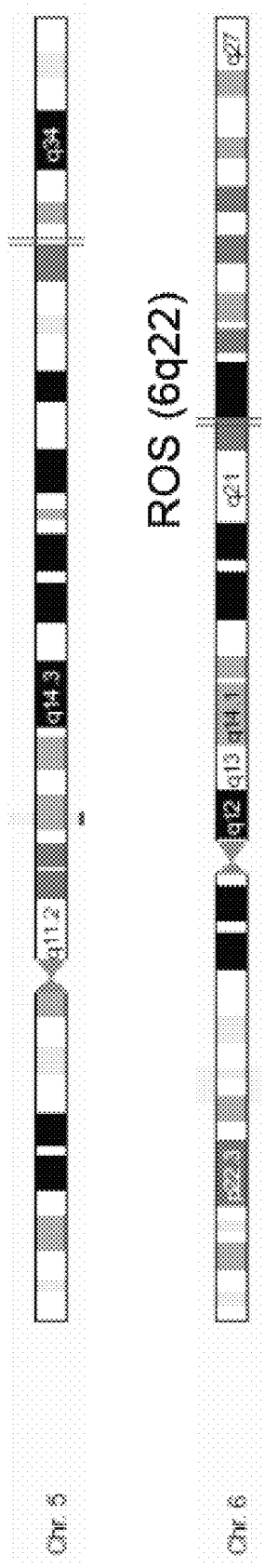
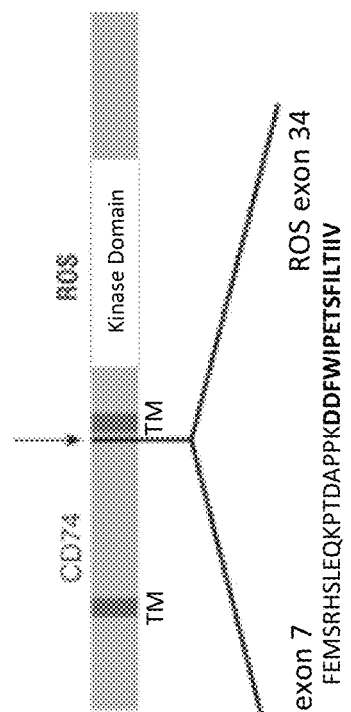
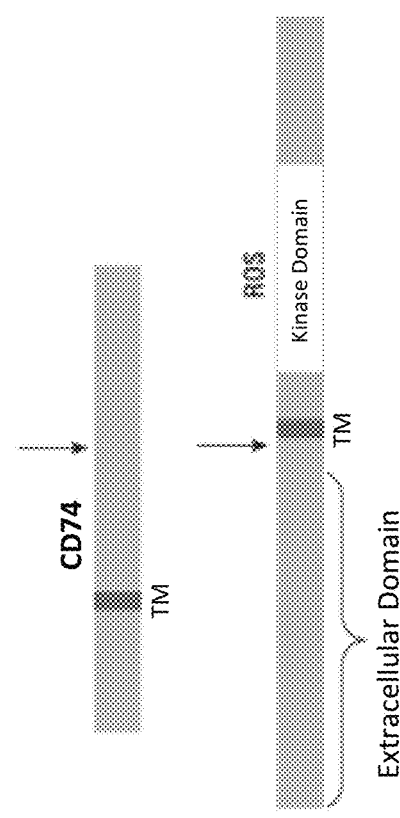

Figure 9

MHRRRSRSCREDQKPVMDDQRDLISNNEQLPMLGRRPGAPESKCSRGALYT
GFSILVTLLLAGQATTAYFLYQQQGRLDKLTVTSQNLQLENLRMKLPKPPKPVS
KMRMATPLLMQALPMGALPQGPMQNATKYGNMTEDHVMHLLQNADPLKVYP
PLKGSFPENLRHLKNTMETIDWKVFESWMHHWLLFEMSRHSLEQKPTDAPPK
DDFWIPETSFILTIIVGIFLVVTIPLTFVWHRRLKNQKSAKEGVTVLINEDKELAEL
RGLAAGVGLANACYAIHTLPTQEEIENLPAFPREKLTLRLLLGSGAFGEVYEGT
AVDILGVGSGEIKVAVKTLKKGSTDQEKIEFLKEAHLMSKFNHPNILKQLGVCL
LNEPQYIILELMEGGDLLTYLRKARMATFYGPLLTVDLVDLCVDISKGCVYLE
RMHFIHRDLAARNCLVSVKDYTSPRIVKIGDFGLARDIYKNDYYRKRGEGLLPV
RWMAPESLMDGIFTTQSDVWSFGILIWEILTLGHQPYPAHSNLDVLNYVQTGG
RLEPPRNCPDDLWNLMTQCWAQEPDQRPTFHRIQDQLQLFRNFFLNSIYKSR
DEANNSGVINESFEGEDGDVICLNSDDIMPVALMETKNREGLNYMVLATECGQ
GEEKSEGPLGSQESESCGLRKEEKEPHADKDFCQEKQVAYCPSGKPEGLNYA
CLTHSGYGDGSD

ATGCACAGGAGGAGAAGCAGGAGCTGTCGGGAAGATCAGAAGCCAGTCAT
GGATGACCAGCGCGACCTTATCTCCAACAATGAGCAACTGCCCATGCTGGG
CCGGCGCCCTGGGGCCCCGGAGAGCAAGTGCAGCCGCGGAGCCCTGTAC
ACAGGCTTTTCCATCCTGGTGACTCTGCTCCTCGCTGGCCAGGCCACCACC
GCCTACTTCCTGTACCAGCAGCAGGGCCGGCTGGACAAACTGACAGTCAC
CTCCCAGAACCTGCAGCTGGAGAACCTGCGCATGAAGCTTCCCAAGCCTCC
CAAGCCTGTGAGCAAGATGCGCATGGCCACCCCGCTGCTGATGCAGGCGC
TGCCCATGGGAGCCCTGCCCCAGGGGCCCATGCAGAATGCCACCAAGTAT
GGCAACATGACAGAGGACCATGTGATGCACCTGCTCCAGAATGCTGACCCC
CTGAAGGTGTACCCGCCACTGAAGGGGAGCTTCCCGGAGAACCTGAGACA
CCTTAAGAACACCATGGAGACCATAGACTGGAAGGTCTTTGAGAGCTGGAT
GCACCATTGGCTCCTGTTTGAAATGAGCAGGCACTCCTTGGAGCAAAAGCC
CACTGACGCTCCACCGAAAGATGATTTTTGGATACCAGAAACAAGTTTCATA
CTTACTATTATAGTTGGAATATTTCTGGTTGTTACAATCCCACTGACCTTTGT
CTGGCATAGAAGATTAAAGAATCAAAAAGTGCCAAGGAAGGGGTGACAGT
GCTTATAAACGAAGACAAAGAGTTGGCTGAGCTGCGAGGTCTGGCAGCCG
GAGTAGGCCTGGCTAATGCCTGCTATGCAATACATACTCTTCCAACCCAAGA
GGAGATTGAAAATCTTCCTGCCTTCCCTCGGGAAAAACTGACTCTGCGTCT
CTTGCTGGGAAGTGGAGCCTTTGGAGAAGTGTATGAAGGAACAGCAGTG
GACATCTTAGGAGTTGGAAGTGGAGAAATCAAAGTAGCAGTGAAGACTTT
GAAGAAGGGTTCCACAGACCAGGAGAAGATTGAATTCCTGAAGGAGGCA
CATCTGATGAGCAAATTTAATCATCCAACATTCTGAAGCAGCTTGGAGTT
TGTCTGCTGAATGAACCCCAATACATTATCCTGGAACTGATGGAGGGAGG
AGACCTTCTTACTTATTTGCGTAAAGCCCGGATGGCAACGTTTATGGTCC
TTTACTCACCTTGGTTGACCTTGTAGACCTGTGTGTAGATATTTCAAAAGG

Figure 9 (cont.)

CTGTGTCTACTTGGAACGGATGCATTTCATTCACAGGGATCTGGCAGCTAG
AAATTGCCTTGTTTCCGTGAAAGACTATACCAGTCCACGGATAGTGAAGAT
TGGAGACTTTGGACTCGCCAGAGACATCTATAAAAATGATTACTATAGAAA
GAGAGGGGAAGGCCTGCTCCCAGTTCGGTGGATGGCTCCAGAAAGTTTG
ATGGATGGAATCTTCACTACTCAATCTGATGTATGGTCTTTTGGAATTCTGA
TTTGGAGATTTTAACTCTTGGTCATCAGCCTTATCCAGCTCATTCCAACCT
TGATGTGTTAAACTATGTGCAAACAGGAGGGAGACTGGAGCCACCAAGAA
ATTGTCCTGATGATCTGTGGAATTTAATGACCCAGTGCTGGGCTCAAGAAC
CCGACCAAAGACCTACTTTTCATAGAATTCAGGACCAACTTCAGTTATTCA
GAAATTTTTCTTAAATAGCATTTATAAGTCCAGAGATGAAGCAAACAACAGT
GGAGTCATAAATGAAAGCTTTGAAGGTGAAGATGGCGATGTGATTTGTTTGA
ATTCAGATGACATTATGCCAGTTGCTTTAATGGAAACGAAGAACCGAGAAGG
GTTAAACTATATGGTACTTGCTACAGAATGTGGCCAAGGTGAAGAAAAGTCT
GAGGGTCCTCTAGGCTCCCAGGAATCTGAATCTTGTGGTCTGAGGAAAGAA
GAGAAGGAACCACATGCAGACAAAGATTTCTGCCAAGAAAACAAGTGGCT
TACTGCCCTTCTGGCAAGCCTGAAGGCCTGAACTATGCCTGTCTCACTCAC
AGTGGATATGGAGATGGGTCTGATTAA

Figure 10

MHRRRSRSCREDQKPVMDDQRDLISNNEQLPMLGRRPGAPESKCSRGALY
TGFSILVTLLLAGQATTAYFLYQQQGRLDKLTVTSQNLQLENLRMKLPKP
PKPVSKMRMATPLLMQALPMGALPQGPMQNATKYGNMTEDHVMHLLQNAD
PLKVYPPLKGSFPENLRHLKNTMETIDWKVFESWMHHWLLFEMSRHSLEQ
KPTDAPPKVLTKCQEEVSHIPAVHPGSFRPKCDENGNYLPLQCYGSIGYC
WCVFPNGTEVPNTRSRGHHNCSESLELEDPSSGLGVTKQDLGPAPL

CAGGGTCCCAGATGCACAGGAGGAGAAGCAGGAGCTGTCGGGAAGATCAG
AAGCCAGTCATGGATGACCAGCGCGACCTTATCTCCAACAATGAGCAACT
GCCCATGCTGGGCCGGCGCCCTGGGGCCCCGGAGAGCAAGTGCAGCCGCG
GAGCCCTGTACACAGGCTTTTCCATCCTGGTGACTCTGCTCCTCGCTGGC
CAGGCCACCACCGCCTACTTCCTGTACCAGCAGCAGGGCCGGCTGGACAA
ACTGACAGTCACCTCCCAGAACCTGCAGCTGGAGAACCTGCGCATGAAGC
TTCCCAAGCCTCCCAAGCCTGTGAGCAAGATGCGCATGGCCACCCCGCTG
CTGATGCAGGCGCTGCCCATGGGAGCCCTGCCCCAGGGGCCCATGCAGAA
TGCCACCAAGTATGGCAACATGACAGAGGACCATGTGATGCACCTGCTCC
AGAATGCTGACCCCCTGAAGGTGTACCCGCCACTGAAGGGGAGCTTCCCG
GAGAACCTGAGACACCTTAAGAACACCATGGAGACCATAGACTGGAAGGT
CTTTGAGAGCTGGATGCACCATTGGCTCCTGTTTGAAATGAGCAGGCACT
CCTTGGAGCAAAAGCCCACTGACGCTCCACCGAAAGTACTGACCAAGTGC
CAGGAAGAGGTCAGCCACATCCCTGCTGTCCACCCGGGTTCATTCAGGCC
CAAGTGCGACGAGAACGGCAACTATCTGCCACTCCAGTGCTATGGGAGCA
TCGGCTACTGCTGGTGTGTCTTCCCCAACGGCACGGAGGTCCCCAACACC
AGAAGCCGCGGGCACCATAACTGCAGTGAGTCACTGGAACTGGAGGACCC
GTCTTCTGGGCTGGGTGTGACCAAGCAGGATCTGGGCCCAGCTCCTTTG

Figure 11A

MKNIYCLIPKLVNFATLGCLWISVVQCTVLNSCLKSCVTNLGQQLDLGTPHNLSEPCIQG
CHFWNSVDQKNCALKCRESCEVGCSSAEGAYEEEVLENADLPTAPFASSIGSHNMTLRWK
SANFSGVKYIIQWKYAQLLGSWTYTKTVSRPSYVVKPLHPFTEYIFRVVWIFTAQLQLYS
PPSPSYRTHPHGVPETAPLIRNIESSSPDTVEVSWDPPQFPGGPILGYNLRLISKNQKLD
AGTQRTSFQFYSTLPNTIYRFSIAAVNEVGEGPEAESSITTSSSAVQQEEQWLFLSRKTS
LRKRSLKHLVDEAHCLRLDAIYHNITGISVDVHQQIVYFSEGTLIWAKKAANMSDVSDLR
IFYRGSGLISSISIDWLYQRMYFIMDELVCVCDLENCSNIEEITPPSISAPQKIVADSYN
GYVFYLLRDGIYRADLPVPSGRCAEAVRIVESCTLKDFAIKPQAKRIIYFNDTAQVFMST
FLDGSASHLILPRIPFADVKSFACENNDFLVTDGKVIFQQDALSFNEFIVGCDLSHIEEF
GFGNLVIFGSSSQLHPLPGRPQELSVLFGSHQALVQWKPPALAIGANVILISDIIELFEL
GPSAWQNWTYEVKVSTQDPPEVTHIFLNISGTMLNVPELQSAMKYKVSVRASSPKRPGPW
SEPSVGTTLVPASEPPFIMAVKEDGLWSKPLNSFGPGEFLSSDIGNVSDMDWYNNSLYYS
DTKGDVFVWLLNGTDISENYHLPSIAGAGALAFEWLGHFLYWAGKTYVIQRQSVLTGHTD
IVTHVKLLVNDMVVDSVGGYLYWTTLYSVESTRLNGESSLVLQTQPWFSGKKVIALTLDL
SDGLLYWLVQDSQCIHLYTAVLRGQSTGDTTITEFAAWSTSEISQNALMYYSGRLFWING
FRIITTQEIGQKTSVSVLEPARFNQFTIIQTSLKPLPGNFSFTPKVIPDSVQESSFRIEG
NASSFQILWNGPPAVDWGVVFYSVEFSAHSKFLASEQHSLPVFTVEGLEPYALFNLSVTP
YTYWGKGPKTSLSLRAPETVPSAPENPRIFILPSGKCCNKNEVVVEFRWNKPKHENGVLT
KFEIFYNISNQSITNKTCEDWIAVNVTPSVMSFQLEGMSPRCFIAFQVRAFTSKGPGPYA
DVVKSTTSEINPFPHLITLLGNKIVFLDMDQNQVVWTFSAERVISAVCYTADNEMGYYAE
GDSLFLLHLHNRSSSELFQDSLVFDITVITIDWISRHLYFALKESQNGMQVFDVDLEHKV
KYPREVKIHNRNSTIISFSVYPLLSRLYWTEVSNFGYQMFYYSIISHTLHRILQPTATNQ
QNKRNQCSCNVTEFELSGAMAIDTSNLEKPLIYFAKAQEIWAMDLEGCQCWRVITVPAML
AGKTLVSLTVDGDLIYWIITAKDSTQIYQAKKGNGAIVSQVKALRSRHILAYSSVMQPFP
DKAFLSLASDTVEPTILNATNTSLTIRLPLAKTNLTWYGITSPTPTYLVYYAEVNDRKNS
SDLKYRILEFQDSIALIEDLQPFSTYMIQIAVKNYYSDPLEHLPPGKEIWGKTKNGVPEA
VQLINTTVRSDTSLIISWRESHKPNGPKESVRYQLAISHLALIPETPLRQSEFPNGRLTL
LVTRLSGGNIYVLKVLACHSEEMWCTESHPVTVEMFNTPEKPYSLVPENTSLQFNWKAPL
NVNLIRFWVELQKWKYNEFYHVKTSCSQGPAYVCNITNLQPYTSYNVRVVVVYKTGENST
SLPESFKTKAGVPNKPGIPKLLEGSKNSIQWEKAEDNGCRITYYILEIRKSTSNNLQNQN
LRWKMTFNGSCSSVCTWKSKNLKGIFQFRVVAANNLGFGEYSGISENIILVGDDFWIPET
SFILTIIVGIFLVVTIPLTFVWHRRLKNQKSAKEGVTVLINEDKELAELRGLAAGVGLAN
ACYAIHTLPTQEEIENLPAFPREKLTLRLLLGSGAFGEVYEGTAVDILGVGSGEIKVAVK
TLKKGSTDQEKIEFLKEAHLMSKFNHPNILKQLGVCLLNEPQYIILELMEGGDLLTYLRK
ARMATFYGPLLTLVDLVDLCVDISKGCVYLERMHFIHRDLAARNCLVSVKDYTSPRIVKI
GDFGLARDIYKNDYYRKRGEGLLPVRWMAPESLMDGIFTTQSDVWSFGILIWEILTLGHQ
PYPAHSNLDVLNYVQTGGRLEPPRNCPDDLWNLMTQCWAQEPDQRPTFHRIQNQLQLFRN
FFLNSIYQCRDEANNSGVINESFEGEDGDVICLNSDDIMPVVLMETKNREGLNYMVLATE
CGQGEEKSEGPLGSQESESCGLRKEEKEPHADKDFCQEKQVAYCPSGKPEGLNYACLTHS
GYGDGSD

Figure 11B

```
   1 caagctttca agcattcaaa ggtctaaatg aaaaaggcta agtattattt caaaaggcaa
  61 gtatatccta atatagcaaa acaaacaaag caaaatccat cagctactcc tccaattgaa
 121 gtgatgaagc ccaaataatt catatagcaa aatggagaaa attagaccgg ccatctaaaa
 181 atctgccatt ggtgaagtga tgaagaacat ttactgtctt attccgaagc ttgtcaattt
 241 tgcaactctt ggctgcctat ggatttctgt ggtgcagtgt acagttttaa atagctgcct
 301 aaagtcgtgt gtaactaatc tgggccagca gcttgacctt ggcacaccac ataatctgag
 361 tgaaccgtgt atccaaggat gtcacttttg gaactctgta gatcagaaaa actgtgcttt
 421 aaagtgtcgg gagtcgtgtg aggttggctg tagcagcgcg gaaggtgcat atgaagagga
 481 agtactggaa aatgcagacc taccaactgc tcccttttgct tcttccattg gaagccacaa
 541 tatgacatta cgatggaaat ctgcaaactt ctctggagta aaatacatca ttcagtggaa
 601 atatgcacaa cttctgggaa gctggactta tactaagact gtgtccagac cgtcctatgt
 661 ggtcaagccc ctgcacccct tcactgagta cattttccga gtggtttgga tcttcacagc
 721 gcagctgcag ctctactccc ctccaagtcc cagttacagg actcatcctc atggagttcc
 781 tgaaactgca cctttgatta ggaatattga gagctcaagt cccgacactg tggaagtcag
 841 ctgggatcca cctcaattcc caggtggacc tattttgggt tataacttaa ggctgatcag
 901 caaaaatcaa aaattagatg cagggacaca gagaaccagt ttccagtttt actccacttt
 961 accaaatact atctacaggt tttctattgc agcagtaaat gaagttggtg agggtccaga
1021 agcagaatct agtattacca cttcatcttc agcagttcaa caagaggaac agtggctctt
1081 tttatccaga aaaacttctc taagaaagag atctttaaaa catttagtag atgaagcaca
1141 ttgccttcgg ttggatgcta taccataa tattacagga atatctgttg atgtccacca
1201 gcaaattgtt tatttctctg aaggaactct catatgggcg aagaaggctg ccaacatgtc
1261 tgatgtatct gacctgagaa ttttttacag aggttcagga ttaatttctt ctatctccat
1321 agattggctt tatcaaagaa tgtatttcat catggatgaa ctggtatgtg tctgtgattt
1381 agagaactgc tcaaacatcg aggaaattac tccaccctct attagtgcac ctcaaaaaat
1441 tgtggctgat tcatacaatg ggtatgtctt ttacctcctg agagatggca tttatagagc
1501 agaccttcct gtaccatctg gccggtgtgc agaagctgtg cgtattgtgg agagttgcac
1561 gttaaaggac tttgcaatca agccacaagc caagcgaatc atttacttca atgacactgc
1621 ccaagtcttc atgtcaacat ttctggatgg ctctgcttcc catctcatcc tacctcgcat
1681 cccctttgct gatgtgaaaa gttttgcttg tgaaaacaat gactttcttg tcacagatgg
1741 caaggtcatt ttccaacagg atgctttgtc ttttaatgaa ttcatcgtgg gatgtgacct
1801 gagtcacata gaagaatttg ggtttggtaa cttggtcatc tttggctcat cctccagct
1861 gcaccctctg ccaggccgcc cgcaggagct ttcggtgctg tttggctctc accaggctct
1921 tgttcaatgg aagcctcctg cccttgccat aggagccaat gtcatcctga tcagtgatat
1981 tattgaactc tttgaattag gccttctgc ctggcagaac tggacctatg aggtgaaagt
2041 atccacccaa gaccctcctg aagtcactca tatttcttg aacataagtg gaaccatgct
2101 gaatgtacct gagctgcaga gtgctatgaa atacaaggtt tctgtgagag caagttctcc
2161 aaagaggcca ggccctggt cagagccctc agtgggtact accctggtgc cagctagtga
2221 accaccattt atcatggctg tgaaagaaga tgggctttgg agtaaaccat taaatagctt
2281 tggccagga gagttcttat cctctgatat aggaaatgtg tcagacatgg attggtataa
2341 caacagcctc tactacagtg acacgaaagg cgacgttttt gtgtggctgc tgaatgggac
2401 ggatatctca gagaattatc acctacccag cattgcagga gcaggggctt tagcttttga
2461 gtggctgggt cactttctct actgggctgg aaagacatat gtgatacaaa ggcagtctgt
2521 gttgacggga cacacagaca ttgttaccca cgtgaagcta ttggtgaatg acatggtggt
2581 ggattcagtt ggtggatatc tctactggac cacactctat tcagtggaaa gcaccagact
2641 aaatggggaa agttcccttg tactacagac acagccttgg ttttctggga aaaaggtaat
2701 tgctctaact ttagacctca gtgatgggct cctgtattgg ttggttcaag acagtcaatg
2761 tattcacctg tacacagctg ttcttcgggg acagaccagt gggatacca ccatcacaga
2821 atttgcagcc tggagtactt ctgaaatttc ccagaatgca ctgatgtact atagtggtcg
2881 gctgttctgg atcaatggct ttaggattat cacaactcaa gaaataggtc agaaaaccag
2941 tgtctctgtt ttggaaccag ccagatttaa tcagttcaca attattcaga catcccttaa
3001 gcccctgcca gggaactttt cctttacccc taaggttatt ccagattctg ttcaagagtc
3061 ttcatttagg attgaaggaa atgcttcaag ttttcaaatc ctgtggaatg gtccccctgc
3121 ggtagactgg ggtgtagttt tctacagtgt agaatttagt gctcattcta agttcttggc
3181 tagtgaacaa cactctttac ctgtatttac tgtggaagga ctggaacctt atgccttatt
3241 taatctttct gtcactcctt ataccactg gggaaagggc cccaaaacat ctctgtcact
3301 tcgagcacct gaaacagttc catcagcacc agagaacccc agaatattta tattaccaag
3361 tggaaaatgc tgcaacaaga atgaagttgt ggtggaattt aggtggaaca aacctaagca
3421 tgaaaatggg gtgttaacaa aatttgaaat tttctacaat atatccaatc aaagtattac
3481 aaacaaaaca tgtgaagact ggattgctgt caatgtcact ccctcagtga tgtcttttca
3541 acttgaaggc atgagtccca gatgctttat tgccttccag gttagggcct ttacatctaa
3601 ggggccagga ccatatgctg acgttgtaaa gtctacaaca tcagaaatca acccatttcc
```

Figure 11B (cont.)

```
3661 tcacctcata actcttcttg gtaacaagat agttttttta gatatggatc aaaatcaagt
3721 tgtgtggacg ttttcagcag aaagagttat cagtgccgtt tgctacacag ctgataatga
3781 gatgggatat tatgctgaag gggactcact ctttcttctg cacttgcaca atcgctctag
3841 ctctgagctt ttccaagatt cactggtttt tgatatcaca gttattacaa ttgactggat
3901 ttcaaggcac ctctactttg cactgaaaga atcacaaaat ggaatgcaag tatttgatgt
3961 tgatcttgaa cacaaggtga aatatcccag agaggtgaag attcacaata ggaattcaac
4021 aataatttct ttttctgtat atcctctttt aagtcgcttg tattggacag aagtttccaa
4081 ttttggctac cagatgttct actacagtat tatcagtcac accttgcacc gaattctgca
4141 acccacagct acaaaccaac aaaacaaaag gaatcaatgt tcttgtaatg tgactgaatt
4201 tgagttaagt gggagcaatgg ctattgatac ctctaaccta gagaaaccat tgatatactt
4261 tgccaaagca caagagatct gggcaatgga tctgaaggc tgtcagtgtt ggagagttat
4321 cacagtacct gctatgctcg caggaaaaac ccttgttagc ttaactgtgg atggagatct
4381 tatatactgg atcatcacag caaaggacag cacacagatt tatcaggcaa agaaaggaaa
4441 tgggccatc gtttcccagg tgaaggccct aaggagtagg catatcttgg cttacagttc
4501 agttatgcag ccttttccag ataaagcgtt tctgtctcta gcttcagaca ctgtggaacc
4561 aactatactt aatgccacta acactagcct cacaatcaga ttacctctgg ccaagacaaa
4621 cctcacatgg tatggcatca ccagccctac tccaacatac ctggtttatt atgcagaagt
4681 taatgacagg aaaaacagct ctgacttgaa atatagaatt ctggaatttc aggacagtat
4741 agctcttatt gaagatttac aaccattttc aacatacatg atacagatag ctgtaaaaaa
4801 ttattattca gatcctttgg aacatttacc accaggaaaa gagatttggg gaaaaactaa
4861 aaatggagta ccagaggcag tgcagctcat taatacaact gtgcggtcag acaccagcct
4921 cattatatct tggagagaat ctcacaagcc aaatggacct aaagaatcag tccgttatca
4981 gttgcaatc tcacacctgg ccctaattcc tgaaactcct ctaagacaaa gtgaatttcc
5041 aaatggaagg ctcactctcc ttgttactag actgtctggt ggaaatattt atgtgttaaa
5101 ggttcttgcc tgccactctg aggaaatgtg gtgtacagag agtcatcctg tcactgtgga
5161 aatgtttaac acaccagaga aaccttattc cttggttcca gagaacacta gtttgcaatt
5221 taattggaag gctccattga atgttaacct catcagattt tgggttgagc tacagaagtg
5281 gaaatacaat gagttttacc atgttaaaac ttcatgcagc caaggtcctg cttatgtctg
5341 taatatcaca aatctacaac cttatacttc atataatgtc agagtagtgg tggtttataa
5401 gacgggagaa aatagcacct cacttccaga aagctttaag acaaaagctg gagtcccaaa
5461 taaaccaggc attcccaaat tactagaagg gagtaaaaat tcaatacagt gggagaaagc
5521 tgaagataat ggatgtagaa ttacatacta tatccttgag ataagaaaga gcacttcaaa
5581 taatttacag aaccagaatt taaggtggaa gatgacattt aatggatcct gcagtagtgt
5641 ttgcacatgg aagtccaaaa acctgaaagg aatatttcag ttcagagtag tagctgcaaa
5701 taatctaggg tttggtgaat atagtggaat cagtgagaat attatattag ttggagatga
5761 ttttttggata ccagaaacaa gtttcatact tactattata gttggaatat ttctggttgt
5821 tacaatccca ctgaccttg tctggcatag aagattaaag aatcaaaaaa gtgccaagga
5881 agggtgaca gtgcttataa acgaagacaa agagttggct gagctgcgag gtctggcagc
5941 cggagtaggc ctggctaatg cctgctatgc aatacatact cttccaaccc aagaggagat
6001 tgaaaatctt cctgccttcc ctcgggaaaa actgactctg cgtctcttgc tgggaagtgg
6061 agcctttgga gaagtgtatg aaggaacagc agtggacatc ttaggagttg gaagtggaga
6121 aatcaaagta gcagtgaaga cttttgaaga gggttccaca gaccaggaga agattgaatt
6181 cctgaaggag gcacatctga tgagcaaatt taatcatccc aacattctga agcagcttgg
6241 agtttgtctg ctgaatgaac ccaatacat tatcctggaa ctgatggagg gaggagacct
6301 tcttacttat ttgcgtaaag cccggatggc aacgttttat ggtcctttac tcacccttggt
6361 tgaccttgta gacctgtgtg tagatatttc aaaaggctgt ctacttggg aacggatgca
6421 tttcattcac agggatctgg cagctagaaa ttgccttgtt tccgtgaaag actataccag
6481 tccacggata gtgaagattg gagactttgg actcgccaga gacatctata aaaatgatta
6541 ctatagaaag agaggggaag gcctgctccc agttcggtgg atggctccag aaagtttgat
6601 ggatggaatc ttcactactc aatctgatgt atggtctttt ggaattctga tttgggagat
6661 tttaactctt ggtcatcagc ctatccagc tcattccaac cttgatgtgt taaactatgt
6721 gcaaacagga gggagactgg agccaccaag aaattgtcct gatgatctgt ggaatttaat
6781 gacccagtgc tgggctcaag aacccgacca agacctact ttcatagaa ttcaggacca
6841 acttcagtta ttcagaaatt ttttcttaaa tagcatttat aagtccgag atgaagcaaa
6901 caacagtgga gtcataaatg aaagctttga aggtgaagat ggcgatgtga tttgtttgaa
6961 ttcagatgac attatgccag ttgctttaat ggaaacgaag aaccgagaag ggttaaacta
7021 tatggtactt gctacagaat gtggccaagg tgaagaaaag tctgagggtc tctaggctc
7081 ccaggaatct gaatcttgtg gtctgaggaa agaagagaag gaaccacatg cagacaaaga
7141 tttctgccaa gaaaaacaag tggcttactg cccttctggc aagcctgaag gcctgaacta
7201 tgcctgtctc actcacagtg gatatggaga tgggtctgat taatagcgtt gtttgggaaa
7261 tagagagttg agataaacac tctcattcag tagttactga agaaaactc tgctagaatg
7321 ataaatgtca tggtggtcta taactccaaa taaacaatgc aacgttcc
```

CD74-ROS

CD74-F1: GCAGAATGCCACCAAGTATGGCAA
ROS-GSP3: TGCCAGACAAAGGTCAGTGGGATT

Figure 16 A-F
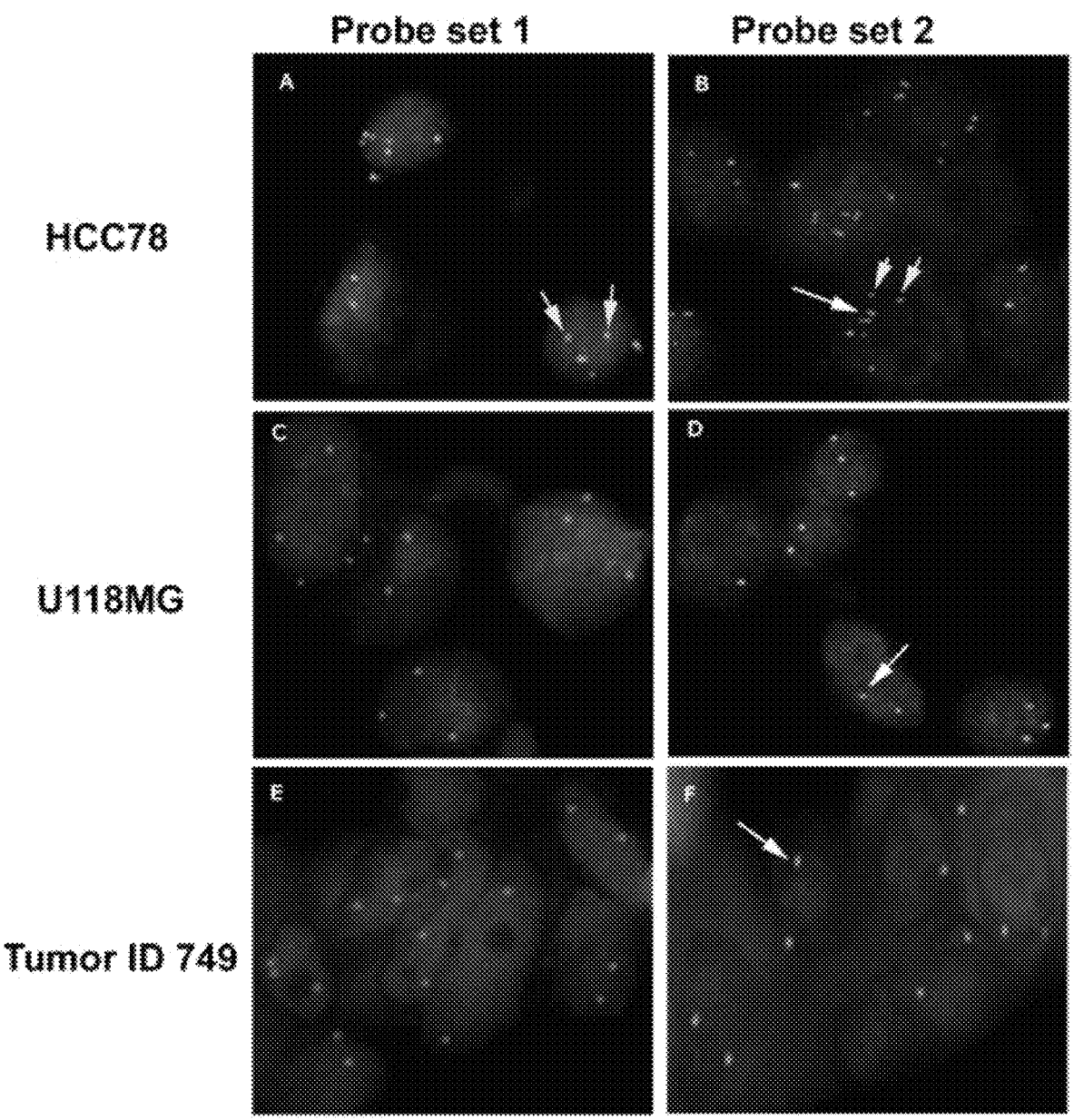

Figure 17

```
>lcl|9303
Length=167

Score =  272 bits (147),  Expect = 3e-77
Identities = 147/147 (100%), Gaps = 0/147 (0%)
Strand=Plus/Plus Query  556  GCTGTTCTTCCAAGGCTTCGAAGTAGTATATGGGCGCCAAGACTTAGCTTCCCAAGTACTTGGCATAAGGAA  615
            |||||||||||||||||||||||||||||||||||||||||||||||||||||||||||||||||||||||
Sbjct  3    GCTGTTCTTCCAAGGCTTCGAAGTAGTATATGGGCGCCAAGACTTAGCTTCCCAAGTACTTGGCATAAGGAA  62

Query  616  CTGGCAGGAAGTACTCTTCCAACCCAAGACGGAAGATTGAAAATCTTCCTTCCCTCCG  675
            |||||||||||||||||||||||||||||||||||||||||||||||||||||||||
Sbjct  63   CTGGCAGGAAGTACTCTTCCAACCCAAGACGGAAGATTGAAAATCTTCCTTCCCTCCG  122

Query  676  GAAAAACTGACTCTGCGGTCTCTTGCTG  702
            ||||||||||||||||||||||||||||
Sbjct  123  GAAAAACTGACTCTGCGGTCTCTTGCTG  149
```

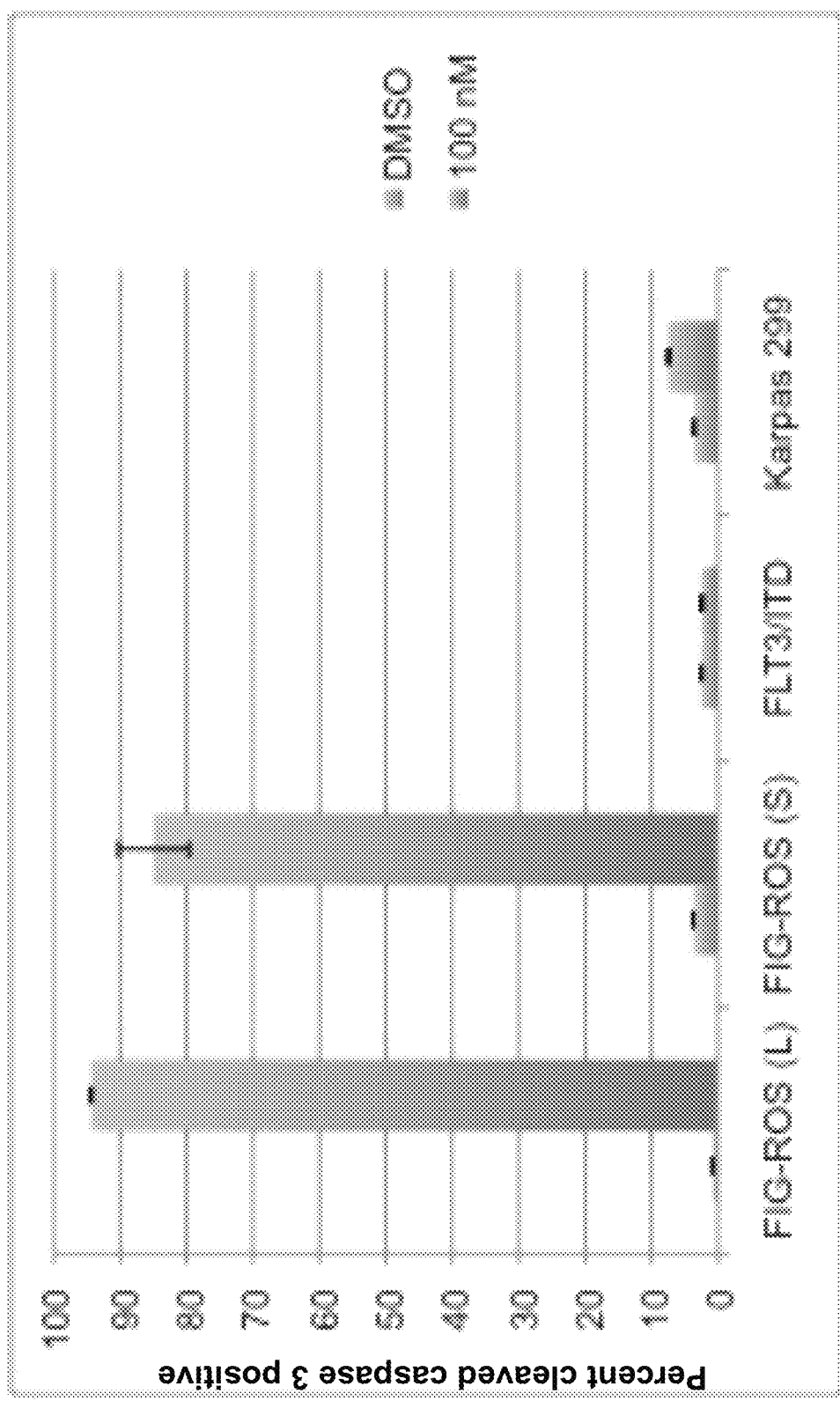

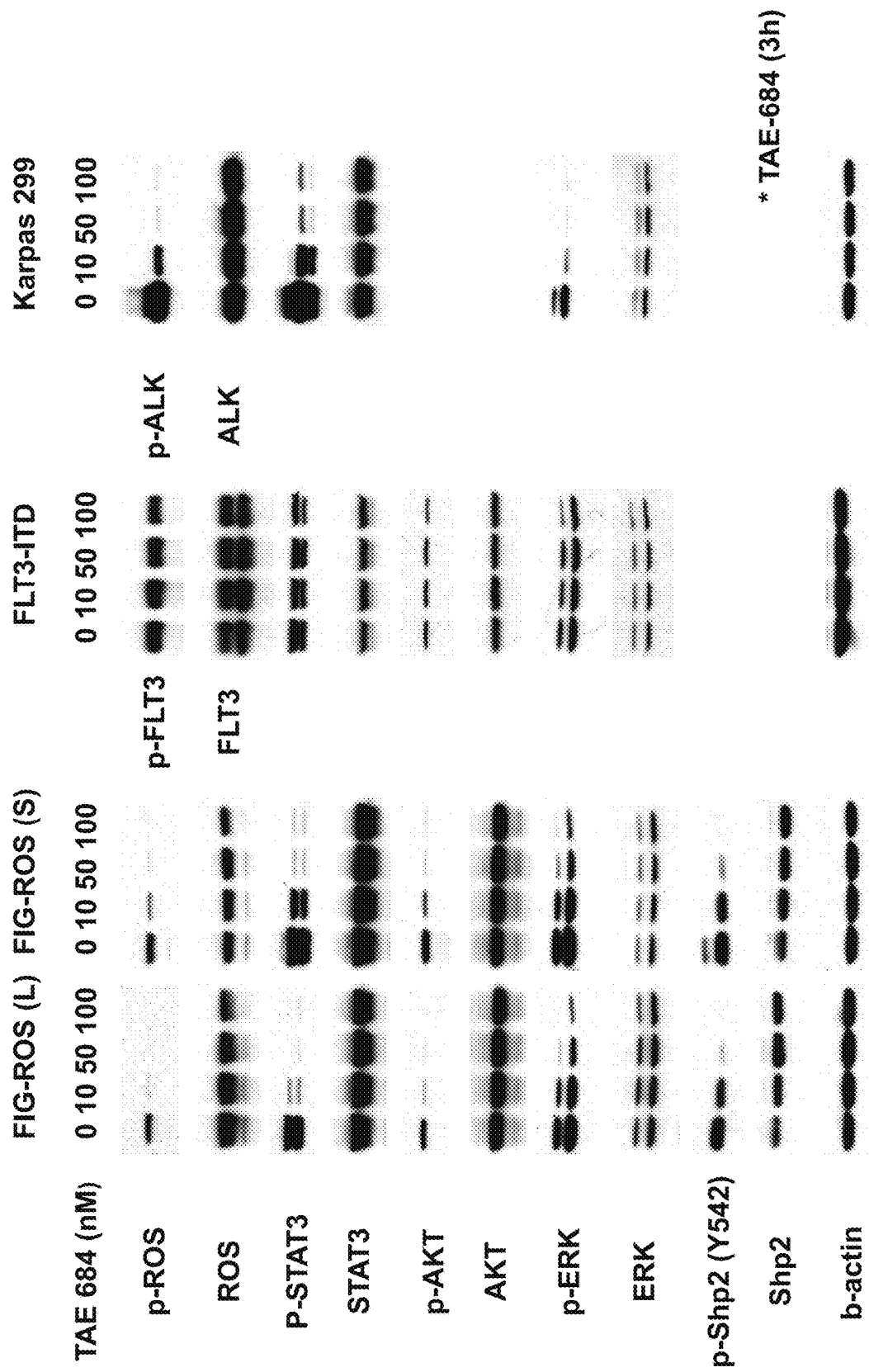
Figure 20: Phosphorylation of FIG-ROS is inhibited by TAE-684

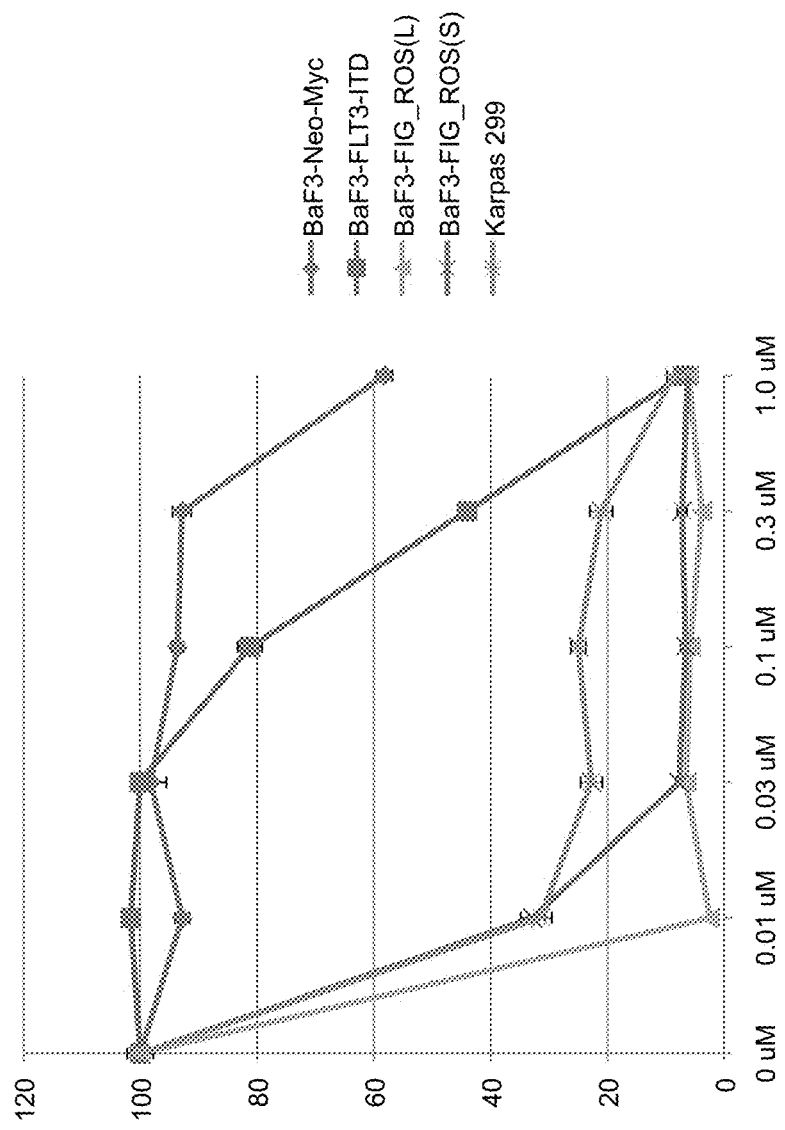

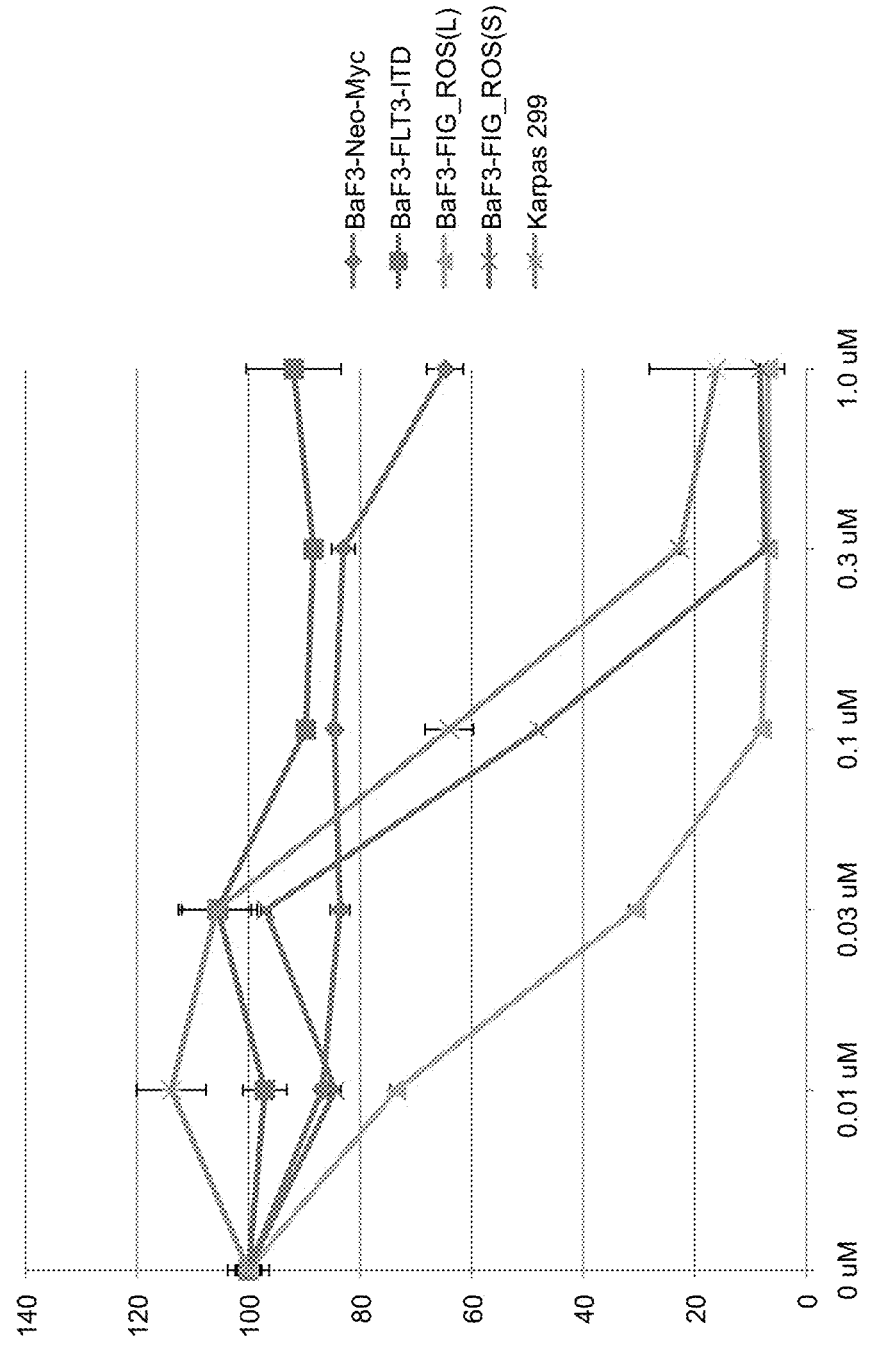

ROS KINASE IN LUNG CANCER

CROSS REFERENCE TO RELATED APPLICATIONS

This application is a divisional of U.S. patent application Ser. No. 13/113,676 filed May 23, 2011, now abandoned, which is a continuation-in-part of U.S. patent application Ser. No. 12/581,126 filed Oct. 17, 2009, which itself is a continuation-in-part of U.S. patent application Ser. No. 12/218,834, filed Jul. 18, 2008, now U.S. Pat. No. 8,383, 799, which itself claims priority to and the benefit of PCT Patent Application No. PCT/US2007/001360 filed Jan. 19, 2007 and U.S. Provisional Patent Application Ser. No. 60/760,634, filed Jan. 20, 2006. This application also is a continuation-in-part of PCT Patent Application No. PCT/US2010/024109 filed Feb. 12, 2010 which itself claims priority to and benefit of U.S. Provisional Patent Application Ser. No. 61/207,484 filed Feb. 12, 2009. This application also is a continuation-in-part of US patent application Ser. No. 12/738,210 filed Apr. 15, 2010, now U.S. Pat. No. 9,096,855, which is a US national stage filing of PCT Patent Application No. PCT/US08/11968 filed Oct. 20, 2008 which itself claim priority to and benefit of U.S. Provisional Patent Application Ser. No. 60/999,668 filed Oct. 18, 2007. This application also claims priority to and benefit of U.S. Provisional Patent Application Ser. No. 61/347,251 filed May 21, 2010. The entire disclosures of each of these above-listed US and PCT patent applications are hereby incorporated by reference.

INCORPORATION BY REFERENCE OF SEQUENCE LISTING

The Sequence Listing in the ASCII text file, named as 28119Z_CST315CON_SequenceListing of 122 KB, created on May 30, 2018, and submitted to the United States Patent and Trademark Office via EFS-Web, is incorporated herein by reference.

BACKGROUND OF THE INVENTION

The invention relates generally to proteins and genes involved in lung cancer (e.g., human lung cancer), and to the detection, diagnosis and treatment of lung cancer.

Many cancers are characterized by disruptions in cellular signaling pathways that lead to aberrant control of cellular processes including growth and proliferation. These disruptions are often caused by changes in the activity of particular signaling proteins, such as kinases.

Aberrant expression of protein kinase proteins can be the causative agent of (and the driver of) cancer. Aberrant expression can be caused by the fusion of the protein (or kinase portion thereof) with a secondary protein (or portion there), expression of a truncated portion of the protein, or by abnormal regulation of expression of the full-length protein.

It is known that gene translocations resulting in kinase fusion proteins with aberrant signaling activity can directly lead to certain cancers (see, e.g., Mitelman et al., Nature Reviews Cancer 7: 233-245, 2007, Futreal et al., Nat Rev Cancer 4(3): 177-183 (2004), and Falini et al., *Blood* 99(2): 409-426 (2002). For example, the BCR-ABL oncoprotein, a tyrosine kinase fusion protein, is the causative agent and drives human chronic myeloid leukemia (CML). The BCR-ABL oncoprotein, which is found in at least 90-95% of CML cases, is generated by the translocation of gene sequences from the c-ABL protein tyrosine kinase on chromosome 9 into BCR sequences on chromosome 22, producing the so-called Philadelphia chromosome. See, e.g. Kurzock et al., *N. Engl. J. Med.* 319: 990-998 (1988). The translocation is also observed in acute lymphocytic leukemia (ALL) and acute myeloid leukemia (AML) cases. These discoveries spurred FDA approval of imatinib mesylate (sold under the trademark Gleevec® by Novartis) and dasatinig (sold by Bristol-Mysers Squibb under the trademark Sprycel®), small molecule inhibitors of the ABL kinase, for the treatment of CML and ALL. These drugs are examples of drugs designed to interfere with the signaling pathways that drive the growth of tumor cells. The development of such drugs represents a significant advance over the conventional therapies for CML and ALL, chemotherapy and radiation, which are plagued by well known side-effects and are often of limited effect since they fail to specifically target the underlying causes of the cancer.

Thus, it would be useful to identify proteins that drive cancers in order to detect cancers at an early stage, when they are more likely to respond to therapy. Additionally, identification of such proteins will, among other things, desirably enable new methods for selecting patients for targeted therapies, as well as for the screening and development of new drugs that inhibit such proteins and, thus, treat cancer.

The oncogenic role of receptor tyrosine kinases (RTKs) have been implicated in many types of solid tumors, including lung cancer. Lung cancer, which has several subtypes including non-small cell lung cancer and small cell lung cancer, is the most common cause of death due to cancer in both men and women throughout the world. According to the U.S. National Cancer Institute, approximately one out of every 14 men and women in the U.S. will be diagnosed with cancer of the lung at some point in their lifetime. Two particularly deadly forms of lung cancer are small cell lung carcinoma (SCLC) and non-small cell lung carcinoma.

Unfortunately, lung cancer is often not diagnosed at an early stage, and it often does not respond completely to surgery even when combined with chemotherapy or radiotherapy. For example, NSCLC is the leading cause of cancer death in the United States, and accounts for about 87% of all lung cancers. There are about 151,000 new cases of NSCLC in the United States annually, and it is estimated that over 120,000 patients will die annually from the disease in the United States alone. See "*Cancer Facts and Figures* 2005," American Cancer Society. NSCLC, which comprises three distinct subtypes, is often only detected after it has metastasized, and thus the mortality rate is 75% within two years of diagnosis.

Thus, it would be useful to discover new ways to identify lung cancer at an early stage, and new ways (and new reagents) to treat lung cancer.

SUMMARY OF THE INVENTION

The invention is based upon the discovery of aberrant ROS expression and/or activity in cancer, particularly lung cancer. Aberrant expression of ROS in mammalian lung cancer may be due to, for example, expression of full length ROS kinase in mammalian lung cancer since healthy, normal lung tissue and cells do not express ROS kinase protein or ROS kinase activity. Aberrant expression of ROS in mammlian lung cancer may also be due to the presence of either truncated ROS (e.g., comprising a part of ROS kinase including the kinase domain) or one of the ROS fusion proteins disclosed herein. All disclosed expression of ROS in lung cancer result in the expression of the ROS kinase domain; thus all the disclosed ROS fusion polypeptides have active ROS kinase activity.

Accordingly, in a first aspect, the invention provides a method for detecting the presence of a polypeptide with ROS kinase activity in a biological sample from a mammalian lung cancer or a suspected mammalian lung cancer. The method includes the steps of: obtaining a biological sample from a mammalian lung cancer or suspected mammalian lung cancer; and utilizing at least one reagent that specifically binds to said polypeptide with ROS kinase activity to determine whether said polypeptide is present in said biological sample, wherein detection of specific binding of said reagent to said biological sample indicates said polypeptide is present in said biological sample.

In another embodiment, the reagent is an antibody. In some embodiments, the reagent (e.g., the antibody) is detectably labeled. In another embodiment, the reagent specifically binds to a full length ROS polypeptide. In another embodiment, the reagent specifically binds to a ROS kinase domain. In another embodiment, the reagent specifically binds to a ROS fusion polypeptide (e.g., specifically binds to a CD74-ROS fusion polypeptide, an SLC34A2-ROS(S) polypeptide, an SLC34A2-ROS(L) polypeptide, an SLC34A2-ROS(VS) polypeptide, a FIG-ROS (L) polypeptide, a FIG-ROS(S) polypeptide, or a FIG-ROS(VL) polypeptide.

In various embodiments of the methods of the invention, the polypeptide having ROS kinase activity is a full-length ROS polypeptide. In another embodiment, the polypeptide is a ROS fusion polypeptide. In another embodiment, the ROS fusion polypeptide is selected from the group consisting of a CD74-ROS fusion polypeptide, an SLC34A2-ROS(S) polypeptide, an SLC34A2-ROS(L) polypeptide, an SLC34A2-ROS(VS) polypeptide, a FIG-ROS (L) polypeptide, a FIG-ROS(S) polypeptide, and a FIG-ROS(VL) polypeptide. In various embodiments, the polypeptide having ROS kinase activity comprises the amino acid sequence of SEQ ID NO: 1, SEQ ID NO: 61, SEQ ID NO: 58, SEQ ID NO: 56, SEQ ID NO: 60, SEQ ID NO: 28, SEQ ID NO: 7, SEQ ID NO: 5, or SEQ ID NO: 22.

In some embodiments, the method is implemented in a format selected from the group consisting of a flow cytometry assay, an in vitro kinase assay, an immunohistochemistry (IHC) assay, an immunofluorescence (IF) assay, an Enzyme-linked immunosorbent assay (ELISA) assay, and a Western blotting analysis assay.

In one embodiment, the kinase activity of said polypeptide is detected. In another embodiment, the reagent is a heavy-isotope labeled (AQUA) peptide. In another embodiment, the heavy-isotope labeled (AQUA) peptide comprises an amino acid sequence comprising a fusion junction of an ROS fusion polypeptide. In another embodiment, the method is implemented using mass spectrometry analysis.

In another aspect, the invention provides to a method for detecting the presence of a polynucleotide encoding a polypeptide with ROS kinase activity in a biological sample from a mammalian lung cancer or suspected mammalian lung cancer. The method includes the steps of: (a) obtaining a biological sample from a mammalian lung cancer or suspected mammalian lung cancer and (b) utilizing a reagent that specifically binds to said polynucleotide encoding said polypeptide with ROS kinase activity to determine whether said polynucleotide is present in said biological sample, wherein detection of specific binding of said reagent to said biological sample indicates said polynucleotide encoding said polypeptide with ROS kinase activity is present in said biological sample.

In some embodiments, the polynucleotide comprises a nucleotide sequence selected from the group consisting of SEQ ID NO: 2, 6, 8, 23, 29, 55, 57, and 59.

In some embodiments, the reagent is a nucleic acid probe. In some embodiments, the reagent is detectably labeled. In another embodiment, the nucleic acid probe is a fluorescence in-situ hybridization (FISH) probe and said method is implemented in a FISH assay. In another embodiment, the nucleic acid probe is a polymerase chain reaction (PCR) probe and said method is implemented in a PCR assay. In a further embodiment, the reagent is detectably labeled.

In various embodiments of the methods of the invention, the polypeptide having ROS kinase activity is a full-length ROS polypeptide. In another embodiment, the polypeptide is a ROS fusion polypeptide. In another embodiment, the ROS fusion polypeptide is selected from the group consisting of a CD74-ROS fusion polypeptide, an SLC34A2-ROS(S) polypeptide, an SLC34A2-ROS(L) polypeptide, an SLC34A2-ROS(VS) polypeptide, a FIG-ROS (L) polypeptide, a FIG-ROS(S) polypeptide, and a FIG-ROS(VL) polypeptide. In various embodiments, the polypeptide having ROS kinase activity comprises the amino acid sequence of SEQ ID NO: 1, SEQ ID NO: 61, SEQ ID NO: 58, SEQ ID NO: 56, SEQ ID NO: 60, SEQ ID NO: 28, SEQ ID NO: 7, SEQ ID NO: 5, or SEQ ID NO: 22.

In various embodiments of the methods of the invention, the lung cancer is human lung cancer (e.g., non-small cell lung carcinoma or small cell lung carinoma). In a further embodiment, the biological sample is selected from the group consisting of a lung biopsy, a bronchioalveolar lavage, a tumor resection, a fine needle aspirate, a pleural effusion, and a circulating tumor cell.

In various embodiments of the methods of the invention, the mammalian lung cancer or suspected mammalian lung cancer is a non-small cell lung carcinoma. In various embodiments, mammalian lung cancer or suspected mammalian lung cancer is from a human.

In various embodiments of the methods of the invention, the biological sample is diagnosed as being from a mammalian lung cancer or suspected mammalian lung cancer driven by ROS kinase activity. In some embodiments, the mammalian lung cancer or suspected mammalian lung cancer is likely to respond to a ROS-inhibiting therapeutic. In various embodiments, the patient from whom said biological sample is obtained, where the reagent specifically binds to the biological sample, is diagnosed as having a mammalian lung cancer or suspected mammalian lung cancer driven by ROS kinase activity. In some embodiments, the patient is diagnosed as being likely to respond to a ROS-inhibiting therapeutic. One non-limiting example of a ROS-inhibiting therapeutic is crizotinib (also known as PF-02341066). Additional non-limiting examples of ROS-inhibiting therapeutics include NVT TAE-684, AP26113, CEP-14083, CEP-14513, CH5424802, CEP11988, WHI-P131 and WHI-P154.

In another aspect, the invention provides a method for inhibiting the progression of a mammalian cancer or suspected mammalian cancer that expresses a polypeptide having ROS kinase activity, said method comprising the step of inhibiting the expression and/or activity of said polypeptide in said mammalian cancer or suspected mammalian cancer.

In another aspect, the invention provides a method for inhibiting the progression of a mammalian cancer or suspected mammalian cancer comprising a polynucleotide encoding a polypeptide having ROS kinase activity, said method comprising the step of inhibiting the expression of said polynucleotide in said mammalian cancer or suspected mammalian cancer.

In various embodiments, the lung cancer or suspected lung cancer is from a human. In some embodiments, the expression and/or activity of the polypeptide or the polynucleotide is inhibited by a ROS-inhibiting therapeutic selected from the group consisting of PF-02341066, NVT TAE-684, AP26113, CEP-14083, CEP-14513, CEP11988, CH5424802, WHI-P131 and WHI-P154.

In yet another aspect, the invention provides a method of identifying a patient with lung cancer or suspected of having lung cancer as a patient likely to respond to a ROS-inhibiting therapeutic, comprising: contacting a biological sample from a lung of said patient with a reagent that specifically binds a polypeptide having ROS kinase activity, detecting whether the reagent specifically binds to the biological sample, wherein detection of binding of the reagent to the biological sample identifies the patient as a patient likely to respond to a ROS-inhibiting therapeutic.

In yet another aspect, the invention provides a method of treating a patient for lung cancer, comprising: detecting the presence of a polypeptide having ROS kinase activity in a biological sample from a lung of a patient having or suspected of having lung cancer; and administering a therapeutically effective amount of a ROS-inhibiting therapeutic to the patient, thereby treating the subject for lung cancer.

In yet another aspect, the invention provides a method of treating a patient for lung cancer, comprising: detecting the presence in a biological sample from a lung of a patient having or suspected of having lung cancer of a polypeptide selected from the group consisting of a polypeptide having ROS kinase activity and a polypeptide having ALK kinase activity; and administering a therapeutically effective amount of an ALK/ROS-inhibiting therapeutic to the patient, thereby treating the subject for lung cancer.

In a further aspect, the invention provides a method for identifying a patient with lung cancer or suspected of having lung cancer as a patient likely to respond to a ROS-inhibiting therapeutic, comprising: contacting a biological sample from a lung of said patient with a first reagent that specifically binds a polypeptide having ROS kinase activity and a second reagent that specifically binds to a polypeptide having ALK knase activity and detecting whether the first reagent or the second reagent specifically binds to the biological sample, wherein detection of binding of either the first reagent or the second reagent to the biological sample identifies the patient as a patient likely to respond to a ROS-inhibiting therapeutic.

In a further aspect, the invention provides a method for identifying a patient with lung cancer or suspected of having lung cancer as a patient likely to respond to an ALK-inhibiting therapeutic, comprising: contacting a biological sample from a lung of said patient with a first reagent that specifically binds a polypeptide having ROS kinase activity and a second reagent that specifically binds to a polypeptide having ALK knase activity and detecting whether the first reagent or the second reagent specifically binds to the biological sample, wherein detection of binding of either the first reagent or the second reagent to the biological sample identifies the patient as a patient likely to respond to an ALK-inhibiting therapeutic.

In various embodiments, the first reagent specifically binds to full length ROS kinase protein. In various embodiments, the second reagent specifically binds to full length ALK kinase protein. In various embodiments, the first reagent specifically binds to the kinase domain of ROS kinase protein. In various embodiments, the second reagent specifically binds to the kinase domain of ALK kinase protein. In some embodiments, the first reagent is an antibody. In some embodiments, the second reagent is an antibody.

In various embodiments of all of the aspect of the invention, the patient is a human patient and the lung cancer (or suspected lung cancer) is from a human. In some embodiments, the lung cancer is NSCLC or SCLC. In some embodiments, the ROS-inhibiting therapeutic or the ALK-inhibiting therpauetic is PF-02341066, NVT TAE-684, or AP26113. In some embodiments, the ROS-inhibiting therapeutic or ALK-inhibiting therapeutic is AP26113, CEP-14083, CEP-14513, CEP11988, CH5424802, WHI-P131 and WHI-P154.

In various embodiments, the biological sample is selected from the group consisting of a lung biopsy, a bronchioalveolar lavage, a circulating tumor cell, a tumor resection, a fine needle aspirate, and a pleural effusion.

In further aspects, the invention provides a method for determining whether a compound inhibits the progression of a mammalian lung cancer or suspected mammalian lung cancer characterized by the expression of a polypeptide with ROS activity, said method comprising the step of determining whether said compound inhibits the expression of said polypeptide in said cancer. In another aspect, the invention provides a method for inhibiting the progression of a mammalian cancer or suspected mammalian cancer characterized by the expression of a polypeptide with ROS activity, said method comprising the step of inhibiting the expression and/or activity of said polypeptide in said mammalian lung cancer or suspected mammalian lung cancer. In some embodiments, the cancer is from a human.

BRIEF DESCRIPTION OF THE DRAWINGS

This patent or application file contains drawings executed in color. Copies of this patent or patent application publication with color drawings will be provided by the Office upon request and payment of the necessary fee.

FIGS. 2A-2C—show siRNA inhibition of mutant ROS kinase in a human NSCLC cell lines: Panel A shows a graph of cell inhibition following siRNA transfection, Panel B is an immunoblot showing specific knock-down of ROS and increased apoptosis (in the mutant ROS-driven cell line), and Panel C is an immunoblot showing decreased activity of signaling molecules downstream of ROS.

FIG. 4A—is the amino acid sequence (1 letter code) of the long variant of human SLC34A2-ROS fusion protein (SEQ ID NO: 5) (top panel) with coding DNA sequence also indicated (SEQ ID NO: 6) (bottom panel); the residues of the SLC34A2 moiety are in italics, while the residues of the kinase domain of ROS are in bold.

FIG. 4B—is the amino acid sequence (1 letter code) of the short variant of human SLC34A2-ROS fusion protein (SEQ ID NO: 7) (top panel) with coding DNA sequence also indicated (SEQ ID NO: 8) (bottom panel); the residues of the SLC34A2 moiety are in italics, while the residues of the kinase domain of ROS are in bold.

FIG. 5—is the amino acid sequence (1 letter code) of human SLC34A2 protein (SEQ ID NO: 3) (SwissProt Accession No. 095436) (top panel) with coding DNA sequence also indicated (SEQ ID NO: 4) (GeneBank Accession No. NM_006424) (bottom panel); the residues involved in the translocation are underlined.

FIG. 6A—is the amino acid sequence (1 letter code) of human ROS kinase (SEQ ID NO: 1) (SwissProt Accession No. P08922); the residues involved in the SLC34A2-ROS (long) variant translocation are underlined, the underlined bold residues are those involved in the (short) variant translocation, and the underlined, bold, red residues are those involved in the predicted (very short) variant translocation.

FIG. 6B—is the coding DNA sequence of human ROS kinase (SEQ ID NO: 2) (GeneBank Accession No. NM_002944); the residues involved in the first SLC34A2-ROS (long) variant translocation are underlined, the underlined bold residues are those involved in the second (short) variant translocation, and the underlined, bold, capitalized residues are those involved in the (very short) variant translocation.

FIGS. 8A-8C—show the location of the CD74 gene and ROS gene on chromosomes 5q and 6q respectively (panel A), and the domain locations of full length CD74 and ROS proteins as well as those in the CD74-ROS fusion protein (panels B and C (with SEQ ID NO:30 shown below panel C)). The fusion junction occurs at residue 1853 upstream of the transmembrane domain of ROS.

FIG. 9—is the amino acid sequence (1 letter code) of the human CD74-ROS fusion protein (SEQ ID NO: 22) (top panel) with coding DNA sequence also indicated (SEQ ID NO: 23) (bottom panel); the residues of the CD74 moiety are underlined, while the residues of the kinase domain of ROS are in bold.

FIG. 10—is the amino acid sequence (1 letter code) of human CD74 protein (SEQ ID NO: 24) (SwissProt Accession No. P04233) (top panel) with coding DNA sequence also indicated (SEQ ID NO: 25) (GeneBank Accession No. NM_001025159) (bottom panel); the residues involved in the translocation are underlined.

FIG. 11A—is the amino acid sequence (1 letter code) of human ROS kinase (SEQ ID NO: 1) (SwissProt Accession No. P08922); the residues involved in the CD74-ROS translocation are underlined.

FIG. 11B—is the coding DNA sequence of human ROS kinase (SEQ ID NO: 2) (GeneBank Accession No. NM_002944); the residues involved in the CD74-ROS translocation are underlined.

FIG. 14A shows the locations on the ROS gene where the FISH probes hybridize, and FIG. 14B shows the rearrangement of the ROS gene in a human NSCLC cell line (left) and a human NSCLC tumor, resulting in separate orange and green signals.

FIGS. 16A-16F are photographs showing the results of FISH analysis of HCC78 cells (panels A and B), U118MG cells (panels C and D) and FFPE tumor ID 749 (panels E and F). HCC78 cells probed with probe set 1 (A) and probe set 2 (B) shows results expected from the SLC34A2-ROS fusion present in these cells. Yellow arrows point to split signals indicative of balanced translocation in HCC78 cells and white arrows point to intact chromosome. U118MG cells probed with probe set 1 (C) and probe set 2 (D) shows results expected from the FIG-ROS fusion present in these cells. FFPE tumor 749 probed with probe set 1 (E) and probe set 2 (F) is identical to U118MG cells. In both U-118 MG and Tumor ID 749 probed with probe set 1 only the c-ros (orange) probe anneals and the deleted region (green probe) is not present (panels C and E, respectively). In U-118 MG and Tumor ID 749 probed with probe set 2 (panels E and F, respectively), the c-ros (orange) and fig (green) probes come together indicating a fig-ros fusion.

FIG. 17 shows the results of cDNA sequencing of the ROS fusion protein from tumor 749 (in "sbjt" line) and its alignment with the FIG-ROS(S) nucleotide sequence (as "query").

FIG. 19 is a bar graph showing that BaF3 expressing either FIG-ROS(S) or FIG-ROS(L) die by apoptosis in the presence of TAE-684.

FIG. 20 is a depiction of a Western blotting analysis showing that phosphorylation of both FIG-ROS(S) and FIG-ROS(L), as well as their downstream signaling molecules, are inhibited by TAE-684.

FIGS. 21A and 21B are line graphs showing the cellular growth response in the presence of TAE-684 (FIG. 21A) or crizotinib (FIG. 21B) at 0 uM, 0.01 uM, 0.03M, 0.10 uM, 0.3 uM, 1.0 uM of BaF3 cells transduced with neo-myc (negative control; blue diamonds); BaF3 expressing FIG-ROS(S) (purple X's), BaF3 expressing FIG-ROS(L) (green triangles), BaF3 expressing FLT3ITD (red squares), and Karpas 299 cells (blue asterisks).

DETAILED DESCRIPTION OF THE PREFERRED EMBODIMENTS

Figure 1:
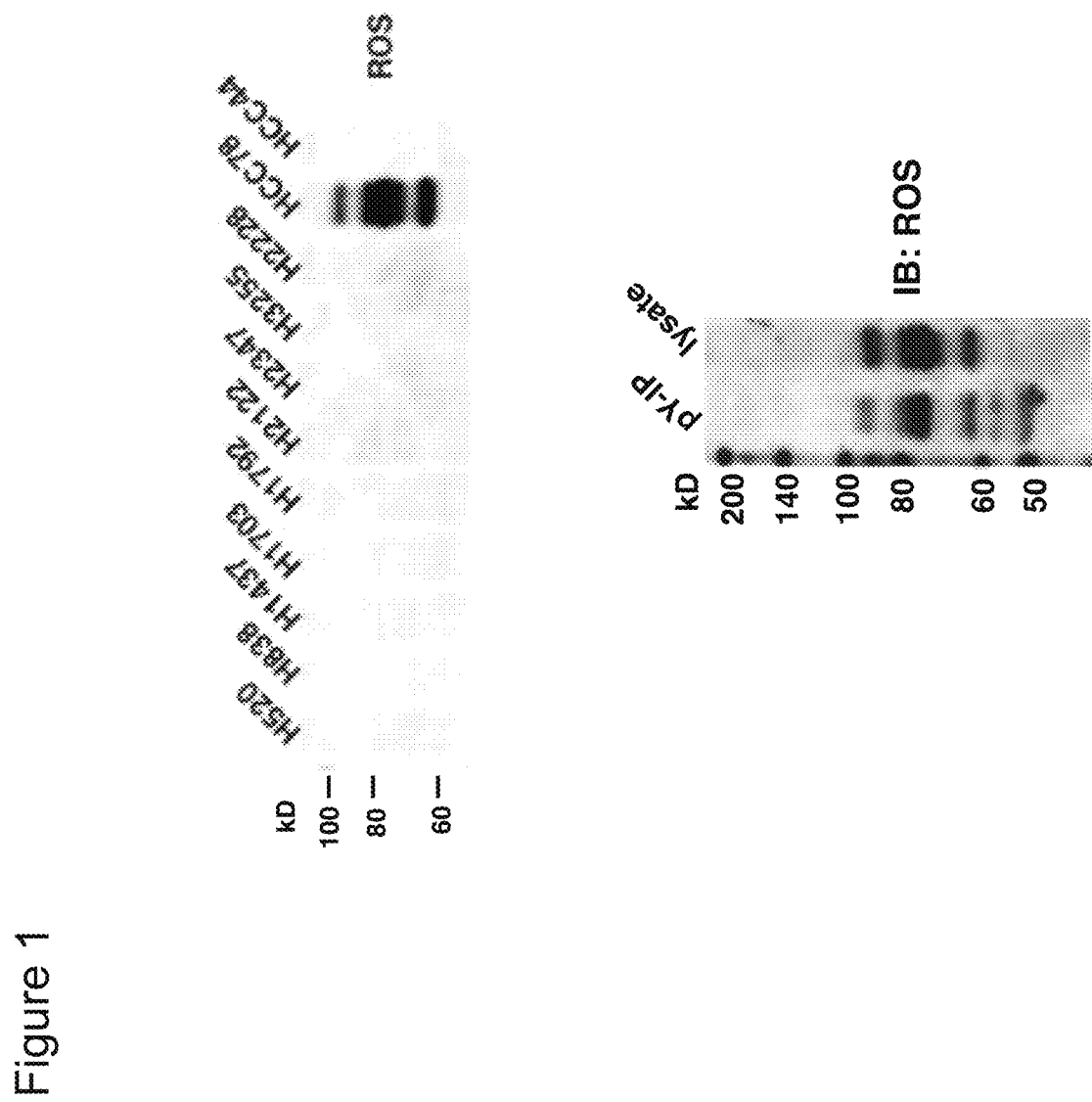
FIG. 1—is a Western blot analysis of extracts from human NSCLC cell line (HCC78) showing expression of a form of ROS having much lower molecular weight than full length/wild-type ROS.

The invention is based upon the discovery of aberrant ROS kinase expression in human lung cancer. As ROS kinase is not expressed in normal lung tissue or cells, the aberrant ROS kinase activity is expected the drive the proliferation and survival of the lung cancer in which it is expressed. Such cancers may be identified (e.g., diagnosed) and/or treated in accordance with the teachings provided herein.

Based on these discoveries, a patient whose lung cancer (or suspected lung cancer) expresses a protein with ROS activity (e.g., full length ROS protein or a ROS fusion protein) where lung tissue of healthy patients do not express such proteins with ROS activity may respond favorably to administration of an ROS inhibitor (e.g., the growth of the cancer may slow or stop as compared to an untreated patient suffering from the same cancer).

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

The further aspects, advantages, and embodiments of the invention are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of antibody and recombinant DNA technology, all of which are incorporated herein by reference in their entirety, include Harlow and Lane, Antibodies, a Laboratory Manual, Cold Spring Harbor Laboratory Press, New York (1988), Ausubel et al. Current Protocols in Molecular Biology, John Wiley & Sons, New York, N.Y. (1989 and updates through September 2010), Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology, all of which are incorporated herein by reference in their entirety, include Goodman and Gilman's The Pharmacological Basis of Therapeutics, 11th Ed., McGraw Hill Companies Inc., New York (2006).

In a first aspect, the invention provides a method for detecting the presence of a polypeptide with ROS kinase activity in a biological sample from a mammalian lung cancer or a suspected mammalian lung cancer. The method includes the steps of: obtaining a biological sample from a mammalian lung cancer or suspected mammalian lung cancer; and utilizing at least one reagent that specifically binds to said polypeptide with ROS kinase activity to determine whether said polypeptide is present in said biological sample, wherein detection of specific binding of said reagent to said biological sample indicates said polypeptide is present in said biological sample.

Human ROS kinase protein (encoded by the ROS1 gene) is a 2347 amino acid long receptor tyrosine kinase that is prone to aberrant expression leading to cancer. A description of full length human ROS kinase (with the amino acid sequence of the human ROS protein) can be found at UniProt Accession No. P08922. As shown in Table 1, the signal peptide, extracellular, transmembrane, and kinase domains of ROS are found at the following amino acid residues in SEQ ID NO: 1:

TABLE 1

| Domain | Amino acid residues in SEQ ID NO: 1 |
|---|---|
| Signal peptide | 1-27 |
| Extracellular domain | 28-1859 |
| Transmembrane domain | 1860-1882 |
| Kinase domain | 1945-2222 |

Additionally, there are multiple known naturally-occurring variants of ROS (see, e.g., Greenman et al., Nature 446: 153-158, 2007). The nucleotide and amino acid sequences of murine full-length ROS are known (see, e.g., UniProt Accession No. Q78DX7). Using routine experimentation, the ordinarily skilled biologist would be readily able to determine corresponding sequences in non-human mammalian ROS homologues.

By "wild-type" ROS is meant the expression and/or activation of full length ROS kinase (i.e., for human ROS, the 2347 amino acid long polypeptide or 2320 amino acid long polypeptide following removal of the signal peptide sequence) in healthy (or normal) tissue (e.g., non-cancerous tissue) of a normal individual (e.g., a normal individual who is not suffering from cancer). ROS kinase (full length or truncated) does not appear to be expressed in normal lung tissue in humans (e.g., see below in the Examples). However, using the methods described in the below Examples, the inventors have made the surprising discovery of ROS kinase expression in lung cancer. Such expression in an atypical cell (in this case a cancerous cell) where no expression is seen in a typical cell (e.g., a non-cancerous lung cell) is aberrant.

Aberrantly expressed ROS kinase, in the form of a fusion with another protein, namely FIG, has been reported in glioblastoma (see Charest et al., Charest et al., Genes Chromosomes Cancer 37: 58-71, 2003; Charest et al., Proc. Natl. Acad. Sci. USA 100: 916-921, 2003) and in liver cancer (see, e.g., PCT Publication No. WO2010/093928).

As used herein, the term "ROS fusion" refers to a portion of the ROS polypeptide comprising the kinase domain of the ROS protein (or polynucleotide encoding the same) fused to all or a portion of another polypeptide (or polynucleotide encoding the same), where the name of that second polypeptide or polynucleotide is named in the fusion. (The term "fusion" simply means all or a portion of a polypeptide or polynucleotide from first gene fused to all or a portion of a polypeptide or a polynucleotide from a second gene). For example, an SLC34A2-ROS fusion is a fusion between a portion of the SLC34A2 polypeptide (or polynucleotide encoding the same) and a portion of the ROS polypeptide (or polynucleotide encoding the same) comprising the kinase domain ROS. An ROS fusion often results from a chromosomal translocation or inversion. There are numerous known ROS fusions, all of which are ROS fusions of the invention and include, without limitation, the SLC34A2-ROS fusion proteins whose members include SLC34A2-ROS(VS), SLC34A2-ROS(S), SLC34A2-ROS(L) (see U.S. Patent Publication No. 20100143918), CD74-ROS (see U.S. Patent Publication No. 20100221737) and the FIG-ROS fusion proteins whose members include FIG-ROS(S), FIG-ROS(L), and FIG-ROS(XL) (see PCT Publication No. WO2010/093928).

All of the known ROS fusion proteins comprise the full kinase domain of full length ROS. Thus, as used herein, by a "polypeptide with ROS kinase activity" (or "polypeptide having ROS kinase activity") is meant a protein (or polypeptide) that includes the full kinase domain of full length ROS protein and, thus, retains ROS kinase activity. Non-limiting examples of proteins with ROS kinase activity include, without limitation, full length ROS protein, the SLC34A2-ROS fusion proteins, whose members include SLC34A2-ROS(VS), SLC34A2-ROS(S), SLC34A2-ROS(L) (see U.S. Patent Publication No. 20100143918), CD74-ROS (see U.S. Patent Publication No. 20100221737) and the FIG-ROS fusion proteins whose members include FIG-ROS(S), FIG-ROS(L), and FIG-ROS(XL) (see PCT Publication No. WO2010/093928), and any truncated or mutated form of ROS kinase that retains the kinase domain of full-length ROS kinase protein. As the kinase domain of ROS is set forth in SEQ ID NO: 61, a "polypeptide with ROS kinase activity" is one whose amino acid sequence comprises SEQ ID NO: 61.

As used herein, by "polypeptide" (or "amino acid sequence" or "protein") refers to a polymer formed from the linking, in a defined order, of preferably, α-amino acids, D-, L-amino acids, and combinations thereof. The link between one amino acid residue and the next is referred to as an amide bond or a peptide bond. Non-limiting examples of polypeptides include refers to an oligopeptide, peptide, polypeptide, or protein sequence, and fragments or portions thereof, and to naturally occurring or synthetic molecules. Polypeptides also include derivatized molecules such as glycoproteins and lipoproteins as well as lower molecular weight polypeptides. "Amino acid sequence" and like terms, such as "polypeptide" or "protein", are not meant to limit the indicated amino acid sequence to the complete, native amino acid sequence associated with the recited protein molecule.

It will be recognized in the art that some amino acid sequences of a polypeptide of the invention (e.g., FIG-ROS(S) polypeptide) can be varied without significant effect of the structure or function of the mutant protein. If such differences in sequence are contemplated, it should be remembered that there will be critical areas on the protein which determine activity (e.g. the kinase domain of ROS). In general, it is possible to replace residues that form the tertiary structure, provided that residues performing a similar function are used. In other instances, the type of residue may be completely unimportant if the alteration occurs at a non-critical region of the protein.

Thus, a polypeptide with ROS activity of the invention further includes variants of the full length ROS protein or the various ROS fusion polypeptides described herein that shows substantial ROS kinase activity. Some non-limiting conservative substitutions include the exchange, one for another, among the aliphatic amino acids Ala, Val, Leu and Ile; exchange of the hydroxyl residues Ser and Thr; exchange of the acidic residues Asp and Glu; exchange of the amide residues Asn and Gln; exchange of the basic residues Lys and Arg; and exchange of the aromatic residues Phe and Tyr. Further examples of conservative amino acid substitutions known to those skilled in the art are: Aromatic: phenylalanine tryptophan tyrosine (e.g., a tryptophan residue is replaced with a phenylalanine); Hydrophobic: leucine isoleucine valine; Polar: glutamine asparagines; Basic: arginine lysine histidine; Acidic: aspartic acid glutamic acid; Small: alanine serine threonine methionine glycine. As indicated in detail above, further guidance concerning which amino acid changes are likely to be phenotypically silent (i.e., are not likely to have a significant deleterious effect on a function) can be found in Bowie et al., Science 247, supra.

In some embodiments, a variant may have "nonconservative" changes, e.g., replacement of a glycine with a tryptophan. Similar variants may also include amino acid deletions or insertions, or both. Guidance in determining which amino acid residues may be substituted, inserted, or deleted without abolishing biological or immunological activity may be found using computer programs well known in the art, for example, DNASTAR software.

The polypeptides having ROS kinase activity of the present invention include the full length human ROS protein (having an amino acid sequence set forth in SEQ ID NO: 1) and the ROS fusion polypeptides having the amino sequences set forth in SEQ ID NOs: 5, 7, 22, 28, 56, 58, and 60 (whether or not including a leader sequence), an amino acid sequence encoding a polypeptide comprising at least six contiguous amino acids encompassing the fusion junction (i.e., the sequences at the junction between the non-ROS partner protein and the ROS protein; see Table 2, as well as polypeptides that have at least 90% similarity, more preferably at least 95% similarity, and still more preferably at least 96%, 97%, 98% or 99% similarity to those described above.

Full length ROS-specific reagents and the ROS fusion polypeptide specific reagents (such as polyclonal and monoclonal antibodies) which are useful in assays for detecting ROS polypeptide expression and/or ROS kinase activity as described below or as ROS-inhibiting therapeutics capable of inhibiting ROS protein function/activity. Further, such polypeptides can be used in the yeast two-hybrid system to "capture" a ROS protein- or a ROS fusion protein-binding proteins, which are also candidate ROS-inhibiting therapeutics according to the present invention. The yeast two hybrid system is described in Fields and Song, *Nature* 340: 245-246 (1989).

In some embodiments, the reagent may further comprise a detectable label (e.g., a fluorescent label or an infrared label). By "detectable label" with respect to a polypeptide, polynucleotide, or reagent (e.g., antibody or FISH probe) disclosed herein means a chemical, biological, or other modification of or to the polypeptide, polynucleotide, or antibody, including but not limited to fluorescence (e.g., FITC or phycoerythrin), infrared, mass (e.g., an isobaric tag), residue, dye (chromophoric dye), radioisotope (e.g., 32P), label, or tag (myc tag or GST tag) modifications, etc., by which the presence of the molecule of interest may be detected. Such a polypeptide, polynucleotide, or reagent thus called "detectably labeled." The detectable label may be attached to the polypeptide, polynucleotide, or binding agent by a covalent (e.g., peptide bond or phosphodiester bond) or non-covalent chemical bond (e.g., an ionic bond).

Reagents useful in the methods of the invention include, without limitation, reagents such as antibodies or AQUA peptides, or binding fractions thereof, that specifically bind to full length ROS protein or one of the many ROS fusion proteins expressed in lung cancer. By "specifically binding" or "specifically binds" means that a reagent or binding agent of the invention (e.g., a nucleic acid probe, an antibody, or AQUA peptide) interacts with its target molecule (e.g., a ROS fusion polypeptide or polynucleotide, or a full-length ROS polypeptide or polynucleotide), where the interaction is dependent upon the presence of a particular structure (e.g., the antigenic determinant or epitope on the polypeptide or the nucleotide sequence of the polynucleotide); in other words, the reagent is recognizing and binding to a specific polypeptide or polynucleotide structure rather than to all polypeptides or polynucleotides in general. By "binding fragment thereof" means a fragment or portion of a reagent that specifically binds the target molecule (e.g., an Fab fragment of an antibody).

A reagent that specifically binds to the target molecule may be referred to as a target-specific reagent or an anti-target reagent. For example, an antibody that specifically binds to a FIG-ROS(L) polypeptide may be referred to as a FIG-ROS(L)-specific antibody or an anti-FIG-ROS(L) antibody. Similarly, a nucleic acid probe that specifically binds to a FIG-ROS(L) polynucleotide may be referred to as a FIG-ROS(L)-specific nucleic acid probe or an anti-FIG-ROS(L) nucleic acid probe.

In some embodiments, where the target molecule is a polypeptide, a reagent that specifically binds a target molecule has a binding affinity ($K_D$) for its target molecule (e.g., full length ROS or a ROS fusion polypeptide) of $1 \times 10^{-6}$ M or less. In some embodiments, a reagent of the invention that specifically binds to a target molecule has for its target molecule a $K_D$ of $1 \times 10^{-7}$ M or less, or a $K_D$ of $1 \times 10^{-8}$ M or less, or a $K_D$ of $1 \times 10^{-9}$ M or less, or a $K_D$ of $1 \times 10^{-10}$ M or less, of a $K_D$ of $1 \times 10^{-11}$ M or less, of a $K_D$ of $1 \times 10^{-12}$ M or less. In certain embodiments, the $K_D$ of a reagent of the invention that specifically binds to a target molecule is 1 pM to 500 pM, or between 500 pM to 1 µM, or between 1 µM to 100 nM, or between 100 mM to 10 nM for its target molecule. Non-limiting examples of a target molecule to which a reagent of the invention specifically binds to include full length ROS polypeptide or the ROS fusion polypeptide s including the SLC34A2-ROS(S) fusion polypeptide, the SLC34A2-ROS(VS) fusion polypeptide, the SLC34A2-ROS(L) fusion polypeptide, the CD74-ROS fusion polypeptide, the FIG-ROS(L) fusion polypeptide, the FIG-ROS(S) fusion polypeptide, the FIG-ROS(XL) fusion polypeptide, and fragments thereof, particularly those fragments that include the junction between the ROS portion and the portion of the second protein (e.g., SLC34A2, FIG, or CD74) of the ROS fusion polypeptide.

In some embodiments, where the target molecule is a polynucleotide, a reagent of the invention that specifically binds its target molecule is a reagent that hybridizes under stringent conditions to it target polynucleotide. The term "stringent conditions" with respect to nucleotide sequence or nucleotide probe hybridization conditions is the "stringency" that occurs within a range from about $T_m$ minus 5° C. (i.e., 5° C. below the melting temperature ($T_m$) of the reagent or nucleic acid probe) to about 20° C. to 25° C. below $T_m$. Typical stringent conditions are: overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences. By a "reagent (e.g., a polynucleotide or nucleotide probe) that hybridizes under stringent conditions to a target polynucleotide (e.g., a full length ROS polynucleotide)" is intended that the reagent (e.g., the polynucleotide or nucleotide probe (e.g., DNA, RNA, or a DNA-RNA hybrid)) hybridizes along the entire length of the reference polynucleotide or hybridizes to a portion of the reference polynucleotide that is at least about 15 nucleotides (nt), or to at least about 20 nt, or to at least about 30 nt, or to about 30-70 nt of the reference polynucleotide. These nucleotide probes of the invention are useful as diagnostic probes (e.g., for FISH) and primers (e.g., for PCR) as discussed herein.

Non-limiting examples of a target molecule to which a reagent of the invention specifically binds includes the full length ROS polypeptide, e.g., comprising the sequence of SEQ ID NO: 1 (or polynucleotide encoding the same), the kinase domain of a ROS protein, e.g., comprising the sequence of SEQ ID NO: 61 (or polynucleotide encoding the same), the transmembrane domain of ROS polypeptide (or a polynucleotide encoding the same), the FIG-ROS(S) fusion polypeptide, e.g., having comprising the sequence of SEQ ID NO: 58 (or FIG-ROS(S) polynucleotide), the FIG-ROS(L) fusion polypeptide, e.g., comprising the sequence of SEQ ID NO: 56 (or FIG-ROS(L) polynucleotide), the FIG-ROS(VL) fusion polypeptide, e.g., comprising the sequence of SEQ ID NO: 60 (or FIG-ROS(VL) polynucleotide), the SLC34A2-ROS(VS) fusion polypeptide, e.g., comprising the sequence of SEQ ID NO: 28 (or SLC34A2-ROS(VS) polynucleotide), the SLC34A2-ROS(S) fusion polypeptide, e.g., comprising the sequence of SEQ ID NO: 7 (or SLC34A2-ROS(S) polynucleotide), the SLC34A2-ROS(L) fusion polypeptide, e.g., comprising the sequence of SEQ ID NO: 5 (or SLC34A2-ROS(L) polynucleotide), the CD74-ROS fusion polypeptide, e.g., comprising the sequence of SEQ ID NO: 22 (or CD74-ROS polynucleotide), and fragments thereof, particularly those fragments that include the junction between the ROS portion and the portion of the second protein (e.g., SLC34A2, FIG, or CD74) of the ROS fusion polypeptide (see, e.g., Table 2).

The reagents useful in the practice of the disclosed methods, include, among others, full length ROS-specific and ROS fusion polypeptide-specific antibodies and AQUA peptides (heavy-isotope labeled peptides) corresponding to, and suitable for detection and quantification of, the indicated polypeptide's expression in a biological sample. Thus, a "ROS polypeptide-specific reagent" is any reagent, biological or chemical, capable of specifically binding to, detecting and/or quantifying the presence/level of expressed ROS polypeptide in a biological sample. If the reagent specifically binds to a portion of ROS protein (e.g., the kinase domain) that is present in a ROS fusion protein, the ROS polypeptide-specific reagent would also be capable of specifically binding to, detecting and/or quantifying the presence/level of expressed ROS fusion polypeptide in a biological sample. The terms include, but are not limited to, the antibodies and AQUA peptide reagents discussed below, and equivalent binding agents are within the scope of the present invention.

In some embodiments, the reagent that specifically binds to a polypeptide with ROS kinase activity is an antibody. In some embodiments, the reagemt (e.g., antibody) specifically binds to full length ROS polyptide. In some embodiments, the reagent (e.g., an antibody) specifically binds to a full length FIG polypeptide. In some embodiments, the reagent (e.g., an antibody) specifically binds to a full length SLC34A2 polypeptide. In some embodiments, the reagent (e.g., an antibody) specifically binds to a full length CD74 polypeptide. In some embodiments, the reagent (e.g., the antibody) specifically binds to a ROS fusion polypeptide and does not specifically bind to the full length polypeptide of either full length ROS or its fusion partner (e.g., full length FIG, full length CD74, or full length SLC34A2).

Also useful in practicing the methods of the invention are other reagents such as epitope-specific antibodies that specifically bind to an epitope in the extracelluar domain of wild-type ROS protein sequence (and are therefore capable of detecting the presence (or absence) of wild type ROS in a sample) or that specifically bind to an epitope in the kinase domain of wild-type ROS protein sequence (and are therefore capable of detecting the presence (or absence) of any protein with ROS kinase activity in a sample)

The antibodies that specifically binds to full length ROS protein or one of the ROS fusion polypeptides in lung cancer may also bind to highly homologous and equivalent epitopic peptide sequences in other mammalian species, for example murine or rabbit, and vice versa. Antibodies useful in practicing the methods of the invention include (a) monoclonal antibodies, (b) purified polyclonal antibodies that specifically bind to the target polypeptide (e.g., the fusion junction of the fusion polypeptide, (c) antibodies as described in (a)-(b) above that specifically bind equivalent and highly homologous epitopes or phosphorylation sites in other non-human species (e.g., mouse, rat), and (d) fragments of (a)-(c) above that specifically bind to the antigen (or more preferably the epitope) bound by the exemplary antibodies disclosed herein.

The term "antibody" or "antibodies" refers to all types of immunoglobulins, including IgG, IgM, IgA, IgD, and IgE, including binding fragments thereof (i.e., fragments of an antibody that are capable of specifically binding to the antibody's target molecule, such as $F_{ab}$, and $F(ab')_2$ fragments), as well as recombinant, humanized, polyclonal, and monoclonal antibodies and/or binding fragments thereof. Antibodies of the invention can be derived from any species of animal, such as from a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Antibodies of the invention may be also be chimeric antibodies. See, e.g., M. Wroser et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed specific antibodies made according to the method disclosed in U.S. Pat. No. 4,676,980 (Segel et al.).

Natural antibodies are the antibodies produced by a host animal, however the invention contemplates also genetically altered antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics. The term "humanized antibody", as used herein, refers to antibody molecules in which amino acids have been replaced in the non-antigen binding regions in order to more closely resemble a human antibody, while still retaining the original binding ability. Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos.

5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies are also included in the present invention. These recombinant antibodies have the same amino acid sequence as the natural antibodies or have altered amino acid sequences of the natural antibodies. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety). Antibodies can be engineered in numerous ways. They can be made as single-chain antibodies (including small modular immunopharmaceuticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203. The genetically altered antibodies of the invention may be functionally equivalent to the above-mentioned natural antibodies. In certain embodiments, modified antibodies of the invention provide improved stability or/and therapeutic efficacy.

Non-limiting examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of the invention can be modified post-translationally (e.g., acetylation, and/or phosphorylation) or can be modified synthetically (e.g., the attachment of a labeling group). Antibodies with engineered or variant constant or Fc regions can be useful in modulating effector functions, such as, for example, antigen-dependent cytotoxicity (ADCC) and complement-dependent cytotoxicity (CDC). Such antibodies with engineered or variant constant or Fc regions may be useful in instances where a parent singling protein is expressed in normal tissue; variant antibodies without effector function in these instances may elicit the desired therapeutic response while not damaging normal tissue. Accordingly, certain aspects and methods of the present disclosure relate to antibodies with altered effector functions that comprise one or more amino acid substitutions, insertions, and/or deletions. The term "biologically active" refers to a protein having structural, regulatory, or biochemical functions of a naturally occurring molecule. Likewise, "immunologically active" refers to the capability of the natural, recombinant, or synthetic full-length ROS protein or ROS fusion polypeptide (e.g., one of the FIG-ROS fusion polypeptides described herein), or any oligopeptide thereof, to induce a specific immune response in appropriate animals or cells and to bind with specific antibodies.

Also within the invention are antibody molecules with fewer than 4 chains, including single chain antibodies, Camelid antibodies and the like and components of an antibody, including a heavy chain or a light chain. In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the invention are heavy or light chain variable regions, framework regions and CDRs. An antibody of the invention may comprise a heavy chain constant region that comprises some or all of a CH1 region, hinge, CH2 and CH3 region.

One non-limiting epitopic site of a fusion polypeptide-specific antibody of the invention is a peptide fragment consisting essentially of about 11 to 17 amino acids of a fusion polypeptide sequence, which fragment encompasses the fusion junction between the ROS portion of the molecule and the portion of the molecule from the non-ROS fusion partner. It will be appreciated that antibodies that specifically binding shorter or longer peptides/epitopes encompassing the fusion junction of a ROS fusion polypeptide are within the scope of the present invention.

The invention is not limited to use of antibodies, but includes equivalent molecules, such as protein binding domains or nucleic acid aptamers, which bind, in a ROS protein-specific or ROS fusion protein-specific manner, to essentially the same epitope to which a full length ROS-specific or ROS fusion polpeptide-specific antibody useful in the methods of the invention binds. See, e.g., Neuberger et al., *Nature* 312: 604 (1984). Such equivalent non-antibody reagents may be suitably employed in the methods of the invention further described below.

Polyclonal antibodies useful in practicing the methods of the invention may be produced according to standard techniques by immunizing a suitable animal (e.g., rabbit, goat, etc.) with an antigen encompassing a desired fusion-protein specific epitope (e.g. the fusion junction between the non-ROS protein partner and the ROS protein partner in a ROS fusion polypeptide), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)). Polyclonal antibodies produced as described herein may be screened and isolated as further described below.

Monoclonal antibodies may also be beneficially employed in the methods of the invention, and may be produced in hybridoma cell lines according to the well-known technique of Kohler and Milstein. *Nature* 265: 495-97 (1975); Kohler and Milstein, *Eur. Immunol.* 6: 511 (1976); see also, CURRENT PROTOCOLS IN MOLECULAR BIOLOGY, Ausubel et al. Eds. (Wiley and Sins, New York, N.Y. 1989 and yearly updates up to and including 2010). Monoclonal antibodies so produced are highly specific, and improve the selectivity and specificity of assay methods provided by the invention. For example, a solution containing the appropriate antigen (e.g. a synthetic peptide comprising the fusion junction of ROS fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are desired for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$-C-rosyl perrosylated oligopeptides and sets and libraries of such peptides, as well as methods for using such oligopeptide sets and libraries for determining the sequence of a perrosylated oligopeptide that preferentially binds to an acceptor molecule of interest. Thus, non-peptide analogs of the epitope-bearing peptides of the invention also can be made routinely by these methods.

Antibodies useful in the methods of the invention, whether polyclonal or monoclonal, may be screened for epitope and fusion protein specificity according to standard techniques. See, e.g., Czernik et al., *Methods in Enzymology,* 201: 264-283 (1991). For example, the antibodies may be screened against a peptide library by ELISA to ensure specificity for both the desired antigen and, if desired, for reactivity only with the full-length ROS protein, a particular ROS fusion polypeptide (e.g., an SLC34A2-ROS(S) polypeptide), or fragments thereof of the invention. The antibodies may also be tested by Western blotting against cell preparations containing target protein to confirm reactivity with the only the desired target and to ensure no appreciable binding to other proteins. The production, screening, and use of fusion protein-specific antibodies is known to those of skill in the art, and has been described. See, e.g., U.S. Patent Publication No. 20050214301.

Antibodies (e.g., full-length ROS protein-specific or ROS fusion polypeptide-specific) useful in the methods of the invention may exhibit some limited cross-reactivity with similar epitopes in other proteins or polypeptides, such as similar fusion polypeptides. This is not unexpected as most antibodies exhibit some degree of cross-reactivity, and anti-peptide antibodies will often cross-react with epitopes having high homology or identity to the immunizing peptide. See, e.g., Czernik, supra. Cross-reactivity with other fusion proteins is readily characterized by Western blotting alongside markers of known molecular weight. Amino acid sequences of cross-reacting proteins may be examined to identify sites highly homologous or identical to full length ROS protein sequence or the ROS fusion polypeptide (e.g., a FIG-ROS(S) polypeptide) sequence to which the antibody binds. Undesirable cross-reactivity can be removed by negative selection using antibody purification on peptide columns.

ROS-specific antibodies and ROS fusion polypeptide-specific antibodies of the invention that are useful in practicing the methods disclosed herein are ideally specific for human fusion polypeptide, but are not limited only to binding the human species, per se. The invention includes the production and use of antibodies that also bind conserved and highly homologous or identical epitopes in other mammalian species (e.g., mouse, rat, monkey). Highly homologous or identical sequences in other species can readily be identified by standard sequence comparisons, such as using BLAST, with the human ROS protein sequence (SEQ ID NO: 1), and the human ROS fusion polypeptide sequences disclosed herein (SEQ ID NOs: 5, 7, 22, 28, 56, 58, and 60).

Antibodies employed in the methods of the invention may be further characterized by, and validated for, use in a particular assay format, for example FC, IHC, and/or ICC. The use of full-length ROS protein-specific and/or a ROS fusion polypeptide-specific antibodies in such methods is further described herein. The antibodies described herein, used alone or in the below-described assays, may also be advantageously conjugated to fluorescent dyes (e.g. Alexa488, phycoerythrin), or labels such as quantum dots, for use in multi-parametric analyses along with other signal transduction (phospho-AKT, phospho-Erk 1/2) and/or cell marker (cytokeratin) antibodies, as further described below.

In practicing the methods of the invention, the expression and/or activity of a ROS fusion polypeptide of the invention and/or of full-length ROS in a given biological sample may also be advantageously examined using antibodies specific for (i.e., that specifically bind to) full length ROS protein or antibodies specific for ROS fusion polypeptides. For example, ROS-specific antibodies (i.e., antibodies that specifically bind full-length ROS) are commercially available (see Santa Cruz Biotech., Inc. (Santa Cruz, Calif.) Catalog No. sc-6347; Cell Signaling Technology, Inc. (Danvers, Mass.), Catalog No. 3266); and Abcam (Cambridge, Mass.), Catalog Nos. ab5512 and ab108492, for example). In some embodiments, ROS-specific antibodies used in the methods of the invention specifically bind the kinase domain of ROS and, thus, will detect full-length ROS and all of the ROS fusion polypeptides described herein. In some embodiments, ROS-specific antibodies used in the methods of the invention specifically bind a region on the ROS protein that is C'terminal to the kinase domain of ROS and, thus, will detect full-length ROS and all of the ROS fusion polypeptides described herein. Such antibodies may also be produced according to standard methods.

Detection of expression and/or activity of full-length ROS and/or a ROS fusion polypeptide expression, in a biological sample (e.g. a tumor sample) can provide information on whether the fusion protein alone is driving the tumor, or whether aberrantly expressed full length ROS is also present and driving the tumor. Such information is clinically useful in assessing whether targeting the fusion protein or the full-length protein(s), or both, or is likely to be most beneficial in inhibiting progression of the tumor, and in selecting an appropriate therapeutic or combination thereof. Antibodies specific for the ROS kinase extracellular domain, which is not present in the mutant ROS disclosed herein, may be particularly useful for determining the presence/absence of the mutant ROS kinase.

It will be understood that more than one antibody may be used in the practice of methods described here. For example, one or more ROS fusion polypeptide-specific antibodies together with antibodies specific for another kinase, receptor, or kinase substrate that is suspected of being, or potentially is, activated in a cancer in which a ROS fusion polypeptide is expressed may be simultaneously employed to detect the activity of such other signaling molecules in a biological sample comprising cells from such cancer one or more.

Those of skill in the art will appreciate that fusion polypeptides of the present invention and the epitope-bearing fragments thereof described above can be combined with parts of other molecules to create chimeric polypeptides. For example, an epitope-bearing fragment of full length ROS or a ROS fusion polypeptide may be combined with the constant domain of immunoglobulins (IgG) to facilitate purification of the chimeric polypeptide and increase the in vivo half-life of the chimeric polypeptide (see, e.g., examples of CD4-Ig chimeric proteins in EPA 394,827; Traunecker et al., *Nature* 331: 84-86 (1988)). Fusion proteins that have a disulfide-linked dimeric structure (e.g., from an IgG portion may also be more efficient in binding and neutralizing other molecules than the monomeric polypeptide alone (see Fountoulakis et al., *J Biochem* 270: 3958-3964(1995)).

In some embodiments, a reagent that specifically binds to full length ROS or a ROS fusion polypeptide is a heavy-isotope labeled peptide (i.e., an AQUA peptide) that, for example, corresponds to a peptide sequence comprising the fusion junction of a ROS fusion polypeptide. Such an AQUA peptide may be suitable for the absolute quantification of an expressed FIG-ROS fusion polypeptide in a biological sample. As used herein, the term "heavy-isotope labeled peptide" is used interchangeably with "AQUA peptide". The production and use of AQUA peptides for the absolute quantification or detection of proteins (AQUA) in complex mixtures has been described. See WO/03016861, "Absolute Quantification of Proteins and Modified Forms Thereof by Multistage Mass Spectrometry," Gygi et al. and also Gerber et al., *Proc. Natl. Acad. Sci. U.S.A.* 100: 6940-5 (2003) (the teachings of which are hereby incorporated herein by reference, in their entirety). The term "specifically detects" with respect to such an AQUA peptide means the peptide will only detect and quantify polypeptides and proteins that contain the AQUA peptide sequence and will not substantially detect polypeptides and proteins that do not contain the AQUA peptide sequence.

The AQUA methodology employs the introduction of a known quantity of at least one heavy-isotope labeled peptide standard (which has a unique signature detectable by LC-SRM chromatography) into a digested biological sample in order to determine, by comparison to the peptide standard, the absolute quantity of a peptide with the same sequence and protein modification in the biological sample. Briefly, the AQUA methodology has two stages: peptide internal standard selection and validation and method development; and implementation using validated peptide internal standards to detect and quantify a target protein in sample. The method is a powerful technique for detecting and quantifying a given peptide/protein within a complex biological mixture, such as a cell lysate, and may be employed, e.g., to quantify change in protein phosphorylation as a result of drug treatment, or to quantify differences in the level of a protein in different biological states.

Generally, to develop a suitable internal standard, a particular peptide (or modified peptide) within a target protein sequence is chosen based on its amino acid sequence and the particular protease to be used to digest. The peptide is then generated by solid-phase peptide synthesis such that one residue is replaced with that same residue containing stable isotopes ($^{13}C$, $^{15}N$). The result is a peptide that is chemically identical to its native counterpart formed by proteolysis, but is easily distinguishable by MS via a 7-Da mass shift. The newly synthesized AQUA internal standard peptide is then evaluated by LC-MS/MS. This process provides qualitative information about peptide retention by reverse-phase chromatography, ionization efficiency, and fragmentation via collision-induced dissociation. Informative and abundant fragment ions for sets of native and internal standard peptides are chosen and then specifically monitored in rapid succession as a function of chromatographic retention to form a selected reaction monitoring (LC-SRM) method based on the unique profile of the peptide standard.

The second stage of the AQUA strategy is its implementation to measure the amount of a protein or modified protein from complex mixtures. Whole cell lysates are typically fractionated by SDS-PAGE gel electrophoresis, and regions of the gel consistent with protein migration are excised. This process is followed by in-gel proteolysis in the presence of the AQUA peptides and LC-SRM analysis. (See Gerber et al., supra.) AQUA peptides are spiked in to the complex peptide mixture obtained by digestion of the whole cell lysate with a proteolytic enzyme and subjected to immuno-affinity purification as described above. The retention time and fragmentation pattern of the native peptide formed by digestion (e.g., trypsinization) is identical to that of the AQUA internal standard peptide determined previously; thus, LC-MS/MS analysis using an SRM experiment results in the highly specific and sensitive measurement of both internal standard and analyte directly from extremely complex peptide mixtures.

Since an absolute amount of the AQUA peptide is added (e.g., 250 fmol), the ratio of the areas under the curve can be used to determine the precise expression levels of a protein or phosphorylated form of a protein in the original cell lysate. In addition, the internal standard is present during in-gel digestion as native peptides are formed, such that peptide extraction efficiency from gel pieces, absolute losses during sample handling (including vacuum centrifugation), and variability during introduction into the LC-MS system do not affect the determined ratio of native and AQUA peptide abundances.

An AQUA peptide standard is developed for a known sequence previously identified by the IAP-LC-MS/MS method within in a target protein. If the site is modified, one AQUA peptide incorporating the modified form of the particular residue within the site may be developed, and a second AQUA peptide incorporating the unmodified form of the residue developed. In this way, the two standards may be used to detect and quantify both the modified an unmodified forms of the site in a biological sample.

Peptide internal standards may also be generated by examining the primary amino acid sequence of a protein and determining the boundaries of peptides produced by protease cleavage. Alternatively, a protein may actually be digested with a protease and a particular peptide fragment produced can then sequenced. Suitable proteases include, but are not limited to, serine proteases (e.g. trypsin, hepsin), metallo proteases (e.g., PUMP1), chymotrypsin, cathepsin, pepsin, thermolysin, carboxypeptidases, etc.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Thus, a peptide is preferably at least about 6 amino acids. The size of the peptide is also optimized to maximize ionization frequency. Thus, in some embodiments, the peptide is not longer than about 20 amino acids. In some embodiments, the peptide is between about 7 to 15 amino acids in length. A peptide sequence is also selected that is not likely to be chemically reactive during mass spectrometry, thus sequences comprising cysteine, tryptophan, or methionine are avoided.

A peptide sequence that does not include a modified region of the target region may be selected so that the peptide internal standard can be used to determine the quantity of all forms of the protein. Alternatively, a peptide internal standard encompassing a modified amino acid may be desirable to detect and quantify only the modified form of the target protein. Peptide standards for both modified and unmodified regions can be used together, to determine the extent of a modification in a particular sample (i.e. to determine what fraction of the total amount of protein is represented by the modified form). For example, peptide standards for both the phosphorylated and unphosphorylated form of a protein known to be phosphorylated at a particular site can be used to quantify the amount of phosphorylated form in a sample.

The peptide is labeled using one or more labeled amino acids (i.e., the label is an actual part of the peptide) or less preferably, labels may be attached after synthesis according to standard methods. Preferably, the label is a mass-altering label selected based on the following considerations: The mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. As a result, the labeled amino acids and peptides are readily distinguished from unlabeled ones by the ion/mass pattern in the resulting mass spectrum. Preferably, the ion mass signature component imparts a mass to a protein fragment that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label preferably does not suppress the ionization efficiency of the protein and is not chemically reactive. The label may contain a mixture of two or more isotopically distinct species to generate a unique mass spectrometric pattern at each labeled fragment position. Stable isotopes, such as $^2H$, $^{13}C$, $^{15}N$, $^{17}O$, $^{18}O$, or $^{34}S$, are some non-limiting labels. Pairs of peptide internal standards that incorporate a different isotope label may also be prepared. Non-limiting amino acid residues into which a heavy isotope label may be incorporated include leucine, proline, valine, and phenylalanine.

Peptide internal standards are characterized according to their mass-to-charge (m/z) ratio, and preferably, also according to their retention time on a chromatographic column (e.g., an HPLC column). Internal standards that co-elute with unlabeled peptides of identical sequence are selected as optimal internal standards. The internal standard is then analyzed by fragmenting the peptide by any suitable means, for example by collision-induced dissociation (CID) using, e.g., argon or helium as a collision gas. The fragments are then analyzed, for example by multi-stage mass spectrometry ($MS^n$) to obtain a fragment ion spectrum, to obtain a peptide fragmentation signature. Preferably, peptide fragments have significant differences in m/z ratios to enable peaks corresponding to each fragment to be well separated, and a signature is that is unique for the target peptide is obtained. If a suitable fragment signature is not obtained at the first stage, additional stages of MS are performed until a unique signature is obtained.

Fragment ions in the MS/MS and $MS^3$ spectra are typically highly specific for the peptide of interest, and, in conjunction with LC methods, allow a highly selective means of detecting and quantifying a target peptide/protein in a complex protein mixture, such as a cell lysate, containing many thousands or tens of thousands of proteins. Any biological sample potentially containing a target protein/peptide of interest may be assayed. Crude or partially purified cell extracts are preferably employed. Generally, the sample has at least 0.01 mg of protein, typically a concentration of 0.1-10 mg/mL, and may be adjusted to a desired buffer concentration and pH.

A known amount of a labeled peptide internal standard, preferably about 10 femtomoles, corresponding to a target protein to be detected/quantified is then added to a biological sample, such as a cell lysate. The spiked sample is then digested with one or more protease(s) for a suitable time period to allow digestion. A separation is then performed (e.g. by HPLC, reverse-phase HPLC, capillary electrophoresis, ion exchange chromatography, etc.) to isolate the labeled internal standard and its corresponding target peptide from other peptides in the sample. Microcapillary LC is a one non-limiting method.

Each isolated peptide is then examined by monitoring of a selected reaction in the MS. This involves using the prior knowledge gained by the characterization of the peptide internal standard and then requiring the MS to continuously monitor a specific ion in the MS/MS or $MS^n$ spectrum for both the peptide of interest and the internal standard. After elution, the area under the curve (AUC) for both peptide standard and target peptide peaks are calculated. The ratio of the two areas provides the absolute quantification that can be normalized for the number of cells used in the analysis and the protein's molecular weight, to provide the precise number of copies of the protein per cell. Further details of the AQUA methodology are described in Gygi et al., and Gerber et al. supra.

AQUA internal peptide standards (heavy-isotope labeled peptides) may desirably be produced, as described above, to detect any quantify any unique site (e.g., the fusion junction within a FIG-ROS fusion polypeptide) within a mutant ROS polypeptide of the invention. For example, an AQUA phosphopeptide may be prepared that corresponds to the fusion junction sequence of one of the FIG-ROS fusion polypeptides. Peptide standards for may be produced for the FIG-ROS fusion junction and such standards employed in the AQUA methodology to detect and quantify the fusion junction (i.e. the presence of that FIG-ROS fusion polypeptide) in a biological sample.

For example, one non-limiting AQUA peptide of the invention comprises the amino acid sequence AGSTLP (SEQ ID NO: 66), which corresponds to the three amino acids immediately flanking each side of the fusion junction in the short variant of FIG-ROS fusion polypeptide (i.e., FIG-ROS(S) fusion ppolypeptide), where the amino acids encoded by the FIG gene are italicized and the amino acids encoded by the ROS gene in bold. It will be appreciated that larger AQUA peptides comprising the fusion junction sequence (and additional residues downstream or upstream of it) may also be constructed. Similarly, a smaller AQUA peptide comprising less than all of the residues of such sequence (but still comprising the point of fusion junction itself) may alternatively be constructed. Such larger or shorter AQUA peptides are within the scope of the present invention, and the selection and production of AQUA peptides may be carried out as described above (see Gygi et al., Gerber et al., supra.).

It should be noted that because the sequence of the AQUA peptide spanning the fusion junction of one of the ROS fusion proteins described herein may also be (or be included in) the epitope to which a ROS fusion-specific antibody specifically binds. An "epitope" refers to either an immunogenic epitope (i.e., capable of eliciting an immune response) or an antigenic epitope (i.e., the region of a protein molecule to which an antibody can specifically bind. The number of immunogenic epitopes of a protein generally is less than the number of antigenic epitopes. See, for instance, Geysen et al., *Proc. Natl. Acad. Sci. USA* 81:3998-4002 (1983).

Table 2 provides a list of the sequences of all the fusion junctions of the ROS fusion polypeptides of the invention, where where the amino acids encoded by the non-ROS gene are italicized and the amino acids encoded by the ROS gene in bold.

TABLE 2

| Fusion | Junction Sequence | SEQ ID NO: |
|---|---|---|
| SLC34A2-ROS (very short) | VGVWHR | 62 |
| SLC34A2-ROS (short) | LVGDDF | 63 |
| SLC34A2-ROS (long) | LVGAGV | 64 |
| CD74-ROS | PPKDDF | 65 |
| FIG-ROS (short) | AGSTLP | 66 |
| FIG-ROS (long) | LQVWHR | 67 |
| FIG-ROS (Extra Long) | VLQAGV | 68 |

In some embodiments, the mammalian lung cancer is from a human (i.e., human). In some embodiments, the mammalian lung cancer is NSCLC (non-small cell lung carcinoma). In some embodiments, the mammalian lung cancer is SCLC (small cell lung carcinoma). In further embodiments of the methods of the invention, the mammal is a human, and the human may be a candidate for a ROS-inhibiting therapeutic, for the treatment of a lung cancer. The human candidate may be a patient currently being treated with, or considered for treatment with, an ROS kinase inhibitor. In another embodiment, the mammal is large animal, such as a horse or cow, while in other embodiments, the mammal is a small animal, such as a dog or cat, all of which are known to develop lung cancers, such as NSCLC and SCLC.

As used throughout the specification, the term "biological sample" is used in its broadest sense, and means any biological sample suspected of containing a polypeptide with ROS kinase activity including, without limitation, a ROS fusion polypeptide or a full length ROS protein (with or without the signal peptide sequence) or fragments having ROS kinase activity thereof. Biological samples include, without limitation, saliva, mucous, tears, blood, circulating tumor cells, serum, tissues, bone marrow, lymph/interstitial fluids, buccal cells, mucosal cells, cerebrospinal fluid, semen, feces, plasma, urine, a suspension of cells, or a suspension of cells and viruses or extracts thereof, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support). In some embodiments, the biological sample contains lung cells suspected of being cancerous.

Any biological sample comprising cells (or extracts of cells) from a mammalian cancer is suitable for use in the methods of the invention. In one embodiment, the biological sample comprises cells obtained from a tumor biopsy or a tumor resection. The biopsy or resection may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36(3): 416-22 (1992)).

The biological sample may also comprise cells obtained from an effusion, such as a pleural effusion. Pleural effusions (liquid that forms outside the lung in the thoracic cavity and which contains cancerous cells) are known to form in many patients with advanced lung cancer (including NSCLC), and the presence of such effusion is predictive of a poor outcome and short survival time. Standard techniques for obtaining pleural effusion samples have been described and are well known in the art (see Sahn, *Clin Chest Med.* 3(2): 443-52 (1982)).

The biological sample may comprise cells obtained from a bronchioalveolar lavage. Bronchioalveolar lavage is a standard medical procedure in which a bronchoscope is passed through the mouth or nose into the lungs and fluid is squirted into a small part of the lung and then recollected for examination.

In some embodiments, the biological sample comprises circulating tumor cells. Circulating tumor cells ("CTCs") may be purified, for example, using the kits and reagents sold under the trademarks Vita-Assays™, Vita-Cap™, and CellSearch® (commercially available from Vitatex, LLC (a Johnson and Johnson corporation). Other methods for isolating CTCs are described (see, for example, PCT Publication No. WO/2002/020825, Cristofanilli et al., New Engl. J. of Med. 351 (8):781-791 (2004), and Adams et al., J. Amer. Chem. Soc. 130(27): 8633-8641 (July 2008)). In a particular embodiment, a circulating tumor cell ("CTC") may be isolated and identified as having originated from the lung.

Accordingly, the invention provides a method for isolating a CTC, and then screening the CTC one or more assay formats to identify the presence of a polypeptide with ROS kinase activity or nucleic acid molecule encoding the same (e.g., full length ROS polypeptide or polynucleotide or ROS fusion polypeptide or polynucleotide) in the CTC.

Cellular extracts of the biological samples described herein may be prepared, either crude or partially (or entirely) purified, in accordance with standard techniques, and used in the methods of the invention. Alternatively, biological samples comprising whole cells may be utilized in assay formats such as in vitro kinase assay, ELISA assays, immunohistochemistry (IHC), flow cytometry (FC), and immunofluorescence (IF), immuno-histochemistry (IHC), fluorescence in situ hybridization (FISH) and polymerase chain reaction (PCR), according to standard methods such as those described below (see, also, e.g., Ausubel et al., supra). Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

Thus, biological samples useful in the practice of the methods of the invention may be obtained from any mammal in which a cancer or suspected cancer characterized by the presence of a polypeptide having ROS kinase activity (e.g., a full length ROS polynucleotide or polypeptide or a ROS fusion polynucleotide or polypeptide) is present or might be present or developing. As used herein, the phrase "characterized by" with respect to a cancer (or suspected cancer) and indicated molecule (e.g., a polypeptide with ROS kinase activity) is meant a cancer (or suspected cancer) in which a gene translocation or mutation (e.g., causing aberrant expression of full-length ROS) and/or an expressed polypeptide with ROS kinase activity (e.g., a ROS fusion polypeptide) is present, as compared to another cancer or a normal tissue in which such translocation, aberrant expression of full-length ROS, and/or polypeptide with ROS kinase activity are not present. The presence of such translocation, aberrant expression of full-length ROS, and/or polypeptide with ROS kinase activity may drive (i.e., stimulate or be the causative agent of), in whole or in part, the growth and survival of such cancer or suspected cancer.

Accordingly, any biological sample (e.g., CTC, pleural effusion, needle aspirate, tumor biopsy, etc. . . . ) from a patient that is identified as comprising a polypeptide with ROS kinase activity or polynucleotide encoding the same (e.g., a full length ROS polypeptide or polynucleotide or a ROS fusion polypeptide or polynucleotide) may indicate that the patient's originating cancer (e.g., an lung cancer such as NSCLC or SCLC) is being driven by the polypeptide with ROS kinase activity and thus is likely to respond to a composition comprising at least one ROS kinase-inhibiting therapeutic.

As used herein, by "likely to respond" is meant that a cancer is more likely to show growth retardation or abrogation in response to (e.g., upon contact with or treatment by) a ROS inhibiting therapeutic. In some embodiments, a cancer that is likely to respond to a ROS inhibiting therapeutic is one that dies (e.g., the cancer cells apoptose) in response to the ROS inhibiting therapeutic.

In assessing the presence of a polypeptide with ROS kinase activity (or polynucleotide encoding the same) in a biological sample comprising cells from a mammalian cancer tumor, a control sample representing a cell in which such a polypeptide with ROS kinase activity does not occur (e.g., healthy lung cells) may desirably be employed for comparative purposes. Ideally, the control sample comprises cells from a subset of the particular cancer (e.g., lung cancer) that is representative of the subset in which the polypeptide with ROS kinase activity (or polynucleotide encoding the same) does not occur. Comparing the level in the control sample versus the test biological sample thus identifies whether the mutant polynucleotide and/or polypeptide is/are present. Alternatively, since a polypeptide with ROS kinase activity (or polynucleotide encoding the same) may not be present in the majority of cancers, any tissue that similarly does not express polypeptide with ROS kinase activity (or polynucleotide encoding the same) may be employed as a control.

The methods described below will have valuable diagnostic utility for cancers characterized by the presence of a polypeptide with ROS kinase activity, and treatment decisions pertaining to the same. For example, biological samples may be obtained from a subject that has not been previously diagnosed as having a cancer characterized by the presence of polypeptide with ROS kinase activity, nor has yet undergone treatment for such cancer, and the method is employed to diagnostically identify a tumor in such subject as belonging to a subset of tumors (e.g., NSCLC or SCLC) in which a polypeptide with ROS kinase activity (or polynucleotide encoding the same) is present/expressed.

Alternatively, a biological sample may be obtained from a subject that has been diagnosed as having a cancer characterized by the presence of one type of kinase, such as EFGR, and has been receiving therapy, such as EGFR inhibitor therapy (e.g., Tarceva™, Iressa™) for treatment of such cancer, and the method of the invention is employed to identify whether the subject's tumor is also characterized by the presence of polypeptide with ROS kinase activity (or polynucleotide encoding the same) such as full length ROS protein or one of the many ROS fusion polypeptides (e.g., SLC34A2-ROS(S)), and is therefore likely to fully respond to the existing therapy and/or whether alternative or additional ROS-inhibiting therapy is desirable or warranted. The methods of the invention may also be employed to monitor the progression or inhibition of a polypeptide with ROS kinase activity-expressing cancer following treatment of a subject with a composition comprising a ROS-inhibiting therapeutic or combination of therapeutics.

Such diagnostic assay may be carried out subsequent to or prior to preliminary evaluation or surgical surveillance procedures. The identification method of the invention may be advantageously employed as a diagnostic to identify patients having cancer, such as lung cancer (e.g., non-small cell lung cancer), characterized by the presence of a polypeptide with ROS kinase activity such as a ROS fusion protein (e.g., FIG-ROS(S)), which patients would be most likely to respond to therapeutics targeted at inhibiting ROS kinase activity. The ability to select such patients would also be useful in the clinical evaluation of efficacy of future ROS-inhibiting therapeutics as well as in the future prescription of such drugs to patients.

The ability to selectively identify cancers in which a polypeptide with ROS kinase activity (or polynucleotide encoding the same), such as a ROS fusion protein or a ROS fusion polynucleotide, or a full length ROS polypeptide or full length ROS polynucleotide, is/are present enables important new methods for accurately identifying such tumors for diagnostic purposes, as well as obtaining information useful in determining whether such a tumor is likely to respond to a ROS-inhibiting therapeutic composition, or likely to be partially or wholly non-responsive to an inhibitor targeting a different kinase when administered as a single agent for the treatment of the cancer.

As used herein, by "cancer" or "cancerous" is meant a cell that shows abnormal growth as compared to a normal (i.e., non-cancerous) cell of the same cell type. For example, a cancerous cell may be metastatic or non-metastatic. A cancerous cell may also show lack of contact inhibition where a normal cell of that same cell type shows contact inhibition. In some embodiments, the cancer is lung cancer (e.g., non-small cell lung cancer or small cell lung cancer). As used herein, by "suspected cancer" (as in "suspected mammalian lung cancer") or "tissue suspected of being cancerous" is meant a cell or tissue that has some aberrant characteristics (e.g., hyperplastic or lack of contact inhibition) as compared to normal cells or tissues of that same cell or tissue type as the suspected cancer, but where the cell or tissue is not yet confirmed by a physician or pathologist as being cancerous.

In some embodiments, the various methods of the invention may be carried out in a variety of different assay formats known to those of skill in the art. Some non-limiting examples of methods include immunoassays and peptide and nucleotide assays.

Immunoassays.

Immunoassays useful in the practice of the methods of the invention may be homogenous immunoassays or heterogeneous immunoassays. In a homogeneous assay the immunological reaction usually involves a specific reagent (e.g. a ROS-specific antibody), a labeled analyte, and the biological sample of interest. The signal arising from the label is modified, directly or indirectly, upon the binding of the antibody to the labeled analyte. Both the immunological reaction and detection of the extent thereof are carried out in a homogeneous solution. Immunochemical labels that may be employed include free radicals, radio-isotopes, fluorescent dyes, enzymes, bacteriophages, coenzymes, and so forth. Semi-conductor nanocrystal labels, or "quantum dots", may also be advantageously employed, and their preparation and use has been well described. See generally, K. Barovsky, *Nanotech. Law & Bus.* 1(2): Article 14 (2004) and patents cited therein.

In a heterogeneous assay approach, the materials are usually the biological sample, binding reagent (e.g., an antibody), and suitable means for producing a detectable signal. Biological samples as further described below may be used. The antibody is generally immobilized on a support, such as a bead, plate or slide, and contacted with the sample suspected of containing the antigen in a liquid phase. The support is then separated from the liquid phase and either the support phase or the liquid phase is examined for a detectable signal employing means for producing such signal. The signal is related to the presence of the analyte in the biological sample. Means for producing a detectable signal include the use of radioactive labels, fluorescent labels, enzyme labels, quantum dots, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. ROS-specific antibodies may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent should be sufficient such that the binding of a protein with ROS kinase activity (e.g., a full-length ROS protein or a ROS fusion polypeptide) is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other binding reagents binding reagents may likewise be conjugated to detectable groups such as radiolabels (e.g., $^{35}S$, $^{125}I$, $^{131}I$), enzyme labels (e.g., horseradish peroxidase, rosaline phosphatase), and fluorescent labels (e.g., fluorescein) in accordance with known techniques.

Cell-based assays, such flow cytometry (FC), immunohistochemistry (IHC), or immunofluorescence (IF) are particularly desirable in practicing the methods of the invention, since such assay formats are clinically-suitable, allow the detection of expression of a protein with ROS kinase activity (e.g., a full length ROS polypeptide or a ROS fusion polypeptide) in vivo, and avoid the risk of artifact changes in activity resulting from manipulating cells obtained from, e.g. a tumor sample in order to obtain extracts. Accordingly, in some embodiments, the methods of the invention are implemented in a flow-cytometry (FC), immuno-histochemistry (IHC), or immunofluorescence (IF) assay format.

Flow cytometry (FC) may be employed to determine the expression of polypeptide with ROS kinase activity in a mammalian tumor before, during, and after treatment with a drug targeted at inhibiting ROS kinase activity. For example, tumor cells from a fine needle aspirate may be analyzed by flow cytometry for expression and/or activation of a polypeptide with ROS kinase activity or polynucleotide encoding the same (e.g., a full length ROS polynucleotide or polypeptide or a ROS fusion polynucleotide or polypeptide), as well as for markers identifying cancer cell types, etc., if so desired. Flow cytometry may be carried out according to standard methods. See, e.g. Chow et al., *Cytometry (Communications in Clinical Cytometry)* 46: 72-78 (2001). Briefly and by way of example, the following protocol for cytometric analysis may be employed: fixation of the cells with 2% paraformaldehyde for 10 minutes at 37° C. followed by permeabilization in 90% methanol for 10 minutes on ice. Cells may then be stained with the primary antibody (e.g., a full-length ROS-specific or a ROS fusion polypeptide-specific antibody), washed and labeled with a fluorescent-labeled secondary antibody. The cells would then be analyzed on a flow cytometer (e.g. a Beckman Coulter FC500) according to the specific protocols of the instrument used. Such an analysis would identify the level of expressed full-length ROS or a ROS fusion polypeptide in the tumor. Similar analysis after treatment of the tumor with a ROS-inhibiting therapeutic would reveal the responsiveness of a full-length ROS-expressing tumor or a ROS fusion polypeptide-expressing tumor to the targeted inhibitor of ROS kinase.

Immunohistochemical (IHC) staining may be also employed to determine the expression and/or activation status of polypeptide with ROS kinase activity in a mammalian cancer (e.g., a lung cancer) before, during, and after treatment with a therapeutic targeted at inhibiting ROS kinase activity. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody (e.g., a ROS-specific antibody) and secondary antibody; and finally detecting using avidin/biotin method.

Immunofluorescence (IF) assays may be also employed to determine the expression and/or activation status of a polypeptide with ROS kinase activity (e.g., full length ROS polypeptide or a ROS fusion polypeptide) in a mammalian cancer before, during, and after treatment with a therapeutic targeted at inhibiting ROS kinase activity. IF may be carried out according to well-known techniques. See, e.g., J. M. polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with a primary antibody against (i.e., that specifically binds to) a polypeptide with ROS kinase activity (e.g., a CD74-ROS fusion polypeptide) followed by a secondary antibody labeled with a fluorescent dye such as Alexa 488 and analyzed with an epifluorescent microscope.

A variety of other protocols, including enzyme-linked immunosorbent assay (ELISA), radio-immunoassay (MA), Western blotting analysis, in vitro kinase assay, and fluorescent-activated cell sorting (FACS), for measuring expression and/or activity of a polypeptide with ROS kinase activity are known in the art and provide a basis for diagnosing the presence of the polypeptide with ROS kinase activity (e.g., a full-length ROS, or an ROS fusion polypeptide such as an FIG-ROS(S) fusion polypeptide). Normal or standard values for full-length ROS polypeptide expression are established by combining body fluids or cell extracts taken from normal mammalian subjects, preferably human, with an antibody that specifically binds to full length ROS polypeptide under conditions suitable for complex formation. The amount of standard complex formation may be quantified by various methods, but preferably by photometric means. Quantities of full length ROS polypeptide expressed in subject, control, and disease samples from biopsied tissues are compared with the standard values. Deviation between standard and subject values establishes the parameters for diagnosing disease. Of course, as described herein, since the proteins with ROS kinase activity (e.g., FIG-ROS(S) or SLC34A2-ROS(S)) were discovered in cancerous lung tissue, no normal lung tissue biological samples are expected to contain these proteins with ROS kinase activity (or polynucleotides encoding the same).

In another aspect, the invention provides a method for detecting the presence of a polynucleotide encoding a polypeptide with ROS kinase activity in a biological sample from a mammalian lung cancer or suspected mammalian lung cancer, said method comprising the steps of: (a) obtaining a biological sample from a mammalian lung cancer or suspected mammalian lung cancer and (b) utilizing a reagent that specifically binds to said polynucleotide encoding said polypeptide with ROS kinase activity to determine whether said polynucleotide is present in said biological sample, wherein detection of specific binding of said reagent to said biological sample indicates said polynucleotide encoding said polypeptide with ROS kinase activity is present in said biological sample.

The presence of a polynucleotide encoding a polypeptide having ROS kinase activity can be assessed by any standard methods. In addition, these methods can be combined with methods to detect the polypeptide having ROS kinase activity as described above.

Nucleotide Assays.

Full length ROS polynucleotide or ROS fusion polynucleotide-specific binding reagents useful in practicing the methods of the invention may also be mRNA, oligonucleotide or DNA probes that can directly hybridize to, and detect, fusion or truncated polypeptide expression transcripts in a biological sample. Such probes are discussed in detail herein. Briefly, and by way of example, formalin-fixed, paraffin-embedded (PPFE) patient samples may be probed with a fluorescein-labeled RNA probe followed by washes with formamide, SSC and PBS and analysis with a fluorescent microscope.

Polynucleotides encoding a polypeptide with ROS kinase activity may also be used for diagnostic purposes. The polynucleotides that may be used include oligonucleotide sequences, antisense RNA and DNA molecules, and PNAs. The polynucleotides may be used to detect and quantitate gene expression in biopsied tissues in which expression of a polypeptide with ROS kinase activity (e.g., a ROS fusion polypeptide or full length ROS) may be correlated with disease. The diagnostic assay may be used to distinguish between absence, presence, and excess expression of a polypeptide with ROS kinase activity, and to monitor regulation of levels of a polypeptide with ROS kinase activity during therapeutic intervention.

In one embodiment, hybridization with PCR primers which are capable of detecting polynucleotide sequences, including genomic sequences, encoding a polypeptide with ROS kinase activity (e.g., encoding a ROS fusion polypeptide or full length ROS protein) may be used to identify nucleic acid sequences that encode such polypeptides with ROS kinase activity. The specificity of the probe, whether it is made from a highly specific region, e.g., 10 unique nucleotides in the fusion junction, or a less specific region, e.g., the 3' coding region, and the stringency of the hybridization or amplification (maximal, high, intermediate, or low) will determine whether the probe identifies only naturally occurring sequences encoding ROS kinase polypeptides (e.g., full length ROS or a ROS fusion protein), alleles, or related sequences.

Probes may also be used for the detection of related sequences, and should preferably contain at least 50% of the nucleotides from any of the mutant ROS polypeptide encoding sequences. The hybridization probes (e.g., FISH probes or Southern or Northern blotting probes) of the subject invention may be DNA or RNA and derived from the nucleotide sequences of ROS and all ROS fusion polynucleotides. In some embodiments, where the polypeptide having ROS kinase activity is a ROS fusion protein, the hybridization probes encompassing the fusion junction, or from genomic sequence including promoter, enhancer elements, and introns of the naturally occurring ROS gene and the fusion partner gene (e.g., SLC34A2, FIG, or CD74).

A ROS fusion polynucleotide (i.e., a polynucleotide encoding a ROS fusion polypeptide such as FIG-ROS(S) or CD74-ROS) or full length ROS polynucleotide may be used in Southern or Northern analysis, dot blot, or other membrane-based technologies; in PCR technologies; or in dip stick, pin, ELISA or chip assays utilizing fluids or tissues from patient biopsies to detect altered expression of a polypeptide with ROS kinase activity. Such qualitative or quantitative methods are well known in the art. In a particular aspect, the nucleotide sequences encoding a polypeptide with ROS kinase activity may be useful in assays that detect activation or induction of various lung cancers, including non-small cell lung carcinoma (NSCLC) and small cell lung carcinoma. Polynucleotides encoding a polypeptide with ROS kinase activity may be detectably labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding a polypeptide with ROS kinase activity (e.g., a ROS fusion polypeptide or full length ROS polypeptide) in the sample indicates the presence of the associated disease. Such assays may also be used to evaluate the efficacy of a particular therapeutic treatment regimen in animal studies, in clinical trials, or in monitoring the treatment of an individual patient.

In some embodiments, the methods of the invention are carried out using a PCR assay format. Polymerase chain reaction (PCR) is standard to those of skill in the art. See, e.g., MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989). PCR primers (also called oligomers) may be chemically synthesized, generated enzymatically, or produced from a recombinant source. Oligomers will preferably consist of two nucleotide sequences, one with sense orientation (5' to 3') and another with antisense (3' to 5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of a polypeptide with ROS kinase activity (e.g., ROS fusion polypeptide or full ROS polypeptide) include radiolabeling or biotinylating nucleotides, coamplification of a control nucleic acid, and standard curves onto which the experimental results are interpolated (Melby et al., *J. Immunol. Methods,* 159: 235-244 (1993); Duplaa et al. *Anal. Biochem.* 229-236 (1993)). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the polynucelotides encoding a polypeptide with ROS kinase activity may be used to generate hybridization probes which are useful for mapping the naturally occurring genomic sequence. The sequences may be mapped to a particular chromosome or to a specific region of the chromosome using well known techniques. Such techniques include fluorescence in-situ hybridization (FISH), FACS, or artificial chromosome constructions, such as yeast artificial chromosomes, bacterial artificial chromosomes, bacterial P1 constructions, or single chromosome cDNA libraries, as reviewed in Price, C. M., *Blood Rev.* 7: 127-134 (1993), and Trask, B. J., *Trends Genet.* 7: 149-154 (1991).

In further embodiments, fluorescence in-situ hybridization (FISH) is employed in the methods of the invention (as described in Verma et al. HUMAN CHROMOSOMES: A MANUAL OF BASIC TECHNIQUES, Pergamon Press, New York, N.Y. (1988)). In some embodiments, the FISH assay may be correlated with other physical chromosome mapping techniques and genetic map data. The FISH technique is well known (see, e.g., U.S. Pat. Nos. 5,756,696; 5,447,841; 5,776,688; and 5,663,319). Examples of genetic map data can be found in the 1994 Genome Issue of *Science* (265: 1981f). Correlation between the location of the gene encoding ROS protein and/or, in the case of ROS fusion polypeptides, the gene encoding the fusion partner of a ROS fusion protein (e.g., the FIG gene, the SLC34A2 gene, or the CD74 gene) on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti et al., *Nature* 336: 577-580 (1988)), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

It shall be understood that all of the methods (e.g., PCR and FISH) that detect polynucleotides encoding a polypeptide with ROS kinase activity (e.g., full-length ROS or an ROS fusion polynucleotides such as FIG-ROS(S)), may be combined with other methods that detect polypeptides with ROS kinase activity or polynucleotides encoding a polypeptide with ROS kinase activity. For example, detection of a FIG-ROS (S) fusion polynucleotide in the genetic material of a biological sample (e.g., FIG-ROS(S) in a circulating tumor cell) may be followed by Western blotting analysis or immuno-histochemistry (IHC) analysis of the proteins of the sample to determine if the FIG-ROS(S) polynucleotide was actually expressed as a FIG-ROS(S) fusion polypeptide in the biological sample. Such Western blotting or IHC analyses may be performed using an antibody that specifically binds to the polypeptide encoded by the detected FIG-ROS(S) polynucleotide, or the analyses may be performed using antibodies that specifically bind either to full length FIG (e.g., bind to the N-terminus of the protein) or to full length ROS (e.g., bind an epitope in the kinase domain of ROS). Such assays are known in the art (see, e.g., U.S. Pat. No. 7,468,252).

In another example, the CISH technology of Dako allows chromatogenic in situ hybridization with immuno-histochemistry on the same tissue section. See Elliot et al., Br J Biomed Sci 2008; 65(4): 167-171, 2008 for a comparison of CISH and FISH.

Another aspect of the invention provides a method for diagnosing a patient as having a lung cancer or a suspected lung cancer driven by an ROS kinase. The method includes contacting a biological sample of said lung cancer or a suspected lung cancer (where the biological sample comprising at least one nucleic acid molecule) with a probe that hybridizes under stringent conditions to a nucleic acid molecule encoding a polypeptide with ROS kinase activity such as a full length ROS polynucleotide or a ROS fusion polynucleotide (e.g., a FIG-ROS(S) fusion polynucleotide, a FIG-ROS(L) fusion polynucleotide, a FIG-ROS(VL) fusion polynucleotide, an SLC34A2-ROS(S) fusion polynucleotide, an SLC34A2-ROS(VS) fusion polynucleotide, an SLC34A2-ROS(L) fusion polynucleotide, or a CD74-ROS fusion polynucleotide), and wherein hybridization of said probe to at least one nucleic acid molecule in said biological sample identifies said patient as having a lung cancer or a suspected lung cancer driven by a ROS kinase.

Yet another aspect of the invention provides a method for diagnosing a patient as having a lung cancer or a suspected lung cancer driven by a ROS kinase. The method includes contacting a biological sample of said lung cancer or suspected lung cancer (where said biological sample comprises at least one polypeptide) with a reagent that specifically binds to a polypeptide with ROS kinase activity (e.g., a FIG-ROS(S) fusion polypeptide, a FIG-ROS(L) fusion polypeptide, a FIG-ROS(VL) fusion polypeptide, an SLC34A2-ROS(S) fusion polypeptide, an SLC34A2-ROS(VS) fusion polypeptide, an SLC34A2-ROS(L) fusion polypeptide, or a CD74-ROS fusion polypeptide), wherein specific binding of said reagent to at least one polypeptide in said biological sample identifies said patient as having a lung cancer or a suspected lung cancer driven by a ROS kinase.

In various embodiments, the identification of a lung cancer or suspected lung cancer as being driven by a ROS kinase will identify that patient having that lung cancer or suspected lung cancer as being likely to respond to a ROS-inhibiting therapeutic.

In order to provide a basis for the diagnosis of disease (e.g., a lung cancer) characterized by expression of a polypeptide with ROS kinase activity (e.g., a ROS fusion polypeptide), a normal or standard profile for expression may be established. This may be accomplished by combining body fluids or cell extracts taken from normal subjects, either animal or human, with a polynucleotide sequence, or a fragment thereof, which encodes a polypeptide with ROS kinase activity (e.g., a ROS fusion polypeptide or a full length ROS polypeptide), under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

A similar normal or standard profile for expression or activity level of a polypeptide having ROS kinase activity can be established. For example, for protein expression, the profile can be established using a reagent that specifically binds to the polypeptide can also be established using, e.g., an antibody that specifically binds to the polypeptide (e.g., binds to full length ROS or binds to the fusion junction of a ROS fusion polypeptide) and comparing levels of binding in normal subject with levels of binding in patients symptomatic for lung cancer. Similarly, for ROS kinase activity levels, a standard in vitro kinase assay (see Ausubel et al., supra; Sambrook et al., supra) can be performed on a samples taken from normal patients as compared to samples taken from patients symptomatic for lung cancer.

In various embodiments, the inhibition of ROS expression or kinase activity is determined using a reagent that specifically binds to a ROS fusion polynucleotide, a reagent that specifically binds to ROS fusion polypeptide, a reagent that specifically binds to a full length ROS polynucleotide, or a reagent that specifically binds to a full length ROS polypeptide. In some additional embodiments, the inhibition of ROS expression or kinase activity is determined using a reagent that specifically binds to a full length FIG polynucleotide, a reagent that specifically binds to a full length FIG polypeptide, a reagent that specifically binds to a full length SLC34A2 polynucleotide, or a reagent that specifically binds to a full length SLC34A2 polypeptide, a reagent that specifically binds to a full length CD74 polynucleotide, or a reagent that specifically binds to a full length CD74 polypeptide.

In various embodiments, the expression and/or activity of said polypeptide is inhibited with a composition comprising a therapeutic selected from the group consisting of crizotinib (also known as PF-02341066), NVT TAE-684, AP26113, CEP-14083, CEP-14513, CEP11988, WHI-P131 and WHI-P154.

As used herein, a "ROS inhibitor" or a "ROS-inhibiting compound" means any composition comprising one or more compounds, chemical or biological, which inhibits, either directly or indirectly, the expression and/or activity of a polypeptide with ROS kinase activity. Such inhibition may be in vitro or in vivo. "ROS inhibitor therapeutic" or "ROS-inhibiting therapeutic" means a ROS-inhibiting compound used as a therapeutic to treat a patient harboring a lung cancer (e.g., NSCLC or SCLC) characterized by the presence of a polypeptide with ROS kinase activity such as aberrantly expressed full length ROS protein or a ROS fusion polypeptide (e.g., one of the FIG-ROS fusion proteins) described herein.

In some embodiments of the invention, the ROS inhibitor is a reagent that specifically binds to a ROS fusion polypeptide (e.g., FIG-ROS(S), FIG-ROS(L), FIG-ROS(XL), SLC34A2-ROS(VS), SLC34A2-ROS(S), SLC34A2-ROS(L), or CD74-ROS), a reagent that specifically binds to a full length ROS polypeptide, an siRNA targeting a ROS fusion polynucleotide (e.g., a SLC34A2-ROS(L) fusion polynucleotide) or an siRNA targeting a full length ROS polynucleotide.

The ROS-inhibiting therapeutic may be, for example, a kinase inhibitor, such as a small molecule or antibody inhibitor. It may be a pan-kinase inhibitor with activity against several different kinases, or a kinase-specific inhibitor. Since ROS, ALK, LTK, InsR, and IGF1R belong to the same family of tyrosine kinases, they may share similar structure in the kinase domain. Thus, in some embodiments, an ROS inhibitor of the invention also inhibits the activity of an ALK kinase, an LTK kinase, an insulin receptor, or an IGF1 receptor. ROS-inhibiting compounds are discussed in further detail below. Patient biological samples may be taken before and after treatment with the inhibitor and then analyzed, using methods described above, for the biological effect of the inhibitor on ROS kinase activity, including the phosphorylation of downstream substrate protein. Such a pharmacodynamic assay may be useful in determining the biologically active dose of the drug that may be preferable to a maximal tolerable dose. Such information would also be useful in submissions for drug approval by demonstrating the mechanism of drug action.

In another embodiment, the expression and/or activity of said polypeptide is inhibited with a composition comprising a ROS inhibiting therapeutic selected from the group consisting of PF-02341066), NVT TAE-684, AP26113, CEP-14083, CEP-14513, CEP11988, WHI-P131 and WHI-P154.

In accordance with the present invention, the polypeptide with ROS kinase activity may occur in at least one subgroup of human lung cancer. Accordingly, the progression of a mammalian cancer in which a polypeptide with ROS kinase activity is expressed may be inhibited, in vivo, by inhibiting the activity of ROS kinase in such cancer. ROS activity in cancers characterized by expression of a polypeptide with ROS kinase activity (e.g., an ROS fusion polypeptide or aberrantly expressed full length ROS polypeptide) may be inhibited by contacting the cancer with a therapeutically effective amount of a ROS-inhibiting therapeutic. Accordingly, the invention provides, in part, a method for inhibiting the progression of polypeptide with ROS kinase activity-expressing lung cancer by inhibiting the expression and/or activity of ROS kinase in the lung cancer by contacting the cancer (e.g., a tumor) with a therapeutically effective amount of an ROS-inhibiting therapeutic.

As used herein, by "therapeutically effective amount" or "pharmaceutically effective amount" is mean an amount of an ROS-inhibiting therapeutic that is adequate to inhibit the cancer (or cell thereof) or suspected cancer (or cells thereof), as compared to an untreated cancer or suspected cancer, by either slowing the growth of the cancer or suspected cancer, reducing the mass of the cancer or suspected cancer, reducing the number of cells of the cancer or suspected cancer, or killing the cancer.

A ROS-inhibiting therapeutic may be any composition comprising at least one ROS inhibitor. Such compositions also include compositions comprising only a single ROS-inhibiting compound, as well as compositions comprising multiple therapeutics (including those against other RTKs), which may also include a non-specific therapeutic agent like a chemotherapeutic agent or general transcription inhibitor.

In some embodiments, a ROS-inhibiting therapeutic useful in the practice of the methods of the invention is a targeted, small molecule inhibitor. Small molecule targeted inhibitors are a class of molecules that typically inhibit the activity of their target enzyme by specifically, and often irreversibly, binding to the catalytic site of the enzyme, and/or binding to an ATP-binding cleft or other binding site within the enzyme that prevents the enzyme from adopting a conformation necessary for its activity. Because of the close similarity in structure and function between the ROS kinase and the ALK kinase, any ALK kinase inhibitor is predicted to also inhibit ROS kinase. Additionally, as described below in the examples, a lung cancer driven by ROS kinase will not driven by ALK kinase. Likewise, a lung cancer driven by ALK kinase will not be driven by ROS kinase.

Accordingly, in another aspect, the invention provides a method of treating a patient for lung cancer, comprising: detecting the presence in a biological sample from a lung of a patient having or suspected of having lung cancer of a polypeptide selected from the group consisting of a polypeptide having ROS kinase activity and a polypeptide having ALK kinase activity; and administering an effective amount of an ALK/ROS-inhibiting therapeutic to the patient, thereby treating the subject for lung cancer.

In a further aspect, the invention provides a method for identifying a patient with lung cancer or suspected of having lung cancer as a patient likely to respond to a ROS-inhibiting therapeutic, comprising: contacting a biological sample from a lung of said patient with a first reagent that specifically binds a polypeptide having ROS kinase activity and a second reagent that specifically binds to a polypeptide having ALK knase activity and detecting whether the first reagent or the second reagent specifically binds to the biological sample, wherein detection of binding of either the first reagent or the second reagent to the biological sample identifies the patient as a patient likely to respond to a ROS-inhibiting therapeutic. In various embodiments, the first reagent specifically binds to full length ROS kinase protein. In various embodiments, the second reagent specifically binds to full length ALK kinase protein. In various embodiments, the first reagent specifically binds to the kinase domain of ROS kinase protein. In various embodiments, the second reagent specifically binds to the kinase domain of ALK kinase protein.

As used herein, by "protein having ALK kinase activity" is meant any polypeptide that retains the full kinase domain of ALK and thus, has ALK kinase activity. Non-limiting polypeptides with ALK kinase activity include full length ALK (see U.S. Pat. No. 5,770,421), NPM-ALK, ALO17-ALK, TFG-ALK, MSN-ALK, TPM3-ALK, TPM4-ALK, ATIC-ALK, MYH9-ALK, CLTC-ALK, SEC31L1-ALK, RANBP2-ALK, CARS-ALK, EML4-ALK, KIFSB-ALK, and TFG-ALK (see, e.g., Palmer et al., Biochem. J. 420(3): 345-361, 2009 (and the articles cited therein), Rikova et al., Cell 131: 1190-1203, 2007; Soda et al., Nature 448: 561-566, 2007; Morris et al., Science 263: 1281-1284, 1994; Du et al., J. Mol. Med 84: 863-875, 2007; Panagopoulos et al., Int. J. Cancer 118: 1181-1186, 2006; Cools et al., Genes Chromosomes Cancer 34: 354-362, 2002; Debelenko et al., Lab. Invest. 83: 1255-1265, 2003; Ma et al., Genes Chromosomes Cancer 37: 98-105, 2003; Lawrence et al., Am. J. Pathol. 157: 377-384, 1995; Hernandez et al., Blood 94: 3265-3268, 1999; Takeuchi K., Clin Cancer Res. 15(9): 3143-3149, 2009; Tort et al., Lab. Invest. 81: 419-426, 2001; Trinei et al., Cancer Res. 60: 793-798, 2000; and Touriol et al., Blood 95: 3204-3207, 2000. See also Pulford et al., Journal of Cellular Physiology, 199:330-358, 2004.

In various embodiments, the patient is a human. In various embodiments, the lung cancer is non-small cell lung cancer or is small cell lung cancer.

One useful small-molecule kinase inhibitor is Pfizer, Inc.'s compound Crizotinib (also known as PF-02341066), which inhibits ALK and MET kinase activity, and its properties have been well described. See You et al., Cancer Res 67: 4408 (2007) and U.S. Patent Pub. No. 2008/0300273. Additional small molecule kinase inhibitors that may target ROS include TAE-684 (from Novartis), CH5424802 (Chugai; see Sakamoto, H. et al., Cancer Cell 19: 679-690, 2011), AP26113 (Ariad Pharmaceuticals, Inc.), and CEP-14083, CEP-14513, and CEP-11988 (Cephalon; see Wan et al., Blood 107: 1617-1623, 2006).

PF-02341066 has the structure:

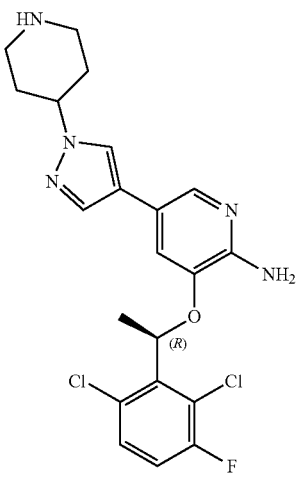

TAE-684, a 5-chloro-2,4-diaminophenylpyrimidine, which has the structure:

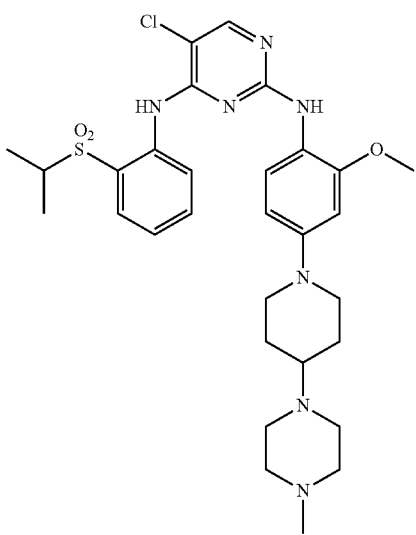 [SMILES: COc1cc(N2CCC(N3CCN(C)CC3)CC2)ccc1Nc1ncc(Cl)c(Nc2ccccc2S(=O)(=O)C(C)C)n1]

and has been shown to inhibit the ROSALK kinase. Grosin, et al., Proc. National Acad. Sci 104(1) 270-275, 2007.

Additional small molecule inhibitors and other inhibitors (e.g., indirect inhibitors) of ROS kinase activity may be rationally designed using X-ray crystallographic or computer modeling of ROS three dimensional structure, or may be found by high throughput screening of compound libraries for inhibition of key upstream regulatory enzymes and/or necessary binding molecules, which results in inhibition of ROS kinase activity. Such approaches are well known in the art, and have been described. ROS inhibition by such therapeutics may be confirmed, for example, by examining the ability of the compound to inhibit ROS activity, but not other kinase activity, in a panel of kinases, and/or by examining the inhibition of ROS activity in a biological sample comprising cancer cells (e.g., lung cancer cells). Methods for identifying compounds that inhibit a cancer characterized by the expression/presence of polypeptide with ROS kinase activity, are further described below.

ROS-inhibiting therapeutics useful in the methods of the invention may also be targeted antibodies that specifically bind to critical catalytic or binding sites or domains required for ROS activity, and inhibit the kinase by blocking access of ligands, substrates or secondary molecules to a and/or preventing the enzyme from adopting a conformation necessary for its activity. The production, screening, and therapeutic use of humanized target-specific antibodies has been well-described. See Merluzzi et al., Adv Clin Path. 4(2): 77-85 (2000). Commercial technologies and systems, such as Morphosys, Inc.'s Human Combinatorial Antibody Library (HuCAL®), for the high-throughput generation and screening of humanized target-specific inhibiting antibodies are available.

The production of various anti-receptor kinase targeted antibodies and their use to inhibit activity of the targeted receptor has been described. See, e.g. U.S. Patent Publication No. 20040202655, U.S. Patent Publication No. 20040086503, U.S. Patent Publication No. 20040033543, Standardized methods for producing, and using, receptor tyrosine kinase activity-inhibiting antibodies are known in the art. See, e.g., European Patent No. EP1423428, Phage display approaches may also be employed to generate ROS-specific antibody inhibitors, and protocols for bacteriophage library construction and selection of recombinant antibodies are provided in the well-known reference text CURRENT PROTOCOLS IN IMMUNOLOGY, Colligan et al. (Eds.), John Wiley & Sons, Inc. (1992-2000), Chapter 17, Section 17.1. See also U.S. Pat. Nos. 6,319,690, 6,300,064, 5,840, 479, and U.S. Patent Publication No. 20030219839.

A library of antibody fragments displayed on the surface of bacteriophages may be produced (see, e.g. U.S. Pat. No. 6,300,064) and screened for binding to a polypeptide with ROS kinase activity such as the ROS fusion polypeptides described herein. An antibody fragment that specifically binds to a ROS fusion polypeptide (e.g., a SLC34A2-ROS(S) fusion polypeptide) or a full length ROS polypeptide is identified as a candidate molecule for blocking constitutive activation of that fusion polypeptide in a cell. See European Patent No. EP1423428.

ROS-binding targeted antibodies identified in screening of antibody libraries as describe above may then be further screened for their ability to block the activity of ROS, both in vitro kinase assay and in vivo in cell lines and/or tumors. ROS inhibition may be confirmed, for example, by examining the ability of such antibody therapeutic to inhibit ROS kinase activity in a panel of kinases, and/or by examining the inhibition of ROS activity in a biological sample comprising cancer cells, as described above. In some embodiments, a ROS-inhibiting compound of the invention reduces ROS kinase activity, but reduces the kinase activity of other kinases to a lesser extent (or not at all). Methods for screening such compounds for ROS kinase inhibition are further described above.

ROS-inhibiting compounds that useful in the practice of the disclosed methods may also be compounds that indirectly inhibit ROS activity by inhibiting the activity of proteins or molecules other than ROS kinase itself. Such inhibiting therapeutics may be targeted inhibitors that modulate the activity of key regulatory kinases that phosphorylate or de-phosphorylate (and hence activate or deactivate) ROS itself, or interfere with binding of ligands. As with other receptor tyrosine kinases, ROS regulates downstream signaling through a network of adaptor proteins and downstream kinases. As a result, induction of cell growth and survival by ROS activity may be inhibited by targeting these interacting or downstream proteins.

ROS kinase activity may also be indirectly inhibited by using a compound that inhibits the binding of an activating molecule necessary for full length ROS or an ROS fusion polypeptide (e.g., an CD74-ROS fusion polypeptide) to adopt its active conformation (i.e., such that the ROS kinase domain is able to be activated). For example, the production and use of anti-PDGF antibodies has been described. See U.S. Patent Publication No. 20030219839, "Anti-PDGF Antibodies and Methods for Producing Engineered Antibodies," Bowdish et al. Inhibition of ligand (PDGF) binding to the receptor directly down-regulates the receptor activity.

ROS inhibiting compounds or therapeutics may also comprise anti-sense and/or transcription inhibiting compounds that inhibit ROS kinase activity by blocking transcription of the gene encoding full-length ROS or a ROS fusion protein. The inhibition of various receptor kinases, including VEGFR, EGFR, and IGFR, and FGFR, by antisense therapeutics for the treatment of cancer has been described. See, e.g., U.S. Pat. Nos. 6,734,017; 6, 710,174, 6,617,162; 6,340,674; 5,783,683; 5,610,288.

Antisense oligonucleotides may be designed, constructed, and employed as therapeutic agents against target genes in accordance with known techniques. See, e.g. Cohen, J., *Trends in Pharmacol. Sci.* 10(11): 435-437 (1989); Marcus-Sekura, *Anal. Biochem.* 172: 289-295 (1988); Weintraub, H., *Sci. AM* Pp. 40-46 (1990); Van Der Krol et al., *BioTechniques* 6(10): 958-976 (1988); Skorski et al., *Proc. Natl. Acad. Sci. USA* (1994) 91: 4504-4508. Inhibition of human carcinoma growth in vivo using an antisense RNA inhibitor of EGFR has recently been described. See U.S. Patent Publication No. 20040047847. Similarly, a ROS-inhibiting therapeutic comprising at least one antisense oligonucleotide against a mammalian ROS gene or a mammalian ROS fusion protein-encoding polynucleotide may be prepared according to standard methods. Pharmaceutical compositions comprising ROS-inhibiting antisense compounds may be prepared and administered as further described below.

Small interfering RNA molecule (siRNA) compositions, which inhibit translation, and hence activity, of ROS through the process of RNA interference, may also be desirably employed in the methods of the invention. RNA interference, and the selective silencing of target protein expression by introduction of exogenous small double-stranded RNA molecules comprising sequence complimentary to mRNA encoding the target protein, has been well described. See, e.g. U.S. Patent Publication No. 20040038921, U.S. Patent Publication No. 20020086356, and U.S. Patent Publication 20040229266.

Double-stranded RNA molecules (dsRNA) have been shown to block gene expression in a highly conserved regulatory mechanism known as RNA interference (RNAi). Briefly, the RNAse III Dicer processes dsRNA into small interfering RNAs (siRNA) of approximately 22 nucleotides, which serve as guide sequences to induce target-specific mRNA cleavage by an RNA-induced silencing complex RISC (see Hammond et al., *Nature* (2000) 404: 293-296). RNAi involves a catalytic-type reaction whereby new siRNAs are generated through successive cleavage of longer dsRNA. Thus, unlike antisense, RNAi degrades target RNA in a non-stoichiometric manner. When administered to a cell or organism, exogenous dsRNA has been shown to direct the sequence-specific degradation of endogenous messenger RNA (mRNA) through RNAi.

A wide variety of target-specific siRNA products, including vectors and systems for their expression and use in mammalian cells, are now commercially available. See, e.g., the web sites of Promega, Inc. and Dharmacon, Inc. Detailed technical manuals on the design, construction, and use of dsRNA for RNAi are available. See, e.g., Dharmacon's "RNAi Technical Reference & Application Guide"; Promega's "RNAi: A Guide to Gene Silencing." ROS-inhibiting siRNA products are also commercially available, and may be suitably employed in the method of the invention. See, e.g., Dharmacon, Inc., Lafayette, Colo. (Cat Nos. M-003162-03, MU-003162-03, D-003162-07 thru -10 (products under the names of siGENOME™ SMARTselection and SMARTpool® siRNAs)).

It has recently been established that small dsRNA less than 49 nucleotides in length, and preferably 19-25 nucleotides, comprising at least one sequence that is substantially identical to part of a target mRNA sequence, and which dsRNA optimally has at least one overhang of 1-4 nucleotides at an end, are most effective in mediating RNAi in mammals. See U.S. Patent Publication Nos. 20040038921 and 20040229266. The construction of such dsRNA, and their use in pharmaceutical preparations to silence expression of a target protein, in vivo, are described in detail in such publications.

If the sequence of the gene to be targeted in a mammal is known, 21-23 nt RNAs, for example, can be produced and tested for their ability to mediate RNAi in a mammalian cell, such as a human or other primate cell. Those 21-23 nt RNA molecules shown to mediate RNAi can be tested, if desired, in an appropriate animal model to further assess their in vivo effectiveness. Target sites that are known, for example target sites determined to be effective target sites based on studies with other nucleic acid molecules, for example ribozymes or antisense, or those targets known to be associated with a disease or condition such as those sites containing mutations or deletions, can be used to design siRNA molecules targeting those sites as well.

Alternatively, the sequences of effective dsRNA can be rationally designed/predicted screening the target mRNA of interest for target sites, for example by using a computer folding algorithm. The target sequence can be parsed in silico into a list of all fragments or subsequences of a particular length, for example 23 nucleotide fragments, using a custom Perl script or commercial sequence analysis programs such as Oligo, MacVector, or the GCG Wisconsin Package.

Various parameters can be used to determine which sites are the most suitable target sites within the target RNA sequence. These parameters include but are not limited to secondary or tertiary RNA structure, the nucleotide base composition of the target sequence, the degree of homology between various regions of the target sequence, or the relative position of the target sequence within the RNA transcript. Based on these determinations, any number of target sites within the RNA transcript can be chosen to screen siRNA molecules for efficacy, for example by using in vitro RNA cleavage assays, cell culture, or animal models. See, e.g., U.S. Patent Publication No. 20030170891. An algorithm for identifying and selecting RNAi target sites has also recently been described. See U.S. Patent Publication No. 20040236517.

Commonly used gene transfer techniques include calcium phosphate, DEAE-dextran, electroporation and microinjection and viral methods (Graham et al. (1973) *Virol.* 52: 456; McCutchan et al., (1968), *J. Natl. Cancer Inst.* 41: 351; Chu et al. (1987), *Nucl. Acids Res.* 15: 1311; Fraley et al. (1980), *J. Biol. Chem.* 255: 10431; Capecchi (1980), *Cell* 22: 479). DNA may also be introduced into cells using cationic liposomes (Feigner et al. (1987), *Proc. Natl. Acad. Sci USA* 84: 7413). Commercially available cationic lipid formulations include Tfx 50 (Promega Corp., Fitchburg, Wis.) or Lipofectamin 200 (Life Technologies, Carlsbad, Calif.). Alternatively, viral vectors may be employed to deliver dsRNA to a cell and mediate RNAi. See U.S. Patent Publication No. 20040023390.

Transfection and vector/expression systems for RNAi in mammalian cells are commercially available and have been well described. See, e.g., Dharmacon, Inc. (Lafayette, Colo.), DharmaFECT™ system; Promega, Inc., siSTRIKE™ U6 Hairpin system; see also Gou et al. (2003) *FEBS.* 548, 113-118; Sui, G. et al. A DNA vector-based RNAi technology to suppress gene expression in mammalian cells (2002) *Proc. Natl. Acad. Sci.* 99, 5515-5520; Yu et al. (2002) *Proc. Natl. Acad. Sci.* 99, 6047-6052; Paul, C. et al. (2002) *Nature Biotechnology* 19, 505-508; McManus et al. (2002) *RNA* 8, 842-850.

siRNA interference in a mammal using prepared dsRNA molecules may then be effected by administering a pharmaceutical preparation comprising the dsRNA to the mammal. The pharmaceutical composition is administered in a dosage sufficient to inhibit expression of the target gene. dsRNA can typically be administered at a dosage of less than 5 mg dsRNA per kilogram body weight per day, and is sufficient to inhibit or completely suppress expression of the target gene. In general a suitable dose of dsRNA will be in the range of 0.01 to 2.5 milligrams per kilogram body weight of the recipient per day, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. A pharmaceutical composition comprising the dsRNA is administered once daily, or in multiple sub-doses, for example, using sustained release formulations well known in the art. The preparation and administration of such pharmaceutical compositions may be carried out accordingly to standard techniques, as further described below.

Such dsRNA may then be used to inhibit ROS expression and activity in a cancer, by preparing a pharmaceutical preparation comprising a therapeutically-effective amount of such dsRNA, as described above, and administering the preparation to a human subject having a lung cancer or suspected lung cancer (e.g., a NSCLC or SCLC) expressing a polypeptide with ROS kinase activity (such as, for example, aberrant expression of full length ROS protein or expression of a ROS fusion protein), for example, via direct injection to the tumor. The similar inhibition of other receptor tyrosine kinases, such as VEGFR and EGFR using siRNA inhibitors has recently been described. See U.S. Patent Publication No. 20040209832, U.S. Patent Publication No. 20030170891, and U.S. Patent Publication No. 20040175703.

ROS-inhibiting therapeutics useful in the practice of the methods of the invention may be administered to a mammal by any means known in the art including, but not limited to oral or peritoneal routes, including intravenous, intramuscular, intraperitoneal, subcutaneous, transdermal, airway (aerosol), rectal, vaginal and topical (including buccal and sublingual) administration.

For oral administration, a ROS-inhibiting therapeutic will generally be provided in the form of tablets or capsules, as a powder or granules, or as an aqueous solution or suspension. Tablets for oral use may include the active ingredients mixed with pharmaceutically acceptable carriers and excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredients is mixed with water or an oil such as peanut oil, liquid paraffin or olive oil. For intramuscular, intraperitoneal, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. The carrier may consist exclusively of an aqueous buffer ("exclusively" means no auxiliary agents or encapsulating substances are present which might affect or mediate uptake of the ROS-inhibiting therapeutic). Such substances include, for example, micellar structures, such as liposomes or capsids, as described below. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

ROS-inhibiting therapeutic compositions may also include encapsulated formulations to protect the therapeutic (e.g., a dsRNA compound or an antibody that specifically binds a ROS fusion polypeptide) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075. An encapsulated formulation may comprise a viral coat protein. The viral coat protein may be derived from or associated with a virus, such as a polyoma virus, or it may be partially or entirely artificial. For example, the coat protein may be a Virus Protein 1 and/or Virus Protein 2 of the polyoma virus, or a derivative thereof.

ROS-inhibiting therapeutics can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, *Trends Cell Bio.,* 2, 139; DELIVERY STRATEGIES FOR ANTISENSE OLIGONUCLEOTIDE THERAPEUTICS, ed. Akbtar, 1995, Maurer et al., 1999, *Mol. Membr. Biol.,* 16, 129-140; Hofland and Huang, 1999, *Handb. Exp. Pharmacol.,* 137, 165-192; and Lee et al., 2000, ACS Symp. Ser., 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

ROS-inhibiting therapeutics (i.e., a ROS-inhibiting compound being administered as a therapeutic) can be administered to a mammalian tumor by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, Clin. Cancer Res., 5, 2330-2337 and PCT Publication No. WO 99/3 1262.

Pharmaceutically acceptable formulations of ROS-inhibitor therapeutics include salts of the above described compounds, e.g., acid addition salts, for example, salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell. For example, pharmacological compositions injected into the blood stream should be soluble. Other factors are known in the art, and include considerations such as toxicity and forms that prevent the composition or formulation from exerting its effect.

Administration routes that lead to systemic absorption (e.g., systemic absorption or accumulation of drugs in the blood stream followed by distribution throughout the entire body), are desirable and include, without limitation: intravenous, subcutaneous, intraperitoneal, inhalation, oral, intrapulmonary and intramuscular. Each of these administration routes exposes the ROS-inhibiting therapeutic to an accessible diseased tissue or tumor. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, 1999, Fundam. Clin. Pharmacol., 13, 16-26); biodegradable polymers, such as poly (DL-lactide-coglycolide) microspheres for sustained release delivery after intracerebral implantation (Emerich et al, 1999, Cell Transplant, 8, 47-58) (Rosermes, Inc. Cambridge, Mass.); and loaded nanoparticles, such as those made of polybutylcyanoacrylate, which can deliver drugs across the blood brain barrier and can alter neuronal uptake mechanisms (Prog Neuro-psychopharmacol Biol Psychiatry, 23, 941-949, 1999). Other non-limiting examples of delivery strategies for the ROS-inhibiting compounds useful in the method of the invention include material described in Boado et al., 1998, J. Pharm. Sci., 87, 1308-1315; Tyler et al., 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058.

Therapeutic compositions comprising surface-modified liposomes containing poly (ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

Therapeutic compositions may include a pharmaceutically effective amount of the desired compounds in a pharmaceutically acceptable carrier or diluent. Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). For example, preservatives, stabilizers, dyes and flavoring agents can be provided. These include sodium benzoate, sorbic acid and esters of p-hydroxybenzoic acid. In addition, antioxidants and suspending agents can be used.

In some embodiments, the ROS-inhibiting therapeutic and/or the ALK/ROS-inhibiting therapeutic is administered in an effective amount. By "effective amount" or "effective dose" is meant the amount of the therapeutic required to prevent, inhibit the occurrence, or treat (alleviate a symptom to some extent, preferably all of the symptoms) of a disease state (e.g., lung cancer). The effective dose depends on the type of disease, the therapeutic used, the route of administration, the type of mammal being treated, the physical characteristics of the specific mammal under consideration, concurrent medication, and other factors that those skilled in the medical arts will recognize. Generally, an effective amount is an amount between 0.1 mg/kg and 100 mg/kg body weight/day of active ingredients is administered dependent upon potency of the negatively charged polymer.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form varies depending upon the host treated and the particular mode of administration. Dosage unit forms generally contain between from about 1 mg to about 500 mg of an active ingredient. It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

A ROS-inhibiting therapeutic useful in the practice of the invention may comprise a single compound as described above, or a combination of multiple compounds, whether in the same class of inhibitor (e.g., antibody inhibitor), or in different classes (e.g., antibody inhibitors and small-molecule inhibitors). Such combination of compounds may increase the overall therapeutic effect in inhibiting the progression of a fusion protein-expressing cancer. For example, the therapeutic composition may a small molecule inhibitor, such as Crizotinib (also known as PF-02341066) produced by Pfizer, Inc. (see U.S. Pub. No. 2008/0300273) alone, or in combination with other Crizotinib analogues targeting ROS activity and/or small molecule inhibitors of ROS, such as NVP-TAE684 produced by Novartis, Inc., or the CH5424802 compound described in Sakamoto et al., Cancer Cell 19: 679-690, 2011. The therapeutic composition may also comprise one or more non-specific chemotherapeutic agent in addition to one or more targeted inhibitors. Such combinations have recently been shown to provide a synergistic tumor killing effect in many cancers. The effectiveness of such combinations in inhibiting ROS activity and tumor growth in vivo can be assessed as described below.

The invention also provides, in part, a method for determining whether a compound inhibits the progression of a cancer (e.g., a lung cancer) characterized by a polypeptide with ROS kinase activity or polynucleotide encoding the same by determining whether the compound inhibits the ROS kinase activity of the polypeptide in the cancer. In some embodiments, inhibition of activity of ROS is determined by examining a biological sample comprising cells from bone marrow, blood, or a tumor. In another embodiment, inhibition of activity of ROS is determined using at least reagent that specifically binds to a ROS polypeptide (e.g., a ROS-specific antibody) or a reagent that specifically binds to a ROS polypeptide-encoding polynucleotide (e.g., an siRNA or an ROS antisense).

The tested compound may be any type of therapeutic or composition as described above. Methods for assessing the efficacy of a compound, both in vitro and in vivo, are well established and known in the art. For example, a composition may be tested for ability to inhibit ROS in vitro using a cell or cell extract in which ROS kinase is activated. A panel of compounds may be employed to test the specificity of the compound for ROS (as opposed to other targets, such as EGFR or PDGFR).

Another technique for drug screening which may be used provides for high throughput screening of compounds having suitable binding affinity to a protein of interest, as described in PCT Publication No. WO 84/03564. In this method, as applied to polypeptides having ROS activity (e.g., full length ROS protein or one of the multiple ROS fusion proteins), large numbers of different small test compounds are synthesized on a solid substrate, such as plastic pins or some other surface. The test compounds are reacted with a polypeptide of the invention, or fragments thereof, and washed. Bound polypeptide (e.g., SLC34A2-ROS(VS), SLC34A2-ROS(S), SLC34A2-ROS(L), CD74-ROS, FIG-ROS(S), FIG-ROS(L), or FIG-ROS(XL) fusion polypeptides or full length ROS polypeptide) is then detected by methods well known in the art. A purified polypeptide can also be coated directly onto plates for use in the aforementioned drug screening techniques. Alternatively, non-neutralizing antibodies can be used to capture the peptide and immobilize it on a solid support.

A compound found to be an effective inhibitor of ROS activity in vitro may then be examined for its ability to inhibit the progression of a cancer expressing a polypeptide with kinase activity (such as lung cancer or other cancer such as a liver cancer, lung cancer, colon cancer, kidney cancer, or a pancreatic cancer), in vivo, using, for example, mammalian xenografts harboring human lung, liver, pancreatic, kidney, lung, or colon tumors that are express a polypeptide with ROS kinase activity. In this procedure, cancer cell lines known to express a protein having ROS kinase activity (e.g., full length ROS or one of the ROS fusion proteins) may be placed subcutaneously in an animal (e.g., into a nude or SCID mouse, or other immune-compromised animal). The cells then grow into a tumor mass that may be visually monitored. The animal may then be treated with the drug. The effect of the drug treatment on tumor size may be externally observed. The animal is then sacrificed and the tumor removed for analysis by IHC and Western blot. Similarly, mammalian bone marrow transplants may be prepared, by standard methods, to examine drug response in hematological tumors expressing a protein with ROS kinase activity. In this way, the effects of the drug may be observed in a biological setting most closely resembling a patient. The drug's ability to alter signaling in the tumor cells or surrounding stromal cells may be determined by analysis with phosphorylation-specific antibodies. The drug's effectiveness in inducing cell death or inhibition of cell proliferation may also be observed by analysis with apoptosis specific markers such as cleaved caspase 3 and cleaved PARP.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, the compounds exhibit high therapeutic indices.

In practicing the disclosed method for determining whether a compound inhibits progression of a tumor characterized by the presence of a polypeptide with ROS kinase activity (or polynucleotide encoding the same), biological samples comprising cells from mammalian xenografts (or bone marrow transplants) may also be advantageously employed. Non-limiting xenografts (or transplant recipients) are small mammals, such as mice, harboring human tumors (or leukemias) that express a polypeptide with ROS kinase activity (e.g., a ROS fusion polypeptide (such as CD74-ROS or FIG-ROS(S)) or full length ROS). Xenografts harboring human tumors are well known in the art (see Kal, *Cancer Treat Res.* 72: 155-69 (1995)) and the production of mammalian xenografts harboring human tumors is well described (see Winograd et al., *In Vivo.* 1(1): 1-13 (1987)). Similarly the generation and use of bone marrow transplant models is well described (see, e.g., Schwaller, et al., *EMBO J.* 7: 5321-333 (1998); Kelly et al., *Blood* 99: 310-318 (2002)).

The following Examples are provided only to further illustrate the invention, and are not intended to limit its scope, except as provided in the claims appended hereto. The present invention encompasses modifications and variations of the methods taught herein which would be obvious to one of ordinary skill in the art. Materials, reagents and the like to which reference is made are obtainable from commercial sources, unless otherwise noted.

Example 1

Identification of ROS Kinase Activity in an NSCLC Cell Line by Global Phosphopeptide Profiling The global phosphorylation profile of kinase activation in several human NSCLC cell lines, including HCC78, were examined using the IAP technique for the isolation and mass spectrometric characterization of modified peptides from complex mixtures (see U.S. Pat. Nos. 7,300,753 and 7,198, 896). The IAP technique was performed using a phosphotyrosine-specific antibody (commercially available from CELL SIGNALING TECHNOLOGY, INC., Danver, Mass., Cat. #9411) to isolate, and subsequently characterize, phosphotyrosine-containing peptides from extracts of the NSCLC cell lines.

Specifically, the IAP approach was employed to facilitate the identification of activated tyrosine kinases in the NSCLC cell lines, in order to identify novel drivers of this disease.
Cell Culture.

HCC78 cells were obtained from DSMZ (the German National Resource Centre for Biological Material), grown in RPMI-1640 medium (Invitrogen) with 10% fetal bovine serum (FBS) (Sigma).
Phosphopeptide Immunoprecipitation.

A total of $2 \times 10^8$ cells were lysed in urea lysis buffer (20 mM HEPES pH 8.0, 9M urea, 1 mM sodium vanadate, 2.5 mM sodium pyrophosphate, 1 mM beta-glycerophosphate) at $1.25 \times 10^8$ cells/ml and sonicated. Sonicated lysates were cleared by centrifugation at 20,000×g, and proteins were reduced and alkylated as described previously (see Rush et al., Nat. Biotechnol. 23(1): 94-101 (2005)). Samples were diluted with 20 mM HEPES pH 8.0 to a final urea concentration of 2M. Trypsin (1 mg/ml in 0.001 M HCl) was added to the clarified lysate at 1:100 v/v. Samples were digested overnight at room temperature.

Following digestion, lysates were acidified to a final concentration of 1% TFA. Peptide purification was carried out using Sep-Pak $C_{18}$ columns as described previously (see Rush et al., supra.). Following purification, all elutions (8%, 12%, 15%, 18%, 22%, 25%, 30%, 35% and 40% acetonitrile in 0.1% TFA) were combined and lyophilized. Dried peptides were resuspended in 1.4 ml MOPS buffer (50 mM MOPS/NaOH pH 7.2, 10 mM $Na_2HPO_4$, 50 mM NaCl) and insoluble material removed by centrifugation at 12,000×g for 10 minutes.

The phosphotyrosine monoclonal antibody P-Tyr-100 (Cell Signaling Technology) from ascites fluid was coupled non-covalently to protein G agarose beads (Roche) at 4 mg/ml beads overnight at 4° C. After coupling, antibody-resin was washed twice with PBS and three times with MOPS buffer. Immobilized antibody (40 μl, 160 μg) was added as a 1:1 slurry in MOPS IP buffer to the solubilized peptide fraction, and the mixture was incubated overnight at 4° C. The immobilized antibody beads were washed three times with MOPS buffer and twice with dd$H_2O$. Peptides were eluted twice from beads by incubation with 40 μl of 0.15% TFA for 20 minutes each, and the fractions were combined.
Analysis by LC-MS/MS Mass Spectrometry.

Peptides in the IP eluate (40 μl) were concentrated and separated from eluted antibody using Stop and Go extraction tips (StageTips) (see Rappsilber et al., Anal. Chem., 75(3): 663-70 (2003)). Peptides were eluted from the microcolumns with 1 μl of 60% MeCN, 0.1% TFA into 7.6 μl of 0.4% acetic acid/0.005% heptafluorobutyric acid (HFBA). The sample was loaded onto a 10 cm×75 μm PicoFrit capillary column (New Objective) packed with Magic C18 AQ reversed-phase resin (Michrom Bioresources) using a Famos autosampler with an inert sample injection valve (Dionex). The column was developed with a 45-min linear gradient of acetonitrile in 0.4% acetic acid, 0.005% HFBA delivered at 280 nl/min (Ultimate, Dionex).

Tandem mass spectra were collected in a data-dependent manner with an LCQ Deca XP Plus ion trap mass spectrometer (ThermoFinnigan), using a top-four method, a dynamic exclusion repeat count of 1, and a repeat duration of 0.5 min.
Database Analysis & Assignments.

MS/MS spectra were evaluated using TurboSequest (ThermoFinnigan) (in the Sequest Browser package (v. 27, rev. 12) supplied as part of BioWorks 3.0). Individual MS/MS spectra were extracted from the raw data file using the Sequest Browser program CreateDta, with the following settings: bottom MW, 700; top MW, 4,500; minimum number of ions, 20; minimum TIC, $4 \times 10^5$; and precursor charge state, unspecified. Spectra were extracted from the beginning of the raw data file before sample injection to the end of the eluting gradient. The IonQuest and VuDta programs were not used to further select MS/MS spectra for Sequest analysis. MS/MS spectra were evaluated with the following TurboSequest parameters: peptide mass tolerance, 2.5; fragment ion tolerance, 0.0; maximum number of differential amino acids per modification, 4; mass type parent, average; mass type fragment, average; maximum number of internal cleavage sites, 10; neutral losses of water and ammonia from b and y ions were considered in the correlation analysis. Proteolytic enzyme was specified except for spectra collected from elastase digests.

Searches were done against the NCBI human database released on Aug. 24, 2004 containing 27,175 proteins allowing oxidized methionine (M+16) and phosphorylation (Y+80) as dynamic modifications.

In proteomics research, it is desirable to validate protein identifications based solely on the observation of a single peptide in one experimental result, in order to indicate that the protein is, in fact, present in a sample. This has led to the development of statistical methods for validating peptide assignments, which are not yet universally accepted, and guidelines for the publication of protein and peptide identification results (see Carr et al., Mol. Cell Proteomics 3: 531-533 (2004)), which were followed in this Example. However, because the immunoaffinity strategy separates phosphorylated peptides from unphosphorylated peptides, observing just one phosphopeptide from a protein is a common result, since many phosphorylated proteins have only one tyrosine-phosphorylated site.

For this reason, it is appropriate to use additional criteria to validate phosphopeptide assignments. Assignments are likely to be correct if any of these additional criteria are met: (i) the same sequence is assigned to co-eluting ions with different charge states, since the MS/MS spectrum changes markedly with charge state; (ii) the site is found in more than one peptide sequence context due to sequence overlaps from incomplete proteolysis or use of proteases other than trypsin; (iii) the site is found in more than one peptide sequence context due to homologous but not identical protein isoforms; (iv) the site is found in more than one peptide sequence context due to homologous but not identical proteins among species; and (v) sites validated by MS/MS analysis of synthetic phosphopeptides corresponding to assigned sequences, since the ion trap mass spectrometer produces highly reproducible MS/MS spectra. The last criterion is routinely employed to confirm novel site assignments of particular interest.

All spectra and all sequence assignments made by Sequest were imported into a relational database. Assigned sequences were accepted or rejected following a conservative, two-step process. In the first step, a subset of high-scoring sequence assignments was selected by filtering for XCorr values of at least 1.5 for a charge state of +1, 2.2 for +2, and 3.3 for +3, allowing a maximum RSp value of 10. Assignments in this subset were rejected if any of the following criteria were satisfied: (i) the spectrum contained at least one major peak (at least 10% as intense as the most intense ion in the spectrum) that could not be mapped to the assigned sequence as an a, b, or y ion, as an ion arising from neutral-loss of water or ammonia from a b or y ion, or as a multiply protonated ion; (ii) the spectrum did not contain a series of b or y ions equivalent to at least six uninterrupted residues; or (iii) the sequence was not observed at least five times in all the studies we have conducted (except for overlapping sequences due to incomplete proteolysis or use of proteases other than trypsin). In the second step, assignments with below-threshold scores were accepted if the low-scoring spectrum showed a high degree of similarity to a high-scoring spectrum collected in another study, which simulates a true reference library-searching strategy. All spectra supporting the final list of assigned sequences (not shown here) were reviewed by at least three scientists to establish their credibility.

The foregoing IAP analysis identified 454 non-redundant phosphotyrosine-containing peptides, 395 phosphotyrosine sites, and 240 tyrosine phosphorylated proteins, the majority of which are novel, from HCC78 cells (data not shown). Among tyrosine phosphorylated kinases were several of those detected are not normally detected by MS analysis in other NSCLC cell lines (unpublished data), including ROS kinase.

Example 2

Detection of Mutant ROS Kinase Expression in a Human Cancer Sample Using Global Phosphopeptide Profiling In order to further confirm the incidence of the ROS fusion mutation in human NSCLC, several human NSCLC tumors were examined, using the IAP technique of global phosphopeptide profiling described above (see Example 1), to identify ROS phosphopeptides in these tumors. Tumor samples (dissected tumors snap frozen and kept in liquid nitrogen) were obtained from a clinical collaborator in China (Second Xiangya Hospital, Central South University Changsha, Hunan, P.R. China).

Briefly, between about 300 milligrams-500 milligrams of tumor tissue were homogenized. For example, the tissue was homogenized and lysed in urea lysis buffer (20 mM HEPES pH 8.0, 9M urea, 1 mM sodium vanadate, 2.5 mM sodium pyrophosphate, 1 mM beta-glycerophosphate) at $1.25 \times 10^8$ cells/ml and sonicated. Sonicated lysates were cleared by centrifugation at 20,000×g, and proteins were reduced and alkylated as described previously (see Rush et al., Nat. Biotechnol. 23(1): 94-101 (2005)). Samples were diluted with 20 mM HEPES pH 8.0 to a final urea concentration of 2M. Trypsin (1 mg/ml in 0.001 M HCl) was added to the clarified lysate at 1:100 v/v. Samples were digested overnight at room temperature.

Global phosphotyrosine profiling of these samples was carried out as described in Example 1 above. The results of the profiling showed that one of the tumor samples had both ROS phospho-peptides and SLC34A2 phospho-peptides (see Table 1 below (other detected phosphopeptides not shown) and also downstream molecules such as IRS-1 and IRS-2 phosphopeptides. The tyrosine profiling signature of this tumor is very similar to that of NSCLC cell line HCC78 (see Table 3, as expected. FISH analysis also showed that the tumor has a ROS translocation (see Example 10 below). RT-PCR, DNA sequencing assay can be used to further confirm that ROS activation in this patient (and other patients harboring the ROS translocation) is due to the aberrant transcript of SLC34A2/ROS.

TABLE 3

Phosphopeptide Profiling of Human NSCLC Tumors.

| Name | Accession | Site | Peptides | SEQ ID NO. | HCC78 (cell line) | cs042 (tumor) |
|---|---|---|---|---|---|---|
|  |  |  | GLAAGVGLANACy AIHTLPTQEEIENLP | 35 |  |  |
| ROS | P08922 | 1923 | AFPR DIyKNDYYR; DIyKNDYyR; DIyKNDyYR; DIyKNDyyRKRGEGL |  36; 37 | 1 | 1 |
| ROS | P08922 | 2110 | LPVR DIYKNDyYR; DIyKNDyYR; DIyKNDyyRKRGEGL | 36; 37 | 12 | 4 |

TABLE 3-continued

Phosphopeptide Profiling of Human NSCLC Tumors.

| Name | Accession | Site | Peptides | SEQ ID NO. | HCC78 (cell line) | cs042 (tumor) |
|---|---|---|---|---|---|---|
| ROS | P08922 | 2114 | LPVR DIyKNDYyR; DIyKNDyyRKRGEGL | 36; 37 | 11 | 3 |
| ROS | P08922 | 2115 | LPVR EGLNyMVLATECGQ GEEK; NREGLNyMVLATEC GQGEEK; EGLNyMVLATECGQ GEEKSEGPLGSQESE SCGLR; NREGLNyMVLATEC GQGEEKSEGPLGSQ | 38; 39; 40; 41 | 1 | 1 |
| ROS | P08922 | 2274 | ESESCGLR QVAyCPSGKPEGLN | 42 | 20 | |
| ROS | P08922 | 2323 | YACLTHSGYGDGSD; QVAyCPSGKPEGLN YACLTHSGyGDGSD; QVAyCPSGKPEGLN yACLTHSGYGDGSD QVAYCPSGKPEGLN yACLTHSGYGDGSD; QVAYCPSGKPEGLN yACLTHSGyGDGSD; QVAyCPSGKPEGLN | 42 | 4 | 1 |
| ROS | P08922 | 2334 | yACLTHSGYGDGSD QVAYCPSGKPEGLN yACLTHSGyGDGSD; QVAyCPSGKPEGLN | 42 | 7 | 2 |
| ROS | P08922 | 2342 | YACLTHSGyGDGSD GGHHRPDSSTLHTD DGyMPMSPGVAPVP | 43 | 3 | |
| IRS-1 | P35568 | 612 | SGR | | | 1 |
| IRS-1 | P35568 | 632 | KGSGDyMPMSPK VDPNGyMMMSPSG GCSPDIGGGPSSSSS | 44 45 | 2 | 1 |
| IRS-1 | P35568 | 662 | SSNAVPSGTSYGK QRPVPQPSSASLDEy | 46 | 3 | |
| IRS-2 | Q9Y4H2 | 598 | TLMR SSSSNLGADDGyMP MTPGAALAGSGSGS | 47 | | 1 |
| IRS-2 | Q9Y4H2 | 653 | CR SDDyMPMSPASVSA | 48 | 4 | 5 |
| IRS-2 | Q9Y4H2 | 675 | PK ASSPAESSPEDSGyM | 49 | 3 | 4 |
| IRS-2 | Q9Y4H2 | 742 | R APYTCGGDSDQyVL MSSPVGR; SYKAPYTCGGDSDQ | 50 | 3 | 3 |
| IRS-2 | Q9Y4H2 | 823 | yVLMSSPVGR IELLPSySTATLIDEP | 51 | 2 | 5 |
| SLC34A2 | O95436 | 54 | TEVDDPWNLPTLQD SGIK | | 1 | 1 |

Example 3

Western Blot Analysis of ROS Kinase Expression in an NSCLC Cell Line

The observation that the HCC78 NSCLC cell line—but not the other NSCLC cell lines—expresses activated ROS kinase was confirmed by Western blot analysis of cell extracts using antibodies specific for ROS and other receptor tyrosine kinases (RTKs) and downstream kinases.

HCC78 cells were lysed in 1× cell lysis buffer (Cell Signaling Technology) supplemented with Protease Arrest™ (G Biosciences) and separated by electrophoresis. All antibodies and reagents for immunoblotting were from Cell Signaling Technology, Inc. (Danvers, Mass.). Western blotting was carried out as described in "Western Immunoblotting Protocol" (Cell Signaling Technology, Inc., 2005-2006 catalogue). Anti-ROS antibody was obtain from Santa Cruz Biotechnology, Inc.

FIG. 1 shows the western blot results. Only HCC78 express ROS protein among many different NSCLC cell lines. ROS protein in HCC78 has much smaller molecular weight than wild type ROS protein, which indicates of a fusion protein.

Western blot confirms ROS fusion protein is tyrosine phosphorylated. Protein lysate from HCC78 cells was immunoprecipitated by phospho-tyrosine antibody, and immunoblotted with total ROS antibody. The same bands were detected from pY-IP as from total lysate by ROS antibody, with IP'ed bands having a little slower migration, which also indicates phosphorylation of the protein.

Example 4

Growth Inhibition of Abnormal ROS Kinase-Expressing Mammalian NSCLC Cell Lines Using siRNA In order to confirm that the truncated form of ROS is driving cell growth and survival in the HCC78 cell line, the ability of siRNA silencing to inhibit growth of these cells was examined. The expression of ROS was down regulated by RNA interference. The following ROS siRNA was ordered from Proligo, Inc., with corresponding ROS sequences indicated in parentheses:

(ROS1(6318-6340))
(SEQ ID NO: 31)
5'AAGCCCGGAUGGCAACGUUTT3';

(ROS1(7181-7203))
(SEQ ID NO: 32)
5'AAGCCUGAAGGCCUGAACUTT3'.

$2\times10^5$ cells were seeded in 12 well plates the day before the transfection. 100 nM ROS1 siRNA was transfected using Minis TransIT-TKO Transfection Reagent. 48 hours after transfection, cells were switched to starvation medium for additional 24 hours. Cells were harvested by trypsinization and counted then, and cell lysate was used in WB to check ROS protein level.

Immunoblot analysis revealed the expression of ROS was specifically and significantly reduced at 72 hours following transfection of the siRNA into HCC78 cells, and control cell line H2066 does not express ROS protein (see FIG. 2B, panel B). This was accompanied by a decrease in the phosphorylation of downstream substrates, such as p-Erk1/2 and p-Akt, as expected (see FIG. 2C, panel C). Moreover, as expected, treatment with ROS siRNA resulted in increased apoptosis of the HCC78 cell line (but not in the control cell line H2066) as determined by detection of cleaved PARP (see FIG. 2B, panel B). 80% of the cells were killed 3 days following transfection with ROS siRNA as shown in FIG. 2A, panel A. Such results indicate that the mutant/truncated ROS kinase in the HCC78 cell line is driving the proliferation and growth of these NSCLC cells, and that such growth and proliferation may be inhibited by using siRNA to inhibit ROS kinase expression.

Example 5

Isolation & Sequencing of SLC34A2-ROS Fusion Gene

Given the presence of the truncated form of ROS kinase detected in an NSCLC cell line (HCC78), 5' rapid amplification of cDNA ends on the sequence encoding the kinase domain of ROS was conducted in order to determine whether a chimeric ROS transcript was present.

Rapid Amplification of Complementary DNA Ends

RNeasy Mini Kit (Qiagen) was used to extract RNA from HCC78 cell line. DNA was extracted with the use of DNeasy Tissue Kit (Qiagen). Rapid amplification of cDNA ends was performed with the use of 5' RACE system (Invitrogen) with primers ROS-GSP1 for cDNA synthesis and ROS-GSP2 and ROS-GSP3 for a nested PCR reaction.

PCR Assay

For RT-PCR, first-strand cDNA was synthesized from 2.5 µg of total RNA with the use of SuperScript® III first-strand synthesis system (Invitrogen) with oligo $(dT)_{20}$ (commercially available from Invitrogen, Carlsbad, Calif., Catalog No. 18080) Then, the SLC34A2-ROS fusion gene was amplified with the use of primer pairs SLCROS-F1 and SLCROS-R1, SLCROS-F2 and SLCROS-R2.

Constructs

The open reading frame of the SLC34A2-ROS fusion gene was amplified by PCR from cDNA of HCC78 cells with the use of Platinum Taq DNA polymerase high fidelity (Invitrogen) and primer pairs SLC-Fb and ROS-Rb (with Bgl II restriction site). This PCR product was cloned in the retroviral vector MSCV-Neo. Primers were:

ROS-GSP1:
(SEQ ID NO: 9)
ACCCTTCTCGGTTCTTCGTTTCCA

ROS-GSP2:
(SEQ ID NO: 10)
GCAGCTCAGCCAACTCTTTGTCTT

ROS-GSP3:
(SEQ ID NO: 11)
TGCCAGACAAAGGTCAGTGGGATT

SLCROS-F1:
(SEQ ID NO: 18)
TCCATCCCAGCACCTGCGGAG

SLCROS-R1:
(SEQ ID NO: 20)
CTCAACTCTCTATTTCCCAAACAACGC

SLCROS-F2:
(SEQ ID NO: 19)
CATGGCTCCCTGGCCTGAATTG

SLCROS-R2:
(SEQ ID NO: 21)
CAACGCTATTAATCAGACCCATCTCC

-continued

SLC-Fb:
(SEQ ID NO: 33)
GAAGATCTCTGACCATGGCTCCCTGGCCTGAA

ROS-Rb:
(SEQ ID NO: 34)
GAAGATCTACGCTATTAATCAGACCCATCTCC

Figure 3A:
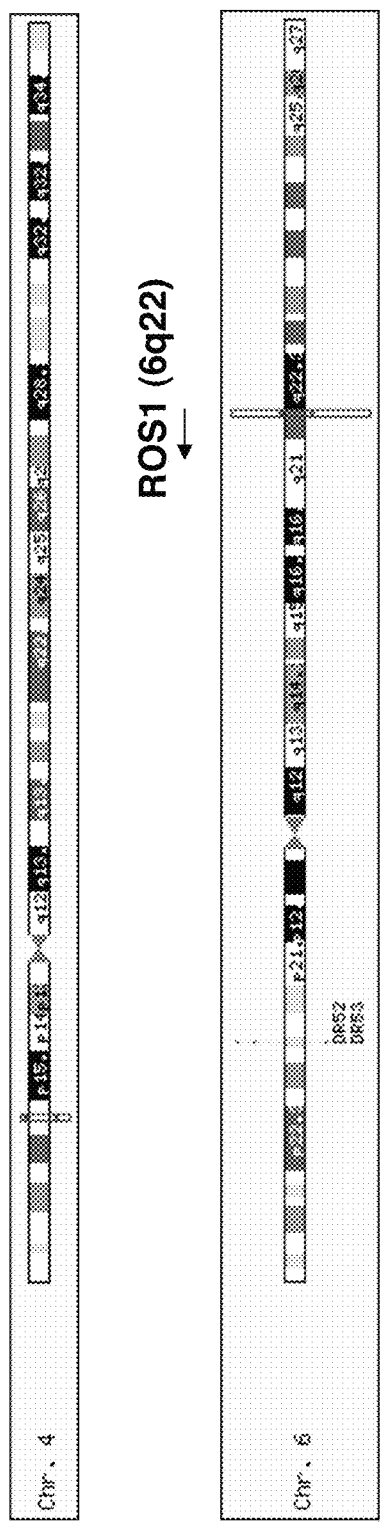
FIGS. 3A-3B—show the location of the SLC34A2 gene and ROS gene on chromosomes 4p and 6q respectively (FIG. 3A), and the domain locations of full length SLC34A2 and ROS proteins (FIG. 3B).
Figure 3B:
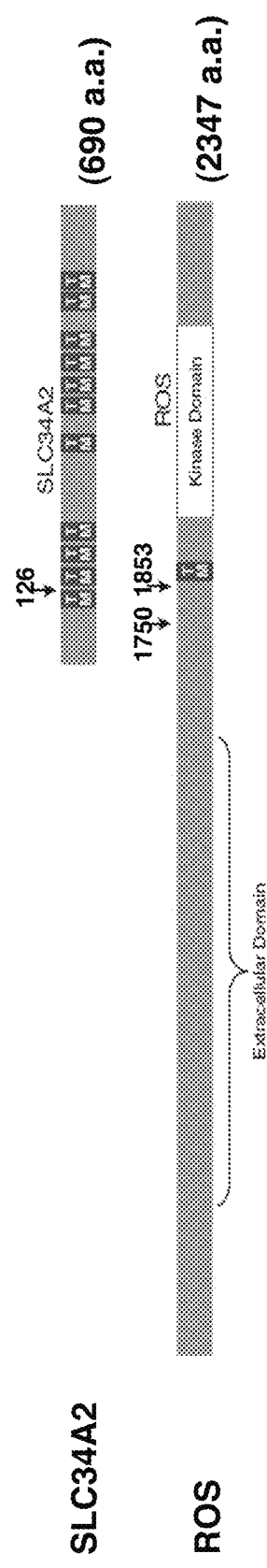
Figure 3C:
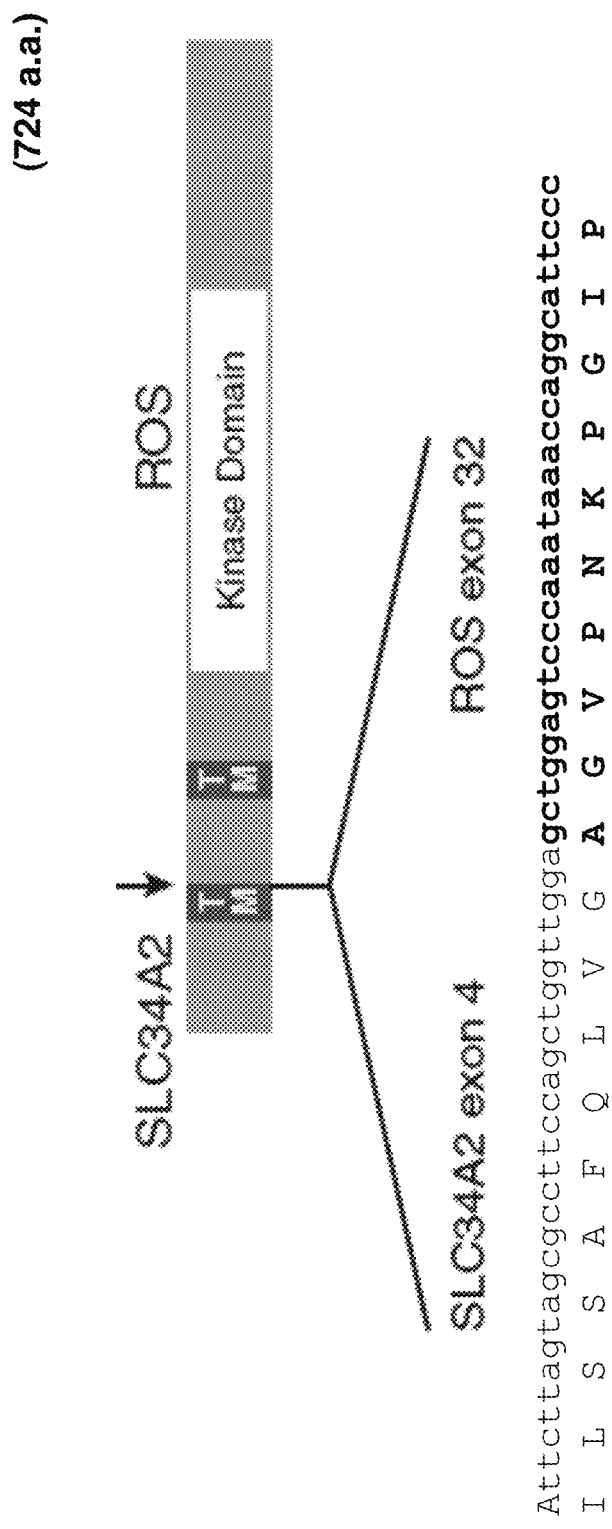
FIG. 3C—is a schematic diagram showing the long SCL34A2-ROS variant, where exons 1-4 of SCL34A2 combine with exons 32-43 of ROS. The fusion junction occurs at residue 1750 upstream of the transmembrane domain of ROS, and the nucleotides and amino acid residues (SEQ ID NO: 12 and SEQ ID NO: 13, respectively) flanking the fusion junction are shown at the bottom of FIG. 3C (with the nucleotides and amino acid residues from SCL34A2 in regular font and the nucleotides and amino acid residues from ROS in bolded text).
Figure 3D:
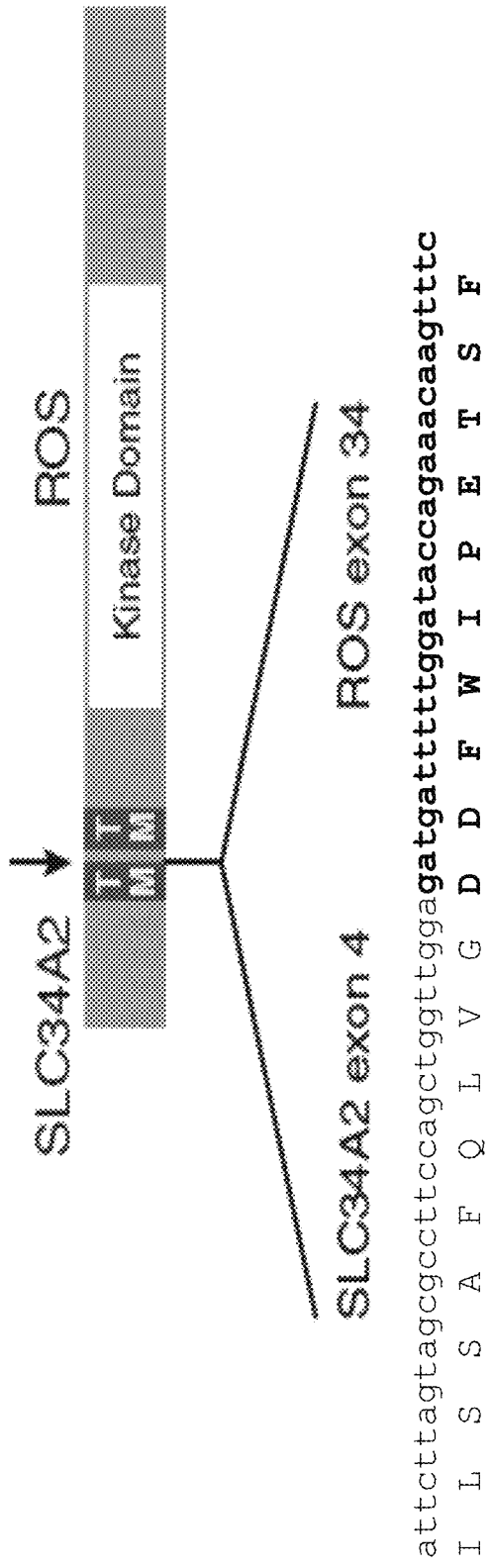
FIG. 3D—is a schematic diagram showing the short SCL34A2-ROS variant, where exons 1-4 of SCL34A2 combine with exons 32-43 of ROS. The fusion junction occurs at residue 1853 just upstream of the transmembrane domain of ROS, and the nucleotides and amino acid residues (SEQ ID NO: 14 and SEQ ID NO: 15, respectively) flanking the fusion junction are shown at the bottom of FIG. 3D (with the nucleotides and amino acid residues from SCL34A2 in regular font and the nucleotides and amino acid residues from ROS in bolded text).
Figure 3E:
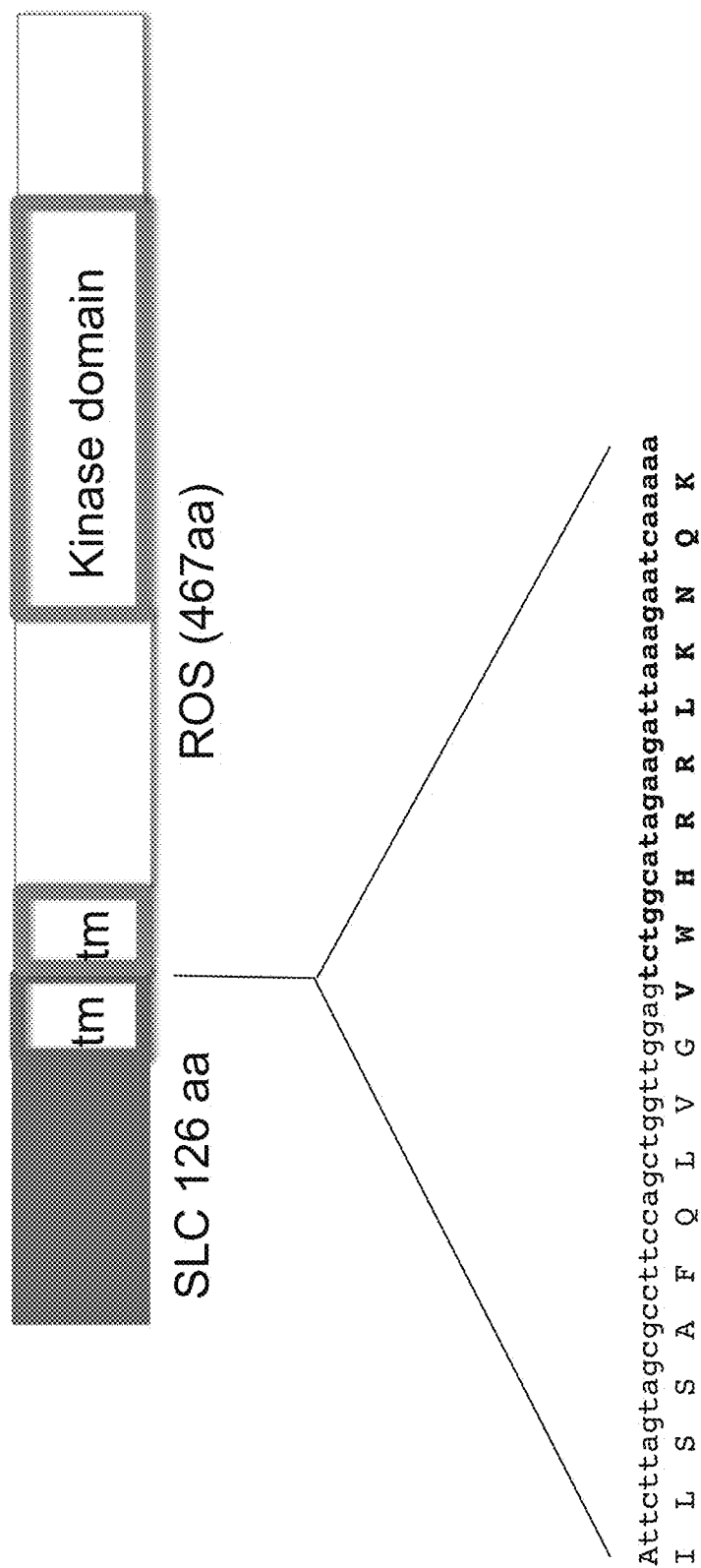
FIG. 3E—is a schematic diagram showing the predicted very short SCL34A2-ROS variant, where exons 1-4 of SCL34A2 combine with exons 35-43 of ROS. The fusion junction is predicted to occur at residue 1882 of ROS, at the N-terminal border of the transmembrane domain of ROS, and the nucleotides and amino acid residues (SEQ ID NO: 16 and SEQ ID NO: 17, respectively) flanking the fusion junction are shown at the bottom of FIG. 3E (with the nucleotides and amino acid residues from SCL34A2 in regular font and the nucleotides and amino acid residues from ROS in bolded text).

The PCR amplification product was detected after 2 rounds. Analysis of the sequence 5' to ROS by 5' RACE then identified that the kinase was fused to the N-terminus of SLC34A2. Sequence analysis of the resultant product revealed that the c-terminal of ROS was fused to SLC34A2 gene N-terminus (see FIGS. 3C and 3D). The SLC34A2-ROS fusion gene was in-frame and fused the first 126 amino acids of SLC34A2 to the last 598 or 495 amino acids of ROS (see FIG. 3B, with the arrow at 1750 showing the break for the C'terminal 598 amino acids and the arrow at 1853 showing the break for the C'terminal 495 amino acids), respectively resulting in two variant fusion protein (long, short). An analysis of the gene structure predicted another variant, the very short variant, which is expected to comprise the first 126 amino acids of SLC34A2 with the last 467 amino acids of ROS (see FIG. 3E). SLC34A2 was located on chromosome 4p15, whereas ROS was on chromosome 6q22. Thus, the fusion gene was created by t(4;6) (p15;q22). See FIG. 3A.

The amino acid and nucleic acid sequences of the predicted SLC34A2-ROS(VS) (i.e., very short variant) are provided in SEQ ID NOs: 28 and 29, respectively.

The sequences of the SLC34A2 fusions are shown in FIG. 4A (long variant, amino acid sequence upper, nucleic acid sequence lower) and FIG. 4B (short variant, amino acid upper, nucleic acid lower). The amino acid and nucleic acid sequence of human SLC34A2 protein are provided in FIG. 5, where the residues involved in the translocation are underline.

Similarly, the amino acid sequence and nucleic acid sequence of human ROS protein are shown in FIGS. 6A and 6B, respectively. In FIGS. 6A and 6B, the residues involved in the long variant are underlined, the underlined bold residues are those involved in the (short) variant translocation, and the underlined, bold, red residues are those predicted to be involved in the predicted (very short) variant translocation.

The fusion of SLC34A2 and ROS for the short and long versions were confirmed by reverse-transcriptase-PCR on RNA.

Example 6

SLC34A2-ROS Fusion Protein Drives Growth and Survival of Transfected 293 Cells

In order to confirm that expression of the SLC34A2-ROS fusion protein can transform normal cells into a cancerous phenotype, human embryonic kidney cells (293 cells) were transfected with the cDNA construct described above, encoding the long variant of SLC34A2-ROS fusion protein.

Figure 7:
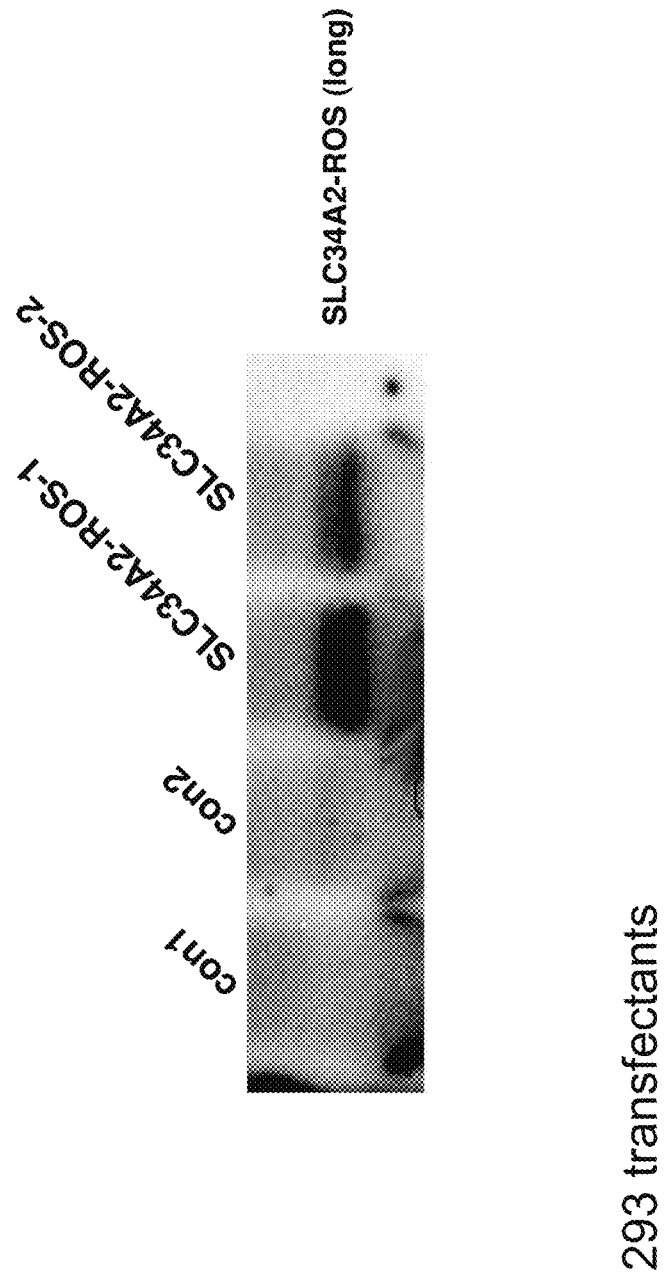
FIG. 7—is a gel showing expression of the SLC34A2-ROS fusion protein (first (long) variant) in transfected 293 cells (human embryonic kidney), as compared to controls (lanes 1 and 2).

The SLC34A2-ROS cDNA construct described above (encoding the long variant fusion protein) was inserted into a MSCV virus vector and transfected into HEK293 cells using SuperFect transfection reagent (commercially available from Qiaqen, Valencia, Calif.). 48 hours later, transfected HEK293 cells were harvested and checked by Western blot to confirm the expression of the recombinant SLC34A2-ROS fusion protein (long variant) of the expected molecular weight (see FIG. 7).

Example 7

SLC34A2-ROS Fusion Protein Drives Growth and Survival of Transformed Mammalian Cell Line In order to confirm that expression of the SLC34A2-ROS fusion protein can transform normal cells into a cancerous phenotype, 3T3 cells may be transformed with a cDNA construct described above. Cells are maintained in DMEM medium (Invitrogen) with 10% fetal calf serum (FCS) (Invitrogen, Carslbad, Calif.).

Production of retroviral supernatant and transduction are carried out as previously described. See Schwaller et al., Embo J. 17(18): 5321-33 (1998). 3T3 cells are transduced with retroviral supernatant containing either the MSCV-Neo or MSCV-Neo/SLC34A2-ROS (long) or MSCV-Neo/ROS (short) vectors, respectively, and selected for G418 (500 ug/ml). Stably transfected cells will be used in soft agar assay to confirm SLC34A2-ROS will transform 3T3 cells.

Such analysis would confirm whether the expression of SLC34A2-ROS fusion protein transforms 3T3 cells so that the cell growth will become attachment independent. Western blot analysis is then performed to check phosphorylation status of ROS, SLC34A2, SHP-1 and other possible ROS downstream targets.

Example 8

Isolation & Sequencing of CD74-ROS Fusion Gene

A second batch of several human NSCLC tumors (including the tumor from patient CD042) were also screened using the IAP technique of global phosphopeptide profiling using the methods described in Examples 1 and 2. Phosphorylated ROS kinase was detected in patient CD042. To determine whether this ROS kinase present in this patient was a fusion between the SLC34A2 protein and the ROS kinase protein, 5' rapid amplification of cDNA ends on the sequence encoding the kinase domain of ROS was conducted in order to determine whether a chimeric ROS transcript was present in those patients. Interestingly, as described below, another ROS fusion gene was found using this method, namely a fusion between CD74 and ROS.

As described in Example 4, RNeasy Mini Kit (Qiagen, Valencia, Calif.) was used to extract RNA from the tumor tissue. The 5' RACE system (commercially available from Invitrogen (part of Life Technologies, Inc.), Carlsbad, Calif.) was used with primers ROS-GSP1 for cDNA synthesis and ROS-GSP2 and ROS-GSP3 for a nested PCR reaction PCR Assay For RT-PCR, first-strand cDNA was synthesized from 2.5 µg of total RNA with the use of SuperScript® III first-strand synthesis system (Invitrogen) with oligo (dT)$_{20}$ (Invitrogen Cat. No. 18080). Then, the CD74-ROS fusion gene was amplified with the use of primer pairs CD74-F1 and ROS-GSP3:

ROS-GSP1:
(SEQ ID NO: 9)
ACCCTTCTCGGTTCTTCGTTTCCA

ROS-GSP2:
(SEQ ID NO: 10)
GCAGCTCAGCCAACTCTTTGTCTT

ROS-GSP3:
(SEQ ID NO: 11)
TGCCAGACAAAGGTCAGTGGGATT

-continued

CD74-F1:
(SEQ ID NO: 26)
GCAGAATGCCACCAAGTATGGCAA

Sequence analysis of the resultant product revealed that the c-terminal of ROS was fused to CD74 gene N-terminus (see FIGS. 8B and C, panels B and C). The CD74-ROS fusion gene was in-frame and fused the first 208 amino acids of CD74 to the last 495 amino acids of ROS (see FIG. 8, panel B), resulting in a fusion protein. CD74 was located on chromosome 5q32, whereas ROS was on chromosome 6q22 (see FIG. 8A, panel A). Thus, the fusion gene was created by t(5,6)(q32;q22).

The sequence of CD74-ROS is provided in FIG. 9 (upper, amino acid sequence; lower, nucleotide sequence). As shown in FIG. 9, the residues from CD74 are underlined while the residues of the ROS kinase domain are shown in bold-face type.

FIG. 10 shows the sequence (amino acid upper and nucleic acid lower) of human CD74, where the residues present in the CD74-ROS fusion are underlined. Similarly, FIGS. 11A and 11B show the amino acid and nucleic acid sequence of human ROS, where the residues present in the CD74-ROS fusion are underlined.

Figure 12:
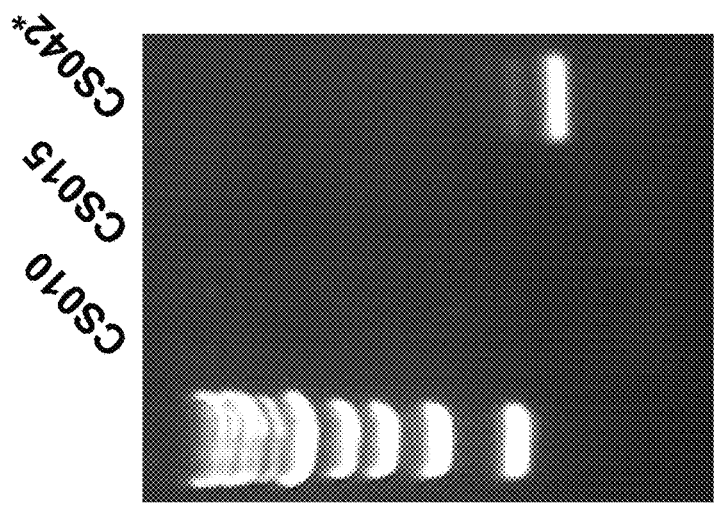
FIG. 12—is the gel depicting the detection of the fusion gene formed by the CD74 and ROS translocation by RT-PCR; with primer sequences shown for CD74-F1 (top) and ROS-GSP3 (bottom) (SEQ ID NOs: 26 and 27, respectively).

The fusion of CD74 and ROS was confirmed by reverse-transcriptase-PCR on RNA. FIG. 12 is an agarose gel showing the RT-PCR product resulting from PCR with the indicated primers.

Example 9

Detection of ROS Kinase Protein by Immunohistochemistry (IHC)

To determine whether or not the ROS fusion proteins discovered in NSCLC could be detected by immunohistochemistry, a ROS-specific rabbit monoclonal antibody was used. The ROS-specific antibody (namely rabbit monoclonal antibody ROS1 D4D6) that was used in these studies has been described previously (see PCT Publication No. WO2010/093928), and specifically binds a region on the human ROS kinase protein that is C-terminal to the kinase domain of the ROS protein. While the D4D6 antibody is not yet commercially available, similar ROS-specific antibodies are commercially available from a variety of suppliers including, without limitation, the Ros (C-20) antibody, Catalog No. sc-6347 from Santa Cruz Biotechnology, Inc., (Santa Cruz, Calif.) and the ROS (69D6) antibody, Catalog No #3266 from Cell Signaling Technology, Inc. (Danvers, Mass.).

For these studies, a cohort of 556 human samples of NSCLC tumors were prepared as paraffin blocks. All tumor samples were evaluated by two independent pathologists, and were found to comprise 246 adenocarcinoma, 64 bronchioaveolar carcinoma, 226 squamous and 20 large cell carcinoma cases.

Immunohistochemistry: 4-6 μm tissue sections were deparaffinized and rehydrated through xylene and graded ethanol, respectively (e.g., through three changes of xylene for 5 minutes each, then rehydrated through two changes of 100% ethanol and 2 changes of 95% ethanol, each for 5 minutes). Slides were rinsed in diH$_2$O, then subjected to antigen retrieval in a Decloaking Chamber (Biocare Medical, Concord, Calif.) using 1.0 mM EDTA, pH 8.0 and manufacturer's settings: SP1 125° C. for 30 seconds and SP2 90° C. for 10 seconds. Slides were quenched in 3% H$_2$O$_2$ for 10 minutes, then washed in diH$_2$O. After blocking in Tris buffered saline positive 0.5% Tween-20 (TBST)/5% goat serum in a humidified chamber, slides were incubated overnight at 4° C. with ROS1 (D4D6) XP™ Rabbit mAb at 0.19 μg/ml diluted in SignalStain® Antibody Diluent (#8112 Cell Signaling Technology, Danvers, Mass.). After washing with TBST, detection was performed with either Envisionpositive (Dako, Carpinteria, Calif.) or SignalStain® Boost IHC Detection Reagent (HRP, Rabbit) (catalog #8114 Cell Signaling Technology, Danvers, Mass.) with a 30 minute incubation at room temperature in a humidified chamber. For the SignalStain® Boost IHC slides, After washing the slides (e.g., three times in TBST) the slides were next exposed to NovaRed (Vector Laboratories, Burlingame, Calif.) prepared per the manufacturer's instructions.

Slides were developed for 1 minute and then rinsed in diH$_2$O. Slides were counterstained by incubating in hematoxylin (ready to use commercially available from Invitrogen (Carlsbad, Calif.) Catalog #00-8011) for 1 minute, rinsed for 30 seconds in diH$_2$O, incubated for 20 seconds in bluing reagent (Richard Allan Scientific, Kalamazoo, Mich. (a Thermo Scientific company), Catalog #7301), and then finally washed for 30 seconds in diH$_2$O. Slides were dehydrated in 2 changes of 95% ethanol for 20 seconds each and 2 changes of 100% ethanol for 2 minutes each. Slides were cleared in 2 changes of xylene for 20 seconds each, then air dried. Coverslips were mounted using VectaMount (Vector Laboratories, Burlingame, Calif.). Slides were air dried, then evaluated under the microscope. Images (20×) were acquired using an Olympus CX41 microscope equipped with an Olympus DP70 camera and DP Controller software.

Out of the 556 NSCLC tumors screened by immunohistochemistry with the ROS-specific Rmab ROS1 D4D6, 9 ROS1-positive tumors were identified. The breakdown was as follows:

Of the 246 adenocarcinomas, 8 (or 3.3%) were positive for ROS1 kinase.

Of the 20 large cell carinomas, 1 (or 5.0%) were positive for ROS1 kinase.

Figure 13:
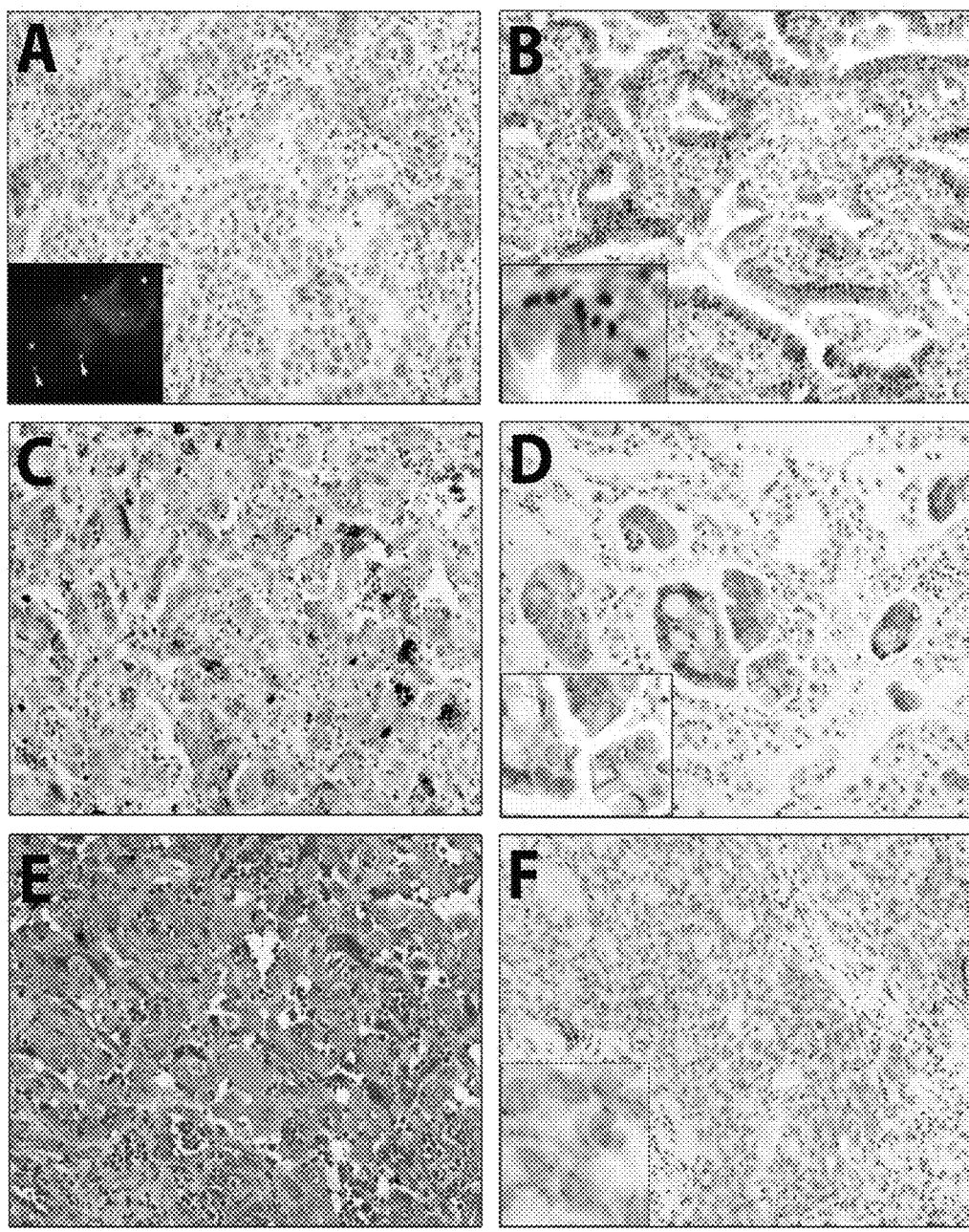
FIGS. 13A-13F—are photographs showing immunohistochemistry and FISH of ROS protein and ROS nucleic acid in non-small cell lung cancer (NSCLC) FFPE tumor tissues. The variation in ROS protein localization are shown as follows: (A) diffuse cytoplasmic with yellow arrows in inset (A) illustrating balanced translocation of the c-ros locus by FISH. (B) Strong punctate localization of ROS in adenocarcinoma with zoom (i.e., enlarged image) in inset. (C) Cytoplasmic localization of ROS staining in large cell carcinoma and corresponding hematoxylin and eosin stain in panel E. (D) Adenocarcinoma with unique cytoplasm staining and membrane localization with zoom in inset showing membrane staining. (E) Hematoxylin and eosin stain corresponding to ROS staining in panel C. (F) Punctate vesicular staining with zoom in inset showing vessicle staining.

A variety of ROS IHC staining patterns ranging from weak cytoplasmic to strong perinuclear aggregates were observed (see FIGS. 13A-F). In 5/9 (55%) cases ROS localized diffusely in the cytoplasm (FIG. 13A). Strong cytoplasmic staining was observed in 1 large cell carcinoma (FIG. 13C). Two cases had unique phenotypes distinct from each other with one being diffuse cytoplasmic with areas of punctate plasma membrane staining (FIG. 13D) and the other vesicular staining throughout (FIG. 13F). It should also be noted that in rare cases non-neoplastic cells such as macrophages and bronchial epithelial cells stained with ROS D4D6. ROS expression was absent in the surrounding stromal tissue.

Example 10

Detection of a ROS Fusion in Human Cancer Samples Using FISH Assay

The presence of either the SLC34A2-ROS fusion protein and/or the CD74-ROS protein (or another ROS fusion protein) in human NSCLC tumor samples was detected using a fluorescence in situ hybridization (FISH) assay, as previously described. See, e.g., Verma et al. HUMAN CHROMOSOMES: A MANUAL OF BASIC TECHNIQUES, Pergamon Press, New York, N.Y. (1988). Over 200 paraffin-embedded human NSCLC tumor samples were examined.

For analyzing rearrangements involving ROS, a dual color break-apart probe was designed. A proximal probe (BAC clone RP1-179P9) and two distal probes (BAC clone RP11-323017, RP1-94G16) (all of which are commercially available, for example, from Invitrogen Inc., Carlsbad, Calif., as Catalog Nos. RPCI1.C and RPCI11.C) were obtained. The locations at which these probes bind to the ROS gene are shown schematically in FIGS. 14A-B. As shown in FIG. 19A, the proximal probe was labeled with Spectrum Orange dUTP, and the distal probes were labeled with Spectrum Green dUTP. Labeling of the probes was done with the Nick Translation DNA Labeling Kit according to manufacturer's instructions (Enzo Life Sciences, Farmingdale, N.Y.). FISH was performed on 4-µm thick FFPE tissue sections according to standard methods. For example, the paraffin embedded tissue sections were re-hydrated and subjected to microwave antigen retrieval in 0.01M Citrate buffer (pH 6.0) for 11 minutes. Sections were digested with Protease (4 mg/ml Pepsin, 2000-3000 U/mg) for 25 minutes at 37° C., dehydrated and hybridized with the FISH probe set at 37° C. for 18 hours. After washing, 4',6-diamidino-2-phenylindole (DAPI; mg/ml) in Vectashield mounting medium (Vector Laboratories, Burlingame, Calif.) was applied for nuclear counterstaining.

FISH-positive cases for ROS were defined as >15% split signals in tumor cells. The Nikon C1 Confocal microscope, 60× objective and trifilter (dapi, TRITC, FITC) was used for scoring each case. For image acquisition the Olympus BX-51 widefield fluorescence microscope with 40× objective and Metamorph software was used to generate tricolor images.

Figure 14:
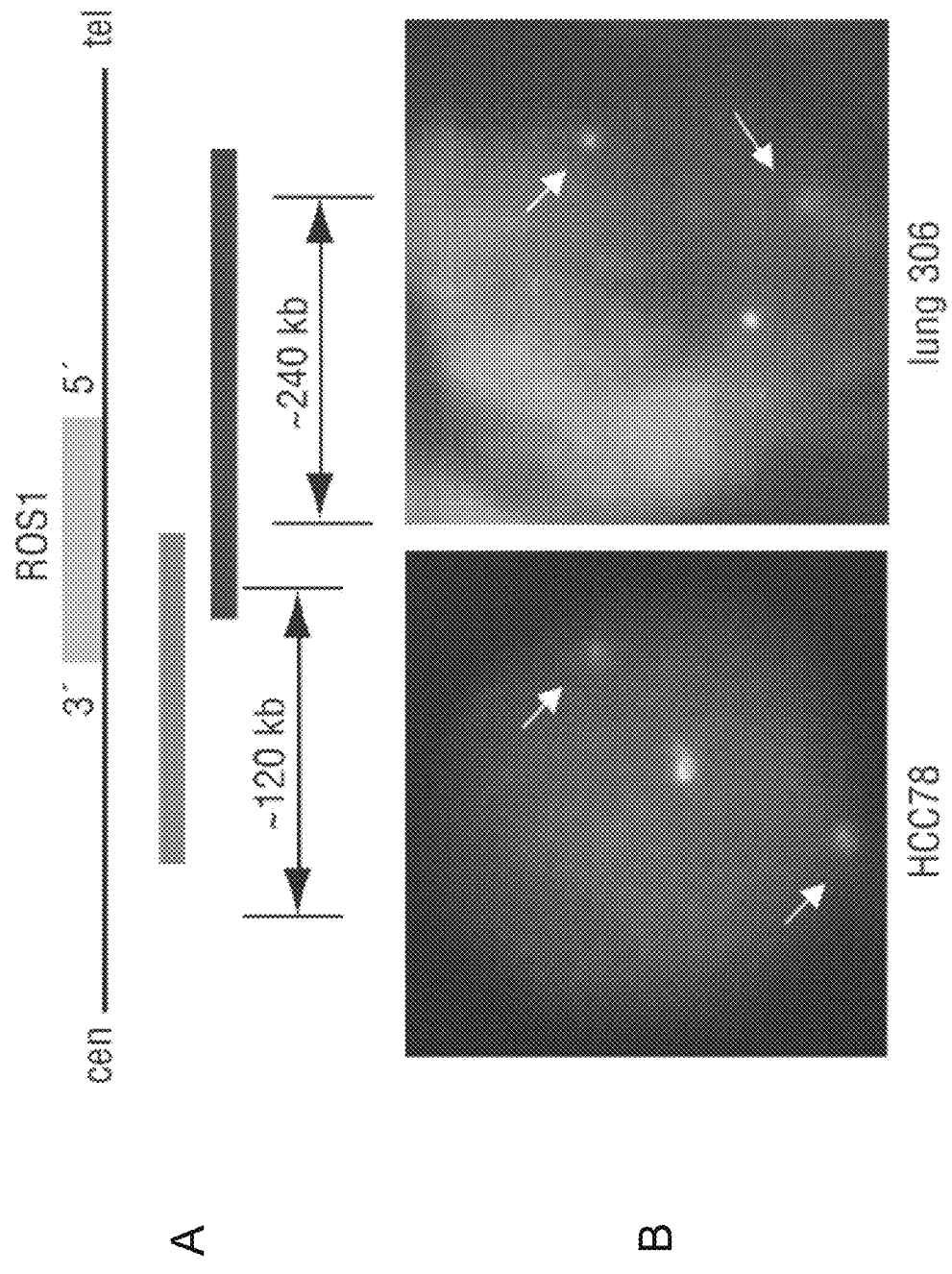
FIGS. 14A and 14B—is an image showing specific detection of the ROS fusion/translocation (in a human NSCLC cell line) by FISH using a 2-color break-a-part probe.

Thus, the ROS rearrangement probe contains two differently labeled probes on opposite sides of the breakpoint of the ROS gene in the wild type (WT) sequence (see FIG. 14A). When hybridized, the native ROS region will appear as an orange/green fusion signal, while rearrangement at this locus (as occurs in the SLC34A2-ROS fusion protein) will result in separate orange and green signals.

As shown in FIG. 14B, a rearranged ROS gene was found in HCC78 (FIG. 14B, left panel) which, as described above, contains a gene rearrangement resulting in the SLC34A2-ROS fusion. In one of the human lung samples, namely lung 306, a similar ROS gene rearrangement was found which may be SLC34A2-ROS or CD74-ROS.

The FISH analysis revealed a low incidence of this ROS mutation in the sample population studied. Of the initial 123 tumors screened, two out of 123 tumors or 1.6% of tumors contained the ROS fusion mutations. However, given the high incidence of NSCLC worldwide (over 15,100 new cases in the U.S. annually, alone), there are expected to be a significant number of patients that harbor this mutant ROS, which patients may benefit from a ROS-inhibiting therapeutic regime.

Example 11

Discovery of FIG-ROS Positive NSCLC Tumor

From Example 9, one of the tumor samples, namely Tumor 749, showed ROS1 staining that was localized to vesicular compartments (see FIG. 13F). This staining pattern is distinct from all other ROS1 positive tumors, which pointed to the possibility of a different ROS1 fusion partner.

To determine what the FISH pattern of this Tumor 749 was, a third distal probe RP11-213A17, was obtained from Invitrogen to further investigate whether the ROS mutation in this tumor might be due to a FIG-ROS fusion. Fusions between the FIG gene and the ROS gene have been described in glioblastoma, cholangiocarcinoma, and liver cancer (see Charest et al., Genes Chromosomes Cancer 37: 58-71, 2003; Charest et al., Proc. Natl. Acad. Sci. USA 100: 916-921, 2003; and PCT Publica NO. WO2010/093928), but this fusion has never been described in lung before. Since the fusion between the FIG gene and the ROS gene results not a translocation or inversion but, rather, results from an intrachromosomal deletion on chromosome 6 of 240 kilobases, a new set of FISH probes was designed.

Figure 15:
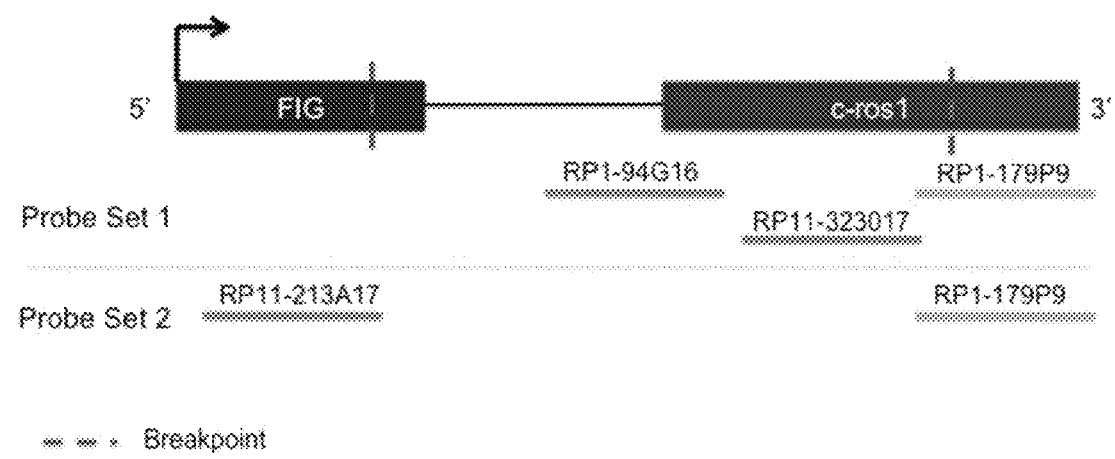
FIG. 15 is a schematic diagram showing where the DNA probes of the two probe sets hybridize to the ROS gene and the FIG gene. The proximal probe of both probe sets, namely RP1-179P9, will give an orange signal while all three distal probes will give a green signal. Probe set 1 was derived from c-ros, and if a balanced translocation occurs, the orange will separated from the green; however if a FIG-ROS translocation occurs, the green signal will disappear. Probe set 2 was derived from c-ros (orange RP1-179P9) and fig (green RP11-213A17).

The FISH probes used in the IHC confirmation testing described previously (see Example 11 above) identified those tumors and cells with ROS balanced translocations that could be due to the presence of one of the SLC34A2-ROS fusion protein or the CD74-ROS fusion protein. The FISH pattern in lung 749 suggested that the rearrangement was not one of these two fusions but potentially that of FIG-ROS. To determine if lung ID 749 was indeed FIG-ROS positive, another FISH probe set was designed (FIG. 15). As described above in Example 11, Probe set 1 containing 179P9 and 323017 BACs flanked either side of the ROS breakpoint in the ROS fusion proteins described herein (e.g., after exon 34, 35, or 36 of ROS) (see FIG. 15 and FIG. 14A). In SLC34A-ROS positive HCC78 cells (see FIG. 14B, left panel and FIG. 16A), probe set 1 results in a balanced translocation. In the FIG-ROS positive human U118MG glioblastoma cell line, the 323017 BAC did not hybridize, since this section of chromosome 6 is deleted, resulting in only orange signals (FIG. 16C). Probe set 2 contained 179P9 located on ROS and 213A7 located on the FIG gene, thus U118MG shows both orange and green signals with this probe set (see FIG. 16D). HCC78 cells showed 1 chromosome with a balanced translocation (e.g., from a SLC34A2-ROS fusion; see the two yellow arrows in FIG. 16B) and the white arrow in FIG. 16B points to a normal chromosome with the green and orange signals close together since the FIG gene and the ROS gene are, in fact, close together on the same chromosome (see FIG. 16B). The wild-type chromosome displayed a separated signal due to the distance between the probes. Lung ID 749, when probed with either probe set 1 (FIG. 16E) or probe set 2 (see FIG. 16F), mimicked that of U118MG cells (FIGS. 16C and D). These data were the first to shown the FIG-ROS fusion as an intrachromosomal deletion on chromosome 6 in NSCLC.

Example 12

Isolation & Sequencing of the FIG-ROS(S) Fusion Gene From Lung Tumor 749

To isolate and sequence the ROS fusion from tumor 749 (which was a Formalin-Fixed, Paraffin-Embedded Tumor), the following protocol was used.

RT-PCR from FFPE tumor samples: RNA from 3×10 µm sections was extracted following standard protocols (RNeasy FFPE Kit, Qiagen). First strand cDNA was synthesized from 500 ng of total RNA with the use of SuperScript III first strand synthesis system (Invitrogen) with gene specific primers. Then the FIG-ROS fusion cDNA was amplified with the use of PCR primer pairs FIG-F3 and ROS-GSP3.1 for the short isoform and FIG-F7 and ROS-GSP3.2 for the long isoforms. GAPDH primers were purchased from Qiagen (Valencia, Calif.).

Primers
ROS-GSP3.1:
(SEQ ID NO: 52)
CAGCAAGAGACGCAGAGTCAGTTT

ROS-GSP3.2:
(SEQ ID NO: 10)
GCAGCTCAGCCAACTCTTTGTCTT

FIG-F3:
(SEQ ID NO: 53)
GCTGTTCTCCAGGCTGAAGTATATGG

-continued

FIG-F7:
(SEQ ID NO: 54)
GTAACCCTGGTGCTAGTTGCAAAG

The primers for FIG were selected because based on the FISH patterns observed in tumor 749 and the published information on the FIG-ROS fusion, tumor 749 was expected to be a FIG-ROS fusion.

As predicted, the ROS fusion protein in tumor 749 was indeed a FIG-ROS fusion, specifically the FIG-ROS (S) fusion previously described (see PCT Publication No. WO2010/0923828). FIG. 17 shows an alignment of the sequence from the FFPE block from tumor 749 (in the "sbjct" line) with the sequence from the FIG-ROS(S) described in PCT Publication No. WO2010/0923828 (in "query" line). As shown in FIG. 17, the identity was 100% with 0 gaps. Since FIG-ROS(S) contains the entire kinase domain of ROS kinase, this FIG-ROS(S) is expected to retain kinase activity and, thus, is a protein with ROS kinase activity as described herein.

The amino acid sequence of FIG-ROS(S) is set forth in SEQ ID NO: 58 and the nucleotide sequence of FIG-ROS(S) is set forth in SEQ ID NO: 57.

FIG-ROS(L) in liver cancer has also been described (see PCT Publication No. WO2010/0923828). The amino acid and nucleotide sequence of FIG-ROS(L) is set forth in SEQ ID NOs 56 and 55, respectively. In addition, based on analysis of the gene structure of the FIG and the ROS genes, a third FIG-ROS variant (namely FIG-ROS(XL) has been proposed (see PCT Publication No. WO2010/0923828). The amino acid and nucleotide sequence of FIG-ROS(XL) is set forth in SEQ ID NOs 60 and 59, respectively. Given this finding of FIG-ROS(S) in NSCLC, other variants of FIG-ROS fusion protein may also be found in NSCLC.

Example 13

Detection of ROS Kinase Expression in a Human Lung Cancer Sample Using PCR Assay The presence of aberrantly expressed full length ROS protein or a ROS fusion protein (e.g., one of the SLC34A2-ROS fusion proteins, CD74-ROS fusion protein, or one of the FIG-ROS fusion proteins) in a human lung cancer sample may be detected using either genomic or reverse transcriptase (RT) polymerase chain reaction (PCR), previously described. See, e.g., Cools et al., N. Engl. J. Med. 348: 1201-1214 (2003).

Briefly and by way of example, tumor or pleural effusion samples may be obtained from a patient having NSCLC using standard techniques. PCR probes against truncated ROS kinase, SLC34A2-ROS fusion protein, CD74-ROS, or FIG-ROS are constructed. RNeasy Mini Kit (Qiagen) may be used to extract RNA from the tumor or pleural effusion samples. DNA may be extracted with the use of DNeasy Tissue Kit (Qiagen). For RT-PCR, first-strand cDNA is synthesized from, e.g., 2.5 mg of total RNA with the use, for example, of SuperScript® III first-strand synthesis system (Invitrogen) with oligo (dT)$_{20}$. Then, the ROS gene or ROS fusion gene (e.g., SLC34A2-ROS, CD74-ROS, or FIG-ROS) is amplified with the use of primer pairs, e.g. SLC34A2-F1 and ROS-P3 (see Example 5 above). For genomic PCR, amplification of the fusion gene may be performed with the use of Platinum Taq DNA polymerase high fidelity (Invitrogen) with primer pairs, e.g. SLC34A2-F1 and ROS-R1, or SLC34A2-F1 and ROS-R2.

Such an analysis will identify a patient having a cancer characterized by expression of the truncated ROS kinase (and/or ROS fusion protein such as FIG-ROS, SLC34A2-ROS, or CD74-ROS), which patient is a candidate for treatment using a ROS-inhibiting therapeutic.

Example 14

Sensitivity of ROS Kinase Fusions to TAE-684 and Crizotinib

The small molecule, TAE-684, a 5-chloro-2,4-diamino-phenylpyrimidine, inhibits the ALK kinase. The structure of TAE-684 is provided in Galkin, et al., Proc. National Acad. Sci 104(1) 270-275, 2007, incorporated by reference. Another small molecule, namely crizotinib, also inhibits the ALK kinase, as well as the MET kinase. The structure of crizotinib (also called PF-02341066) is provided in Zou H Y et al., Cancer Research 67: 4408-4417, 2007 and U.S. Patent Publication No. 20080300273, incorporated by reference.

Whether TAE-684 and/or crizotinib also inhibits ROS fusion polypeptides was determined.

BaF3 and Karpas 299 cells were obtained from DSMZ (Deutsche Sammlung von Mikroorganismen and Zellkulturen GmbH, Germany). BaF3 cells, which need interleukin-3 to survive, were maintained at 37° C. in RPMI-1640 medium (Invitrogen) with 10% fetal bovine serum (FBS) (Sigma) and 1.0 ng/ml murine IL-3 (R&D Systems). Karpas 299 cells (a lymphoma cell line) were grown in RPMI-1640 with 10% FBS.

BaF3 cells were transduced with retrovirus encoding FIG-ROS(S), FIG-ROS(L), or FLT-3ITD (the Internal tandem duplication mutation in FLT3 causes AML leukemia), and selected for IL3 independent growth. Karpas 299 cells, which express NPM-ALK, was used as a positive control. Retroviruses were generated as previously described (see PCT Publication No. WO 2010/093928, incorporated by reference).

A MTS assay was performed using the CellTiter 96 Aqueous One Solution Reagent (Promega, Catalog No G3582). Briefly, 1×10⁵ cells/well in 24 well plates were grown in 1 mL medium that included 0 nM, 3 nM, 10 nM, 30 nM, 100 nM, 300 nM or 1000 nM TAE-684. After 72 hours, 20 µl of the CellTiter 96 Aqueous One Solution Reagent was added into each well of a 96 well assay plate (flat bottom), and then 100 µl of cells grown with or without treatment. Media-only wells were used as controls. The 96 well plate was incubated for 1-4 hours at 37° C., and then viable cells were counted by reading the absorbance at 490 nm using a 96 well plate reader.

Figure 18:
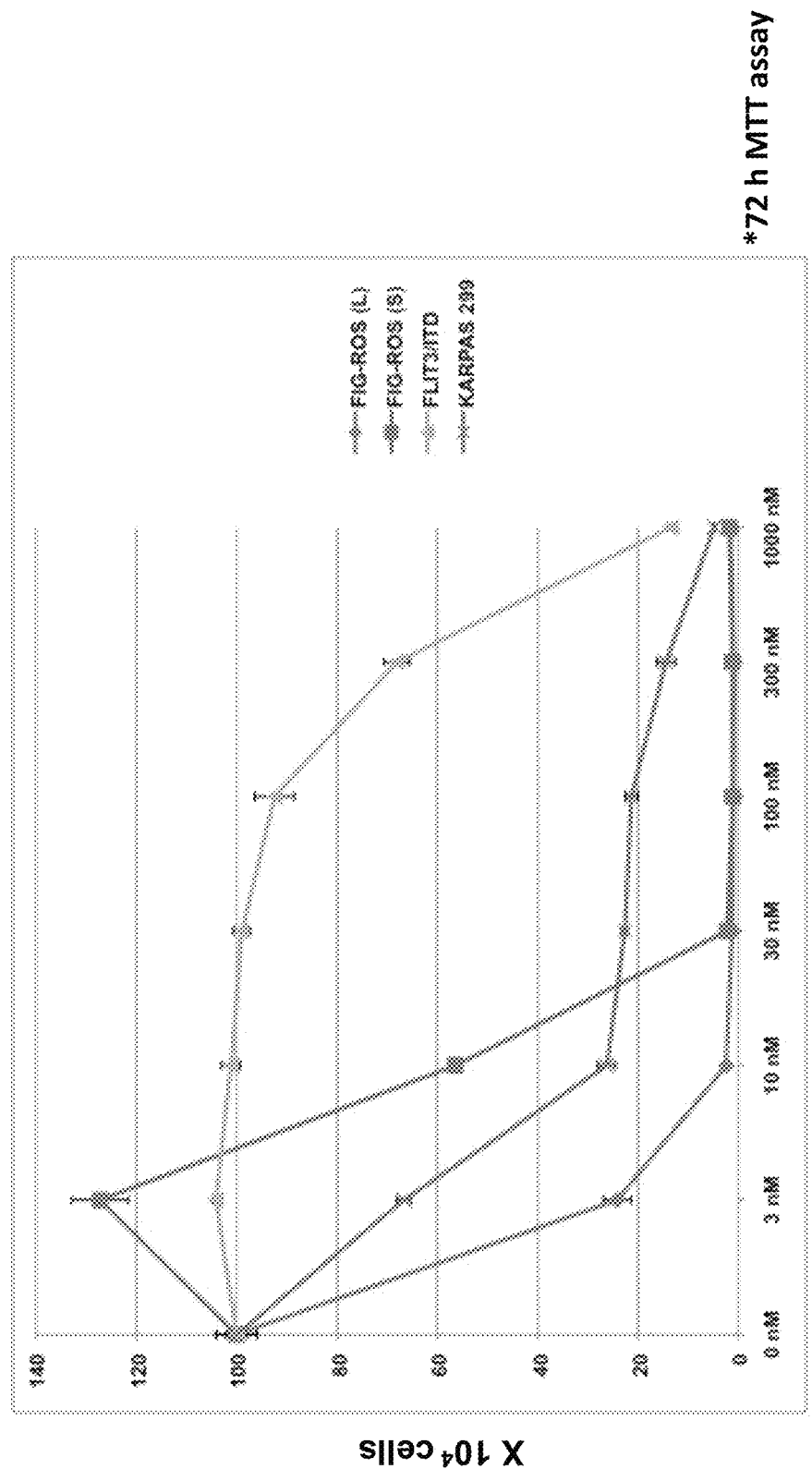
FIG. 18 is a line graph showing the cellular growth response in the presence of 0 nM, 3 nM, 10 nM, 30 nM, 100 nM, 300 nM or 1000 nM TAE-684 of BaF3 expressing FIG-ROS(S) (red squares), BaF3 expressing FIG-ROS(L) (blue diamonds), BaF3 expressing FLT3ITD (green triangles), and Karpas 299 cells (purple Xs).

As shown in FIG. 18, the BaF3 cells transduced with retrovirus expressing one of the FIG-ROS polypeptides stopped growing in the presence of TAE-684. FIG-ROS(S) was less susceptible to TAE-684 than FIG-ROS(L). Karpas 299 cells also responded (i.e., stopped growing) in the presence of TAE-684. The BaF3 cells transduced with FLT3/ITD were not susceptible to TAE-684. The IC50 values from two experiments are as follows in Table 4, with data from a final cell line, namely BaF3 cells expressing myc-tagged neomycin, available only in the second experiment.

TABLE 4

| | TAE-684 | |
|---|---|---|
| | IC50 | IC50 |
| FIG-ROS (L) | 1.78 nM | 2.84 nM |
| FIG-ROS (S) | 10.16 nM | 15.01 nM |
| FLT3/ITD | 419.35 nM | 316.44 nM |
| Neo-Myc | NA | 1641.84 nM |
| Karpas-299 | 4.85 nM | 4.36 nM |

The mechanism of death of the BaF3 and Karpas 299 cells was next assessed by measuring the percentage of cleaved-caspase 3 positive cells by flow cytometry assay using cleaved caspase-3 as a marker for apoptosis. These results were obtained using the protocol publicly available from Cell Signaling Technology, Inc. (Danvers, Mass.). As shown in FIG. 19, the presence of TAE-684 caused the BaF3 cells expressing FIG-ROS(S) or FIG-ROS(L) to die by apoptosis. Karpas 299 cells, which stopped growing in the presence of TAE-684, did not die by apoptosis—they simply underwent cell cycle arrest. Thus, the mechanism by which TAE-684 inhibits FIG-ROS fusion polypeptides is different from the mechanism by which TAE-684 inhibits the ALK kinase.

To further identify the mechanism of action of TAE-684 on the FIG-ROS fusion polypeptides, all four cell lines (i.e., Karpas 299 cells and BaF3 cells transduced with retrovirus encoding FIG-ROS(S), FIG-ROS(L), and FLT-3ITD) were subjected to Western blotting analysis following treatment with 0, 10, 50, or 100 nM TAE-684 for three hours. All antibodies were from Cell Signaling Technology, Inc. (Danvers, Mass.)

As shown in FIG. 20, phosphorylation of both FIG-ROS(S) and FIG-ROS(L) in FIG-ROS(S) and FIG-ROS(L) expressing BaF3 cells was inhibited by TAE-684. In addition, phosphorylation of STAT3, AKT, and ERK, and Shp2 were inhibited in FIG-ROS(S) and FIG-ROS(L) expressing BaF3 cells. The phosphorylation of STAT3, AKT, and ERK, and Shp2 was not affected in the BaF3 cells transduced with the FLT-3ITD retrovirus. TAE-684 also inhibited ALK and ERK phosphorylation in Karpas 299 cells. Since ROS, ALK, LTK, InsR, and IGF1R belong to the same family of tyrosine kinases, they may share similar structure in the kinase domain. Kinase inhibitors or antibodies designed against ALK, LTK, InsR, and IGF1R may have therapeutic effects against ROS kinase.

A parallel set of experiments was next done on the same cells using the same protocols with the addition of another negative control, namely BaF3 cells transduced with the neo-myc tag, to compare two ALK therapeutics, namely TAE-684 and crizotinib.

As shown in FIG. 21A (TAE-684) and FIG. 21B (crizotinib), the FIG-ROS fusion protein-containing BaF3 cells were more sensitive to TAE-684 than to crizotinib at the same concentration of each therapeutic. It may be that crizotinib is not as effective as a similar dose of TAE-684, since even the positive control, namely the NPM-ALK fusion protein-expressing Karpas 299 cells, were not sensitive to crizotinib as compared to TAE-684 at the same concentrations. Both of the negative controls (i.e., BaF3 transduced with FLT3-ITD or BaF3 transduced with neo-myc) were less sensitive to crizotinib and to TAE-684 than the FIG-ROS protein-expressing BaF3 cells and the NPM-ALK protein-expressing Karpas 299.

Figure 22:
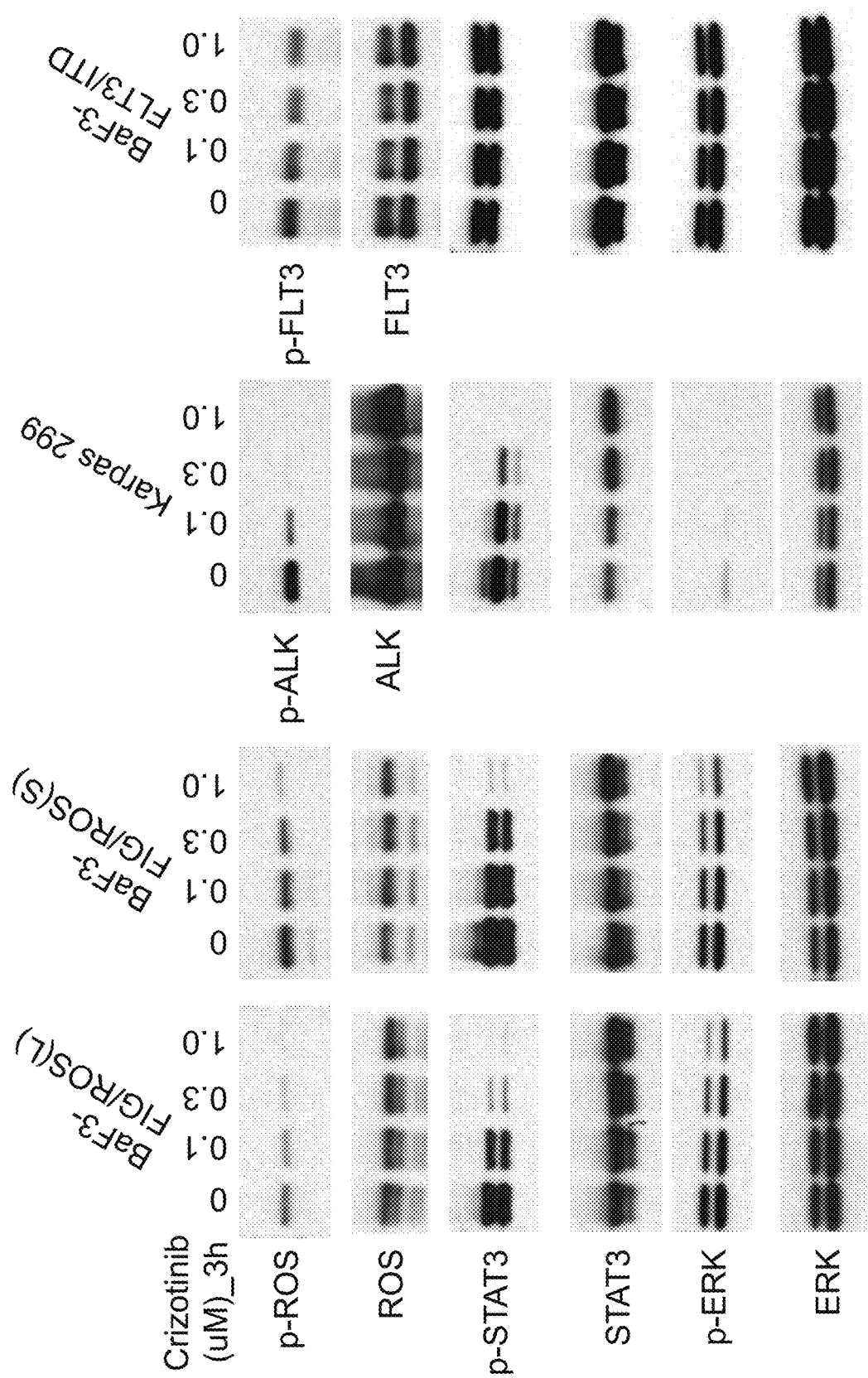
FIG. 22 is a depiction of a Western blotting analysis showing that phosphorylation of both FIG-ROS(S) and FIG-ROS(L), as well as ALK and additional signaling molecules are inhibited by crizotinib.

Western blotting analysis following treatment with 0, 0.1, 0.3, or 1.0 uM crizotinib for three hours was next performed using antibodies available from Cell Signaling Technology, Inc. As shown in FIG. 22, phosphorylation of both FIG-ROS(S) and FIG-ROS(L) in FIG-ROS(S) and FIG-ROS(L) expressing BaF3 cells was inhibited by crizotinib. In addition, phosphorylation of STAT3 and ERK, were inhibited by crizotinib in FIG-ROS(S) and FIG-ROS(L) expressing BaF3 cells. The phosphorylation of STAT3 and ERK was not affected in the BaF3 cells transduced with the FLT-3ITD retrovirus following crizotinib treatment. Crizotinib also inhibited ALK, STAT3 and ERK phosphorylation in Karpas 299 cells. Since ROS, ALK, LTK, InsR, and IGF1R belong to the same family of tyrosine kinases, they may share similar structure in the kinase domain. Kinase inhibitors or antibodies designed against ALK, LTK, InsR, and IGF1R may have therapeutic effects against ROS kinase.

Example 15

Survey of NSCLC Expressing ALK and/or ROS

In addition to ROS kinase, NSCLC have also been described which contain proteins having ALK activity (see, e.g., U.S. Pat. Nos. 7,700,339; 7,605,131; 7,728,120). Using the IHC methods described above in Example 9, numerous FFPE samples of human NSCLC tumors were screened for specific binding by anti-ROS or anti-ALK antibodies. Such antibodies are commercially available from numerous sources.

The same samples were also screened with FISH for the ROS gene or for the ALK gene using standard methods. For example, a FISH protocol for the ROS gene is described in the Examples above. A FISH protocol for the ALK is described in U.S. Pat. No. 7,700,339, herein incorporated by reference. Likewise, another FISH assay is described in US Patent Publication No. 20110110923, incorporated herein by reference). The results of the screening are shown below in Tables 5 (ROS positive samples) and 6 (ALK positive samples).

TABLE 5

Histopathology of ROS1 positive samples

| Patient No. | Tumor ID | Diagnosis | Histologic pattern (%) | ROS1 FISH |
|---|---|---|---|---|
| 1 | 147 | Adenocarcinoma | BAC (40), papillary (30), Acinar (20), Solid (10) | + |
| 2 | 306 | Adenocarcinoma | Acinar (70), papillary (20), and solid (10) | + |
| 3 | 570 | Adenocarcinoma | Acinar (90), BAC (5), micropapillary (5) | + |
| 4 | 400037 | Adenocarcinoma | Acinar | + |
| 5 | 668 | Adenocarcinoma | Solid (80), Acinar (10), BAC (10) | + |
| 6 | 702 | Adenocarcinoma | Papillary (40), Acinar (30), Solid (30) | + |
| 7 | 749 | Adenocarcinoma | Solid (80), Acinar (20) | +, green deletion |
| 8 | 760 | Adenocarcinoma | Signet cells | + |
| 9 | 575 | Large Cell | | Not scoreable |

TABLE 6

Histopathology of ALK positive cases.

| Patient No. | Tumor ID | Diagnosis | Histologic Pattern (%) | ALK FISH |
|---|---|---|---|---|
| 1 | 187 | Adenocarcinoma | Solid Focal signet cell ring features | + |

TABLE 6-continued

Histopathology of ALK positive cases.

| Patient No. | Tumor ID | Diagnosis | Histologic Pattern (%) | ALK FISH |
|---|---|---|---|---|
| 2 | 307 | Adenocarcinoma | BAC (30), Acinar (10), papillary (10), solid (50) clear cell and mucinous features | + |
| 3 | 587 | Adenocarcinoma | Acinar (85), solid (10), papillary (5) | Not scoreable |
| 4 | 618 | Adenocarcinoma | Solid | + |
| 5 | 645 | Adenocarcinoma | Solid (70), BAC (30) | + |
| 6 | 652 | Adenocarcinoma | Papillary (60), Micropapillary (40) | + |
| 7 | 663 | Adenocarcinoma | Papillary (50) BAC (50) | + |
| 8 | 664 | Adenocarcinoma | Acinar | + |
| 9 | 666 | Adenocarcinoma | Solid (90), Papillary (10) | + |
| 10 | 670 | Adenocarcinoma | Solid (60), Papillary (40) | + |
| 11 | 680 | Adenocarcinoma | Solid (70) and acinar (30) with signet ring cell features | + |
| 12 | 759 | Adenocarcinoma | Solid with signet ring cells | + |
| 13 | 580 | Adenocarcinoma (uncertain) | | + |
| 14 | 70 | Adenocarcinoma | Solid | + |
| 15 | 383 | Adenocarcinoma | BAC (40), papillary (30), Acinar (30) | + |
| 16 | 395 | Adenocarcinoma | Solid | + |
| 17 | 278 | Squamous; large cell carcinoma (uncertain) | | + |
| 18 | 330 | Large cell neuroendocrine carcinoma | | + |
| 19 | 503 | Squamous | | + |
| 20 | 615 | Squamous | | + |
| 21 | 644 | Squamous | | + |
| 22 | 691 | Squamous | | + |

Based on this screening of human NSCLC by both IHC and by FISH, it was found that ALK and ROS expression in these tumors is mutually exclusive. In other words, if an NSCLC tumor is driven by ALK, it will not express ROS. Likewise, if an NSCLC tumor is driven by ROS, it will not express ALK. Thus, a therapeutic such as crizotinib or TAE-684 that inhibits both ROS activity and ALK activity will be particularly effective in treating NSCLC.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method, comprising:

performing a PCR assay using a biological sample from primary human lung cancer, wherein
   (i) said PCR assay utilizes a pair of primers which hybridize to a polynucleotide encoding a FIG-ROS fusion polypeptide,
   (ii) said polynucleotide comprises a coding nucleotide sequence selected from the group consisting of SEQ ID NO: 57, SEQ ID NO: 55, and SEQ ID NO: 59,
   (iii) said primers comprise a forward primer which hybridizes under stringent conditions to the 5' side of the fusion junction of said polynucleotide, and a reverse primer which hybridizes under said stringent conditions to the 3' side of the fusion junction of said polynucleotide, and
   (iv) said stringent conditions comprise hybridization at 42° C. in a solution containing 50% formamide, 5×SSC, 50 mM sodium phosphate (pH 7.6), 5×Denhardt's solution, 10% dextran sulfate, and 20 micrograms/ml denatured, sheared salmon sperm DNA, followed by washing in 0.1×SSC at about 65° C.;

detecting an amplification product; and determining the presence of a FIG-ROS fusion polynucleotide in said sample based on detection of the presence of the amplification product.

2. The method of claim 1, wherein the PCR assay is RT-PCR and utilizes mRNA in said sample as template.

3. The method of claim 1, wherein the lung cancer is non-small cell lung carcinoma (NSCLC).

4. The method of claim 1, wherein the biological sample is selected from the group consisting of lung cancer tissue biopsy, pleural effusion, and bronchioalveolar lavage.

* * * * *

SEQUENCE LISTING

```
<160> NUMBER OF SEQ ID NOS: 68

<210> SEQ ID NO 1
<211> LENGTH: 2347
<212> TYPE: PRT
<213> ORGANISM: Artificial Sequence
<220> FEATURE:
<223> OTHER INFORMATION: Synthetic Peptide

<400> SEQUENCE: 1

Met Lys Asn Ile Tyr Cys Leu Ile Pro Lys Leu Val Asn Phe Ala Thr
1               5                   10                  15

Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125
```

-continued

```
Tyr Ile Ile Gln Trp Lys Tyr Ala Gln Leu Leu Gly Ser Trp Thr Tyr
130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
                180                 185                 190

Val Pro Glu Thr Ala Pro Leu Ile Arg Asn Ile Glu Ser Ser Ser Pro
                195                 200                 205

Asp Thr Val Glu Val Ser Trp Asp Pro Pro Gln Phe Pro Gly Gly Pro
210                 215                 220

Ile Leu Gly Tyr Asn Leu Arg Leu Ile Ser Lys Asn Gln Lys Leu Asp
225                 230                 235                 240

Ala Gly Thr Gln Arg Thr Ser Phe Gln Phe Tyr Ser Thr Leu Pro Asn
                245                 250                 255

Thr Ile Tyr Arg Phe Ser Ile Ala Ala Val Asn Glu Val Gly Glu Gly
                260                 265                 270

Pro Glu Ala Glu Ser Ser Ile Thr Thr Ser Ser Ser Ala Val Gln Gln
                275                 280                 285

Glu Glu Gln Trp Leu Phe Leu Ser Arg Lys Thr Ser Leu Arg Lys Arg
290                 295                 300

Ser Leu Lys His Leu Val Asp Glu Ala His Cys Leu Arg Leu Asp Ala
305                 310                 315                 320

Ile Tyr His Asn Ile Thr Gly Ile Ser Val Asp Val His Gln Gln Ile
                325                 330                 335

Val Tyr Phe Ser Glu Gly Thr Leu Ile Trp Ala Lys Lys Ala Ala Asn
                340                 345                 350

Met Ser Asp Val Ser Asp Leu Arg Ile Phe Tyr Arg Gly Ser Gly Leu
                355                 360                 365

Ile Ser Ser Ile Ser Ile Asp Trp Leu Tyr Gln Arg Met Tyr Phe Ile
370                 375                 380

Met Asp Glu Leu Val Cys Val Cys Asp Leu Glu Asn Cys Ser Asn Ile
385                 390                 395                 400

Glu Glu Ile Thr Pro Pro Ser Ile Ser Ala Pro Gln Lys Ile Val Ala
                405                 410                 415

Asp Ser Tyr Asn Gly Tyr Val Phe Tyr Leu Leu Arg Asp Gly Ile Tyr
                420                 425                 430

Arg Ala Asp Leu Pro Val Pro Ser Gly Arg Cys Ala Glu Ala Val Arg
                435                 440                 445

Ile Val Glu Ser Cys Thr Leu Lys Asp Phe Ala Ile Lys Pro Gln Ala
450                 455                 460

Lys Arg Ile Ile Tyr Phe Asn Asp Thr Ala Gln Val Phe Met Ser Thr
465                 470                 475                 480

Phe Leu Asp Gly Ser Ala Ser His Leu Ile Leu Pro Arg Ile Pro Phe
                485                 490                 495

Ala Asp Val Lys Ser Phe Ala Cys Glu Asn Asn Asp Phe Leu Val Thr
                500                 505                 510

Asp Gly Lys Val Ile Phe Gln Gln Asp Ala Leu Ser Phe Asn Glu Phe
                515                 520                 525

Ile Val Gly Cys Asp Leu Ser His Ile Glu Glu Phe Gly Phe Gly Asn
530                 535                 540
```

```
Leu Val Ile Phe Gly Ser Ser Gln Leu His Pro Leu Pro Gly Arg
545                 550                 555                 560

Pro Gln Glu Leu Ser Val Leu Phe Gly Ser His Gln Ala Leu Val Gln
                565                 570                 575

Trp Lys Pro Pro Ala Leu Ala Ile Gly Ala Asn Val Ile Leu Ile Ser
                580                 585                 590

Asp Ile Ile Glu Leu Phe Glu Leu Gly Pro Ser Ala Trp Gln Asn Trp
                595                 600                 605

Thr Tyr Glu Val Lys Val Ser Thr Gln Asp Pro Glu Val Thr His
                610                 615                 620

Ile Phe Leu Asn Ile Ser Gly Thr Met Leu Asn Val Pro Glu Leu Gln
625                 630                 635                 640

Ser Ala Met Lys Tyr Lys Val Ser Val Arg Ala Ser Ser Pro Lys Arg
                645                 650                 655

Pro Gly Pro Trp Ser Glu Pro Ser Val Gly Thr Thr Leu Val Pro Ala
                660                 665                 670

Ser Glu Pro Pro Phe Ile Met Ala Val Lys Glu Asp Gly Leu Trp Ser
                675                 680                 685

Lys Pro Leu Asn Ser Phe Gly Pro Gly Glu Phe Leu Ser Ser Asp Ile
                690                 695                 700

Gly Asn Val Ser Asp Met Asp Trp Tyr Asn Asn Ser Leu Tyr Tyr Ser
705                 710                 715                 720

Asp Thr Lys Gly Asp Val Phe Val Trp Leu Leu Asn Gly Thr Asp Ile
                725                 730                 735

Ser Glu Asn Tyr His Leu Pro Ser Ile Ala Gly Ala Gly Ala Leu Ala
                740                 745                 750

Phe Glu Trp Leu Gly His Phe Leu Tyr Trp Ala Gly Lys Thr Tyr Val
                755                 760                 765

Ile Gln Arg Gln Ser Val Leu Thr Gly His Thr Asp Ile Val Thr His
                770                 775                 780

Val Lys Leu Leu Val Asn Asp Met Val Val Asp Ser Val Gly Gly Tyr
785                 790                 795                 800

Leu Tyr Trp Thr Thr Leu Tyr Ser Val Glu Ser Thr Arg Leu Asn Gly
                805                 810                 815

Glu Ser Ser Leu Val Leu Gln Thr Gln Pro Trp Phe Ser Gly Lys Lys
                820                 825                 830

Val Ile Ala Leu Thr Leu Asp Leu Ser Asp Gly Leu Leu Tyr Trp Leu
                835                 840                 845

Val Gln Asp Ser Gln Cys Ile His Leu Tyr Thr Ala Val Leu Arg Gly
                850                 855                 860

Gln Ser Thr Gly Asp Thr Thr Ile Thr Glu Phe Ala Ala Trp Ser Thr
865                 870                 875                 880

Ser Glu Ile Ser Gln Asn Ala Leu Met Tyr Tyr Ser Gly Arg Leu Phe
                885                 890                 895

Trp Ile Asn Gly Phe Arg Ile Ile Thr Thr Gln Glu Ile Gly Gln Lys
                900                 905                 910

Thr Ser Val Ser Val Leu Glu Pro Ala Arg Phe Asn Gln Phe Thr Ile
                915                 920                 925

Ile Gln Thr Ser Leu Lys Pro Leu Pro Gly Asn Phe Ser Phe Thr Pro
                930                 935                 940

Lys Val Ile Pro Asp Ser Val Gln Glu Ser Ser Phe Arg Ile Glu Gly
945                 950                 955                 960
```

```
Asn Ala Ser Ser Phe Gln Ile Leu Trp Asn Gly Pro Pro Ala Val Asp
                965                 970                 975

Trp Gly Val Val Phe Tyr Ser Val Glu Phe Ser Ala His Ser Lys Phe
            980                 985                 990

Leu Ala Ser Glu Gln His Ser Leu Pro Val Phe Thr Val Glu Gly Leu
        995                 1000                1005

Glu Pro Tyr Ala Leu Phe Asn Leu Ser Val Thr Pro Tyr Thr Tyr
    1010                1015                1020

Trp Gly Lys Gly Pro Lys Thr Ser Leu Ser Leu Arg Ala Pro Glu
    1025                1030                1035

Thr Val Pro Ser Ala Pro Glu Asn Pro Arg Ile Phe Ile Leu Pro
    1040                1045                1050

Ser Gly Lys Cys Cys Asn Lys Asn Glu Val Val Glu Phe Arg
    1055                1060                1065

Trp Asn Lys Pro Lys His Glu Asn Gly Val Leu Thr Lys Phe Glu
    1070                1075                1080

Ile Phe Tyr Asn Ile Ser Asn Gln Ser Ile Thr Asn Lys Thr Cys
    1085                1090                1095

Glu Asp Trp Ile Ala Val Asn Val Thr Pro Ser Val Met Ser Phe
    1100                1105                1110

Gln Leu Glu Gly Met Ser Pro Arg Cys Phe Ile Ala Phe Gln Val
    1115                1120                1125

Arg Ala Phe Thr Ser Lys Gly Pro Gly Pro Tyr Ala Asp Val Val
    1130                1135                1140

Lys Ser Thr Thr Ser Glu Ile Asn Pro Phe Pro His Leu Ile Thr
    1145                1150                1155

Leu Leu Gly Asn Lys Ile Val Phe Leu Asp Met Asp Gln Asn Gln
    1160                1165                1170

Val Val Trp Thr Phe Ser Ala Glu Arg Val Ile Ser Ala Val Cys
    1175                1180                1185

Tyr Thr Ala Asp Asn Glu Met Gly Tyr Tyr Ala Glu Gly Asp Ser
    1190                1195                1200

Leu Phe Leu Leu His Leu His Asn Arg Ser Ser Ser Glu Leu Phe
    1205                1210                1215

Gln Asp Ser Leu Val Phe Asp Ile Thr Val Ile Thr Ile Asp Trp
    1220                1225                1230

Ile Ser Arg His Leu Tyr Phe Ala Leu Lys Glu Ser Gln Asn Gly
    1235                1240                1245

Met Gln Val Phe Asp Val Asp Leu Glu His Lys Val Lys Tyr Pro
    1250                1255                1260

Arg Glu Val Lys Ile His Asn Arg Asn Ser Thr Ile Ile Ser Phe
    1265                1270                1275

Ser Val Tyr Pro Leu Leu Ser Arg Leu Tyr Trp Thr Glu Val Ser
    1280                1285                1290

Asn Phe Gly Tyr Gln Met Phe Tyr Tyr Ser Ile Ile Ser His Thr
    1295                1300                1305

Leu His Arg Ile Leu Gln Pro Thr Ala Thr Asn Gln Gln Asn Lys
    1310                1315                1320

Arg Asn Gln Cys Ser Cys Asn Val Thr Glu Phe Glu Leu Ser Gly
    1325                1330                1335

Ala Met Ala Ile Asp Thr Ser Asn Leu Glu Lys Pro Leu Ile Tyr
    1340                1345                1350
```

-continued

```
Phe Ala Lys Ala Gln Glu Ile Trp Ala Met Asp Leu Glu Gly Cys
1355                1360                1365

Gln Cys Trp Arg Val Ile Thr Val Pro Ala Met Leu Ala Gly Lys
1370                1375                1380

Thr Leu Val Ser Leu Thr Val Asp Gly Asp Leu Ile Tyr Trp Ile
1385                1390                1395

Ile Thr Ala Lys Asp Ser Thr Gln Ile Tyr Gln Ala Lys Lys Gly
1400                1405                1410

Asn Gly Ala Ile Val Ser Gln Val Lys Ala Leu Arg Ser Arg His
1415                1420                1425

Ile Leu Ala Tyr Ser Ser Val Met Gln Pro Phe Pro Asp Lys Ala
1430                1435                1440

Phe Leu Ser Leu Ala Ser Asp Thr Val Glu Pro Thr Ile Leu Asn
1445                1450                1455

Ala Thr Asn Thr Ser Leu Thr Ile Arg Leu Pro Leu Ala Lys Thr
1460                1465                1470

Asn Leu Thr Trp Tyr Gly Ile Thr Ser Pro Thr Pro Thr Tyr Leu
1475                1480                1485

Val Tyr Tyr Ala Glu Val Asn Asp Arg Lys Asn Ser Ser Asp Leu
1490                1495                1500

Lys Tyr Arg Ile Leu Glu Phe Gln Asp Ser Ile Ala Leu Ile Glu
1505                1510                1515

Asp Leu Gln Pro Phe Ser Thr Tyr Met Ile Gln Ile Ala Val Lys
1520                1525                1530

Asn Tyr Tyr Ser Asp Pro Leu Glu His Leu Pro Pro Gly Lys Glu
1535                1540                1545

Ile Trp Gly Lys Thr Lys Asn Gly Val Pro Glu Ala Val Gln Leu
1550                1555                1560

Ile Asn Thr Thr Val Arg Ser Asp Thr Ser Leu Ile Ile Ser Trp
1565                1570                1575

Arg Glu Ser His Lys Pro Asn Gly Pro Lys Glu Ser Val Arg Tyr
1580                1585                1590

Gln Leu Ala Ile Ser His Leu Ala Leu Ile Pro Glu Thr Pro Leu
1595                1600                1605

Arg Gln Ser Glu Phe Pro Asn Gly Arg Leu Thr Leu Leu Val Thr
1610                1615                1620

Arg Leu Ser Gly Gly Asn Ile Tyr Val Leu Lys Val Leu Ala Cys
1625                1630                1635

His Ser Glu Glu Met Trp Cys Thr Glu Ser His Pro Val Thr Val
1640                1645                1650

Glu Met Phe Asn Thr Pro Glu Lys Pro Tyr Ser Leu Val Pro Glu
1655                1660                1665

Asn Thr Ser Leu Gln Phe Asn Trp Lys Ala Pro Leu Asn Val Asn
1670                1675                1680

Leu Ile Arg Phe Trp Val Glu Leu Gln Lys Trp Lys Tyr Asn Glu
1685                1690                1695

Phe Tyr His Val Lys Thr Ser Cys Ser Gln Gly Pro Ala Tyr Val
1700                1705                1710

Cys Asn Ile Thr Asn Leu Gln Pro Tyr Thr Ser Tyr Asn Val Arg
1715                1720                1725

Val Val Val Val Tyr Lys Thr Gly Glu Asn Ser Thr Ser Leu Pro
1730                1735                1740
```

```
Glu Ser Phe Lys Thr Lys Ala Gly Val Pro Asn Lys Pro Gly Ile
1745                1750                1755

Pro Lys Leu Leu Glu Gly Ser Lys Asn Ser Ile Gln Trp Glu Lys
1760                1765                1770

Ala Glu Asp Asn Gly Cys Arg Ile Thr Tyr Tyr Ile Leu Glu Ile
1775                1780                1785

Arg Lys Ser Thr Ser Asn Asn Leu Gln Asn Gln Asn Leu Arg Trp
1790                1795                1800

Lys Met Thr Phe Asn Gly Ser Cys Ser Ser Val Cys Thr Trp Lys
1805                1810                1815

Ser Lys Asn Leu Lys Gly Ile Phe Gln Phe Arg Val Val Ala Ala
1820                1825                1830

Asn Asn Leu Gly Phe Gly Glu Tyr Ser Gly Ile Ser Glu Asn Ile
1835                1840                1845

Ile Leu Val Gly Asp Asp Phe Trp Ile Pro Glu Thr Ser Phe Ile
1850                1855                1860

Leu Thr Ile Ile Val Gly Ile Phe Leu Val Val Thr Ile Pro Leu
1865                1870                1875

Thr Phe Val Trp His Arg Arg Leu Lys Asn Gln Lys Ser Ala Lys
1880                1885                1890

Glu Gly Val Thr Val Leu Ile Asn Glu Asp Lys Glu Leu Ala Glu
1895                1900                1905

Leu Arg Gly Leu Ala Ala Gly Val Gly Leu Ala Asn Ala Cys Tyr
1910                1915                1920

Ala Ile His Thr Leu Pro Thr Gln Glu Glu Ile Glu Asn Leu Pro
1925                1930                1935

Ala Phe Pro Arg Glu Lys Leu Thr Leu Arg Leu Leu Leu Gly Ser
1940                1945                1950

Gly Ala Phe Gly Glu Val Tyr Glu Gly Thr Ala Val Asp Ile Leu
1955                1960                1965

Gly Val Gly Ser Gly Glu Ile Lys Val Ala Val Lys Thr Leu Lys
1970                1975                1980

Lys Gly Ser Thr Asp Gln Glu Lys Ile Glu Phe Leu Lys Glu Ala
1985                1990                1995

His Leu Met Ser Lys Phe Asn His Pro Asn Ile Leu Lys Gln Leu
2000                2005                2010

Gly Val Cys Leu Leu Asn Glu Pro Gln Tyr Ile Ile Leu Glu Leu
2015                2020                2025

Met Glu Gly Gly Asp Leu Leu Thr Tyr Leu Arg Lys Ala Arg Met
2030                2035                2040

Ala Thr Phe Tyr Gly Pro Leu Leu Thr Leu Val Asp Leu Val Asp
2045                2050                2055

Leu Cys Val Asp Ile Ser Lys Gly Cys Val Tyr Leu Glu Arg Met
2060                2065                2070

His Phe Ile His Arg Asp Leu Ala Ala Arg Asn Cys Leu Val Ser
2075                2080                2085

Val Lys Asp Tyr Thr Ser Pro Arg Ile Val Lys Ile Gly Asp Phe
2090                2095                2100

Gly Leu Ala Arg Asp Ile Tyr Lys Asn Asp Tyr Tyr Arg Lys Arg
2105                2110                2115

Gly Glu Gly Leu Leu Pro Val Arg Trp Met Ala Pro Glu Ser Leu
2120                2125                2130
```

| Met | Asp | Gly | Ile | Phe | Thr | Thr | Gln | Ser | Asp | Val | Trp | Ser | Phe | Gly |
|---|---|---|---|---|---|---|---|---|---|---|---|---|---|---|
| | 2135 | | | | 2140 | | | | | 2145 | | | | |

Ile Leu Ile Trp Glu Ile Leu Thr Leu Gly His Gln Pro Tyr Pro
    2150                  2155                    2160

Ala His Ser Asn Leu Asp Val Leu Asn Tyr Val Gln Thr Gly Gly
    2165                  2170                    2175

Arg Leu Glu Pro Pro Arg Asn Cys Pro Asp Asp Leu Trp Asn Leu
    2180                  2185                    2190

Met Thr Gln Cys Trp Ala Gln Glu Pro Asp Gln Arg Pro Thr Phe
    2195                  2200                    2205

His Arg Ile Gln Asp Gln Leu Gln Leu Phe Arg Asn Phe Phe Leu
    2210                  2215                    2220

Asn Ser Ile Tyr Lys Ser Arg Asp Glu Ala Asn Asn Ser Gly Val
    2225                  2230                    2235

Ile Asn Glu Ser Phe Glu Gly Glu Asp Gly Asp Val Ile Cys Leu
    2240                  2245                    2250

Asn Ser Asp Asp Ile Met Pro Val Ala Leu Met Glu Thr Lys Asn
    2255                  2260                    2265

Arg Glu Gly Leu Asn Tyr Met Val Leu Ala Thr Glu Cys Gly Gln
    2270                  2275                    2280

Gly Glu Glu Lys Ser Glu Gly Pro Leu Gly Ser Gln Glu Ser Glu
    2285                  2290                    2295

Ser Cys Gly Leu Arg Lys Glu Glu Lys Glu Pro His Ala Asp Lys
    2300                  2305                    2310

Asp Phe Cys Gln Glu Lys Gln Val Ala Tyr Cys Pro Ser Gly Lys
    2315                  2320                    2325

Pro Glu Gly Leu Asn Tyr Ala Cys Leu Thr His Ser Gly Tyr Gly
    2330                  2335                    2340

Asp Gly Ser Asp
    2345

```
<210> SEQ ID NO 2
<211> LENGTH: 7368
<212> TYPE: DNA
<213> ORGANISM: Artificial Sequence
<220> FEATURE:
<223> OTHER INFORMATION: Synthetic Oligonucleotide

<400> SEQUENCE: 2
```

| | | | | | |
|---|---|---|---|---|---|
| caagctttca | agcattcaaa | ggtctaaatg | aaaaaggcta | agtattattt | caaaaggcaa          60 |
| gtatatccta | atatagcaaa | acaaacaaag | caaaatccat | cagctactcc | tccaattgaa         120 |
| gtgatgaagc | ccaaataatt | catatagcaa | aatggagaaa | attagaccgg | ccatctaaaa         180 |
| atctgccatt | ggtgaagtga | tgaagaacat | ttactgtctt | attccgaagc | ttgtcaattt         240 |
| tgcaactctt | ggctgccat  | ggatttctgt | ggtgcagtgt | acagttttaa | atagctgcct         300 |
| aaagtcgtgt | gtaactaatc | tgggccagca | gcttgacctt | ggcacaccac | ataatctgag         360 |
| tgaaccgtgt | atccaaggat | gtcacttttg | gaactctgta | gatcagaaaa | actgtgcttt         420 |
| aaagtgtcgg | gagtcgtgtg | aggttggctg | tagcagcgcg | gaaggtgcat | atgaagagga         480 |
| agtactggaa | aatgcagacc | taccaactgc | tccctttgct | tcttccattg | aagccacaa          540 |
| tatgacatta | cgatggaaat | ctgcaaactt | ctctggagta | aaatacatca | ttcagtggaa         600 |
| atatgcacaa | cttctgggaa | gctggactta | tactaagact | gtgtccagac | cgtcctatgt         660 |
| ggtcaagccc | ctgcaccccc | tcactgagta | catttttccga | gtggtttgga | tcttcacagc         720 |

-continued

```
gcagctgcag ctctactccc ctccaagtcc cagttacagg actcatcctc atggagttcc      780
tgaaactgca cctttgatta ggaatattga gagctcaagt cccgacactg tggaagtcag      840
ctgggatcca cctcaattcc caggtggacc tattttgggt tataacttaa ggctgatcag      900
caaaaatcaa aaattagatg caggacacag agaaccagt ttccagtttt actccacttt       960
accaaatact atctacaggt tttctattgc agcagtaaat gaagttggtg agggtccaga     1020
agcagaatct agtattacca cttcatcttc agcagttcaa caagaggaac agtggctctt     1080
tttatccaga aaacttctc taagaaagag atctttaaaa catttagtag atgaagcaca      1140
ttgccttcgg ttggatgcta tataccataa tattacagga atatctgttg atgtccacca     1200
gcaaattgtt tatttctctg aaggaactct catatgggcg aagaaggctg ccaacatgtc     1260
tgatgtatct gacctgagaa ttttttacag aggttcagga ttaatttctt ctatctccat     1320
agattggctt tatcaaagaa tgtatttcat catggatgaa ctggtatgtg tctgtgattt     1380
agagaactgc tcaaacatcg aggaaattac tccaccctct attagtgcac ctcaaaaaat     1440
tgtggctgat tcatacaatg ggtatgtctt ttacctcctg agagatggca tttatagagc     1500
agaccttcct gtaccatctg gccggtgtgc agaagctgtg cgtattgtgg agagttgcac     1560
gttaaaggac tttgcaatca agccacaagc caagcgaatc atttacttca atgacactgc     1620
ccaagtcttc atgtcaacat ttctggatgg ctctgcttcc catctcatcc tacctcgcat     1680
cccctttgct gatgtgaaaa gttttgcttg tgaaaacaat gactttcttg tcacagatgg     1740
caaggtcatt ttccaacagg atgctttgtc ttttaatgaa ttcatcgtgg gatgtgacct     1800
gagtcacata gaagaatttg ggtttggtaa cttggtcatc tttggctcat cctcccagct     1860
gcaccctctg ccaggccgcc cgcaggagct ttcggtgctg tttggctctc accaggctct     1920
tgttcaatgg aagcctcctg cccttgccat aggagccaat gtcatcctga tcagtgatat     1980
tattgaactc tttgaattag gcccttctgc ctggcagaac tggacctatg aggtgaaagt     2040
atccacccaa gaccctcctg aagtcactca tattttcttg aacataagtg gaaccatgct     2100
gaatgtacct gagctgcaga gtgctatgaa atacaaggtt tctgtgagag caagttctcc     2160
aaagaggcca ggcccctggt cagagccctc agtgggtact accctggtgc cagctagtga     2220
accaccattt atcatggctg tgaaagaaga tgggctttgg agtaaaccat aaatagctt      2280 tggcccagga gagttcttat cctctgatat aggaaatgtg tcagacatgg attggtataa     2340
caacagcctc tactacagtg acacgaaagg cgacgttttt gtgtggctgc tgaatgggac     2400
ggatatctca gagaattatc acctacccag cattgcagga gcaggggctt tagcttttga     2460
gtggctgggt cactttctct actgggctgg aaagacatat gtgatacaaa ggcagtctgt     2520
gttgacggga cacacagaca ttgttaccca cgtgaagcta ttggtgaatg acatggtggt     2580
ggattcagtt ggtggatatc tctactggac cacactctat tcagtggaaa gcaccagact     2640
aaatggggaa agttcccttg tactacagac acagccttgg ttttctggga aaaaggtaat     2700
tgctctaact ttagacctca gtgatgggct cctgtattgg ttggttcaag acagtcaatg     2760
tattcacctg tacacagctg ttcttcgggg acagagcact ggggatacca ccatcacaga     2820
atttgcagcc tggagtactt ctgaaatttc ccagaatgca ctgatgtact atagtggtcg     2880
gctgttctgg atcaatggct ttaggattat cacaactcaa gaaataggtc agaaaaccag     2940
tgtctctgtt ttggaaccag ccagatttaa tcagttcaca attattcaga catcccttaa     3000
gcccctgcca gggaactttt cctttacccc taaggttatt ccagattctg ttcaagagtc     3060
ttcatttagg attgaaggaa atgcttcaag ttttcaaatc ctgtggaatg gtccccctgc     3120
```

```
ggtagactgg ggtgtagttt tctacagtgt agaatttagt gctcattcta agttcttggc    3180
tagtgaacaa cactctttac ctgtatttac tgtggaagga ctggaacctt atgccttatt    3240
taatctttct gtcactcctt atacctactg gggaaagggc cccaaaacat ctctgtcact    3300
tcgagcacct gaaacagttc catcagcacc agagaacccc agaatatta tattaccaag    3360 tggaaaatgc tgcaacaaga atgaagttgt ggtggaattt aggtggaaca aacctaagca    3420
tgaaaatggg gtgttaacaa aatttgaaat tttctacaat atatccaatc aaagtattac    3480
aaacaaaaca tgtgaagact ggattgctgt caatgtcact ccctcagtga tgtcttttca    3540
acttgaaggc atgagtccca gatgctttat tgccttccag gttagggcct ttacatctaa    3600
ggggccagga ccatatgctg acgttgtaaa gtctacaaca tcagaaatca cccatttcc    3660 tcacctcata actcttcttg gtaacaagat agttttttta gatatggatc aaaatcaagt    3720
tgtgtggacg ttttcagcag aaagagttat cagtgccgtt tgctacacag ctgataatga    3780
gatgggatat tatgctgaag gggactcact ctttcttctg cacttgcaca atcgctctag    3840
ctctgagctt ttccaagatt cactggtttt tgatatcaca gttattacaa ttgactggat    3900
ttcaaggcac ctctactttg cactgaaaga atcacaaaat ggaatgcaag tatttgatgt    3960
tgatcttgaa cacaaggtga atatcccag agaggtgaag attcacaata ggaattcaac    4020
aataatttct ttttctgtat atcctctttt aagtcgcttg tattggacag aagtttccaa    4080
ttttggctac cagatgttct actacagtat tatcagtcac accttgcacc gaattctgca    4140
acccacagct acaaaccaac aaaacaaaag gaatcaatgt tcttgtaatg tgactgaatt    4200
tgagttaagt ggagcaatgg ctattgatac ctctaaccta gagaaaccat tgatatactt    4260
tgccaaagca caagagatct gggcaatgga tctggaaggc tgtcagtgtt ggagagttat    4320
cacagtacct gctatgctcg caggaaaaac ccttgttagc ttaactgtgg atggagatct    4380
tatatactgg atcatcacag caaggacag cacacagatt tatcaggcaa agaaaggaaa    4440
tggggccatc gtttcccagg tgaaggccct aaggagtagg catatcttgg cttacagttc    4500
agttatgcag ccttttccag ataaagcgtt tctgtctcta gcttcagaca ctgtggaacc    4560
aactatactt aatgccacta acactagcct cacaatcaga ttacctctgg ccaagacaaa    4620
cctcacatgg tatggcatca ccagccctac tccaacatac ctggtttatt atgcagaagt    4680
taatgacagg aaaaacagct ctgacttgaa atatagaatt ctggaatttc aggacagtat    4740
agctcttatt gaagatttac aaccatttc aacatacatg atacagatag ctgtaaaaaa    4800
ttattattca gatcctttgg aacatttacc accaggaaaa gagatttggg gaaaaactaa    4860
aaatggagta ccagaggcag tgcagctcat taatacaact gtgcggtcag acaccagcct    4920
cattatatct tggagagaat ctcacaagcc aaatggaccc aaagaatcag tccgttatca    4980
gttggcaatc tcacacctgg ccctaattcc tgaaactcct ctaagacaaa gtgaatttcc    5040
aaatggaagg ctcactctcc ttgttactag actgtctggt ggaaatattt atgtgttaaa    5100
ggttcttgcc tgccactctg aggaaatgtg gtgtacagag agtcatcctg tcactgtgga    5160
aatgtttaac acaccagaga accttattc cttggttcca gagaacacta gtttgcaatt    5220
taattggaag gctccattga atgttaacct catcagattt tgggttgagc tacagaagtg    5280
gaaatacaat gagttttacc atgttaaaac ttcatgcagc caaggtcctg cttatgtctg    5340
taatatcaca aatctacaac cttatacttc atataatgtc agagtagtgg tggtttataa    5400
gacgggagaa aatagcacct cacttccaga aagctttaag acaaaagctg gagtcccaaa    5460
taaaccaggc attcccaaat tactagaagg gagtaaaaat tcaatacagt gggagaaagc    5520
```

-continued

```
tgaagataat ggatgtagaa ttacatacta tatccttgag ataagaaaga gcacttcaaa    5580
taatttacag aaccagaatt taaggtggaa gatgacattt aatggatcct gcagtagtgt    5640
ttgcacatgg aagtccaaaa acctgaaagg aatatttcag ttcagagtag tagctgcaaa    5700
taatctaggt tttggtgaat atagtggaat cagtgagaat attatattag ttggagatga    5760
tttttggata ccagaaacaa gtttcatact tactattata gttggaatat ttctggttgt    5820
tacaatccca ctgacctttg tctggcatag aagattaaag aatcaaaaaa gtgccaagga    5880
aggggtgaca gtgcttataa acgaagacaa agagttggct gagctgcgag gtctggcagc    5940
cggagtaggc ctggctaatg cctgctatgc aatacatact cttccaaccc aagaggagat    6000
tgaaaatctt cctgccttcc ctcgggaaaa actgactctg cgtctcttgc tgggaagtgg    6060
agcctttgga gaagtgtatg aaggaacagc agtggacatc ttaggagttg aagtggaga    6120 aatcaaagta gcagtgaaga cttttgaagaa gggttccaca gaccaggaga agattgaatt    6180
cctgaaggag gcacatctga tgagcaaatt taatcatccc aacattctga agcagcttgg    6240
agtttgtctg ctgaatgaac cccaatacat tatcctggaa ctgatggagg gaggagacct    6300
tcttacttat ttgcgtaaag cccggatggc aacgttttat ggtcctttac tcaccttggt    6360
tgaccttgta gacctgtgtg tagatatttc aaaaggctgt gtctacttgg aacggatgca    6420
tttcattcac agggatctgg cagctagaaa ttgccttgtt ccgtgaaag actataccag    6480 tccacggata gtgaagattg gagactttgg actcgccaga gacatctata aaatgattaa    6540
ctatagaaag agaggggaag gcctgctccc agttcggtgg atggctccag aaagtttgat    6600
ggatggaatc ttcactactc aatctgatgt atggtctttt ggaattctga tttgggagat    6660
tttaactctt ggtcatcagc cttatccagc tcattccaac cttgatgtgt taaactatgt    6720
gcaaacagga gggagactgg agccaccaag aaattgtcct gatgatctgt ggaatttaat    6780
gacccagtgc tgggctcaag aacccgacca aagacctact tttcatagaa ttcaggacca    6840
acttcagtta ttcagaaatt ttttcttaaa tagcatttat aagtccagag atgaagcaaa    6900
caacagtgga gtcataaatg aaagctttga aggtgaagat ggcgatgtga tttgtttgaa    6960
ttcagatgac attatgccag ttgctttaat ggaaacgaag aaccgagaag ggttaaaacta    7020 tatggtactt gctacagaat gtggccaagg tgaagaaaag tctgagggtc ctctaggctc    7080
ccaggaatct gaatcttgtg gtctgaggaa agaagagaag gaaccacatg cagacaaaga    7140
tttctgccaa gaaaaacaag tggcttactg cccttctggc aagcctgaag gcctgaacta    7200
tgcctgtctc actcacagtg gatatggaga tgggtctgat taatagcgtt gtttgggaaa    7260
tagagagttg agataaacac tctcattcag tagttactga aagaaaactc tgctagaatg    7320
ataaatgtca tggtggtcta taactccaaa taaacaatgc aacgttcc              7368
```

<210> SEQ ID NO 3
<211> LENGTH: 690
<212> TYPE: PRT
<213> ORGANISM: Artificial Sequence
<220> FEATURE:
<223> OTHER INFORMATION: Synthetic Peptide

<400> SEQUENCE: 3

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30
```

```
Lys Glu Thr Asn Lys Thr Asp Asn Thr Glu Ala Pro Val Thr Lys Ile
            35                  40                  45

Glu Leu Leu Pro Ser Tyr Ser Thr Ala Thr Leu Ile Asp Glu Pro Thr
 50                  55                  60

Glu Val Asp Asp Pro Trp Asn Leu Pro Thr Leu Gln Asp Ser Gly Ile
 65                  70                  75                  80

Lys Trp Ser Glu Arg Asp Thr Lys Gly Lys Ile Leu Cys Phe Phe Gln
                 85                  90                  95

Gly Ile Gly Arg Leu Ile Leu Leu Gly Phe Leu Tyr Phe Phe Val
                100                 105                 110

Cys Ser Leu Asp Ile Leu Ser Ser Ala Phe Gln Leu Val Gly Gly Lys
            115                 120                 125

Met Ala Gly Gln Phe Phe Ser Asn Ser Ser Ile Met Ser Asn Pro Leu
130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
                180                 185                 190

Ser Ile Thr Asn Thr Ile Val Ala Leu Met Gln Val Gly Asp Arg Ser
                195                 200                 205

Glu Phe Arg Arg Ala Phe Ala Gly Ala Thr Val His Asp Phe Asn
            210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
            275                 280                 285

Asn Asp Glu Lys Ala Lys Asn Lys Ser Leu Val Lys Ile Trp Cys Lys
            290                 295                 300

Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
            355                 360                 365

Leu Ile Leu Ser Leu Leu Val Leu Cys Gly Cys Leu Ile Met Ile Val
            370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
            435                 440                 445
```

Ile Thr Ile Glu Arg Ala Tyr Pro Leu Thr Leu Gly Ser Asn Ile Gly
450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Phe Asn Ile
                485                 490                 495

Ser Gly Ile Leu Leu Trp Tyr Pro Ile Pro Phe Thr Arg Leu Pro Ile
                500                 505                 510

Arg Met Ala Lys Gly Leu Gly Asn Ile Ser Ala Lys Tyr Arg Trp Phe
                515                 520                 525

Ala Val Phe Tyr Leu Ile Ile Phe Phe Phe Leu Ile Pro Leu Thr Val
530                 535                 540

Phe Gly Leu Ser Leu Ala Gly Trp Arg Val Leu Val Gly Val Gly Val
545                 550                 555                 560

Pro Val Val Phe Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
                580                 585                 590

Leu Pro Leu Trp Met Arg Ser Leu Lys Pro Trp Asp Ala Val Val Ser
                595                 600                 605

Lys Phe Thr Gly Cys Phe Gln Met Arg Cys Cys Tyr Cys Cys Arg Val
610                 615                 620

Cys Cys Arg Ala Cys Cys Leu Leu Cys Gly Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
                660                 665                 670

Glu Ala Gln Gly Glu Val Pro Ala Ser Asp Ser Lys Thr Glu Cys Thr
                675                 680                 685

Ala Leu
690

<210> SEQ ID NO 4
<211> LENGTH: 2280
<212> TYPE: DNA
<213> ORGANISM: Artificial Sequence
<220> FEATURE:
<223> OTHER INFORMATION: Synthetic Oligonucleotide

<400> SEQUENCE: 4
cgggccaggt tccaggctc ggccgccgcc tccatcccag cacctgcgga gggagcgctg      60
accatggctc cctggcctga attgggagat gcccagccca ccccgataa gtacctcgaa      120 ggggccgcag gtcagcagcc cactgccct gataaaagca agagaccaa caaaacagat      180 aacactgagg cacctgtaac caagattgaa cttctgccgt cctactccac ggctacactg      240
atagatgagc ccactgaggt ggatgacccc tggaacctac ccactcttca ggactcgggg      300
atcaagtggt cagagagaga caccaaaggg aagattctct gtttcttcca agggattggg      360
agattgattt tacttctcgg atttctctac ttttcgtgt gctccctgga tattcttagt      420
agcgccttcc agctggttgg aggaaaaatg gcaggacagt tcttcagcaa cagctctatt      480
atgtccaacc ctttgttggg gctggtgatc ggggtgctgg tgaccgtctt ggtgcagagc      540
tccagcacct caacgtccat cgttgtcagc atggtgtcct cttcattgct cactgttcgg      600
gctgccatcc ccattatcat gggggccaac attggaacgt caatcaccaa cactattgtt      660

-continued

```
gcgctcatgc aggtgggaga tcggagtgag ttcagaagag cttttgcagg agccactgtc    720
catgacttct tcaactggct gtccgtgttg gtgctcttgc ccgtggaggt ggccacccat    780
tacctcgaga tcataaccca gcttatagtg gagagcttcc acttcaagaa tggagaagat    840
gccccagatc ttctgaaagt catcactaag cccttcacaa agctcattgt ccagctggat    900
aaaaaagtta tcagccaaat tgcaatgaac gatgaaaaag cgaaaaacaa gagtcttgtc    960
aagatttggt gcaaaacttt taccaacaag acccagatta acgtcactgt tccctcgact   1020
gctaactgca cctccccttc cctctgttgg acggatggca tccaaaactg gaccatgaag   1080
aatgtgacct acaaggagaa catcgccaaa tgccagcata tctttgtgaa tttccacctc   1140
ccggatcttg ctgtgggcac catcttgctc atactctccc tgctggtcct ctgtggttgc   1200
ctgatcatga ttgtcaagat cctgggctct gtgctcaagg ggcaggtcgc cactgtcatc   1260
aagaagacca tcaacactga tttccccttt ccctttgcat ggttgactgg ctacctggcc   1320
atcctcgtcg gggcaggcat gaccttcatc gtacagagca gctctgtgtt cacgtcggcc   1380
ttgacccccc tgattggaat cggcgtgata accattgaga gggcttatcc actcacgctg   1440
ggctccaaca tcggcaccac caccaccgcc atcctggccg ccttagccag ccctggcaat   1500
gcattgagga gttcactcca gatcgccctg tgccactttt tcttcaacat ctccggcatc   1560
ttgctgtggt acccgatccc gttcactcgc ctgcccatcc gcatggccaa ggggctgggc   1620
aacatctctg ccaagtatcg ctggttcgcc gtcttctacc tgatcatctt cttcttcctg   1680
atcccgctga cggtgtttgg cctctcgctg gccggctggc gggtgctggt tggtgtcggg   1740
gttcccgtcg tcttcatcat catcctggta ctgtgcctcc gactcctgca gtctcgctgc   1800
ccacgcgtcc tgccgaagaa actccagaac tggaacttcc tgccgctgtg gatgcgctcg   1860
ctgaagccct gggatgccgt cgtctccaag ttcaccggct gcttccagat gcgctgctgc   1920
tactgctgcc gcgtgtgctg ccgcgcgtgc tgcttgctgt gtggctgccc caagtgctgc   1980
cgctgcagca agtgctgcga ggacttggag gaggcgcagg aggggcagga tgtccctgtc   2040
aaggctcctg agacctttga taacataacc attagcagag aggctcaggg tgaggtccct   2100
gcctcggact caaagaccga atgcacggcc ttgtagggga cgccccagat tgtcagggat   2160
gggggggatgg tccttgagtt ttgcatgctc tcctccctcc cacttctgca ccctttcacc   2220
acctcgagga gatttgctcc ccattagcga atgaaattga tgcagtccta aaaaaaaaaa   2280
```

<210> SEQ ID NO 5
<211> LENGTH: 724
<212> TYPE: PRT
<213> ORGANISM: Artificial Sequence
<220> FEATURE:
<223> OTHER INFORMATION: Synthetic Peptide

<400> SEQUENCE: 5

```
Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80
```

```
Lys Trp Ser Glu Arg Asp Thr Lys Gly Lys Ile Leu Cys Phe Phe Gln
                85                  90                  95
Gly Ile Gly Arg Leu Ile Leu Leu Gly Phe Leu Tyr Phe Phe Val
            100                 105                 110
Cys Ser Leu Asp Ile Leu Ser Ser Ala Phe Gln Leu Val Gly Ala Gly
            115                 120                 125
Val Pro Asn Lys Pro Gly Ile Pro Lys Leu Leu Glu Gly Ser Lys Asn
130                 135                 140
Ser Ile Gln Trp Glu Lys Ala Glu Asp Asn Gly Cys Arg Ile Thr Tyr
145                 150                 155                 160
Tyr Ile Leu Glu Ile Arg Lys Ser Thr Ser Asn Asn Leu Gln Asn Gln
                165                 170                 175
Asn Leu Arg Trp Lys Met Thr Phe Asn Gly Ser Cys Ser Ser Val Cys
            180                 185                 190
Thr Trp Lys Ser Lys Asn Leu Lys Gly Ile Phe Gln Phe Arg Val Val
        195                 200                 205
Ala Ala Asn Asn Leu Gly Phe Gly Glu Tyr Ser Gly Ile Ser Glu Asn
        210                 215                 220
Ile Ile Leu Val Gly Asp Asp Phe Trp Ile Pro Glu Thr Ser Phe Ile
225                 230                 235                 240
Leu Thr Ile Ile Val Gly Ile Phe Leu Val Val Thr Ile Pro Leu Thr
                245                 250                 255
Phe Val Trp His Arg Arg Leu Lys Asn Gln Lys Ser Ala Lys Glu Gly
                260                 265                 270
Val Thr Val Leu Ile Asn Glu Asp Lys Glu Leu Ala Glu Leu Arg Gly
            275                 280                 285
Leu Ala Ala Gly Val Gly Leu Ala Asn Ala Cys Tyr Ala Ile His Thr
        290                 295                 300
Leu Pro Thr Gln Glu Glu Ile Glu Asn Leu Pro Ala Phe Pro Arg Glu
305                 310                 315                 320
Lys Leu Thr Leu Arg Leu Leu Gly Ser Gly Ala Phe Gly Glu Val
                325                 330                 335
Tyr Glu Gly Thr Ala Val Asp Ile Leu Gly Val Gly Ser Gly Glu Ile
            340                 345                 350
Lys Val Ala Val Lys Thr Leu Lys Lys Gly Ser Thr Asp Gln Glu Lys
        355                 360                 365
Ile Glu Phe Leu Lys Glu Ala His Leu Met Ser Lys Phe Asn His Pro
        370                 375                 380
Asn Ile Leu Lys Gln Leu Gly Val Cys Leu Leu Asn Glu Pro Gln Tyr
385                 390                 395                 400
Ile Ile Leu Glu Leu Met Glu Gly Gly Asp Leu Leu Thr Tyr Leu Arg
                405                 410                 415
Lys Ala Arg Met Ala Thr Phe Tyr Gly Pro Leu Leu Thr Leu Val Asp
                420                 425                 430
Leu Val Asp Leu Cys Val Asp Ile Ser Lys Gly Cys Val Tyr Leu Glu
            435                 440                 445
Arg Met His Phe Ile His Arg Asp Leu Ala Ala Arg Asn Cys Leu Val
        450                 455                 460
Ser Val Lys Asp Tyr Thr Ser Pro Arg Ile Val Lys Ile Gly Asp Phe
465                 470                 475                 480
Gly Leu Ala Arg Asp Ile Tyr Lys Asn Asp Tyr Tyr Arg Lys Arg Gly
                485                 490                 495
```

```
Glu Gly Leu Leu Pro Val Arg Trp Met Ala Pro Glu Ser Leu Met Asp
                500                 505                 510

Gly Ile Phe Thr Thr Gln Ser Asp Val Trp Phe Gly Ile Leu Ile
            515                 520                 525

Trp Glu Ile Leu Thr Leu Gly His Gln Pro Tyr Pro Ala His Ser Asn
        530                 535                 540

Leu Asp Val Leu Asn Tyr Val Gln Thr Gly Gly Arg Leu Glu Pro Pro
545                 550                 555                 560

Arg Asn Cys Pro Asp Asp Leu Trp Asn Leu Met Thr Gln Cys Trp Ala
                565                 570                 575

Gln Glu Pro Asp Gln Arg Pro Thr Phe His Arg Ile Gln Asp Gln Leu
            580                 585                 590

Gln Leu Phe Arg Asn Phe Phe Leu Asn Ser Ile Tyr Lys Ser Arg Asp
        595                 600                 605

Glu Ala Asn Asn Ser Gly Val Ile Asn Glu Ser Phe Glu Gly Glu Asp
610                 615                 620

Gly Asp Val Ile Cys Leu Asn Ser Asp Asp Ile Met Pro Val Ala Leu
625                 630                 635                 640

Met Glu Thr Lys Asn Arg Glu Gly Leu Asn Tyr Met Val Leu Ala Thr
                645                 650                 655

Glu Cys Gly Gln Gly Glu Glu Lys Ser Glu Gly Pro Leu Gly Ser Gln
            660                 665                 670

Glu Ser Glu Ser Cys Gly Leu Arg Lys Glu Glu Lys Glu Pro His Ala
        675                 680                 685

Asp Lys Asp Phe Cys Gln Glu Lys Gln Val Ala Tyr Cys Pro Ser Gly
690                 695                 700

Lys Pro Glu Gly Leu Asn Tyr Ala Cys Leu Thr His Ser Gly Tyr Gly
705                 710                 715                 720

Asp Gly Ser Asp

<210> SEQ ID NO 6
<211> LENGTH: 2175
<212> TYPE: DNA
<213> ORGANISM: Artificial Sequence
<220> FEATURE:
<223> OTHER INFORMATION: Synthetic Oligonucleotide

<400> SEQUENCE: 6
atggctccct ggcctgaatt gggagatgcc cagcccaacc ccgataagta cctcgaaggg      60
gccgcaggtc agcagcccac tgcccctgat aaaagcaaag agaccaacaa aacagataac     120
actgaggcac ctgtaaccaa gattgaactt ctgccgtcct actccacggc tacactgata     180
gatgagccca ctgaggtgga tgaccccctgg aacctaccca ctcttcagga ctcgggatc     240 aagtggtcag agagagacac caaagggaag attctctgtt tcttccaagg gattgggaga     300
ttgattttac ttctcggatt tctctacttt ttcgtgtgct ccctggatat tcttagtagc     360
gccttccagc tggttggagc tggagtccca aataaaccag gcattcccaa attactagaa     420
gggagtaaaa attcaataca gtgggagaaa gctgaagata tggatgtag aattacatac     480 tatatccttg agataagaaa gagcacttca ataatttac agaaccagaa tttaaggtgg     540
aagatgacat ttaatggatc ctgcagtagt gtttgcacat ggaagtccaa aaacctgaaa     600
ggaatatttc agttcagagt agtagctgca ataatctag ggtttggtga atatagtgga     660
atcagtgaga atattatatt agttggagat gattttggaa taccagaaac aagtttcata     720
cttactatta tagttggaat atttctggtt gttacaatcc cactgacctt tgtctggcat     780
```

```
agaagattaa agaatcaaaa aagtgccaag aagggggtga cagtgcttat aaacgaagac    840
aaagagttgg ctgagctgcg aggtctggca gccggagtag gcctggctaa tgcctgctat    900
gcaatacata ctcttccaac ccaagaggag attgaaaatc ttcctgcctt ccctcgggaa    960
aaactgactc tgcgtctctt gctgggaagt ggagcctttg gagaagtgta tgaaggaaca   1020
gcagtggaca tcttaggagt tggaagtgga gaaatcaaag tagcagtgaa gactttgaag   1080
aagggttcca cagaccagga gaagattgaa ttcctgaagg aggcacatct gatgagcaaa   1140
tttaatcatc ccaacattct gaagcagctt ggagtttgtc tgctgaatga accccaatac   1200
attatcctgg aactgatgga gggagggac cttcttactt atttgcgtaa agcccggatg   1260
gcaacgtttt atggtccttt actcaccttg gttgaccttg tagacctgtg tgtagatatt   1320
tcaaaaggct gtgtctactt ggaacggatg catttcattc acagggatct ggcagctaga   1380
aattgccttg tttccgtgaa agactatacc agtccacgga tagtgaagat tggagacttt   1440
ggactcgcca gagacatcta taaaaatgat tactatagaa agagagggga aggcctgctc   1500
ccagttcggt ggatggctcc agaaagtttg atggatggaa tcttcactac tcaatctgat   1560
gtatggtctt ttggaattct gatttgggag attttaactc ttggtcatca gccttatcca   1620
gctcattcca accttgatgt gttaaactat gtgcaaacag agggagact ggagccacca    1680 agaaattgtc ctgatgatct gtggaattta atgacccagt gctgggctca agaacccgac   1740
caaagaccta cttttcatag aattcaggac caacttcagt tattcagaaa ttttttctta   1800
aatagcattt ataagtccag agatgaagca acaacagtg gagtcataaa tgaaagcttt   1860
gaaggtgaag atggcgatgt gatttgtttg aattcagatg acattatgcc agttgcttta   1920
atggaaacga agaaccgaga agggttaaac tatatggtac ttgctacaga atgtggccaa   1980
ggtgaagaaa agtctgaggg tcctctaggc tcccaggaat ctgaatcttg tggtctgagg   2040
aaagaagaga aggaaccaca tgcagacaaa gatttctgcc aagaaaaaca gtggcttac    2100 tgcccttctg gcaagcctga aggcctgaac tatgcctgtc tcactcacag tggatatgga   2160
gatgggtctg attaa                                                    2175
```

<210> SEQ ID NO 7
<211> LENGTH: 621
<212> TYPE: PRT
<213> ORGANISM: Artificial Sequence
<220> FEATURE:
<223> OTHER INFORMATION: Synthetic Peptide

<400> SEQUENCE: 7

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

```
Cys Ser Leu Asp Ile Leu Ser Ser Ala Phe Gln Leu Val Gly Asp Asp
            115                 120                 125
Phe Trp Ile Pro Glu Thr Ser Phe Ile Leu Thr Ile Ile Val Gly Ile
        130                 135                 140
Phe Leu Val Val Thr Ile Pro Leu Thr Phe Val Trp His Arg Arg Leu
145                 150                 155                 160
Lys Asn Gln Lys Ser Ala Lys Glu Gly Val Thr Val Leu Ile Asn Glu
                165                 170                 175
Asp Lys Glu Leu Ala Glu Leu Arg Gly Leu Ala Ala Gly Val Gly Leu
            180                 185                 190
Ala Asn Ala Cys Tyr Ala Ile His Thr Leu Pro Thr Gln Glu Glu Ile
        195                 200                 205
Glu Asn Leu Pro Ala Phe Pro Arg Glu Lys Leu Thr Leu Arg Leu Leu
    210                 215                 220
Leu Gly Ser Gly Ala Phe Gly Glu Val Tyr Glu Gly Thr Ala Val Asp
225                 230                 235                 240
Ile Leu Gly Val Gly Ser Gly Glu Ile Lys Val Ala Val Lys Thr Leu
                245                 250                 255
Lys Lys Gly Ser Thr Asp Gln Glu Lys Ile Glu Phe Leu Lys Glu Ala
            260                 265                 270
His Leu Met Ser Lys Phe Asn His Pro Asn Ile Leu Lys Gln Leu Gly
        275                 280                 285
Val Cys Leu Leu Asn Glu Pro Gln Tyr Ile Ile Leu Glu Leu Met Glu
    290                 295                 300
Gly Gly Asp Leu Leu Thr Tyr Leu Arg Lys Ala Arg Met Ala Thr Phe
305                 310                 315                 320
Tyr Gly Pro Leu Leu Thr Leu Val Asp Leu Val Asp Leu Cys Val Asp
                325                 330                 335
Ile Ser Lys Gly Cys Val Tyr Leu Glu Arg Met His Phe Ile His Arg
            340                 345                 350
Asp Leu Ala Ala Arg Asn Cys Leu Val Ser Val Lys Asp Tyr Thr Ser
        355                 360                 365
Pro Arg Ile Val Lys Ile Gly Asp Phe Gly Leu Ala Arg Asp Ile Tyr
    370                 375                 380
Lys Asn Asp Tyr Tyr Arg Lys Arg Gly Glu Gly Leu Leu Pro Val Arg
385                 390                 395                 400
Trp Met Ala Pro Glu Ser Leu Met Asp Gly Ile Phe Thr Thr Gln Ser
                405                 410                 415
Asp Val Trp Ser Phe Gly Ile Leu Ile Trp Glu Ile Leu Thr Leu Gly
            420                 425                 430
His Gln Pro Tyr Pro Ala His Ser Asn Leu Asp Val Leu Asn Tyr Val
        435                 440                 445
Gln Thr Gly Gly Arg Leu Glu Pro Pro Arg Asn Cys Pro Asp Asp Leu
    450                 455                 460
Trp Asn Leu Met Thr Gln Cys Trp Ala Gln Glu Pro Asp Gln Arg Pro
465                 470                 475                 480
Thr Phe His Arg Ile Gln Asp Gln Leu Gln Leu Phe Arg Asn Phe Phe
                485                 490                 495
Leu Asn Ser Ile Tyr Lys Ser Arg Asp Glu Ala Asn Asn Ser Gly Val
            500                 505                 510
Ile Asn Glu Ser Phe Glu Gly Glu Gly Asp Gly Asp Val Ile Cys Leu Asn
        515                 520                 525
```

```
Ser Asp Asp Ile Met Pro Val Ala Leu Met Glu Thr Lys Asn Arg Glu
    530                 535                 540
Gly Leu Asn Tyr Met Val Leu Ala Thr Glu Cys Gly Gln Gly Glu Glu
545                 550                 555                 560
Lys Ser Glu Gly Pro Leu Gly Ser Gln Glu Ser Glu Ser Cys Gly Leu
                565                 570                 575
Arg Lys Glu Glu Lys Glu Pro His Ala Asp Lys Asp Phe Cys Gln Glu
            580                 585                 590
Lys Gln Val Ala Tyr Cys Pro Ser Gly Lys Pro Glu Gly Leu Asn Tyr
        595                 600                 605
Ala Cys Leu Thr His Ser Gly Tyr Gly Asp Gly Ser Asp
    610                 615                 620

<210> SEQ ID NO 8
<211> LENGTH: 1866
<212> TYPE: DNA
<213> ORGANISM: Artificial Sequence
<220> FEATURE:
<223> OTHER INFORMATION: Synthetic Oligonucleotide

<400> SEQUENCE: 8
atggctccct ggcctgaatt gggagatgcc cagcccaacc ccgataagta cctcgaaggg     60
gccgcaggtc agcagcccac tgcccctgat aaaagcaaag agaccaacaa aacagataac    120
actgaggcac ctgtaaccaa gattgaactt ctgccgtcct actccacggc tacactgata    180
gatgagccca ctgaggtgga tgaccccctgg aacctaccca ctcttcagga ctcggggatc    240
aagtggtcag agagagacac caaagggaag attctctgtt tcttccaagg gattgggaga    300
ttgattttac ttctcggatt tctctacttt ttcgtgtgct ccctggatat tcttagtagc    360
gccttccagc tggttggaga tgattttttgg ataccagaaa caagtttcat acttactatt    420
atagttggaa tatttctggt tgttacaatc ccactgacct ttgtctggca tagaagatta    480
aagaatcaaa aaagtgccaa ggaaggggtg acagtgctta taaacgaaga caaagagttg    540
gctgagctgc gaggtctggc agccggagta ggcctggcta tgcctgcta tgcaatacat    600 actcttccaa cccaagagga gattgaaaat cttcctgcct tccctcggga aaaactgact    660
ctgcgtctct tgctgggaag tggagccttt ggagaagtgt atgaaggaac agcagtggac    720
atcttaggag ttgaagtgg agaaatcaaa gtagcagtga agacttgaa gaagggttcc    780 acagaccagg agaagattga attcctgaag gaggcacatc tgatgagcaa atttaatcat    840
cccaacattc tgaagcagct ggagtttgt ctgctgaatg aaccccaata cattatcctg    900
gaactgatgg agggaggaga ccttcttact tatttgcgta agcccggat ggcaacgttt    960 tatggtcctt tactcacctt ggttgacctt gtagacctgt gtgtagatat ttcaaaaggc   1020
tgtgtctact tggaacggat gcatttcatt cacagggatc tggcagctag aaattgcctt   1080
gtttccgtga agactatac cagtccacgg atagtgaaga ttggagactt tggactcgcc   1140
agagacatct ataaaaatga ttactataga agagaggggg aaggcctgct cccagttcgg   1200
tggatggctc cagaaagttt gatggatgga atcttcacta ctcaatctga tgtatggtct   1260
tttggaattc tgatttggga gattttaact cttggtcatc agccttatcc agctcattcc   1320
aaccttgatg tgttaaacta tgtgcaaaca ggagggagac tggagccacc aagaaattgt   1380
cctgatgatc tgtggaattt aatgacccag tgctgggctc aagaacccga ccaaagacct   1440
acttttcata gaattcagga ccaacttcag ttattcagaa atttttttctt aaatagcatt   1500 tataagtcca gagatgaagc aaacaacagt ggagtcataa atgaaagctt tgaaggtgaa   1560
```

```
gatggcgatg tgatttgttt gaattcagat gacattatgc cagttgcttt aatgaaaacg    1620
aagaaccgag aagggttaaa ctatatggta cttgctacag aatgtggcca aggtgaagaa    1680
aagtctgagg gtcctctagg ctcccaggaa tctgaatctt gtggtctgag gaaagaagag    1740
aaggaaccac atgcagacaa agatttctgc caagaaaaac aagtggctta ctgcccttct    1800
ggcaagcctg aaggcctgaa ctatgcctgt ctcactcaca gtggatatgg agatgggtct    1860
gattaa                                                               1866
```

<210> SEQ ID NO 9
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 9

```
acccttctcg gttcttcgtt tcca                                             24
```

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10

```
gcagctcagc caactctttg tctt                                             24
```

<210> SEQ ID NO 11
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 11

```
tgccagacaa aggtcagtgg gatt                                             24
```

<210> SEQ ID NO 12
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 12

```
attcttagta gcgccttcca gctggttgga gctggagtcc caaataaacc aggcattccc    60
```

<210> SEQ ID NO 13
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 13

```
Ile Leu Ser Ser Ala Phe Gln Leu Val Gly Ala Gly Val Pro Asn Lys
1               5                   10                  15

Pro Gly Ile Pro
            20
```

<210> SEQ ID NO 14
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 14
attcttagta gcgccttcca gctggttgga gatgattttt ggataccaga aacaagtttc    60

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 15

Ile Leu Ser Ser Ala Phe Gln Leu Val Gly Asp Asp Phe Trp Ile Pro
1               5                   10                  15

Glu Thr Ser Phe
            20

<210> SEQ ID NO 16
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 16
attcttagta gcgccttcca gctggttgga gtctggcata aagattaaa gaatcaaaaa     60

<210> SEQ ID NO 17
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 17

Ile Leu Ser Ser Ala Phe Gln Leu Val Gly Val Trp His Arg Arg Leu
1               5                   10                  15

Lys Asn Gln Lys
            20

<210> SEQ ID NO 18
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 18
tccatcccag cacctgcgga g                                              21

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
catggctccc tggcctgaat tg                                             22

-continued

<210> SEQ ID NO 20
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 20
ctcaactctc tatttcccaa acaacgc                                          27

<210> SEQ ID NO 21
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 21
caacgctatt aatcagaccc atctcc                                           26

<210> SEQ ID NO 22
<211> LENGTH: 703
<212> TYPE: PRT
<213> ORGANISM: Artificial Sequence
<220> FEATURE:
<223> OTHER INFORMATION: Synthetic Peptide

<400> SEQUENCE: 22

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Asp Asp Phe Trp Ile Pro Glu Thr Ser Phe Ile Leu Thr Ile Ile Val
    210                 215                 220

Gly Ile Phe Leu Val Val Thr Ile Pro Leu Thr Phe Val Trp His Arg
225                 230                 235                 240

```
Arg Leu Lys Asn Gln Lys Ser Ala Lys Glu Gly Val Thr Val Leu Ile
            245                 250                 255

Asn Glu Asp Lys Glu Leu Ala Glu Leu Arg Gly Leu Ala Ala Gly Val
        260                 265                 270

Gly Leu Ala Asn Ala Cys Tyr Ala Ile His Thr Leu Pro Thr Gln Glu
    275                 280                 285

Glu Ile Glu Asn Leu Pro Ala Phe Pro Arg Glu Lys Leu Thr Leu Arg
290                 295                 300

Leu Leu Leu Gly Ser Gly Ala Phe Gly Glu Val Tyr Glu Gly Thr Ala
305                 310                 315                 320

Val Asp Ile Leu Gly Val Gly Ser Gly Glu Ile Lys Val Ala Val Lys
                325                 330                 335

Thr Leu Lys Lys Gly Ser Thr Asp Gln Glu Lys Ile Glu Phe Leu Lys
            340                 345                 350

Glu Ala His Leu Met Ser Lys Phe Asn His Pro Asn Ile Leu Lys Gln
        355                 360                 365

Leu Gly Val Cys Leu Leu Asn Glu Pro Gln Tyr Ile Ile Leu Glu Leu
    370                 375                 380

Met Glu Gly Gly Asp Leu Leu Thr Tyr Leu Arg Lys Ala Arg Met Ala
385                 390                 395                 400

Thr Phe Tyr Gly Pro Leu Leu Thr Leu Val Asp Leu Val Asp Leu Cys
                405                 410                 415

Val Asp Ile Ser Lys Gly Cys Val Tyr Leu Glu Arg Met His Phe Ile
            420                 425                 430

His Arg Asp Leu Ala Ala Arg Asn Cys Leu Val Ser Val Lys Asp Tyr
        435                 440                 445

Thr Ser Pro Arg Ile Val Lys Ile Gly Asp Phe Gly Leu Ala Arg Asp
    450                 455                 460

Ile Tyr Lys Asn Asp Tyr Tyr Arg Lys Arg Gly Glu Gly Leu Leu Pro
465                 470                 475                 480

Val Arg Trp Met Ala Pro Glu Ser Leu Met Asp Gly Ile Phe Thr Thr
                485                 490                 495

Gln Ser Asp Val Trp Ser Phe Gly Ile Leu Ile Trp Glu Ile Leu Thr
            500                 505                 510

Leu Gly His Gln Pro Tyr Pro Ala His Ser Asn Leu Asp Val Leu Asn
        515                 520                 525

Tyr Val Gln Thr Gly Gly Arg Leu Glu Pro Pro Arg Asn Cys Pro Asp
    530                 535                 540

Asp Leu Trp Asn Leu Met Thr Gln Cys Trp Ala Gln Glu Pro Asp Gln
545                 550                 555                 560

Arg Pro Thr Phe His Arg Ile Gln Asp Gln Leu Gln Leu Phe Arg Asn
                565                 570                 575

Phe Phe Leu Asn Ser Ile Tyr Lys Ser Arg Asp Glu Ala Asn Asn Ser
            580                 585                 590

Gly Val Ile Asn Glu Ser Phe Glu Gly Glu Asp Gly Asp Val Ile Cys
        595                 600                 605

Leu Asn Ser Asp Asp Ile Met Pro Val Ala Leu Met Glu Thr Lys Asn
    610                 615                 620

Arg Glu Gly Leu Asn Tyr Met Val Leu Ala Thr Glu Cys Gly Gln Gly
625                 630                 635                 640

Glu Glu Lys Ser Glu Gly Pro Leu Gly Ser Gln Glu Ser Glu Ser Cys
                645                 650                 655
```

```
Gly Leu Arg Lys Glu Glu Lys Glu Pro His Ala Asp Lys Asp Phe Cys
            660                 665                 670

Gln Glu Lys Gln Val Ala Tyr Cys Pro Ser Gly Lys Pro Glu Gly Leu
        675                 680                 685

Asn Tyr Ala Cys Leu Thr His Ser Gly Tyr Gly Asp Gly Ser Asp
    690                 695                 700

<210> SEQ ID NO 23
<211> LENGTH: 2112
<212> TYPE: DNA
<213> ORGANISM: Artificial Sequence
<220> FEATURE:
<223> OTHER INFORMATION: Synthetic Oligonucleotide

<400> SEQUENCE: 23
atgcacagga ggagaagcag gagctgtcgg gaagatcaga agccagtcat ggatgaccag      60
cgcgacctta tctccaacaa tgagcaactg cccatgctgg gccggcgccc tggggccccg     120
gagagcaagt gcagccgcgg agccctgtac acaggctttt ccatcctggt gactctgctc     180
ctcgctggcc aggccaccac cgcctacttc ctgtaccagc agcagggccg gctggacaaa     240
ctgacagtca cctcccagaa cctgcagctg agaaacctgc gcatgaagct tcccaagcct     300
cccaagcctg tgagcaagat cgcatggcc accccgctgc tgatgcaggc gctgcccatg     360
ggagccctgc ccaggggcc catgcagaat gccaccaagt atggcaacat gacagaggac     420
catgtgatgc acctgctcca gaatgctgac cccctgaagg tgtacccgcc actgaagggg     480
agcttcccgg agaacctgag acaccttaag aacaccatgg agaccataga ctggaaggtc     540
tttgagagct ggatgcacca ttggctcctg tttgaaatga caggcactc cttggagcaa     600 aagcccactg acgctccacc gaaagatgat ttttggatac cagaaacaag tttcatactt     660
actattatag ttggaatatt tctggttgtt acaatcccac tgaccttgt ctggcataga     720 agattaaaga tcaaaaaag tgccaaggaa ggggtgacag tgcttataaa cgaagacaaa     780
gagttggctg agctgcgagg tctggcagcc ggagtaggcc tggctaatgc ctgctatgca     840
atacatactc ttccaacccca agaggagatt gaaaatcttc ctgccttccc tcgggaaaaa     900
ctgactctgc gtctcttgct gggaagtgga gcctttggag aagtgtatga aggaacagca     960
gtggacatct taggagttgg aagtggagaa atcaaagtag cagtgaagac tttgaagaag    1020
ggttccacag accaggagaa gattgaattc ctgaaggagg cacatctgat gagcaaattt    1080
aatcatccca acattctgaa gcagcttgga gtttgtctgc tgaatgaacc ccaatacatt    1140
atcctggaac tgatggaggg aggagaccct tcttacttat tgcgtaaagc ccggatggca    1200 acgtttatg gtcctttact caccttggtt gaccttgtag acctgtgtgt agatatttca    1260
aaaggctgtg tctacttgga acggatgcat ttcattcaca gggatctggc agctagaaat    1320
tgccttgttt ccgtgaaaga ctataccagt ccacggatag tgaagattgg agactttgga    1380
ctcgccagag acatctataa aaatgattac tatagaaaga gaggggaagg cctgctccca    1440
gttcggtgga tggctccaga aagtttgatg gatggaatct tcactactca atctgatgta    1500
tggtcttttg gaattctgat tgggagatt ttaactcttg gtcatcagcc ttatccagct    1560
cattccaacc ttgatgtgtt aaactatgtg caaacaggag ggagactgga gccaccaaga    1620
aattgtcctg atgatctgtg gaatttaatg acccagtgct gggctcaaga acccgaccaa    1680
agacctactt tcatagaat tcaggaccaa cttcagttat tcagaaattt tttcttaaat    1740
agcatttata gtccagagat tgaagcaaac aacagtggag tcataaatga aagctttgaa    1800
```

-continued

```
ggtgaagatg gcgatgtgat ttgtttgaat tcagatgaca ttatgccagt tgctttaatg    1860
gaaacgaaga accgagaagg gttaaactat atggtacttg ctacagaatg tggccaaggt    1920
gaagaaaagt ctgagggtcc tctaggctcc caggaatctg aatcttgtgg tctgaggaaa    1980
gaagagaagg aaccacatgc agacaaagat ttctgccaag aaaaacaagt ggcttactgc    2040
ccttctggca agcctgaagg cctgaactat gcctgtctca ctcacagtgg atatggagat    2100
gggtctgatt aa                                                          2112

<210> SEQ ID NO 24
<211> LENGTH: 296
<212> TYPE: PRT
<213> ORGANISM: Artificial Sequence
<220> FEATURE:
<223> OTHER INFORMATION: Synthetic Peptide

<400> SEQUENCE: 24

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285

Gln Asp Leu Gly Pro Ala Pro Leu
    290                 295
```

<210> SEQ ID NO 25
<211> LENGTH: 899
<212> TYPE: DNA
<213> ORGANISM: Artificial Sequence
<220> FEATURE:
<223> OTHER INFORMATION: Synthetic Oligonucleotide

<400> SEQUENCE: 25

```
cagggtccca gatgcacagg aggagaagca ggagctgtcg ggaagatcag aagccagtca    60
tggatgacca gcgcgacctt atctccaaca atgagcaact gcccatgctg ggccggcgcc   120
ctggggcccc ggagagcaag tgcagccgcg agccctgta cacaggcttt tccatcctgg    180
tgactctgct cctcgctggc caggccacca ccgcctactt cctgtaccag cagcagggcc   240
ggctggacaa actgacagtc acctcccaga acctgcagct ggagaacctg cgcatgaagc   300
ttcccaagcc tcccaagcct gtgagcaaga tgcgcatggc caccccgctg ctgatgcagg   360
cgctgcccat gggagccctg ccccaggggc ccatgcagaa tgccaccaag tatggcaaca   420
tgacagagga ccatgtgatg cacctgctcc agaatgctga ccccctgaag gtgtacccgc   480
cactgaaggg gagcttcccg gagaacctga cacccttaa gaacaccatg gagaccatag    540
actggaaggt ctttgagagc tggatgcacc attggctcct gtttgaaatg gcaggcact    600
ccttggagca aaagcccact gacgctccac cgaaagtact gaccaagtgc caggaagagg   660
tcagccacat ccctgctgtc cacccgggtt cattcaggcc caagtgcgac gagaacggca   720
actatctgcc actccagtgc tatgggagca tcggctactg ctggtgtgtc ttccccaacg   780
gcacggaggt ccccaacacc agaagccgcg gcaccataa ctgcagtgag tcactggaac    840
tggaggaccc gtcttctggg ctgggtgtga ccaagcagga tctgggccca gctccttg     899
```

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 26

```
gcagaatgcc accaagtatg gcaa                                            24
```

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 27

```
tgccagacaa aggtcagtgg gatt                                            24
```

<210> SEQ ID NO 28
<211> LENGTH: 592
<212> TYPE: PRT
<213> ORGANISM: Artificial Sequence
<220> FEATURE:
<223> OTHER INFORMATION: Synthetic Peptide

<400> SEQUENCE: 28

```
Met Ala Pro Trp Pro Glu Leu Gly Asp Ala Gln Pro Asn Pro Asp Lys
1               5                   10                  15
Tyr Leu Glu Gly Ala Ala Gly Gln Gln Pro Thr Ala Pro Asp Lys Ser
            20                  25                  30
```

```
Lys Glu Thr Asn Lys Thr Asp Asn Thr Glu Ala Pro Val Thr Lys Ile
             35                  40                  45

Glu Leu Leu Pro Ser Tyr Ser Thr Ala Thr Leu Ile Asp Glu Pro Thr
 50                  55                  60

Glu Val Asp Asp Pro Trp Asn Leu Pro Thr Leu Gln Asp Ser Gly Ile
 65                  70                  75                  80

Lys Trp Ser Glu Arg Asp Thr Lys Gly Lys Ile Leu Cys Phe Phe Gln
                 85                  90                  95

Gly Ile Gly Arg Leu Ile Leu Leu Gly Phe Leu Tyr Phe Val
                100                 105                 110

Cys Ser Leu Asp Ile Leu Ser Ser Ala Phe Gln Leu Val Gly Val Trp
             115                 120                 125

His Arg Arg Leu Lys Asn Gln Lys Ser Ala Lys Glu Gly Val Thr Val
         130                 135                 140

Leu Ile Asn Glu Asp Lys Glu Leu Ala Glu Leu Arg Gly Leu Ala Ala
145                 150                 155                 160

Gly Val Gly Leu Ala Asn Ala Cys Tyr Ala Ile His Thr Leu Pro Thr
                 165                 170                 175

Gln Glu Glu Ile Glu Asn Leu Pro Ala Phe Pro Arg Glu Lys Leu Thr
             180                 185                 190

Leu Arg Leu Leu Leu Gly Ser Gly Ala Phe Gly Glu Val Tyr Glu Gly
         195                 200                 205

Thr Ala Val Asp Ile Leu Gly Val Gly Ser Gly Glu Ile Lys Val Ala
     210                 215                 220

Val Lys Thr Leu Lys Lys Gly Ser Thr Asp Gln Glu Lys Ile Glu Phe
225                 230                 235                 240

Leu Lys Glu Ala His Leu Met Ser Lys Phe Asn His Pro Asn Ile Leu
                 245                 250                 255

Lys Gln Leu Gly Val Cys Leu Leu Asn Glu Pro Gln Tyr Ile Ile Leu
             260                 265                 270

Glu Leu Met Glu Gly Gly Asp Leu Leu Thr Tyr Leu Arg Lys Ala Arg
         275                 280                 285

Met Ala Thr Phe Tyr Gly Pro Leu Leu Thr Leu Val Asp Leu Val Asp
     290                 295                 300

Leu Cys Val Asp Ile Ser Lys Gly Cys Val Tyr Leu Glu Arg Met His
305                 310                 315                 320

Phe Ile His Arg Asp Leu Ala Ala Arg Cys Leu Val Ser Val Lys Asp
                 325                 330                 335

Tyr Thr Ser Pro Arg Ile Val Lys Ile Gly Asp Phe Gly Leu Ala Arg
             340                 345                 350

Asp Ile Tyr Lys Asn Asp Tyr Tyr Arg Lys Arg Gly Glu Gly Leu Leu
         355                 360                 365

Pro Val Arg Trp Met Ala Pro Glu Ser Leu Met Asp Gly Ile Phe Thr
     370                 375                 380

Thr Gln Ser Asp Val Trp Ser Phe Gly Ile Leu Ile Trp Glu Ile Leu
385                 390                 395                 400

Thr Leu Gly His Gln Pro Tyr Pro Ala His Ser Asn Leu Asp Val Leu
                 405                 410                 415

Asn Tyr Val Gln Thr Gly Gly Arg Leu Glu Pro Pro Arg Asn Cys Pro
             420                 425                 430

Asp Asp Leu Trp Asn Leu Met Thr Gln Cys Trp Ala Gln Glu Pro Asp
         435                 440                 445
```

```
Gln Arg Pro Thr Phe His Arg Ile Gln Asp Gln Leu Gln Leu Phe Arg
    450                 455                 460

Asn Phe Phe Leu Asn Ser Ile Tyr Lys Ser Arg Asp Glu Ala Asn Asn
465                 470                 475                 480

Ser Gly Val Ile Asn Glu Ser Phe Glu Gly Glu Asp Gly Asp Val Ile
                485                 490                 495

Cys Leu Asn Ser Asp Asp Ile Met Pro Val Ala Leu Met Glu Thr Lys
                500                 505                 510

Asn Arg Glu Gly Leu Asn Tyr Met Val Leu Ala Thr Glu Cys Gly Gln
                515                 520                 525

Gly Glu Glu Lys Ser Gly Pro Leu Gly Ser Gln Glu Ser Glu Ser
    530                 535                 540

Cys Gly Leu Arg Lys Glu Glu Lys Glu Pro His Ala Asp Lys Asp Phe
545                 550                 555                 560

Cys Gln Glu Lys Gln Val Ala Tyr Cys Pro Ser Gly Lys Pro Glu Gly
                565                 570                 575

Leu Asn Tyr Ala Cys Leu Thr His Ser Gly Tyr Gly Asp Gly Ser Asp
                580                 585                 590
```

<210> SEQ ID NO 29
<211> LENGTH: 1782
<212> TYPE: DNA
<213> ORGANISM: Artificial Sequence
<220> FEATURE:
<223> OTHER INFORMATION: Synthetic Oligonucleotide

<400> SEQUENCE: 29

```
atggctccct ggcctgaatt gggagatgcc cagcccaacc ccgataagta cctcgaaggg      60
gccgcaggtc agcagcccac tgcccctgat aaaagcaaag agaccaacaa aacagataac     120
actgaggcac ctgtaaccaa gattgaactt ctgccgtcct actccacggc tacactgata     180
gatgagccca ctgaggtgga tgaccccctgg aacctaccca ctcttcagga ctcgggggatc    240 aagtggtcag agagagacac caaagggaag attctctgtt tcttccaagg gattgggaga     300
ttgattttac ttctctcggatt tctctacttt ttcgtgtgct ccctggatat tcttagtagc     360
gccttccagc tggttggagt ctggcataga agattaaaga atcaaaaaag tgccaaggaa     420
ggggtgacag tgcttataaa cgaagacaaa gagttggctg agctgcgagg tctggcagcc     480
ggagtaggcc tggctaatgc ctgctatgca atacatactc ttccaaccca agaggagatt     540
gaaaatcttc ctgccttccc tcgggaaaaa ctgactctgc gtctcttgct gggaagtgga     600
gcctttggag aagtgtatga aggaacagca gtggacatct aggagttgg aagtggagaa      660 atcaaagtag cagtgaagac tttgaagaag ggttccacag accaggagaa gattgaattc     720
ctgaaggagg cacatctgat gagcaaattt aatcatccca acattctgaa gcagcttgga     780
gtttgtctgc tgaatgaacc ccaatacatt atcctggaac tgatggaggg aggagacctt     840
cttacttatt tgcgtaaagc ccggatggca acgttttatg gtccttttact cacccttggtt    900 gaccttgtag acctgtgtgt agatatttca aaaggctgtg tctacttgga acggatgcat     960
ttcattcaca gggatctggc agctagaaat tgccttgttt ccgtgaaaga ctataccagt    1020
ccacggatag tgaagattgg agactttgga ctcgccagag acatctataa aaatgattac    1080
tatagaaaga gaggggaagg cctgctccca gttcggtgga tggctccaga aagtttgatg    1140 gatgaatct tcactactca atctgatgta tggtcttttg gaattctgat tggggagatt    1200
ttaactcttg gtcatcagcc ttatccagct cattccaacc ttgatgtgtt aaactatgtg    1260
```

-continued

```
caaacaggag ggagactgga gccaccaaga aattgtcctg atgatctgtg gaatttaatg    1320
acccagtgct gggctcaaga acccgaccaa agacctactt ttcatagaat tcaggaccaa    1380
cttcagttat tcagaaattt tttcttaaat agcatttata agtccagaga tgaagcaaac    1440
aacagtggag tcataaatga aagctttgaa ggtgaagatg gcgatgtgat ttgttttgaat   1500 tcagatgaca ttatgccagt tgctttaatg gaaacgaaga accgagaagg gttaaactat    1560
atggtacttg ctacagaatg tggccaaggt gaagaaaagt ctgagggtcc tctaggctcc    1620
caggaatctg aatcttgtgg tctgaggaaa gaagagaagg aaccacatgc agacaaagat    1680
ttctgccaag aaaaacaagt ggcttactgc ccttctggca agcctgaagg cctgaactat    1740
gcctgtctca ctcacagtgg atatggagat gggtctgatt aa                      1782
```

<210> SEQ ID NO 30
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 30

Phe Glu Met Ser Arg His Ser Leu Glu Gln Lys Pro Thr Asp Ala Pro
1               5                   10                  15

Pro Lys Asp Asp Phe Trp Ile Pro Glu Thr Ser Phe Ile Leu Thr Ile
            20                  25                  30

Ile Val

<210> SEQ ID NO 31
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 31
aagcccggag gcaacgtt                                                    18

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
aagccgaagg ccgaactt                                                    18

<210> SEQ ID NO 33
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 33
gaagatctct gaccatggct ccctggcctg aa                                    32

<210> SEQ ID NO 34
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 34
gaagatctac gctattaatc agacccatct cc                                32

<210> SEQ ID NO 35
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 35

Gly Leu Ala Ala Gly Val Gly Leu Ala Asn Ala Cys Tyr Ala Ile His
1               5                   10                  15

Thr Leu Pro Thr Gln Glu Glu Ile Glu Asn Leu Pro Ala Phe Pro Arg
            20                  25                  30

<210> SEQ ID NO 36
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 36

Asp Ile Tyr Lys Asn Asp Tyr Tyr Arg
1               5

<210> SEQ ID NO 37
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 37

Asp Ile Tyr Lys Asn Asp Tyr Tyr Arg Lys Arg Gly Glu Gly Leu Leu
1               5                   10                  15

Pro Val Arg

<210> SEQ ID NO 38
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 38

Glu Gly Leu Asn Tyr Met Val Leu Ala Thr Glu Cys Gly Gln Gly Glu
1               5                   10                  15

Glu Lys

<210> SEQ ID NO 39
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 39

Asn Arg Glu Gly Leu Asn Tyr Met Val Leu Ala Thr Glu Cys Gly Gln
1               5                   10                  15

Gly Glu Glu Lys
            20

```
<210> SEQ ID NO 40
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 40

Glu Gly Leu Asn Tyr Met Val Leu Ala Thr Glu Cys Gly Gln Gly Glu
1               5                   10                  15

Glu Lys Ser Glu Gly Pro Leu Gly Ser Gln Glu Ser Glu Ser Cys Gly
            20                  25                  30

Leu Arg

<210> SEQ ID NO 41
<211> LENGTH: 36
<212> TYPE: PRT
<213> ORGANISM: Artificial Sequence
<220> FEATURE:
<223> OTHER INFORMATION: Synthetic Peptide

<400> SEQUENCE: 41

Asn Arg Glu Gly Leu Asn Tyr Met Val Leu Ala Thr Glu Cys Gly Gln
1               5                   10                  15

Gly Glu Glu Lys Ser Glu Gly Pro Leu Gly Ser Gln Glu Ser Glu Ser
            20                  25                  30

Cys Gly Leu Arg
        35

<210> SEQ ID NO 42
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 42

Gln Val Ala Tyr Cys Pro Ser Gly Lys Pro Glu Gly Leu Asn Tyr Ala
1               5                   10                  15

Cys Leu Thr His Ser Gly Tyr Gly Asp Gly Ser Asp
            20                  25

<210> SEQ ID NO 43
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 43

Gly Gly His His Arg Pro Asp Ser Ser Thr Leu His Thr Asp Asp Gly
1               5                   10                  15

Tyr Met Pro Met Ser Pro Gly Val Ala Pro Val Pro Ser Gly Arg
            20                  25                  30

<210> SEQ ID NO 44
<211> LENGTH: 12
<212> TYPE: PRT
<213> ORGANISM: Artificial Sequence
<220> FEATURE:
<223> OTHER INFORMATION: Synthetic Peptide
```

<400> SEQUENCE: 44

Lys Gly Ser Gly Asp Tyr Met Pro Met Ser Pro Lys
1               5                   10

<210> SEQ ID NO 45
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 45

Val Asp Pro Asn Gly Tyr Met Met Met Ser Pro Ser Gly Gly Cys Ser
1               5                   10                  15

Pro Asp Ile Gly Gly Gly Pro Ser Ser Ser Ser Ser Ser Asn Ala
            20                  25                  30

Val Pro Ser Gly Thr Ser Tyr Gly Lys
        35                  40

<210> SEQ ID NO 46
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 46

Gln Arg Pro Val Pro Gln Pro Ser Ser Ala Ser Leu Asp Glu Tyr Thr
1               5                   10                  15

Leu Met Arg

<210> SEQ ID NO 47
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 47

Ser Ser Ser Ser Asn Leu Gly Ala Asp Asp Gly Tyr Met Pro Met Thr
1               5                   10                  15

Pro Gly Ala Ala Leu Ala Gly Ser Gly Ser Gly Ser Cys Arg
            20                  25                  30

<210> SEQ ID NO 48
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 48

Ser Asp Asp Tyr Met Pro Met Ser Pro Ala Ser Val Ser Ala Pro Lys
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Synthetic Peptide

```
<400> SEQUENCE: 49

Ala Ser Ser Pro Ala Glu Ser Ser Pro Glu Asp Ser Gly Tyr Met Arg
1               5                   10                  15

<210> SEQ ID NO 50
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 50

Ala Pro Tyr Thr Cys Gly Gly Asp Ser Asp Gln Tyr Val Leu Met Ser
1               5                   10                  15

Ser Pro Val Gly Arg Ser Tyr Lys Ala Pro Tyr Thr Cys Gly Gly Asp
                20                  25                  30

Ser Asp Gln Tyr Val Leu Met Ser Ser Pro Val Gly Arg
            35                  40                  45

<210> SEQ ID NO 51
<211> LENGTH: 34
<212> TYPE: PRT
<213> ORGANISM: Artificial Sequence
<220> FEATURE:
<223> OTHER INFORMATION: Synthetic Peptide

<400> SEQUENCE: 51

Ile Glu Leu Leu Pro Ser Tyr Ser Thr Ala Thr Leu Ile Asp Glu Pro
1               5                   10                  15

Thr Glu Val Asp Asp Pro Trp Asn Leu Pro Thr Leu Gln Asp Ser Gly
                20                  25                  30

Ile Lys

<210> SEQ ID NO 52
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 52
cagcaagaga cgcagagtca gttt                                          24

<210> SEQ ID NO 53
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 53
gctgttctcc aggctgaagt atatgg                                        26

<210> SEQ ID NO 54
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 54
gtaaccctgg tgctagttgc aaag                                          24
```

-continued

<210> SEQ ID NO 55
<211> LENGTH: 2637
<212> TYPE: DNA
<213> ORGANISM: Artificial Sequence
<220> FEATURE:
<223> OTHER INFORMATION: Synthetic Oligonucleotide

<400> SEQUENCE: 55

| | | |
|---|---|---|
| atgtcggcgg gcggtccatg cccagcagca gccggagggg gcccaggggg cgcctcctgc | 60 |
| tccgtggggg cccctggcgg ggtatccatg ttccggtggc tggaggtgct ggagaaggag | 120 |
| ttcgacaaag cttttgtgga tgtggatctg ctcctgggag agatcgatcc agaccaagcg | 180 |
| gacatcactt tgaggggcg acagaagatg accagcctga gctcctgctt tgcacagctt | 240 |
| tgccacaaag cccagtctgt gtctcaaatc aaccacaagc tggaggcaca gttggtggat | 300 |
| ctgaaatctg aactgacaga acccaagca gagaaagttg ttttggagaa agaagtacat | 360 |
| gatcagcttt tacagctgca ctctattcag ctgcagcttc atgctaaaac tggtcaaagt | 420 |
| gctgactctg gtaccattaa ggcaaaattg gaaagagagc ttgaggcaaa caaaaaagaa | 480 |
| aaaatgaaag aagcacaact tgaagctgaa gtgaaattgt tgagaaaaga gaatgaagcc | 540 |
| cttcgtagac atatagctgt tctccaggct gaagtatatg ggcgagact agctgccaag | 600 |
| tacttggata aggaactggc aggaagggtc caacagatac aattgctagg acgagatatg | 660 |
| aagggacctg ctcatgataa gctttggaac caattagaag ctgaaataca tttgcatcgt | 720 |
| cacaaaactg tgatccgagc ctgcagagga cgtaatgact tgaaacgacc aatgcaagca | 780 |
| ccaccaggcc atgatcaaga ttccctaaag aaaagccaag gtgttggtcc aattagaaaa | 840 |
| gttctcctcc ttaaggaaga tcatgaaggc cttggcattt caattacagg tgggaaagaa | 900 |
| catggtgttc caatcctcat ctctgagatc catccggggc aacctgctga tagatgcgga | 960 |
| gggctgcacg ttggggatgc tattttggca gtcaacggag ttaacctaag ggacacaaag | 1020 |
| cataaagaag ctgtaactat tctttctcag cagagaggag agattgaatt tgaagtagtt | 1080 |
| tatgtggctc ctgaagtgga ttctgatgat gaaaacgtag agtatgaaga tgagagtgga | 1140 |
| catcgttacc gtttgtacct tgatgagtta aaggaggtg gtaaccctgg tgctagttgc | 1200 |
| aaagacacaa gtggggaaat caagtatta caagtctggc atagaagatt aaagaatcaa | 1260 |
| aaaagtgcca aggaaggggt gacagtgctt ataaacgaag acaaagagtt ggctgagctg | 1320 |
| cgaggtctgg cagccggagt aggcctggct aatgcctgct atgcaataca tactcttcca | 1380 |
| acccaagagg agattgaaaa tcttcctgcc ttccctcggg aaaaactgac tctgcgtctc | 1440 |
| ttgctgggaa gtggagcctt tggagaagtg tatgaaggaa cagcagtgga catcttagga | 1500 |
| gttggaagtg gagaaatcaa agtagcagtg aagactttga agaagggttc cacagaccag | 1560 |
| gagaagattg aattcctgaa ggaggcacat ctgatgagca atttaatca tcccaacatt | 1620 |
| ctgaagcagc ttgagtttg tctgctgaat gaaccccaat acattatcct ggaactgatg | 1680 |
| gagggaggag accttcttac ttatttgcgt aaagcccgga tggcaacgtt ttatggtcct | 1740 |
| ttactcacct tggttgacct tgtagacctg tgtgtagata tttcaaaagg ctgtgtctac | 1800 |
| ttggaacgga tgcatttcat tcacagggat ctggcagcta gaaattgcct tgtttccgtg | 1860 |
| aaagactata ccagtccacg gatagtgaag attggagact ttggactcgc cagagacatc | 1920 |
| tataaaaatg attactatag aaagagaggg gaaggcctgc tcccagttcg gtggatggct | 1980 |
| ccagaaagtt tgatggatgg aatcttcact actcaatctg atgtatggtc ttttggaatt | 2040 |
| ctgatttggg agatttaac tcttggtcat cagccttatc cagctcattc caaccttgat | 2100 |

-continued

```
gtgttaaact atgtgcaaac aggagggaga ctggagccac caagaaattg tcctgatgat    2160
ctgtggaatt taatgaccca gtgctgggct caagaacccg accaaagacc tactttcat    2220 agaattcagg accaacttca gttattcaga aattttttct taaatagcat ttataagtcc    2280
agagatgaag caaacaacag tggagtcata aatgaaagct ttgaaggtga agatggcgat    2340
gtgatttgtt tgaattcaga tgacattatg ccagttgctt taatggaaac gaagaaccga    2400
gaagggttaa actatatggt acttgctaca gaatgtggcc aaggtgaaga aaagtctgag    2460
ggtcctctag gctcccagga atctgaatct tgtggtctga ggaaagaaga gaaggaacca    2520
catgcagaca aagatttctg ccaagaaaaa caagtggctt actgcccttc tggcaagcct    2580
gaaggcctga actatgcctg tctcactcac agtggatatg gagatgggtc tgattaa      2637
```

<210> SEQ ID NO 56
<211> LENGTH: 878
<212> TYPE: PRT
<213> ORGANISM: Artificial Sequence
<220> FEATURE:
<223> OTHER INFORMATION: Synthetic Peptide

<400> SEQUENCE: 56

```
Met Ser Ala Gly Gly Pro Cys Pro Ala Ala Gly Gly Gly Pro Gly
1               5                   10                  15

Gly Ala Ser Cys Ser Val Gly Ala Pro Gly Gly Val Ser Met Phe Arg
            20                  25                  30

Trp Leu Glu Val Leu Glu Lys Glu Phe Asp Lys Ala Phe Val Asp Val
        35                  40                  45

Asp Leu Leu Gly Glu Ile Asp Pro Asp Gln Ala Asp Ile Thr Tyr
    50                  55                  60

Glu Gly Arg Gln Lys Met Thr Ser Leu Ser Ser Cys Phe Ala Gln Leu
65                  70                  75                  80

Cys His Lys Ala Gln Ser Val Ser Gln Ile Asn His Lys Leu Glu Ala
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

Lys Met Lys Glu Ala Gln Leu Glu Ala Glu Val Lys Leu Leu Arg Lys
                165                 170                 175

Glu Asn Glu Ala Leu Arg Arg His Ile Ala Val Leu Gln Ala Glu Val
            180                 185                 190

Tyr Gly Ala Arg Leu Ala Ala Lys Tyr Leu Asp Lys Glu Leu Ala Gly
        195                 200                 205

Arg Val Gln Gln Ile Gln Leu Leu Gly Arg Asp Met Lys Gly Pro Ala
    210                 215                 220

His Asp Lys Leu Trp Asn Gln Leu Glu Ala Glu Ile His Leu His Arg
225                 230                 235                 240

His Lys Thr Val Ile Arg Ala Cys Arg Gly Arg Asn Asp Leu Lys Arg
                245                 250                 255

Pro Met Gln Ala Pro Pro Gly His Asp Gln Asp Ser Leu Lys Lys Ser
            260                 265                 270
```

```
Gln Gly Val Gly Pro Ile Arg Lys Val Leu Leu Lys Glu Asp His
            275                 280                 285
Glu Gly Leu Gly Ile Ser Ile Thr Gly Gly Lys Glu His Gly Val Pro
        290                 295                 300
Ile Leu Ile Ser Glu Ile His Pro Gly Gln Pro Ala Asp Arg Cys Gly
305                 310                 315                 320
Gly Leu His Val Gly Asp Ala Ile Leu Ala Val Asn Gly Val Asn Leu
                325                 330                 335
Arg Asp Thr Lys His Lys Glu Ala Val Thr Ile Leu Ser Gln Gln Arg
            340                 345                 350
Gly Glu Ile Glu Phe Glu Val Val Tyr Val Ala Pro Glu Val Asp Ser
        355                 360                 365
Asp Asp Glu Asn Val Glu Tyr Glu Asp Glu Ser Gly His Arg Tyr Arg
370                 375                 380
Leu Tyr Leu Asp Glu Leu Glu Gly Gly Gly Asn Pro Gly Ala Ser Cys
385                 390                 395                 400
Lys Asp Thr Ser Gly Glu Ile Lys Val Leu Gln Val Trp His Arg Arg
                405                 410                 415
Leu Lys Asn Gln Lys Ser Ala Lys Glu Gly Val Thr Val Leu Ile Asn
            420                 425                 430
Glu Asp Lys Glu Leu Ala Glu Leu Arg Gly Leu Ala Ala Gly Val Gly
        435                 440                 445
Leu Ala Asn Ala Cys Tyr Ala Ile His Thr Leu Pro Thr Gln Glu Glu
            450                 455                 460
Ile Glu Asn Leu Pro Ala Phe Pro Arg Glu Lys Leu Thr Leu Arg Leu
465                 470                 475                 480
Leu Leu Gly Ser Gly Ala Phe Gly Glu Val Tyr Glu Gly Thr Ala Val
                485                 490                 495
Asp Ile Leu Gly Val Gly Ser Gly Glu Ile Lys Val Ala Val Lys Thr
            500                 505                 510
Leu Lys Lys Gly Ser Thr Asp Gln Glu Lys Ile Glu Phe Leu Lys Glu
        515                 520                 525
Ala His Leu Met Ser Lys Phe Asn His Pro Asn Ile Leu Lys Gln Leu
            530                 535                 540
Gly Val Cys Leu Leu Asn Glu Pro Gln Tyr Ile Ile Leu Glu Leu Met
545                 550                 555                 560
Glu Gly Gly Asp Leu Leu Thr Tyr Leu Arg Lys Ala Arg Met Ala Thr
                565                 570                 575
Phe Tyr Gly Pro Leu Leu Thr Leu Val Asp Leu Val Asp Leu Cys Val
            580                 585                 590
Asp Ile Ser Lys Gly Cys Val Tyr Leu Glu Arg Met His Phe Ile His
        595                 600                 605
Arg Asp Leu Ala Ala Arg Asn Cys Leu Val Ser Val Lys Asp Tyr Thr
610                 615                 620
Ser Pro Arg Ile Val Lys Ile Gly Asp Phe Gly Leu Ala Arg Asp Ile
625                 630                 635                 640
Tyr Lys Asn Asp Tyr Tyr Arg Lys Arg Gly Glu Gly Leu Leu Pro Val
                645                 650                 655
Arg Trp Met Ala Pro Glu Ser Leu Met Asp Gly Ile Phe Thr Thr Gln
            660                 665                 670
Ser Asp Val Trp Ser Phe Gly Ile Leu Ile Trp Glu Ile Leu Thr Leu
        675                 680                 685
```

| | | | | | | | | | | | | | |
|---|---|---|---|---|---|---|---|---|---|---|---|---|---|
| Gly | His | Gln | Pro | Tyr | Pro | Ala | His | Ser | Asn | Leu | Asp | Val | Leu | Asn | Tyr |
| | 690 | | | | 695 | | | | | 700 | | | | | |

| Val | Gln | Thr | Gly | Gly | Arg | Leu | Glu | Pro | Pro | Arg | Asn | Cys | Pro | Asp | Asp |
|---|---|---|---|---|---|---|---|---|---|---|---|---|---|---|---|
| 705 | | | | | 710 | | | | | 715 | | | | | 720 |

| Leu | Trp | Asn | Leu | Met | Thr | Gln | Cys | Trp | Ala | Gln | Glu | Pro | Asp | Gln | Arg |
|---|---|---|---|---|---|---|---|---|---|---|---|---|---|---|---|
| | | | | 725 | | | | | 730 | | | | | 735 | |

| Pro | Thr | Phe | His | Arg | Ile | Gln | Asp | Gln | Leu | Gln | Leu | Phe | Arg | Asn | Phe |
|---|---|---|---|---|---|---|---|---|---|---|---|---|---|---|---|
| | | | 740 | | | | | 745 | | | | | 750 | | |

| Phe | Leu | Asn | Ser | Ile | Tyr | Lys | Ser | Arg | Asp | Glu | Ala | Asn | Asn | Ser | Gly |
|---|---|---|---|---|---|---|---|---|---|---|---|---|---|---|---|
| | | | 755 | | | | | 760 | | | | | 765 | | |

| Val | Ile | Asn | Glu | Ser | Phe | Glu | Gly | Asp | Gly | Asp | Val | Ile | Cys | Leu |
|---|---|---|---|---|---|---|---|---|---|---|---|---|---|---|
| | 770 | | | | | 775 | | | | | 780 | | | | |

| Asn | Ser | Asp | Asp | Ile | Met | Pro | Val | Ala | Leu | Met | Glu | Thr | Lys | Asn | Arg |
|---|---|---|---|---|---|---|---|---|---|---|---|---|---|---|---|
| 785 | | | | | 790 | | | | | 795 | | | | | 800 |

| Glu | Gly | Leu | Asn | Tyr | Met | Val | Leu | Ala | Thr | Glu | Cys | Gly | Gln | Gly | Glu |
|---|---|---|---|---|---|---|---|---|---|---|---|---|---|---|---|
| | | | | 805 | | | | | 810 | | | | | 815 | |

| Glu | Lys | Ser | Glu | Gly | Pro | Leu | Gly | Ser | Gln | Ser | Glu | Ser | Cys | Gly |
|---|---|---|---|---|---|---|---|---|---|---|---|---|---|---|
| | | | 820 | | | | | 825 | | | | | 830 | |

| Leu | Arg | Lys | Glu | Glu | Lys | Glu | Pro | His | Ala | Asp | Lys | Asp | Phe | Cys | Gln |
|---|---|---|---|---|---|---|---|---|---|---|---|---|---|---|---|
| | | | 835 | | | | | 840 | | | | | 845 | | |

| Glu | Lys | Gln | Val | Ala | Tyr | Cys | Pro | Ser | Gly | Lys | Pro | Glu | Gly | Leu | Asn |
|---|---|---|---|---|---|---|---|---|---|---|---|---|---|---|---|
| 850 | | | | | 855 | | | | | 860 | | | | | |

| Tyr | Ala | Cys | Leu | Thr | His | Ser | Gly | Tyr | Gly | Asp | Gly | Ser | Asp |
|---|---|---|---|---|---|---|---|---|---|---|---|---|---|
| 865 | | | | | 870 | | | | | 875 | | | |

<210> SEQ ID NO 57
<211> LENGTH: 1893
<212> TYPE: DNA
<213> ORGANISM: Artificial Sequence
<220> FEATURE:
<223> OTHER INFORMATION: Synthetic Oligonucleotide

<400> SEQUENCE: 57

```
atgtcggcgg gcggtccatg cccagcagca gccggagggg gcccaggggg cgcctcctgc      60
tccgtggggg cccctggcgg ggtatccatg ttccggtggc tggaggtgct ggagaaggag     120
ttcgacaaag cttttgtgga tgtggatctg ctcctgggag agatcgatcc agaccaagcg     180
gacatcactt atgagggggcg acagaagatg accagcctga gctcctgctt tgcacagctt     240
tgccacaaag cccagtctgt gtctcaaatc aaccacaagc tggaggcaca gttggtggat     300
ctgaaatctg aactgacaga aacccaagca gagaaagttg ttttggagaa agaagtacat     360
gatcagcttt tacagctgca ctctattcag ctgcagcttc atgctaaaac tggtcaaagt     420
gctgactctg gtaccattaa ggcaaaattg gaaagagagc ttaggcaaa caaaaaagaa      480 aaaatgaaag aagcacaact tgaagctgaa gtgaaattgt tgagaaaaga gaatgaagcc     540
cttcgtagac atatagctgt tctccaggct gaagtatatg gggcgagact agctgccaag     600
tacttggata aggaactggc aggaagtact cttccaaccc aagaggagat tgaaaatctt     660
cctgccttcc ctcgggaaaa actgactctg cgtctcttgc tgggaagtgg agcctttgga     720
gaagtgtatg aaggaacagc agtggacatc ttaggagttg aagtggaga aatcaaagta     780 gcagtgaaga ctttgaagaa gggttccaca gaccaggaga agattgaatt cctgaaggag     840
gcacatctga tgagcaaatt taatcatccc aacattctga gcagcttgg agtttgtctg     900 ctgaatgaac cccaatacat tatcctggaa ctgatggagg gaggagacct tcttacttat     960
ttgcgtaaag cccggatggc aacgttttat ggtccttac tcaccttggt tgaccttgta    1020
```

```
gacctgtgtg tagatatttc aaaaggctgt gtctacttgg aacggatgca tttcattcac    1080
agggatctgg cagctagaaa ttgccttgtt tccgtgaaag actataccag tccacggata    1140
gtgaagattg gagactttgg actcgccaga gacatctata aaaatgatta ctatagaaag    1200
agaggggaag gcctgctccc agttcggtgg atggctccag aaagtttgat ggatggaatc    1260
ttcactactc aatctgatgt atggtctttt ggaattctga tttgggagat tttaactctt    1320
ggtcatcagc cttatccagc tcattccaac cttgatgtgt taaactatgt gcaaacagga    1380
gggagactgg agccaccaag aaattgtcct gatgatctgt ggaatttaat gacccagtgc    1440
tgggctcaag aacccgacca agacctact tttcatagaa ttcaggacca acttcagtta    1500
ttcagaaatt ttttcttaaa tagcatttat aagtccagag atgaagcaaa caacagtgga    1560
gtcataaatg aaagctttga aggtgaagat ggcgatgtga tttgtttgaa ttcagatgac    1620
attatgccag ttgcttaat ggaaacgaag aaccgagaag ggttaaacta tatggtactt    1680
gctacagaat gtggccaagg tgaagaaaag tctgagggtc ctctaggctc ccaggaatct    1740
gaatcttgtg gtctgaggaa agaagagaag gaaccacatg cagacaaaga tttctgccaa    1800
gaaaaacaag tggcttactg cccttctggc aagcctgaag gcctgaacta tgcctgtctc    1860
actcacagtg gatatggaga tgggtctgat taa                                 1893
```

<210> SEQ ID NO 58
<211> LENGTH: 630
<212> TYPE: PRT
<213> ORGANISM: Artificial Sequence
<220> FEATURE:
<223> OTHER INFORMATION: Synthetic Peptide

<400> SEQUENCE: 58

```
Met Ser Ala Gly Gly Pro Cys Pro Ala Ala Gly Gly Gly Pro Gly
1               5                   10                  15

Gly Ala Ser Cys Ser Val Gly Ala Pro Gly Gly Val Ser Met Phe Arg
                20                  25                  30

Trp Leu Glu Val Leu Glu Lys Glu Phe Asp Lys Ala Phe Val Asp Val
            35                  40                  45

Asp Leu Leu Leu Gly Glu Ile Asp Pro Asp Gln Ala Asp Ile Thr Tyr
        50                  55                  60

Glu Gly Arg Gln Lys Met Thr Ser Leu Ser Ser Cys Phe Ala Gln Leu
65                  70                  75                  80

Cys His Lys Ala Gln Ser Val Ser Gln Ile Asn His Lys Leu Glu Ala
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

Lys Met Lys Glu Ala Gln Leu Glu Ala Glu Val Lys Leu Leu Arg Lys
                165                 170                 175

Glu Asn Glu Ala Leu Arg Arg His Ile Ala Val Leu Gln Ala Glu Val
            180                 185                 190

Tyr Gly Ala Arg Leu Ala Ala Lys Tyr Leu Asp Lys Glu Leu Ala Gly
        195                 200                 205
```

-continued

```
Ser Thr Leu Pro Thr Gln Glu Ile Glu Asn Leu Pro Ala Phe Pro
    210                 215                 220
Arg Glu Lys Leu Thr Leu Arg Leu Leu Leu Gly Ser Gly Ala Phe Gly
225                 230                 235                 240
Glu Val Tyr Glu Gly Thr Ala Val Asp Ile Leu Gly Val Gly Ser Gly
                    245                 250                 255
Glu Ile Lys Val Ala Val Lys Thr Leu Lys Lys Gly Ser Thr Asp Gln
                260                 265                 270
Glu Lys Ile Glu Phe Leu Lys Glu Ala His Leu Met Ser Lys Phe Asn
            275                 280                 285
His Pro Asn Ile Leu Lys Gln Leu Gly Val Cys Leu Leu Asn Glu Pro
        290                 295                 300
Gln Tyr Ile Ile Leu Glu Leu Met Glu Gly Gly Asp Leu Leu Thr Tyr
305                 310                 315                 320
Leu Arg Lys Ala Arg Met Ala Thr Phe Tyr Gly Pro Leu Leu Thr Leu
                    325                 330                 335
Val Asp Leu Val Asp Leu Cys Val Asp Ile Ser Lys Gly Cys Val Tyr
                340                 345                 350
Leu Glu Arg Met His Phe Ile His Arg Asp Leu Ala Ala Arg Asn Cys
            355                 360                 365
Leu Val Ser Val Lys Asp Tyr Thr Ser Pro Arg Ile Val Lys Ile Gly
        370                 375                 380
Asp Phe Gly Leu Ala Arg Asp Ile Tyr Lys Asn Asp Tyr Tyr Arg Lys
385                 390                 395                 400
Arg Gly Glu Gly Leu Leu Pro Val Arg Trp Met Ala Pro Glu Ser Leu
                    405                 410                 415
Met Asp Gly Ile Phe Thr Thr Gln Ser Asp Val Trp Ser Phe Gly Ile
                420                 425                 430
Leu Ile Trp Glu Ile Leu Thr Leu Gly His Gln Pro Tyr Pro Ala His
            435                 440                 445
Ser Asn Leu Asp Val Leu Asn Tyr Val Gln Thr Gly Gly Arg Leu Glu
        450                 455                 460
Pro Pro Arg Asn Cys Pro Asp Asp Leu Trp Asn Leu Met Thr Gln Cys
465                 470                 475                 480
Trp Ala Gln Glu Pro Asp Gln Arg Pro Thr Phe His Arg Ile Gln Asp
                    485                 490                 495
Gln Leu Gln Leu Phe Arg Asn Phe Phe Leu Asn Ser Ile Tyr Lys Ser
                500                 505                 510
Arg Asp Glu Ala Asn Asn Ser Gly Val Ile Asn Glu Ser Phe Glu Gly
            515                 520                 525
Glu Asp Gly Asp Val Ile Cys Leu Asn Ser Asp Ile Met Pro Val
        530                 535                 540
Ala Leu Met Glu Thr Lys Asn Arg Glu Gly Leu Asn Tyr Met Val Leu
545                 550                 555                 560
Ala Thr Glu Cys Gly Gln Gly Glu Glu Lys Ser Glu Gly Pro Leu Gly
                    565                 570                 575
Ser Gln Glu Ser Glu Ser Cys Gly Leu Arg Lys Glu Glu Lys Glu Pro
                580                 585                 590
His Ala Asp Lys Asp Phe Cys Gln Glu Lys Gln Val Ala Tyr Cys Pro
            595                 600                 605
```

```
Ser Gly Lys Pro Glu Gly Leu Asn Tyr Ala Cys Leu Thr His Ser Gly
    610                 615                 620

Tyr Gly Asp Gly Ser Asp
625             630

<210> SEQ ID NO 59
<211> LENGTH: 3030
<212> TYPE: DNA
<213> ORGANISM: Artificial Sequence
<220> FEATURE:
<223> OTHER INFORMATION: Synthetic Oligonucleotide

<400> SEQUENCE: 59
atgtcggcgg gcggtccatg cccagcagca gccggagggg gcccaggggg cgcctcctgc        60
tccgtggggg cccctggcgg ggtatccatg ttccggtggc tggaggtgct ggagaaggag       120
ttcgacaaag cttttgtgga tgtggatctg ctcctgggag agatcgatcc agaccaagcg       180
gacatcactt atgagggcg acagaagatg accagcctga gctcctgctt tgcacagctt       240
tgccacaaag cccagtctgt gtctcaaatc aaccacaagc tggaggcaca gttggtggat       300
ctgaaatctg aactgacaga acccaagca gagaaagttg ttttggagaa agaagtacat       360
gatcagcttt tacagctgca ctctattcag ctgcagcttc atgctaaaac tggtcaaagt       420
gctgactctg gtaccattaa ggcaaaattg gaaagagagc ttgaggcaaa caaaaaagaa       480
aaaatgaaag aagcacaact tgaagctgaa gtgaaattgt tgagaaaaga atgaagcc        540 cttcgtagac atatagctgt tctccaggct gaagtatatg ggcgagact agctgccaag       600 tacttggata aggaactggc aggaagggtc aacagatac aattgctagg acgagatatg       660 aagggaccctg ctcatgataa gctttggaac caattagaag ctgaaataca tttgcatcgt       720
cacaaaactg tgatccgagc ctgcagagga cgtaatgact tgaaacgacc aatgcaagca       780
ccaccaggcc atgatcaaga ttccctaaag aaaagccaag tgttggtcc aattagaaaa       840 gttctcctcc ttaaggaaga tcatgaaggc cttggcattt caattacagg tgggaaagaa       900
catggtgttc aatcctcat ctctgagatc catccggggc aacctgctga tagatgcgga       960
gggctgcacg ttggggatgc tattttggca gtcaacggga ttaacctaag ggacacaaag      1020
cataaagaag ctgtaactat tctttctcag cagagaggag agattgaatt tgaagtagtt      1080
tatgtggctc ctgaagtgga ttctgatgat gaaaacgtag agtatgaaga tgagagtgga      1140
catcgttacc gtttgtacct tgatgagtta aaggaggtg gtaaccctgg tgctagttgc      1200
aaagacacaa gtggggaaat caaagtatta caagctggag tcccaaataa accaggcatt      1260
cccaaattac tagaagggag taaaaattca atacagtggg agaaagctga agataatgga      1320
tgtagaatta catactatat ccttgagata agaaagagca cttcaaataa tttacagaac      1380
cagaatttaa ggtggaagat gacatttaat ggatcctgca gtagtgtttg cacatggaag      1440
tccaaaaacc tgaaaggaat atttcagttc agagtagtag ctgcaaataa tctagggttt      1500
ggtgaatata gtggaatcag tgagaatatt atattagttg gagatgattt ttggatacca      1560
gaaacaagtt tcatacttac tattatagtt ggaatatttc tggttgttac aatcccactg      1620
acctttgtct ggcatagaag attaaagaat caaaaaagtg ccaaggaagg ggtgacagtg      1680
cttataaacg aagacaaaga gttggctgag ctgcgaggtc tggcagccgg agtaggcctg      1740
gctaatgcct gctatgcaat acatactctt ccaaccccaag aggagattga aaatcttcct      1800
gccttccctc gggaaaaact gactctgcgt ctcttgctgg aagtggagc ctttggagaa      1860 gtgtatgaag aacagcagt ggacatctta ggagttggaa gtggagaaat caaagtagca      1920
```

```
gtgaagactt tgaagaaggg ttccacagac caggagaaga ttgaattcct gaaggaggca  1980
catctgatga gcaaatttaa tcatcccaac attctgaagc agcttggagt ttgtctgctg  2040
aatgaacccc aatacattat cctggaactg atggagggag gagaccttct tacttatttg  2100
cgtaaagccc ggatggcaac gttttatggt cctttactca ccttggttga ccttgtagac  2160
ctgtgtgtag atatttcaaa aggctgtgtc tacttggaac ggatgcattt cattcacagg  2220
gatctggcag ctagaaattg ccttgtttcc gtgaaagact ataccagtcc acggatagtg  2280
aagattggag actttggact cgccagagac atctataaaa atgattacta tagaaagaga  2340
ggggaaggcc tgctcccagt tcggtggatg gctccagaaa gtttgatgga tggaatcttc  2400
actactcaat ctgatgtatg gtcttttgga attctgattt gggagatttt aactcttggt  2460
catcagcctt atccagctca ttccaacctt gatgtgttaa actatgtgca acaggaggg  2520 agactggagc caccaagaaa ttgtcctgat gatctgtgga atttaatgac ccagtgctgg  2580
gctcaagaac ccgaccaaag acctactttt catagaattc aggaccaact tcagttattc  2640
agaaattttt tcttaaatag catttataag tccagagatg aagcaaacaa cagtggagtc  2700
ataaatgaaa gctttgaagg tgaagatggc gatgtgattt gtttgaattc agatgacatt  2760
atgccagttg ctttaatgga aacgaagaac cgagaagggt taaactatat ggtacttgct  2820
acagaatgtg gccaaggtga agaaaagtct gagggtcctc taggctccca ggaatctgaa  2880
tcttgtggtc tgaggaaaga agagaaggaa ccacatgcag acaaagattt ctgccaagaa  2940
aaacaagtgg cttactgccc ttctggcaag cctgaaggcc tgaactatgc ctgtctcact  3000
cacagtggat atggagatgg gtctgattaa                                    3030
```

<210> SEQ ID NO 60
<211> LENGTH: 1009
<212> TYPE: PRT
<213> ORGANISM: Artificial Sequence
<220> FEATURE:
<223> OTHER INFORMATION: Synthetic Peptide

<400> SEQUENCE: 60

Met Ser Ala Gly Gly Pro Cys Pro Ala Ala Gly Gly Gly Pro Gly
1               5                   10                  15

Gly Ala Ser Cys Ser Val Gly Ala Pro Gly Gly Val Ser Met Phe Arg
            20                  25                  30

Trp Leu Glu Val Leu Glu Lys Glu Phe Asp Lys Ala Phe Val Asp Val
        35                  40                  45

Asp Leu Leu Leu Gly Glu Ile Asp Pro Asp Gln Ala Asp Ile Thr Tyr
    50                  55                  60

Glu Gly Arg Gln Lys Met Thr Ser Leu Ser Ser Cys Phe Ala Gln Leu
65                  70                  75                  80

Cys His Lys Ala Gln Ser Val Ser Gln Ile Asn His Lys Leu Glu Ala
                85                  90                  95

Gln Leu Val Asp Leu Lys Ser Glu Leu Thr Glu Thr Gln Ala Glu Lys
            100                 105                 110

Val Val Leu Glu Lys Glu Val His Asp Gln Leu Gln Leu His Ser
        115                 120                 125

Ile Gln Leu Gln Leu His Ala Lys Thr Gly Gln Ser Ala Asp Ser Gly
    130                 135                 140

Thr Ile Lys Ala Lys Leu Glu Arg Glu Leu Glu Ala Asn Lys Lys Glu
145                 150                 155                 160

```
Lys Met Lys Glu Ala Gln Leu Glu Ala Glu Val Lys Leu Leu Arg Lys
            165                 170                 175

Glu Asn Glu Ala Leu Arg Arg His Ile Ala Val Leu Gln Ala Glu Val
        180                 185                 190

Tyr Gly Ala Arg Leu Ala Ala Lys Tyr Leu Asp Lys Glu Leu Ala Gly
    195                 200                 205

Arg Val Gln Gln Ile Gln Leu Leu Gly Arg Asp Met Lys Gly Pro Ala
210                 215                 220

His Asp Lys Leu Trp Asn Gln Leu Glu Ala Glu Ile His Leu His Arg
225                 230                 235                 240

His Lys Thr Val Ile Arg Ala Cys Arg Gly Arg Asn Asp Leu Lys Arg
                245                 250                 255

Pro Met Gln Ala Pro Pro Gly His Asp Gln Asp Ser Leu Lys Lys Ser
            260                 265                 270

Gln Gly Val Gly Pro Ile Arg Lys Val Leu Leu Lys Glu Asp His
        275                 280                 285

Glu Gly Leu Gly Ile Ser Ile Thr Gly Gly Lys Glu His Gly Val Pro
    290                 295                 300

Ile Leu Ile Ser Glu Ile His Pro Gly Gln Pro Ala Asp Arg Cys Gly
305                 310                 315                 320

Gly Leu His Val Gly Asp Ala Ile Leu Ala Val Asn Gly Val Asn Leu
                325                 330                 335

Arg Asp Thr Lys His Lys Glu Ala Val Thr Ile Leu Ser Gln Gln Arg
            340                 345                 350

Gly Glu Ile Glu Phe Glu Val Val Tyr Val Ala Pro Glu Val Asp Ser
        355                 360                 365

Asp Asp Glu Asn Val Glu Tyr Glu Asp Glu Ser Gly His Arg Tyr Arg
370                 375                 380

Leu Tyr Leu Asp Glu Leu Glu Gly Gly Asn Pro Gly Ala Ser Cys
385                 390                 395                 400

Lys Asp Thr Ser Gly Glu Ile Lys Val Leu Gln Ala Gly Val Pro Asn
                405                 410                 415

Lys Pro Gly Ile Pro Lys Leu Leu Glu Gly Ser Lys Asn Ser Ile Gln
            420                 425                 430

Trp Glu Lys Ala Glu Asp Asn Gly Cys Arg Ile Thr Tyr Tyr Ile Leu
        435                 440                 445

Glu Ile Arg Lys Ser Thr Ser Asn Asn Leu Gln Asn Gln Asn Leu Arg
    450                 455                 460

Trp Lys Met Thr Phe Asn Gly Ser Cys Ser Ser Val Cys Thr Trp Lys
465                 470                 475                 480

Ser Lys Asn Leu Lys Gly Ile Phe Gln Phe Arg Val Val Ala Ala Asn
                485                 490                 495

Asn Leu Gly Phe Gly Glu Tyr Ser Gly Ile Ser Glu Asn Ile Ile Leu
            500                 505                 510

Val Gly Asp Asp Phe Trp Ile Pro Glu Thr Ser Phe Ile Leu Thr Ile
        515                 520                 525

Ile Val Gly Ile Phe Leu Val Val Thr Ile Pro Leu Thr Phe Val Trp
    530                 535                 540

His Arg Arg Leu Lys Asn Gln Lys Ser Ala Lys Glu Gly Val Thr Val
545                 550                 555                 560

Leu Ile Asn Glu Asp Lys Glu Leu Ala Glu Leu Arg Gly Leu Ala Ala
                565                 570                 575
```

```
Gly Val Gly Leu Ala Asn Ala Cys Tyr Ala Ile His Thr Leu Pro Thr
            580                 585                 590

Gln Glu Glu Ile Glu Asn Leu Pro Ala Phe Pro Arg Glu Lys Leu Thr
        595                 600                 605

Leu Arg Leu Leu Leu Gly Ser Gly Ala Phe Gly Glu Val Tyr Glu Gly
    610                 615                 620

Thr Ala Val Asp Ile Leu Gly Val Gly Ser Gly Glu Ile Lys Val Ala
625                 630                 635                 640

Val Lys Thr Leu Lys Lys Gly Ser Thr Asp Gln Glu Lys Ile Glu Phe
                645                 650                 655

Leu Lys Glu Ala His Leu Met Ser Lys Phe Asn His Pro Asn Ile Leu
            660                 665                 670

Lys Gln Leu Gly Val Cys Leu Leu Asn Glu Pro Gln Tyr Ile Ile Leu
        675                 680                 685

Glu Leu Met Glu Gly Gly Asp Leu Leu Thr Tyr Leu Arg Lys Ala Arg
    690                 695                 700

Met Ala Thr Phe Tyr Gly Pro Leu Leu Thr Leu Val Asp Leu Val Asp
705                 710                 715                 720

Leu Cys Val Asp Ile Ser Lys Gly Cys Val Tyr Leu Glu Arg Met His
                725                 730                 735

Phe Ile His Arg Asp Leu Ala Ala Arg Asn Cys Leu Val Ser Val Lys
            740                 745                 750

Asp Tyr Thr Ser Pro Arg Ile Val Lys Ile Gly Asp Phe Gly Leu Ala
        755                 760                 765

Arg Asp Ile Tyr Lys Asn Asp Tyr Tyr Arg Lys Arg Gly Glu Gly Leu
    770                 775                 780

Leu Pro Val Arg Trp Met Ala Pro Glu Ser Leu Met Asp Gly Ile Phe
785                 790                 795                 800

Thr Thr Gln Ser Asp Val Trp Ser Phe Gly Ile Leu Ile Trp Glu Ile
                805                 810                 815

Leu Thr Leu Gly His Gln Pro Tyr Pro Ala His Ser Asn Leu Asp Val
            820                 825                 830

Leu Asn Tyr Val Gln Thr Gly Gly Arg Leu Glu Pro Pro Arg Asn Cys
        835                 840                 845

Pro Asp Asp Leu Trp Asn Leu Met Thr Gln Cys Trp Ala Gln Glu Pro
850                 855                 860

Asp Gln Arg Pro Thr Phe His Arg Ile Gln Asp Gln Leu Gln Leu Phe
865                 870                 875                 880

Arg Asn Phe Phe Leu Asn Ser Ile Tyr Lys Ser Arg Asp Glu Ala Asn
                885                 890                 895

Asn Ser Gly Val Ile Asn Glu Ser Phe Glu Gly Glu Asp Gly Asp Val
            900                 905                 910

Ile Cys Leu Asn Ser Asp Asp Ile Met Pro Val Ala Leu Met Glu Thr
        915                 920                 925

Lys Asn Arg Glu Gly Leu Asn Tyr Met Val Leu Ala Thr Glu Cys Gly
    930                 935                 940

Gln Gly Glu Glu Lys Ser Glu Gly Pro Leu Gly Ser Gln Glu Ser Glu
945                 950                 955                 960

Ser Cys Gly Leu Arg Lys Glu Glu Lys Glu Pro His Ala Asp Lys Asp
                965                 970                 975

Phe Cys Gln Glu Lys Gln Val Ala Tyr Cys Pro Ser Gly Lys Pro Glu
            980                 985                 990
```

```
Gly Leu Asn Tyr Ala Cys Leu Thr His Ser Gly Tyr Gly Asp Gly Ser
            995                1000                1005

Asp

<210> SEQ ID NO 61
<211> LENGTH: 278
<212> TYPE: PRT
<213> ORGANISM: Artificial Sequence
<220> FEATURE:
<223> OTHER INFORMATION: Synthetic Peptide

<400> SEQUENCE: 61

Leu Thr Leu Arg Leu Leu Gly Ser Gly Ala Phe Gly Glu Val Tyr
  1               5                  10                  15

Glu Gly Thr Ala Val Asp Ile Leu Gly Val Gly Ser Gly Glu Ile Lys
                 20                  25                  30

Val Ala Val Lys Thr Leu Lys Lys Gly Ser Thr Asp Gln Glu Lys Ile
             35                  40                  45

Glu Phe Leu Lys Glu Ala His Leu Met Ser Lys Phe Asn His Pro Asn
         50                  55                  60

Ile Leu Lys Gln Leu Gly Val Cys Leu Leu Asn Glu Pro Gln Tyr Ile
 65                  70                  75                  80

Ile Leu Glu Leu Met Glu Gly Gly Asp Leu Leu Thr Tyr Leu Arg Lys
                 85                  90                  95

Ala Arg Met Ala Thr Phe Tyr Gly Pro Leu Leu Thr Leu Val Asp Leu
            100                 105                 110

Val Asp Leu Cys Val Asp Ile Ser Lys Gly Cys Val Tyr Leu Glu Arg
        115                 120                 125

Met His Phe Ile His Arg Asp Leu Ala Ala Arg Asn Cys Leu Val Ser
    130                 135                 140

Val Lys Asp Tyr Thr Ser Pro Arg Ile Val Lys Ile Gly Asp Phe Gly
145                 150                 155                 160

Leu Ala Arg Asp Ile Tyr Lys Asn Asp Tyr Tyr Arg Lys Arg Gly Glu
                165                 170                 175

Gly Leu Leu Pro Val Arg Trp Met Ala Pro Glu Ser Leu Met Asp Gly
            180                 185                 190

Ile Phe Thr Thr Gln Ser Asp Val Trp Ser Phe Gly Ile Leu Ile Trp
        195                 200                 205

Glu Ile Leu Thr Leu Gly His Gln Pro Tyr Pro Ala His Ser Asn Leu
    210                 215                 220

Asp Val Leu Asn Tyr Val Gln Thr Gly Gly Arg Leu Glu Pro Pro Arg
225                 230                 235                 240

Asn Cys Pro Asp Asp Leu Trp Asn Leu Met Thr Gln Cys Trp Ala Gln
                245                 250                 255

Glu Pro Asp Gln Arg Pro Thr Phe His Arg Ile Gln Asp Gln Leu Gln
            260                 265                 270

Leu Phe Arg Asn Phe Phe
        275

<210> SEQ ID NO 62
<211> LENGTH: 6
<212> TYPE: PRT
<213> ORGANISM: Artificial Sequence
<220> FEATURE:
<223> OTHER INFORMATION: Synthetic Peptide
```

```
<400> SEQUENCE: 62

Val Gly Val Trp His Arg
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 63

Leu Val Gly Asp Asp Phe
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 64

Leu Val Gly Ala Gly Val
1               5

<210> SEQ ID NO 65
<211> LENGTH: 6
<212> TYPE: PRT
<213> ORGANISM: Artificial Seuqnece
<220> FEATURE:
<223> OTHER INFORMATION: Synthetic Peptide

<400> SEQUENCE: 65

Pro Pro Lys Asp Asp Phe
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 66

Ala Gly Ser Thr Leu Pro
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 67

Leu Gln Val Trp His Arg
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide
```

```
<400> SEQUENCE: 68

Val Leu Gln Ala Gly Val
1               5
```